(12) United States Patent
Garibay et al.

(10) Patent No.: US 8,648,041 B2
(45) Date of Patent: Feb. 11, 2014

(54) DOUBLE-ACYLATED GLP-1 DERIVATIVES

(75) Inventors: Patrick William Garibay, Holte (DK); Lars Linderoth, Alleroed (DK); Jesper Lau, Farum (DK); Per Sauerberg, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 48 days.

(21) Appl. No.: 12/970,196

(22) Filed: Dec. 16, 2010

(65) Prior Publication Data

US 2011/0166321 A1 Jul. 7, 2011

Related U.S. Application Data

(60) Provisional application No. 61/288,601, filed on Dec. 21, 2009.

(30) Foreign Application Priority Data

Dec. 16, 2009 (EP) ..................................... 09179390

(51) Int. Cl.
*A61K 38/22* (2006.01)
*C07K 14/575* (2006.01)

(52) U.S. Cl.
USPC ............ 514/7.2; 514/11.7; 530/324; 530/345

(58) Field of Classification Search
None
See application file for complete search history.

(56) References Cited

U.S. PATENT DOCUMENTS

| 5,545,618 A | 8/1996 | Buckley et al. | |
|---|---|---|---|
| 2008/0076705 A1 * | 3/2008 | Kodra et al. | 514/3 |

FOREIGN PATENT DOCUMENTS

| JP | 2010-530962 A | 9/2010 |
|---|---|---|
| WO | 9808871 A1 | 3/1998 |
| WO | 99/43707 A1 | 9/1999 |
| WO | WO 99/43706 | 9/1999 |
| WO | 00/07617 A1 | 2/2000 |
| WO | 00/16797 A2 | 3/2000 |
| WO | 2004/067548 A2 | 8/2004 |
| WO | 2005/027978 A2 | 3/2005 |
| WO | 2006/082204 A1 | 8/2006 |
| WO | 2006096515 A2 | 9/2006 |
| WO | WO 2006/097537 | 9/2006 |
| WO | 2006/127948 A2 | 11/2006 |
| WO | 2007/128817 A2 | 11/2007 |
| WO | 2009/030738 A1 | 3/2009 |
| WO | 2009/030771 A1 | 3/2009 |
| WO | WO 2009/030771 | 3/2009 |
| WO | 2009/083549 A1 | 7/2009 |

OTHER PUBLICATIONS

Knudsen et al., "Potent Derivatives of Glucagon-Like Peptide-1 with Pharmacokinetic Properties Suitable for Once Daily Administration," Journal of Medicinal Chemistry, 2000, vol. 43, No. 9, pp. 1664-1669.
Dolensky et al., "New Building Blocks for Fluorinated Imidazole," Jorunal of Organic Chemistry, vol. 66(13), pp. 4687-4691 (2001).
Dumelin et al.., "A Portable Albumin Binder From a DNA-Encoded Chemical Library", Angewandte Chemie (International Edition in English), vol. 47(17), pp. 3196-3201 (2008).
Chae et al., "The Fatty Acid Conjugated Exendin-4 Analogs for Type 2 Antidiabetic Therapeutics", Journal of the Controlled Release, vol. 144, pp. 10-16 (2010).

* cited by examiner

*Primary Examiner* — Jeffrey E Russel
(74) *Attorney, Agent, or Firm* — Richard W. Bork

(57) ABSTRACT

The invention relates to a derivative of a GLP-1 analogue, which analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$, which derivative comprises two albumin binding moieties attached to $K^{26}$ and $K^{37}$, respectively, wherein the albumin binding moiety comprises a protracting moiety selected from:
Chem. 1, Chem. 2, Chem. 3 or Chem. 4; or a pharmaceutically acceptable salt, amide, or ester thereof.

30 Claims, No Drawings

DOUBLE-ACYLATED GLP-1 DERIVATIVES

CROSS REFERENCE TO RELATED APPLICATIONS

The present application claims the benefit under 35 U.S.C. 119 of Danish application EP09179390.1 filed Dec. 16, 2009, and of U.S. provisional application 61/288,601, filed Dec. 21, 2009, the contents of which are hereby incorporated by reference.

FIELD OF THE INVENTION

The present invention relates to derivatives of Glucagon-Like Peptide 1 (GLP-1) and their pharmaceutical use, viz. to double-acylated GLP-1 derivatives acylated at position 26 and 37, and their pharmaceutical use.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun. 26, 2013. The Sequence Listing is made up of 6 kilobytes, and the information contained in the attached "SEQUENCE LISTING" is identical to the information in the specification as originally filed. No new matter is added.

BACKGROUND OF THE INVENTION

Journal of Medicinal Chemistry (2000), vol. 43, no. 9, p. 1664-669 discloses derivatives of GLP-1(7-37) that are double-acylated at $K^{26,34}$-see Table 1.

WO 98/08871 discloses a number of GLP-1 derivatives including some that are double-acylated at $K^{26,34}$, see Examples 3, 7, 17, 24, 32, 33, and 36. Liraglutide, a mono-acylated GLP-1 derivative for once daily administration which is marketed as of 2009 by Novo Nordisk A/S, is also disclosed in WO 98/08871 (Example 37). WO 99/43706 discloses a number of mono- and double-acylated GLP-1 derivatives including some $K^{26,37}$ derivatives (see p. 148-178).

WO 2005/027978 discloses a number of GLP-1 derivatives including a few that are double-acylated at one and the same residue, $K^{37}$, see Examples 8 and 9.

WO 2009/030738 discloses a number of GLP-1 derivatives including one double-acylated at $K^{31}$, $Dap^{34}$, see Example 37.

Journal of Controlled Release (2010), vol. 144, p. 10-16 relates to acylated exendin-4 analogs and discloses, among others, a double-acylated exendin-4 ($K^{12,27}$-diLUA-Exendin-4) is disclosed (LUA is lauric acid, C12).

WO 06/097537 discloses a number of GLP-1 derivatives including semaglutide (Example 4), a mono-acylated GLP-1 derivative for once weekly administration which is under development by Novo Nordisk A/S.

Angewandte Chemie International Edition 2008, vol. 47, p. 3196-3201 reports the discovery and characterisation of a class of 4-(p-iodophenyl)butyric acid derivatives which purportedly display a stable noncovalent binding interaction with both mouse serum albumin (MSA) and human serum albumin (HSA).

SUMMARY OF THE INVENTION

The invention relates to derivatives of GLP-1 peptides.

The derivatives are acylated at the native lysine at position 26, as well as at a lysine substituted for the native glycine at position 37. The side chains are albumin binding moieties. They comprise a protracting moiety, preferably selected from fatty diacids, and fatty acids with a distal phenyl, phenoxy, or thiophene group, all optionally substituted. A carboxy group of the fatty acid or fatty diacid is acylated, optionally via a linker, to a lysine residue of the GLP-1 peptide, preferably at the epsilon-amino group thereof. The GLP-1 peptide may be an analogue of GLP-1(7-37) (SEQ ID NO: 1) having a total of up to ten amino acid differences as compared to GLP-1(7-37), for example one or more additions, one or more deletions, and/or one or more substitutions.

More in particular, the invention relates to a derivative of a GLP-1 analogue, which analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$; which derivative comprises two albumin binding moieties attached to $K^{26}$ and $K^{37}$, respectively, wherein each albumin binding moiety comprises a protracting moiety selected from Chem. 1, Chem. 2, Chem. 3, and Chem. 4:

Chem. 1:

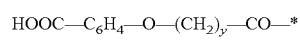

Chem. 2:

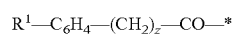

Chem. 3:

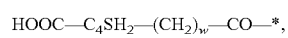

Chem. 4:

in which x is an integer in the range of 6-18, y is an integer in the range of 3-17, z is an integer in the range of 1-5, $R^1$ is a group having a molar mass not higher than 150 Da, and w is an integer in the range of 6-18; with the proviso that when the protracting moiety is Chem. 1, the albumin binding moiety further comprises a linker of formula Chem. 5:

Chem. 5:

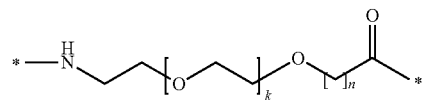

wherein k is an integer in the range of 1-5, and n is an integer in the range of 1-5; or a pharmaceutically acceptable salt, amide, or ester thereof.

The invention also relates to such derivative for use as a medicament, in particular for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

The invention furthermore relates to intermediate products in the form of GLP-1 peptides and side chains, which are relevant for the preparation of certain GLP-1 peptides and derivatives of the invention.

The derivatives of the invention are biologically active. Also, or alternatively, they have a protracted pharmacokinetic profile. Also, or alternatively, they are stable against degradation by gastro intestinal enzymes. Also, or alternatively, they have a high oral bioavailability. These properties are of importance in the development of next generation GLP-1 compounds for subcutaneous, intravenous, and/or in particular oral administration.

DESCRIPTION OF THE INVENTION

The invention relates to derivatives of GLP-1 peptides. The derivatives are acylated at the native lysine at position 26, as well as at a lysine substituted for the native glycine at position 37. The side chains are albumin binding moieties. They comprise a protracting moiety, preferably selected from fatty diacids, and fatty acids with a distal, or terminal, phenyl, thiophene, or phenoxy group, all optionally substituted. A carboxy group of the fatty acid or fatty diacid is acylated, optionally via a linker, to a lysine residue of the GLP-1 peptide, preferably at the epsilon-amino group thereof. The GLP-1 peptide may be an analogue of GLP-1(7-37) (SEQ ID NO: 1) having a total of up to ten amino acid differences as compared to GLP-1(7-37), for example one or more additions, one or more deletions, and/or one or more substitutions.

More in particular, in a first aspect, the invention relates to a derivative of a GLP-1 analogue, which analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$, which derivative comprises two albumin binding moieties attached to $K^{26}$ and $K^{37}$, respectively, wherein the albumin binding moiety comprises a protracting moiety selected from Chem. 1, Chem. 2, Chem. 3, and Chem. 4:

HOOC—$(CH_2)_x$—CO—*      Chem. 1:

HOOC—$C_6H_4$—O—$(CH_2)_y$—CO—*      Chem. 2:

$R^1$—$C_6H_4$—$(CH_2)_z$—CO—*      Chem. 3:

HOOC—$C_4SH_2$—$(CH_2)_w$—CO—*      Chem. 4:

in which x is an integer in the range of 6-18, y is an integer in the range of 3-17, z is an integer in the range of 1-5, $R^1$ is a group having a molar mass not higher than 150 Da, and w is an integer in the range of 6-18; with the proviso that when the protracting moiety is Chem. 1, the albumin binding moiety further comprises a linker of formula Chem. 5:

Chem. 5:

$$*-\overset{H}{N}\diagdown\diagup[\text{O}\diagdown\diagup]_k\text{O}\diagdown\diagup[\diagdown\diagup]_n\overset{O}{\|}\text{C}-*$$

wherein k is an integer in the range of 1-5, and n is an integer in the range of 1-5; or a pharmaceutically acceptable salt, amide, or ester thereof.

Thus, in a first aspect, the invention relates to a derivative of a GLP-1 analogue, wherein the GLP-1 analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$, which derivative comprises two albumin binding moieties attached to $K^{26}$ and $K^{37}$, respectively, wherein the albumin binding moiety comprises a protracting moiety selected from Chem. 2, Chem. 3, and Chem. 4:

HOOC—$C_6H_4$—O—$(CH_2)_y$—CO—*      Chem. 2:

$R^1$—$C_6H_4$—$(CH_2)_z$—CO—*      Chem. 3:

HOOC—$C_4SH_2$—$(CH_2)_w$—CO—*      Chem. 4:

in which y is an integer in the range of 3-17, z is an integer in the range of 1-5, $R^1$ is a group having a molar mass not higher than 150 Da, and w is an integer in the range of 6-18; or a pharmaceutically acceptable salt, amide, or ester thereof.

In a second aspect, the invention relates to a derivative of a GLP-1 analogue, wherein the GLP-1 analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$, which derivative comprises two albumin binding moieties attached to $K^{26}$ and $K^{37}$, respectively, wherein the albumin binding moiety comprises i) a protracting moiety of formula Chem. 1:

HOOC—$(CH_2)_x$—CO—*      Chem. 1:

in which x is an integer in the range of 6-18; and ii) a linker of formula Chem. 5:

Chem. 5:

$$*-\overset{H}{N}\diagdown\diagup[\text{O}\diagdown\diagup]_k\text{O}\diagdown\diagup[\diagdown\diagup]_n\overset{O}{\|}\text{C}-*$$

wherein k is an integer in the range of 1-5, and n is an integer in the range of 1-5;
or a pharmaceutically acceptable salt, amide, or ester thereof.

In a third aspect, the invention relates to a derivative of a GLP-1 analogue, wherein the GLP-1 analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$; which derivative comprises two protracting moieties attached to $K^{26}$ and $K^{37}$, respectively, via a linker, wherein the protracting moiety is selected from Chem. 1, Chem. 2, Chem. 3, and Chem. 4:

HOOC—$(CH_2)_x$—CO—*      Chem. 1:

HOOC—$C_6H_4$—O—$(CH_2)_y$—CO—*      Chem. 2:

$R^1$—$C_6H_4$—$(CH_2)_z$—CO—*      Chem. 3:

HOOC—$C_4SH_2$—$(CH_2)_w$—CO—*      Chem. 4:

in which x is an integer in the range of 6-18, y is an integer in the range of 3-17, z is an integer in the range of 1-5, $R^1$ is a group having a molar mass not higher than 150 Da, and w is an integer in the range of 6-18; and the linker comprises Chem. 5:

Chem. 5:

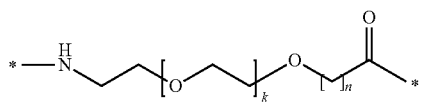

wherein k is an integer in the range of 1-5, and n is an integer in the range of 1-5; or a pharmaceutically acceptable salt, amide, or ester thereof.

The invention also relates to an intermediate product in the form of a GLP-1 analogue which comprises the following modifications as compared to GLP-1(7-37) (SEQ ID NO: 1): (i) (8Aib, 31H, 34Q, 37K); (ii) (des7-8, 34R, 37K, 38E); (iii) (des7-8, 34R, 37K); (iv) (8Aib, 9G, 34R, 37K); (v) (8Aib, 23R, 34R, 37K); (vi) (31H, 34Q, 37K); (vii) (9Q, 34R, 37K); (iix) (30E, 34R, 37K); (ix) (34R, 37K, 38G); (x) (34R, 36G, 37K); or (xi) (34R, 37K, 38E); or a pharmaceutically acceptable salt, amide, or ester of any of the analogues thereof.

The invention also relates to an intermediate product comprising a protracting moiety selected from Chem. 2c, Chem. 3b, and Chem. 4b:

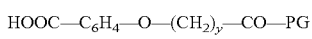 Chem. 2c:

 Chem. 3b:

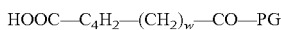 Chem. 4b:

in which y is an integer in the range of 3-17, z is an integer in the range of 1-5, $R^1$ is a group having a molar mass not higher than 150 Da, w is an integer in the range of 6-18, and *—CO—PG is an activated ester; wherein, optionally, the distal *—COOH group of the protracting moiety, if present, is functionalised as a non-reactive ester; or a pharmaceutically acceptable salt, amide, or ester thereof.

And finally the invention also relates to the pharmaceutical use of the analogues and derivatives of the invention, in particular for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

In what follows, Greek letters may be represented by their symbol or the corresponding written name, for example: α=alpha; β=beta; ε=epsilon; γ=gamma; ω=omega; etc. Also, the Greek letter of μ my be represented by "u", e.g. in μl=ul, or in μM=uM.

An asterisk (*) in a chemical formula designates i) a point of attachment, ii) a radical, and/or iii) an unshared electron.

GLP-1 Analogues

The term "GLP-1 analogue" or "analogue of GLP-1" as used herein refers to a peptide, or a compound, which is a variant of the human Glucagon-Like Peptide-1 (GLP-1(7-37)), the sequence of which is included in the sequence listing as SEQ ID NO: 1. The peptide having the sequence of SEQ ID NO: 1 may also be designated "native" GLP-1.

In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 analogues of the derivatives of the invention may be described by reference to i) the number of the amino acid residue in native GLP-1(7-37) which corresponds to the amino acid residue which is modified (i.e., the corresponding position in native GLP-1), and to ii) the actual modification. The following are non-limiting examples of suitable analogue nomenclature.

A non-limiting example of a GLP-1 analogue of the derivative of the invention is an analogue that only is modified so as to comprise a first lysine residue at a position corresponding to position 37 of GLP-1(7-37). The amino acid sequence of this analogue is otherwise identical to that of native GLP-1, and this analogue may be designated $K^{37}$-GLP-1(7-37). This designation represents the amino acid sequence of native GLP-1 where glycine at position 37 has been substituted with lysine.

This GLP-1 analogue of the derivative of the invention furthermore comprises a second lysine residue at a position corresponding to position 26 of GLP-1(7-37). As the amino acid sequence of this analogue is otherwise identical to that of native GLP-1, such analogue is, still, designated $K^{37}$-GLP-1(7-37), as $K^{26}$ is implied by the reference to native GLP-1(7-37), SEQ ID NO: 1.

Accordingly, $K^{37}$-GLP-1(7-37) designates a GLP-1(7-37) analogue wherein the naturally occurring glycine at position 37 has been substituted with lysine.

The term "analogue of $K^{37}$-GLP-1(7-37)" refers to an analogue of GLP-1(7-37) which comprises the modification $K^{37}$ and at least one additional modification, as compared to GLP-1(7-37).

The GLP-1 analogue forming part of the derivative of the invention comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$. In other words, it is a modified GLP-1(7-37) peptide in which a number of amino acid residues have been changed when compared to native GLP-1(7-37) (SEQ ID NO: 1). These changes, or modifications, may represent, independently, one or more amino acid substitutions, additions, and/or deletions.

Another non-limiting example of an analogue of a derivative of the invention is [Aib$^8$,Arg$^{34}$,Lys$^{37}$]GLP-1(7-37), which designates a GLP-1(7-37) analogue, in which the alanine at position 8 has been substituted with α-aminoisobutyric acid (Aib), the lysine at position 34 has been substituted with arginine, and the glycine at position 37 has been substituted with lysine. This analogue may also be designated (8Aib, R34, K37) GLP-1(7-37).

An additional non-limiting example of an analogue of a derivative of the invention is an analogue "which comprises 34E, 34Q, or 34R" which refers to a GLP-1 analogue which has either a glutamic acid (E), a glutamine (Q), or an arginine (R) at a position corresponding to position 34 of native GLP-1 (SEQ ID NO: 1), and which may comprise further modifications as compared to SEQ ID NO: 1.

A still further non-limiting example of an analogue of a derivative of the invention is the analogue of GLP-1(7-37) (SEQ ID NO: 1) which is simply designated "(8Aib, 31H, 34Q, 37K)". This designation refers to an analogue which is identical to SEQ ID NO: 1 except for these four substitutions, i.e. an analogue in which the alanine at position 8 has been substituted with α-aminoisobutyric acid (Aib), the tryptophan at position 31 has been substituted with histidine, the lysine at position 34 has been substituted with glutamine, and the glycine at position 37 has been substituted with lysine. This analogue does not comprise further modifications as compared to SEQ ID NO: 1.

A still further non-limiting example of an analogue of a derivative of the invention is an analogue comprising des7 (or Des), which refers to an analogue of GLP-1(7-37) in which the N-terminal amino acid, histidine, has been deleted. This analogue may also be designated GLP-1(8-37).

Similarly, (des7+des8); (des7, des8); (des7-8); or (Des$^7$, Des$^8$) in relation to an analogue of GLP-1(7-37), where the reference to GLP-1(7-37) may be implied, refers to an analogue in which the amino acids corresponding to the two N-terminal amino acids of native GLP-1, histidine and alanine, have been deleted. This analogue may also be designated GLP-1(9-37).

A still further non-limiting example of an analogue of a derivative of the invention is an analogue comprising Imp$^7$, and/or (Aib$^8$ or S$^8$), which refers to a GLP-1(7-37) analogue, which, when compared to native GLP-1, comprises a substitution of histidine at position 7 with imidazopropionic acid (Imp); and/or a substitution of alanine at position 8 with α-aminoisobutyric acid (Aib), or with serine.

Analogues "comprising" certain specified modifications may comprise further modifications, when compared to SEQ ID NO: 1. Two examples, non-limiting, of analogues comprising Imp$^7$, and/or (Aib$^8$ or S$^8$), and forming part of derivatives of the invention are the peptide parts of Chem. 47 and Chem. 58.

Non-limiting examples of an analogue of GLP-1(7-37) comprising (des7+des8), Arg34, Lys37, and Glu38 are the following: [Des$^7$, Des$^8$, Arg$^{34}$, Lys$^{37}$]GLP-1(7-37)-Glu$^{38}$ peptide; and N$^9$-{2-[2-(1H-Imidazol-4-yl)-ethylcarbamoyl]-2-methyl-propionyl}[Arg$^{34}$, Lys$^{37}$]GLP-1(9-37)Glu$^{38}$-peptide. In the latter compound a dipeptide mimetic of the N-terminus of native GLP-1 (His-Ala) is attached to the new N-terminus, Glu 9, via an amide bond.

Suitable His- or His-Ala mimetics that may be used as a kind of a substitute for the deleted N-terminal amino acids, if any, comprise a heterocyclic, nitrogen-containing, aromatic ring structure, e.g. pyridine or imidazole. Preferred His- or His-Ala mimetics are derivatives of an imidazole or a pyridine, other than His and His-Ala, in one embodiment having a substituent with a free carboxylic acid group, which can form an amide bond with an amino group of the N-terminal amino acid of the peptide. The term imidazole refers to imidazoles as a class of heterocycles with similar ring structure but varying substituents, and vice-versa for pyridine.

As is apparent from the above examples, amino acid residues may be identified by their full name, their one-letter code, and/or their three-letter code. These three ways are fully equivalent.

The expressions "a position equivalent to" or "corresponding position" may be used to characterise the site of modification in a modified GLP-1(7-37) sequence by reference to native GLP-1(7-37) (SEQ ID NO: 1). Equivalent or corresponding positions, as well as the number of modifications, are easily deduced, e.g. by simple handwriting and eye-balling; and/or a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM50 and the default identity matrix may be used, and the penalty for the first residue in a gap may be set at −12, or preferably at −10, and the penalties for additional residues in a gap at −2, or preferably at −0.5.

An example of such alignment is inserted hereinbelow, in which sequence no. 1 is SEQ ID NO: 1, and sequence no. 2 (SEQ ID NO: 2) is the analogue (des7-8, 34R, 37K, 38E) thereof:

```
# 1: GLP-1 (7-37)
# 2: GLP-1 (7-37)_Analogue
# Matrix: EBLOSUM62
# Gap_penalty: 10.0
# Extend_penalty: 0.5
# Length: 32
# Identity:   27/32 (84.4%)
# Similarity: 28/32 (87.5%)
# Gaps:       3/32 (9.4%)
# Score: 138.0

1      1 HAEGTFTSDVSSYLEGQAAKEFIAWLVKGRG- 31
         ||||||||||||||||||||||||||||:||.
2      1 --EGTFTSDVSSYLEGQAAKEFIAWLVRGRKE 30
```

In case of non-natural amino acids such as Imp and/or Aib being included in the sequence, or in case of His-Ala mimetics, these may, for alignment purposes, be replaced with X. If desired, X can later be manually corrected.

The term "peptide", as e.g. used in the context of the GLP-1 analogues of the derivatives of the invention, refers to a compound which comprises a series of amino acids interconnected by amide (or peptide) bonds.

In a particular embodiment the peptide is to a large extent, or predominantly, composed of amino acids interconnected by amide bonds (e.g., at least 50%, 60%, 70%, 80%, or at least 90%, by molar mass). In another particular embodiment the peptide consists of amino acids interconnected by peptide bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 28 amino acids.

In particular embodiments, the peptide is composed of at least five constituent amino acids, preferably composed of at least 10, at least 15, at least 20, at least 25, or most preferably composed of at least 28 amino acids.

In additional particular embodiments, the peptide is a) composed of, or b) consists of, i) 29, ii) 30, iii) 31, or iv) 32 amino acids.

In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteogenic amino acids (encoded by the genetic code, including natural amino acids, and standard amino acids), as well as non-proteogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of amino acids which are not encoded by the genetic code are gamma-carboxyglutamate, ornithine, and phosphoserine. Non-limiting examples of synthetic amino acids are the D-isomers of the amino acids such as D-alanine (in what follows sometimes abbreviated "a" as f.ex. in "a8", which accordingly refers to D-Ala$^8$) and D-leucine, Aib (α-aminoisobutyric acid), β-alanine, and desamino-histidine (desH, alternative name imidazopropionic acid, abbreviated Imp).

In what follows, all amino acids for which the optical isomer is not stated is to be understood to mean the L-isomer (unless otherwise specified).

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assay described in Example 50 herein.

GLP-1 Derivatives

The term "derivative" as used herein in the context of a GLP-1 peptide or analogue means a chemically modified GLP-1 peptide or analogue, in which one or more substituents have been covalently attached to the peptide. The substituent may also be referred to as a side chain.

In a particular embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient. Thus, the substituent, or side chain, as a whole is preferably referred to as an albumin binding moiety.

In particular embodiments, the side chain has at least 10 carbon atoms, or at least 15, 20, 25, 30, 35, or at least 40 carbon atoms. In further particular embodiments, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms.

In another particular embodiment the albumin binding moiety comprises a portion which is particularly relevant for the albumin binding and thereby the protraction, which portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion inbetween the protracting moiety and the point of attachment to the peptide, which portion may be referred to as a linker, linker moiety, spacer, or the like. The linker may be optional, and hence in that case the albumin binding moiety may be identical to the protracting moiety.

In particular embodiments, the albumin binding moiety and/or the protracting moiety is lipophilic, and/or negatively charged at physiological pH (7.4).

The albumin binding moiety, the protracting moiety, or the linker may be covalently attached to a lysine residue of the GLP-1 peptide by acylation. Additional or alternative conjugation chemistry includes alkylation, ester formation, or amide formation, or coupling to a cysteine residue, such as by maleimide or haloacetamide (such as bromo-/fluoro-/iodo-) coupling.

In a preferred embodiment, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

A derivative comprising two protracting moieties attached to $K^{26}$ and $K^{37}$, optionally via a linker, may be referred to as a derivative which has been acylated twice, double-acylated, or dual acylated at the epsilon-amino groups of the lysine residues at positions corresponding to position 26 and 37, respectively, of GLP-1(7-37).

For the present purposes, the terms "albumin binding moiety", "protracting moiety", and "linker" may include the unreacted as well as the reacted forms of these molecules. Whether or not one or the other form is meant is clear from the context in which the term is used.

In one aspect, each protracting moiety comprises, or consists of, a protracting moiety independently selected from Chem. 1, Chem. 2, Chem. 3, and Chem. 4:

$$HOOC-(CH_2)_x-CO-* \quad \text{Chem. 1:}$$

$$HOOC-C_6H_4-O-(CH_2)_y-CO-* \quad \text{Chem. 2:}$$

$$R^1-C_6H_4-(CH_2)_z-CO-* \quad \text{Chem. 3:}$$

$$HOOC-C_4SH_2-(CH_2)_w-CO-* \quad \text{Chem. 4:}$$

in which x is an integer in the range of 6-18, y is an integer in the range of 3-17, z is an integer in the range of 1-5, $R^1$ is a group having a molar mass not higher than 150 Da, and w is an integer in the range of 6-18.

In one embodiment, $*-(CH_2)_x-*$ refers to straight or branched, preferably straight, alkylene in which x is an integer in the range of 6-18.

In another embodiment, $*-(CH_2)_y-*$ refers to straight or branched, preferably straight, alkylene in which y is an integer in the range of 3-17.

In a third embodiment, $*-(CH_2)_z-*$ refers to straight or branched, preferably straight, alkylene in which z is an integer in the range of 1-5.

In a still further embodiment, $*-(CH_2)_w-*$ refers to straight or branched, preferably straight, alkylene in which w is an integer in the range of 6-18.

In another aspect the albumin binding moiety comprises, or consists of, a protracting moiety selected from fatty diacids, and fatty acids with a distal (terminal) phenyl or phenoxy group, both optionally substituted. Optional substituents to the phenyl, and/or the phenoxy group, have a molar mass not higher than 150 Da, preferably not higher than 125 Da, more preferably not higher than 100 Da, even more preferably not higher than 75 Da, or most preferably not higher than 50 Da. Examples of substituents include, without limitation, carboxy, hydroxyl, lower linear or branched C1-C5 alkyl such as methyl and tert. butyl, and halogen such as iodine.

For the attachment to the GLP-1 peptide, the acid group of the fatty acid, or one of the acid groups of the fatty diacid, forms an amide bond with the epsilon amino group of a lysine residue in the GLP-1 peptide, preferably via a linker.

The term "fatty acid" refers to aliphatic monocarboxylic acids having from 4 to 28 carbon atoms, it is preferably unbranched, and/or even numbered, and it may be saturated or unsaturated.

The term "fatty diacid" refers to fatty acids as defined above but with an additional carboxylic acid group in the omega position. Thus, fatty diacids are dicarboxylic acids.

In a preferred embodiment the protracting moiety is selected from HOOC—$(CH_2)_n$—CO—*, HOOC—$C_6H_4$—O—$(CH_2)_m$—CO—*, and $R^1$—$C_6H_4$—$(CH_2)_p$—CO—*, in which n is an integer in the range of 8-16, m is an integer in the range of 7-17, p is an integer in the range of 1-5, and $R^1$ is a group having a molar mass not higher than 150 Da.

The nomenclature is as is usual in the art, for example in the above formulas *—COOH as well as HOOC—* refers to carboxy; *—$C_6H_4$—* to phenylene; *—CO—*, as well as *—OC—*, to carbonyl (O=C<**); $C_6H_5$—O—* to phenoxy; $C_4H_4$ S or $C_4H_4$ to thiophene; and *—$C_4SH_2$* to a di-radical thereof (any thiophenylene). In particular embodiments, the aromatics, such as the phenoxy, and the phenylene radicals, may be, independently, ortho, meta, or para. In another embodiment, the thiophenylene di-radical may be 2,3-; 2,4-; or 2,5-.

The molar mass (M) of a chemical substance (such as the group $R^1$) is the mass of one mole of the substance. The molar mass is quoted in dalton, symbol Da, with the definition 1 Da=1 g/mol.

Molar mass may be calculated from standard atomic weights, and is often listed in chemical catalogues. The molar mass of a compound is given by the sum of the standard atomic weights of the atoms which form the compound multiplied by the molar mass constant, $M_u$ which equals 1 g/mol. As an example, the molecular mass of tert. butyl $(C_4H_9)$ is $M(C_4H_9)=([4×12.01]+[9×1.008])×1$ g/mol=57 Da.

Standard atomic weights are published by the International Union of Pure and Applied Chemistry (IUPAC), and also reprinted in a wide variety of textbooks, commercial catalogues, wallcharts etc.

As explained above, the GLP-1 derivatives of the present invention are double-acylated, i.e. two albumin binding moieties are covalently attached to the GLP-1 peptide. The points of attachment are the native lysine residue at the position corresponding to position 26 of GLP-1(7-37), and a lysine residue which has been substituted for the native glycine residue at the position corresponding to position 37 of GLP-1(7-37).

In a particular embodiment, the two albumin binding moieites (i.e. the entire side chains) are similar, preferably substantially identical, or, most preferably, identical.

In another particular embodiment, the two protracting moieties are similar, preferably substantially identical, or, most preferably, identical.

In a still further particular embodiment, the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as the albumin binding moieities, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b) or c) is used.

In particular embodiments, whether a), b) or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008-both from Accelrys Software Inc., San Diego, US, and the guides www.tripos.com/tripos_resources/fileroot/pdfs/Unity_111408.pdf, and www.tripos.com/data/SYBYL/SYBYL_072505.pdf.

An example of a similarity calculation is inserted hereinbelow, in which the entire side chain of Chem. 23 was compared with a methyl ester thereof, viz. the mono methyl ester of the glutamine linker moiety (Chem 23a):

Chem. 23a:

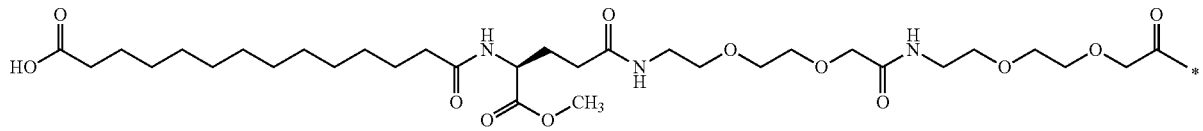

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

Each of the two linkers of the derivative of the invention may comprise the following first linker element:

Chem. 5:

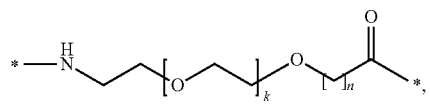

wherein k is an integer in the range of 1-5, and n is an integer in the range of 1-5.

In a particular embodiment, when k=1 and n=1, this linker element may be designated OEG, or a di-radical of 8-amino-3,6-dioxaoctanic acid, and/or it may be represented by the following formula:

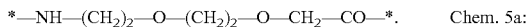   Chem. 5a:

In another particular embodiment, each linker of the derivative of the invention may further comprise, independently, a second linker element, preferably a Glu di-radical, such as Chem. 6 and/or Chem. 7:

Chem. 6:

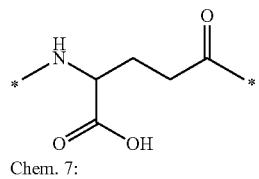

Chem. 7:

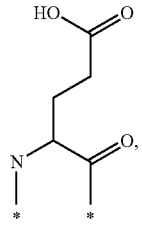

wherein the Glu di-radical may be included p times, where p is an integer in the range of 1-3.

Chem. 6 may also be referred to as gamma-Glu, or briefly gGlu, due to the fact that it is the gamma carboxy group of the amino acid glutamic acid which is here used for connection to another linker element, or to the epsilon-amino group of lysine. As explained above, the other linker element may, for example, be another Glu residue, or an OEG molecule. The amino group of Glu in turn forms an amide bond with the carboxy group of the protracting moiety, or with the carboxy group of, e.g., an OEG molecule, if present, or with the gamma-carboxy group of, e.g., another Glu, if present.

Chem. 7 may also be referred to as alpha-Glu, or briefly aGlu, or simply Glu, due to the fact that it is the alpha carboxy group of the amino acid glutamic acid which is here used for connection to another linker element, or to the epsilon-amino group of lysine.

The above structures of Chem. 6 and Chem. 7 cover the L-form, as well as the D-form of Glu. In particular embodiments, Chem. 6 and/or Chem. 7 is/are, independently, a) in the L-form, or b) in the D-form.

In another particular embodiment, each linker of the derivative of the invention may further comprise, independently, the following third linker element:

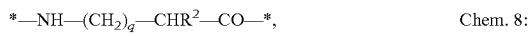   Chem. 8:

in which q is an integer in the range of 2-12, and $R^2$ is hydrogen (H) or amino ($NH_2$).

In Chem. 8, the group $*-(CH_2)_q-*$ may represent straight or branched, preferably straight, alkylene, wherein q is an integer in the range of 2-12.

In still further particular embodiments the linker has a) from 5 to 41 C-atoms; and/or b) from 4 to 28 hetero atoms. Particular and non-limiting examples of hetero atoms are N-, and O-atoms. H-atoms are not hetero atoms.

Alternatively, the linker moiety, if present, has from 5 to 30 C-atoms, preferably from 5 to 25 C-atoms, more preferably from 5 to 20 C-atoms, or most preferably from 5 to 17 C-atoms. In additional preferred embodiments, the linker moiety, if present, has from 4 to 20 hetero atoms, preferably from 4 to 18 hetero atoms, more preferably from 4 to 14 hetero atoms, or most preferably from 4 to 12 hetero atoms.

Alternatively, the linker comprises at least one OEG molecule, and/or at least one glutamic acid residue, or rather the corresponding radicals.

In a particular embodiment, each linker consists of one time Chem. 6 and two times Chem. 5, interconnected via amide bonds and in the sequence indicated, the linker being connected at its free amino end to the free carbonyl group of the protracting moiety, and at its free carbonyl end to the epsilon amino group of $K^{26}$ or $K^{37}$ of the GLP-1 analogue.

In another particular embodiment, each linker consists of two times Chem. 5 and one time Chem. 6, interconnected via amide bonds and in the sequence indicated, the linker being connected at its free amino end to the free carbonyl group of the protracting moiety, and at its free carbonyl end to the epsilon amino group of $K^{26}$ or $K^{37}$ of the GLP-1 analogue.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030,738 on p. 116-118. A preferred assay is the LOCI assay described in Example 52, 55, and 58 herein.

Pharmaceutically Acceptable Salt, Amide, or Ester

The derivatives, analogues, and intermediate products of the invention may be in the form of a pharmaceutically acceptable salt, amide, or ester.

Salts are e.g. formed by a chemical reaction between a base and an acid, e.g.: $2NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Intermediate Products

One type of intermediate product of the invention takes the form of a GLP-1 analogue which comprises the following modifications as compared to GLP-1(7-37) (SEQ ID NO: 1): (i) (8Aib, 31H, 34Q, 37K); (ii) (des7-8, 34R, 37K, 38E); (iii) (des7-8, 34R, 37K); (iv) (8Aib, 9G, 34R, 37K); (v) (8Aib, 23R, 34R, 37K); (vi) (31H, 34Q, 37K); (vii) (9Q, 34R, 37K); (iix) (30E, 34R, 37K); (ix) (34R, 37K, 38G); (x) (34R, 36G, 37K); or (xi) (34R, 37K, 38E); or a pharmaceutically acceptable, salt, amide, or ester thereof.

Another type of intermediate product of the invention takes the form of an albumin binding moiety, or a side chain intermediate, comprising a protracting moiety selected from Chem. 2c, Chem. 3b, and Chem. 4b:

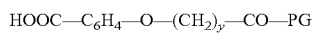 Chem. 2c:

 Chem. 3b:

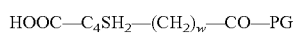 Chem. 4b:

in which y is an integer in the range of 3-17, z is an integer in the range of 1-5, $R^1$ is a group having a molar mass not higher than 150 Da, w is an integer in the range of 6-18, whee PG is a protection group, preferably *—CO—PG is an activated ester; wherein, optionally, the other (distal) *—COOH group of the protracting moiety, if present, is preferably also protected as is known in the art, for example functionalised as a non-reactive ester; or a pharmaceutically acceptable salt, amide, or ester thereof.

In a particular embodiment, the side chain intermediate comprises
a) a protracting moiety selected from Chem. 2, Chem. 3, and Chem. 4:

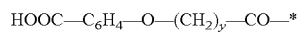 Chem. 2:

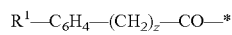 Chem. 3:

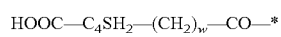 Chem. 4:

in which y is an integer in the range of 3-17, z is an integer in the range of 1-5, $R^1$ is a group having a molar mass not higher than 150 Da, and w is an integer in the range of 6-18; and b) one or more linkers selected from Chem. 5b, Chem. 6, and Chem. 7:

Chem. 5b:

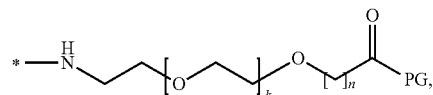

Chem. 6a:

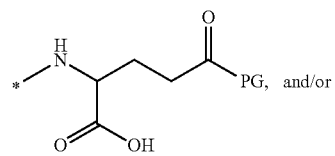 PG, and/or

Chem. 7a:

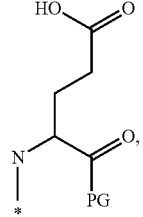

wherein k is an integer in the range of 1-5, and n is an integer in the range of 1-5; and PG is a protection group; wherein, optionally, the *—COOH group of the protracting moiety is preferably also protected as is known in the art, preferably functionalised as a non-reactive ester; or a pharmaceutically acceptable salt, amide, or ester thereof.

In a particular embodiment, PG is a group that reversibly renders the compound such as the protracting moiety unreactive, and that can be removed selectively.

Non-limiting examples of PG groups are —OH, or groups functionalised as an activated ester, for example, without limitation, OPfp, OPnp, and OSuc.

Other suitable activated esters may be selected, e.g., according to the teaching of M. Bodanszky, "Principles of Peptide Synthesis", 2nd ed., Springer Verlag, 1993.

Functional Properties

In a first functional aspect, the derivatives of the invention have a good potency. Also, or alternatively, in a second functional aspect, they have a protracted pharmacokinetic profile. Also, or alternatively, in a third functional aspect, they are stable against degradation by gastro intestinal enzymes. Also, or alternatively, in a fourth functional aspect, they have a high oral bioavailability.

Biological Activity (Potency)

According to the first functional aspect, the derivatives of the invention, as well as the constituent GLP-1 peptides as such (such as $K^{37}$-GLP-1(7-37) or analogues thereof), are biologically active, or potent.

In a particular embodiment, potency and/or activity refers to in vitro potency, i.e. performance in a functional GLP-1 receptor assay, more in particular to the capability of stimulating cAMP formation in a cell line expressing the cloned human GLP-1 receptor.

The stimulation of the formation of cAMP in a medium containing the human GLP-1 receptor may preferably be determined using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 50.

The term half maximal effective concentration ($EC_K$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$, the better the potency.

In a particular embodiment, the medium has the following composition (final in-assay concentrations): 50 mM TRIS-HCl; 5 mM HEPES; 10 mM $MgCl_2$, $6H_2O$; 150 mM NaCl; 0.01% Tween™ 0.1% BSA ; 0.5 mM IBMX; 1 mM ATP; 1 uM GTP; pH 7.4.

An alternative medium is: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% Tween-20, pH 7.4.

In a further particular embodiment, the derivative of the invention has an $EC_{50}$ at or below 3000 µM, more preferably below 2000 µM, even more preferably below 1000 µM, or most preferably below 500 µM.

In another particular embodiment the derivatives of the invention are potent in vivo, which may be determined as is known in the art in any suitable animal model, as well as in clinical trials.

The diabetic db/db mouse is one example of a suitable animal model, and the blood glucose lowering effect may be determined in such mice in vivo, e.g. as described in Example 53, or as described in Example 43 of WO09/030,738.

Also, or alternatively, the effect on glucose mediated insulin secretion in vivo may be determined in pharmacodynamic studies in minipigs (IVGTT), e.g. as described in Example 55.

Also, or alternatively, the effect on feed intake in vivo may be determined in pharmacodynamic studies in pigs, e.g. as described in Example 56.

Protraction—Receptor Binding/Low and High Albumin

According to the second functional aspect, the derivatives of the invention are protracted.

The ability of the derivatives of the invention to bind to the GLP-1 receptor in the presence of a low and a high concentration of albumin, respectively, may be determined as described in Example 51.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$IC_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low). On the other hand, albumin binding may not always be desirable, or the binding to albumin may become too strong. Therefore, the desirable ranges for $IC_{50}$ (low albumin), $IC_{50}$ (high albumin)/, and the ratio high/low may vary from compound to compound, depending on the intended use and the circumstances surrounding such use, and on other compound properties of potential interest.

In a particular embodiment, the GLP-1 receptor binding affinity ($IC_{50}$) in the presence of 0.005% HSA (low albumin) is below 1000.00 nM, preferably below 600.00 nM, more preferably below 100.00 nM, or most preferably below 50.00 nM.

A suitable assay for determining receptor binding at high and low albumin concentration is disclosed in Example 51 herein.

Protraction—Half Life In Vivo in Rats

According to the second functional aspect, the derivatives of the invention are protracted. In a particular embodiment, protraction may be determined as half-life ($T_{1/2}$) in vivo in rats after i.v. administration. In additional embodiments, the half-life is at least 4 hours, preferably at least 6 hours, even more preferably at least 8 hours, or most preferably at least 10 hours.

A suitable assay for determining half-life in vivo in rats after i.v. administration is disclosed in Example 58 herein.

Protraction—Half Life In Vivo in Minipigs

According to the second functional aspect, the derivatives of the invention are protracted. In a particular embodiment protraction may be determined as half-life ($T_{1/2}$) in vivo in minipigs after i.v. administration. In additional embodiments, the half-life is at least 12 hours, preferably at least 24 hours, more preferably at least 36 hours, even more preferably at least 48 hours, or most preferably at least 60 hours.

A suitable assay for determining half-life in vivo in minipigs after i.v. administration is disclosed in Example 54 herein.

Degradation by Gastro Intestinal Enzymes

According to the third functional aspect, the derivatives of the invention are stable, or stabilised, against degradation by one or more gastro intestinal enzymes.

Gastro intestinal enzymes include, without limitation, exo and endo peptidases, such as pepsin, trypsin, chymotrypsin, elastases, and carboxypeptidases. The stability may be tested against these gastro intestinal enzymes in the form of purified enzymes, or in the form of extracts from the gastrointestinal system.

In a particular embodiment, the derivative of the invention has an in vitro half-life ($T_{1/2}$), in an extract of rat small intestines, divided by the corresponding half-life ($T_{1/2}$) of GLP-1(7-37), of at least 1, preferably above 1.0, more preferably at least 1.2, still more preferably at least 2.0, even more preferably at least 3.0, or most preferably at least 4.0. In other words, a ratio(SI) may be defined for each derivative, viz. as the in vitro half-life ($T_{1/2}$) of the derivative in question, in an extract of rat small intestines, divided by the corresponding half-life ($T_{1/2}$) of GLP-1(7-37).

A suitable assay for determining in vitro half-life in an extract of rat small intestines is disclosed in Example 57 herein.

Oral Bioavailability

According to the fourth functional aspect, the derivatives of the invention have a high oral bioavailability.

The oral bioavailability of commercial GLP-1 derivatives is very low. The oral bioavailability of GLP-1 derivatives under development for i.v. or s.c. administration is also low.

Accordingly, there is a need in the art for GLP-1 derivatives of an improved oral bioavailability. Such derivatives could be suitable candidates for oral administration, as long as their potency is generally satisfactory, and/or as long as their half-life is also generally satisfactory.

The present inventors identified a novel class of GLP-1 derivatives, which have a surprisingly high oral bioavailability, and at the same time a satisfactory potency, and/or half-life.

Also, or alternatively, these derivatives have a surprisingly high oral bioavailability, and at the same time a high binding affinity (i.e. a low $IC_{50}$ value) to the GLP-1 receptor at a low concentration of albumin.

These features are of importance with a view to obtaining a low daily oral dose of the active pharmaceutical ingredient, which is desirable for various reasons, including, e.g., economy of production, likelihood of potential safety issues, as well as administration comfort issues, and environmental concerns.

Generally, the term bioavailability refers to the fraction of an administered dose of the active pharmaceutical ingredient (API), such as a derivative of the invention that reaches the systemic circulation unchanged. By definition, when an API is administered intravenously, its bioavailability is 100%. However, when it is administered via other routes (such as orally), its bioavailability decreases (due to incomplete absorption and first-pass metabolism). Knowledge about bioavailability is essential when calculating dosages for non-intravenous routes of administration.

Absolute oral bioavailability compares the bioavailability (estimated as the area under the curve, or AUC) of the API in systemic circulation following oral administration, with the bioavailability of the same API following intravenous administration. It is the fraction of the API absorbed through non-intravenous administration compared with the corresponding intravenous administration of the same API. The comparison must be dose normalised if different doses are used; consequently, each AUC is corrected by dividing the corresponding dose administered.

A plasma API concentration vs time plot is made after both oral and intravenous administration. The absolute bioavailability (F) is the dose-corrected AUC-oral divided by AUC-intravenous.

The derivatives of the invention have an absolute oral bioavailability which is higher than that of a) liraglutide, and/or b) semaglutide; preferably at least 10% higher, more preferably at least 20% higher, even more preferably at least 30% higher, or most preferably at least 40% higher. Before testing oral bioavailability the derivatives of the invention may suitably be formulated as is known in the art of oral formulations of insulinotropic compounds, e.g. using any one or more of the formulations described in WO 2008/145728.

A test has been developed, described in Example 52, which was found to be a very good prediction of oral bioavailability. According to this test, after direct injection of the GLP-1 derivative into the intestinal lumen of rats, the concentration (exposure) thereof in plasma is determined, and the ratio of plasma concentration (pmol/l) divided by the concentration of the dosing solution (umol/l) is calculated for t=30 min. This ratio is a measure of intestinal bioavailability, and it has shown to correlate nicely with actual oral bioavailability data.

Additional particular embodiments of the derivatives of the invention are described in the sections headed "particular embodiments" and "additional particular embodiments" before the experimental section.

Production Processes

The production of peptides like GLP-1(7-37) and GLP-1 analogues is well known in the art.

The GLP-1 moiety of the derivatives of the invention (or fragments thereof), such as $K^{37}$-GLP-1(7-37) or an analogue or fragment thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

Pharmaceutical compositions comprising a derivative of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19$^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethane, bicine, tricine, malic acid, succinate, maleic acid, fumaric acid, tartaric acid, aspartic acid, and mixtures thereof. A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml. A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose—Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. A pharmaceutical composition may comprise a chelating agent. The chelating agent may e.g. be selected from salts of ethylenediaminetetraacetic acid (EDTA), citric acid, and aspartic acid, and mixtures thereof. A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.01 mg-100 mg of the derivative, or from 0.01-50 mg, or from 0.01-20 mg, or from 0.01-10 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. A composition may be an oral composition, and the route of administration is per oral.

A composition may be administered in several dosage forms, for example as a solution; a suspension; an emulsion;

a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant. A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention, for use as a medicament.

In particular embodiments, the derivative of the invention-may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1 C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

PARTICULAR EMBODIMENTS

The following are particular embodiments of the invention:
1. A derivative of a GLP-1 analogue,
which analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$, which derivative comprises two albumin binding moieties attached to $K^{26}$ and $K^{37}$, respectively, wherein the albumin binding moiety comprises a protracting moiety selected from Chem. 1, Chem. 2, Chem. 3, and Chem. 4:

$HOOC—(CH_2)_x—CO—*$     Chem. 1:

$HOOC—C_6H_4—O—(CH_2)_y—CO—*$     Chem. 2:

$R^1—C_6H_4—(CH_2)_z—CO—*$     Chem. 3:

$HOOC—C_4SH_2—(CH_2)_w—CO—*$     Chem. 4:

in which x is an integer in the range of 6-18, y is an integer in the range of 3-17, z is an integer in the range of 1-5, $R^1$ is a group having a molar mass not higher than 150 Da, and w is an integer in the range of 6-18;

with the proviso that when the protracting moiety is Chem. 1, the albumin binding moiety further comprises a linker of formula Chem. 5:

Chem. 5:

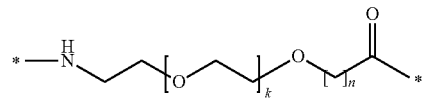

wherein k is an integer in the range of 1-5, and n is an integer in the range of 1-5;

or a pharmaceutically acceptable salt, amide, or ester thereof.

2. The derivative of embodiment 1,
wherein the GLP-1 analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$, which derivative comprises two albumin binding moieties attached to $K^{26}$ and $K^{37}$, respectively, wherein the albumin binding moiety comprises a protracting moiety selected from Chem. 2, Chem. 3, and Chem. 4:

$HOOC—C_6H_4—O—(CH_2)_y—CO—*$     Chem. 2:

$R^1—C_6H_4—(CH_2)_z—CO—*$     Chem. 3:

$HOOC—C_4SH_2—(CH_2)_w—CO—*$     Chem. 4:

in which y is an integer in the range of 3-17, z is an integer in the range of 1-5, $R^1$ is a group having a molar mass not higher than 150 Da, and w is an integer in the range of 6-18;

or a pharmaceutically acceptable salt, amide, or ester thereof.

3. The derivative of embodiment 2, wherein the albumin binding moiety further comprises a linker.

4. The derivative of embodiment 3, wherein the linker comprises i) a Glu di-radical; and/or ii) a linker of formula Chem. 5:

Chem. 5:

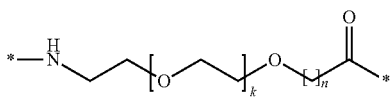

wherein k is an integer in the range of 1-5, and n is an integer in the range of 1-5.

5. The derivative of embodiment 4, wherein the Glu di-radical is selected from Chem. 6, and/or Chem. 7:

Chem. 6:

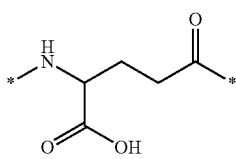

Chem. 7:

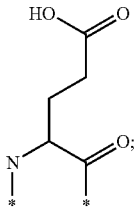

preferably Chem. 6.

6. The derivative of embodiment 1,
wherein the GLP-1 analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$,
which derivative comprises two albumin binding moieties attached to $K^{26}$ and $K^{37}$, respectively, wherein the albumin binding moiety comprises
i) a protracting moiety of formula Chem. 1:

 Chem. 1:

in which x is an integer in the range of 6-18; and
ii) a linker of formula Chem. 5:

Chem. 5:

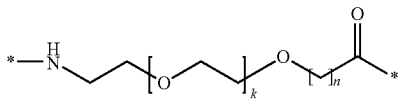

wherein k is an integer in the range of 1-5, and n is an integer in the range of 1-5; or a pharmaceutically acceptable salt, amide, or ester thereof.

7. The derivative of embodiment 1,
wherein the GLP-1 analogue comprises a first K residue at a position corresponding to position 37 of GLP-1(7-37) (SEQ ID NO: 1), a second K residue at a position corresponding to position 26 of GLP-1(7-37), and a maximum of ten amino acid modifications as compared to GLP-1(7-37), wherein the first K residue is designated $K^{37}$, and the second K residue is designated $K^{26}$;
which derivative comprises two protracting moieties attached to $K^{26}$ and $K^{37}$, respectively, via a linker, wherein
the protracting moiety is selected from Chem. 1, Chem. 2, Chem. 3, and Chem. 4:

 Chem. 1:

 Chem. 2:

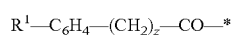 Chem. 3:

 Chem. 4:

in which x is an integer in the range of 6-18, y is an integer in the range of 3-17, z is an integer in the range of 1-5, $R^1$ is a group having a molar mass not higher than 150 Da, and w is an integer in the range of 6-18; and
the linker comprises Chem. 5:

Chem. 5:

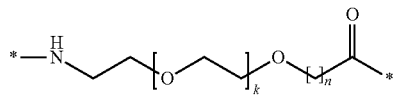

wherein k is an integer in the range of 1-5, and n is an integer in the range of 1-5;
or a pharmaceutically acceptable salt, amide, or ester thereof.

8. The derivative of any one of embodiments 1-7, wherein Chem. 5 is a first linker element.

9. The derivative of any one of embodiments 1-8, wherein k is 1.

10. The derivative of any one of embodiments 1-9, wherein n is 1.

11. The derivative of any one of embodiments 1-10, wherein Chem. 5 is included m times, wherein m is an integer in the range of 1-10.

12. The derivative of embodiment 11, wherein m is an integer in the range of 1-6; preferably in the range of 1-4; more preferably m is 1 or 2; or most preferably m is 2.

13. The derivative of any one of embodiments 11-12, wherein, when m is different from 1, the Chem. 5 elements are interconnected via amide bond(s).

14. The derivative of any one of embodiments 1-13, wherein the linker consists of one or more Chem. 5 elements.

15. The derivative of any one of embodiments 1-13, wherein the linker further comprises a second linker element; preferably a Glu di-radical; more preferably selected from Chem. 6, and/or Chem. 7:

Chem. 6:

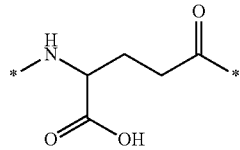

-continued

Chem. 7:

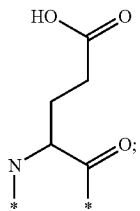

most preferably Chem. 6.

16. The derivative of embodiment 15, wherein the Glu di-radical is included p times, wherein p is an integer in the range of 1-3.

17. The derivative of embodiment 16, wherein p is 1, 2, or 3; preferably 1 or 2; or most preferably 1.

18. The derivative of any one of embodiments 1-17, wherein the Glu di-radical is a radical of L-Glu or D-Glu, preferably of L-Glu.

19. The derivative of any one of embodiments 16-18, wherein the one or more Glu di-radicals and the one or more Chem. 5 elements are interconnected via amide bond(s).

20. The derivative of any one of embodiments 1-19, wherein the linker comprises a further linker element, such as a third linker element.

21. The derivative of embodiment 20, wherein the third linker element is

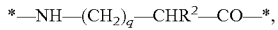

*—NH—(CH$_2$)$_q$—CHR$^2$—CO—*,    Chem. 8:

in which q is an integer in the range of 2-12, and R$^2$ is hydrogen (H), amino (NH$_2$), or a C$_1$—C$_5$ lower alcohol.

22. The derivative of embodiment 21, wherein q is 4, 6, or 10.

23. The derivative of any one of embodiments 21-22, wherein Chem. 8 is a radical of amino hexanoic acid, amino octanoic acid, amino dodecanoic acid, or lysine.

24. The derivative of embodiment 23, wherein the radicalised amino group is at the epsilon position.

25. The derivative of any one of embodiments 1-24, wherein the linker consists of m times Chem. 5 and p times the Glu di-radical.

26. The derivative of embodiment 25, wherein (m,p) is (2,2), (2,1), (2,3), (4,1), (6,1), (1,0), (1,1), (1,2), (0,1), or (0,2); preferably (2,1), (2,0), (1,0), (1,1), (0,1), or (0,2); more preferably (2,1), (2,2), or (1,2); even more preferably (1,1) or (2,1); or most preferably (2,1).

27. The derivative of any one of embodiments 25-26, wherein the m Chem. 5 elements and the p Glu di-radicals are interconnected via amide bonds.

28. The derivative of any one of embodiments 21-24, wherein the linker consists of m times Chem. 5, p times the Glu di-radical, and Chem. 8.

29. The derivative of embodiment 28, wherein (m,p) is (2,1), or (1,1); preferably (2,1).

30. The derivative of any one of embodiments 28-29, wherein the m Chem. 5 elements, the p Glu di-radicals, and the Chem. 8 element are interconnected via amide bonds.

31. The derivative of any one of embodiments 1-30, wherein the linker and the protracting moiety are interconnected via an amide bond.

32. The derivative of any one of embodiments 1-31, wherein the linker and the GLP-1 analogue are interconnected via an amide bond.

33. The derivative of embodiment 32, wherein the linker is attached to the epsilon-amino group of K$^{26}$ or K$^{37}$.

34. The derivative of any one of embodiments 1-33, wherein the linker has
(i) from 5 to 41 C-atoms; preferably from 5-17 C-atoms; such as 5, 6, 11, 12, or 17 C-atoms; for example 5, 6 or 12 C-atoms, or 11 or 17 C-atoms; or most preferably 17 C-atoms; or
(ii) from 5-30 C-atoms, preferably from 5-25 C-atoms, more preferably from 5-20 C-atoms, or most prefarbly from 5-17 C-atoms.

35. The derivative of any one of embodiments 1-34, wherein the linker has
(i) from 4 to 28 hetero atoms; preferably from 4 to 12 hetero atoms; such as 4, 8, or 12 hetero atoms; more preferably 8 or 12 hetero atoms; or most preferably 12 hetero atoms; or
(ii) from 4-20 hetero atoms, preferably from 4-18 hetero atoms, more preferably from 4-14 hetero atoms, or most preferably from 4-12 hetero atoms.

36. The derivative of embodiment 35, wherein the hetero atoms are N—, and/or O-atoms.

37. The derivative of any one of embodiments 34-36, wherein the linker has from 1 to 7 N-atoms; preferably from 1 to 3 N-atoms; such as 1, 2, or 3 N-atoms; for example 1, or 2 N-atoms; or most preferably 3 N-atoms.

38. The derivative of any one of embodiments 34-37, wherein the linker has from 3 to 21 O-atoms; preferably from 3 to 9 O-atoms; such as 3, 6, or 9 O-atoms; for example 3, or 6 O-atoms; or most preferably 9 O-atoms.

39. The derivative of any one of embodiments 1-38, wherein the linker consists of two times Chem. 5, interconnected via an amide bond, and being connected at its *—NH end to the *—CO end of the protracting moiety, and at its *—CO end to the epsilon amino group of K$^{26}$ or K$^{37}$ of the GLP-1 analogue.

40. The derivative of any one of embodiments 1-38, wherein the linker consists of four times Chem. 5, interconnected via amide bonds, and connected at its *—NH end to the *—CO end of the protracting moiety, and at its *—CO end to the epsilon amino group of K$^{26}$ or K$^{37}$ of the GLP-1 analogue.

41. The derivative of any one of embodiments 1-38, wherein the linker consists of two times Chem. 6 and two times Chem. 5, interconnected via amide bonds and in the sequence indicated, the linker being connected at its *—NH end to the *—CO end of the protracting moiety, and at its *—CO end to the epsilon amino group of K$^{26}$ or K$^{37}$ of the GLP-1 analogue.

42. The derivative of any one of embodiments 1-38, wherein the linker consists of two times Chem. 5 and one time Chem. 6, interconnected via amide bonds and in the sequence indicated, the linker being connected at its *—NH end to the *—CO end of the protracting moiety, and at its free *—CO end to the epsilon amino group of K$^{26}$ or K$^{37}$ of the GLP-1 analogue.

43. The derivative of any one of embodiments 1-38, wherein the linker consists of three times Chem. 6 and two times Chem. 5, interconnected via amide bonds and in the sequence indicated, the linker being connected at its *—NH end to the *—CO end of the protracting moiety, and at its free *—CO end to the epsilon amino group of K$^{26}$ or K$^{37}$ of the GLP-1 analogue.

44. The derivative of any one of embodiments 1-38, wherein the linker consists of one time Chem. 6 and two times Chem. 5, interconnected via amide bonds and in the sequence indicated, the linker being connected at its *—NH end to the *—CO end of the protracting moiety, and at its *—CO end to the epsilon amino group of K$^{26}$ or K$^{37}$ of the GLP-1 analogue.

45. The derivative of any one of embodiments 1-38, wherein the linker consists of one time Chem. 6, one time Chem. 5, and one time Chem. 6, interconnected via amide bonds and in the sequence indicated, the linker being connected at its

*—NH end to the *—CO end of the protracting moiety, and at its *—CO end to the epsilon amino group of $K^{26}$ or $K^{37}$ of the GLP-1 analogue.

46. The derivative of any one of embodiments 1-38, wherein the linker consists of one time Chem. 6 and four times Chem. 5, interconnected via amide bonds and in the sequence indicated, the linker being connected at its *—NH end to the *—CO end of the protracting moiety, and at its *—CO end to the epsilon amino group of $K^{26}$ or $K^{37}$ of the GLP-1 analogue.

47. The derivative of any one of embodiments 1-38, wherein the linker consists of one time Chem. 6 and six times Chem. 5, interconnected via amide bonds and in the sequence indicated, the linker being connected at its *—NH end to the *—CO end of the protracting moiety and at its *—CO end to the epsilon amino group of $K^{26}$ or $K^{37}$ of the GLP-1 analogue.

48. The derivative of any one of embodiments 1-38, wherein the linker consists of one time Chem. 6 and one time Chem. 5, interconnected via amide bonds and in the sequence indicated, the linker being connected at its *—NH end to the *—CO end of the protracting moiety, and at its *—CO end to the epsilon amino group of $K^{26}$ or $K^{37}$ of the GLP-1 analogue.

49. The derivative of any one of embodiments 1-38, wherein the linker consists of one time Chem. 5, one time Chem. 6, and one time Chem. 5, interconnected via amide bonds and in the sequence indicated, the linker being connected at its *—NH end to the *—CO end of the protracting moiety, and at its *—CO end to the epsilon amino group of $K^{26}$ or $K^{37}$ of the GLP-1 analogue.

50. The derivative of any one of embodiments 1-38, wherein the linker consists of one time Chem. 7, and two times Chem. 5, interconnected via amide bonds and in the sequence indicated, the linker being connected at its *—NH end to the *—CO end of the protracting moiety, and at its *—CO end to the epsilon amino group of $K^{26}$ or $K^{37}$ of the GLP-1 analogue.

51. The derivative of any one of embodiments 1-38, wherein the linker consists of one time Chem. 5, the linker being connected at its *—NH end to the *—CO end of the protracting moiety, and at its *—CO end to the epsilon amino group of $K^{26}$ or $K^{37}$ of the GLP-1 analogue.

52. The derivative of any one of embodiments 1-38, wherein the linker consists of one time Chem. 6, the linker being connected at its *—NH end to the *—CO end of the protracting moiety, and at its *—CO end to the epsilon amino group of $K^{26}$ or $K^{37}$ of the GLP-1 analogue.

53. The derivative of any one of embodiments 1-38, wherein the linker consists of two times Chem. 6, interconnected via amide bonds, the linker being connected at its *—NH end to the *—CO end of the protracting moiety, and at its *—CO end to the epsilon amino group of $K^{26}$ or $K^{37}$ of the GLP-1 analogue.

54. The derivative of any one of embodiments 1-53, wherein the linker consists of one time Chem. 6, one time Chem. 8, in which preferably q is 10 and $R^2$ is H, one time Chem. 6, and two times Chem. 5, interconnected via amide bonds and in the sequence indicated, the linker being connected at its *—NH end to the *—CO end of the protracting moiety, and at its *—CO end to the epsilon amino group of $K^{26}$ or $K^{37}$ of the GLP-1 analogue.

55. The derivative of any one of embodiments 1-54, wherein the linker consists of one time Chem. 6, one time Chem. 8, in which preferably q is 4 and $R^2$ is H, one time Chem. 6, and two times Chem. 5, interconnected via amide bonds and in the sequence indicated, the linker being connected at its *—NH end to the *—CO end of the protracting moiety, and at its *—CO end to the epsilon amino group of $K^{26}$ or $K^{37}$ of the GLP-1 analogue.

56. The derivative of any one of embodiments 1-55, wherein the linker consists of one time Chem. 6, one time Chem. 8, in which preferably q is 6 and $R^2$ is H, one time Chem. 6, and two times Chem. 5, interconnected via amide bonds and in the sequence indicated, the linker being connected at its *—NH end to the *—CO end of the protracting moiety, and at its *—CO end to the epsilon amino group of $K^{26}$ or $K^{37}$ of the GLP-1 analogue.

57. The derivative of any one of embodiments 15-18, wherein the linker consists of one time Chem. 6, one time Chem. 8, in which preferably q is 4 and $R^2$ is $NH_2$, one time Chem. 6, and two times Chem. 5, interconnected via amide bonds and in the sequence indicated, the linker being connected at its *—NH end to the *—CO end of the protracting moiety, and at its *—CO end to the epsilon amino group of $K^{26}$ or $K^{37}$ of the GLP-1 analogue.

58. The derivative of any one of embodiments 1-57, wherein the protracting moiety is Chem. 1.

59. The derivative of any one of embodiments 1-58, wherein x is an even number.

60. The derivative of any one of embodiments 1-59, wherein x is an integer in the range of 8-16, such as 8, 10, 12, 14, or 16; or preferably in the range of 10-14.

61. The derivative of any one of embodiments 1-60, wherein x is 10, 12, or 14; preferably 14; more preferably 10; or most preferably 12.

62. The derivative of any one of embodiments 1-61, wherein Chem. 1 is represented by Chem. 1a:

Chem. 1a:

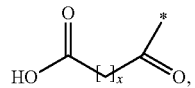

where x is as defined in any one of embodiments 1-61.

63. The derivative of any one of embodiments 1-57, wherein the protracting moiety is Chem. 2.

64. The derivative of any one of embodiments 1-63, wherein y is an odd number.

65. The derivative of any one of embodiments 1-64, wherein y is an integer in the range of 7-17, such as 7, 9, 11, 13, 15, or 17; preferably 7-15, such as, for example, 9, 11 or 15.

66. The derivative of any one of embodiments 1-65, wherein y is 7, 8, 9, 11, or 15.

67. The derivative of any one of embodiments 1-66, wherein y is 7, 9, 11, or 15.

68. The derivative of any one of embodiments 1-67, wherein y is 7.

69. The derivative of any one of embodiments 1-68, wherein y is 9.

70. The derivative of any one of embodiments 1-69, wherein y is 11.

71. The derivative of any one of embodiments 1-70, wherein y is 15.

72. The derivative of any one of embodiments 1-71, wherein Chem. 2 is represented by Chem. 2a, or Chem. 2b:

Chem. 2a:

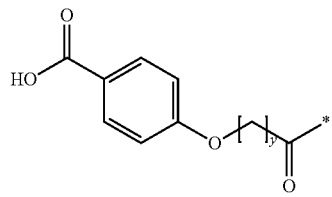

Chem. 2b:

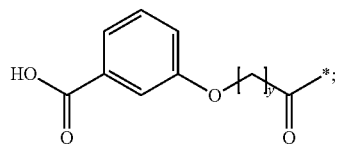

preferably by Chem. 2a;
wherein y is as defined in any one of embodiments 1-71.
73. The derivative of any one of embodiments 1-57, wherein the protracting moiety is Chem. 3.
74. The derivative of any one of embodiments 1-73, wherein z is an odd number; preferably 3.
75. The derivative of any one of embodiments 1-74, wherein $R^1$ is a group having a molar mass not higher than 127 Da.
76. The derivative of any one of embodiments 1-75, wherein $R^1$ is a group having a molar mass in the range of 1-127 Da; preferably 1-125 Da, more preferably 1-100 Da, even more preferably 1-75 Da, or most preferably 1-50 Da.
77. The derivative of any one of embodiments 1-76, wherein $R^1$ is a group having
(ii) a molar mass below 130 Da, preferably below 100 Da, more preferably below 75 Da, even more preferably below 60 Da, or most preferably below 50 Da; or
(iii) a molar mass below 40 Da, preferably below 30 Da, more preferably below 20 Da, or most preferably below 15 Da.
78. The derivative of any one of embodiments 1-77, wherein $R^1$ is —H.
79. The derivative of any one of embodiments 1-78, wherein $R^1$ is a halogen radical.
80. The derivative of any one of embodiments 1-79, wherein $R^1$ is —I.
81. The derivative of any one of embodiments 1-80, wherein $R^1$ is linear or branched C1-C5 alkyl; preferably C1-C4 alkyl; more preferably methyl; or most preferably tert. butyl.
82. The derivative of any one of embodiments 1-81, wherein Chem. 3 is represented by Chem. 3a:

Chem. 3a:

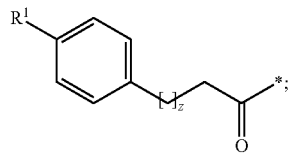

wherein $R^1$ and z are as defined in any one of embodiments 1-81.
83. The derivative of any one of embodiments 1-57, wherein the protracting moiety is Chem. 4.

84. The derivative of any one of embodiments 1-83, wherein w is an even number.
85. The derivative of any one of embodiments 1-84, wherein w is an integer in the range of 8-16; or preferably in the range of 10-14.
86. The derivative of any one of embodiments 1-85, wherein w is 10, 12, or 14; preferably 14; more preferably 10; or most preferably 12.
87. The derivative of any one of embodiments 1-86, wherein Chem. 4 is represented by Chem. 4a:

Chem. 4a:

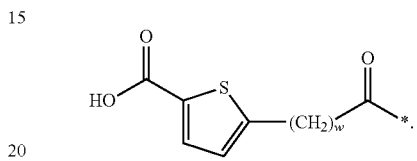

wherein w is as defined in any one of embodiments 1-86.
88. The derivative of any one of embodiments 1-87, wherein the two protracting moieites are substantially identical; such as at least 80%, at least 85%, at least 90%, at least 95%, or at least 99% identical.
89. The derivative of any one of embodiments 1-88, wherein the two protracting moieties have a similarity of at least 0.5; preferably at least 0.6; more preferably at least 0.7, or at least 0.8; even more preferably at least 0.9; or most preferably at least 0.99, such as a similarity of 1.0.
90. The derivative of any one of embodiments 1-89, wherein the two linkers are substantially identical; such as at least 80%, at least 85%, at least 90%, at least 95%, or at least 99% identical.
91. The derivative of any one of embodiments 1-90, wherein the two linkers have a similarity of at least 0.5; preferably at least 0.6; more preferably at least 0.7, or at least 0.8; even more preferably at least 0.9; or most preferably at least 0.99, such as a similarity of 1.0.
92. The derivative of any one of embodiments 1-91, wherein the two albumin binders, such as the two side chains consisting of protracting moiety and linker, are substantially identical; such as at least 80%, at least 85%, at least 90%, at least 95%, or at least 99% identical.
93. The derivative of any one of embodiments 1-92, wherein the two albumin binders, such as the two side chains consisting of protracting moiety and linker, have a similarity of at least 0.5; preferably at least 0.6; more preferably at least 0.7, or at least 0.8; even more preferably at least 0.9; or most preferably at least 0.99, such as a similarity of 1.0.
94. The derivative of any one of embodiments 88-93, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity, or identity, of the two fingerprints.
95. The derivative of any one of embodiments 1-94, wherein a) the positions corresponding to position 37 and 26 of GLP-1(7-37) (SEQ ID NO: 1), and/or b) the number of amino acid modifications as compared to GLP-1(7-37) (SEQ ID NO: 1)

are identified by handwriting and eyeballing.

96. The derivative of any one of embodiments 1-95, wherein
   a) the positions corresponding to position 37 and 26 of GLP-1(7-37) (SEQ ID NO: 1), and/or
   b) the number of amino acid modifications as compared to GLP-1(7-37) (SEQ ID NO: 1)
are identified by use of a standard protein or peptide alignment program.

97. The derivative of embodiment 96, wherein the alignment program is a Needleman-Wunsch alignment.

98. The derivative of any one of embodiments 96-97, wherein the default scoring matrix and the default identity matrix is used.

99. The derivative of any one of embodiments 96-98, wherein the scoring matrix is BLOSUM62.

100. The derivative of any one of embodiments 96-99, wherein the penalty for the first residue in a gap is −10 (minus ten).

101. The derivative of any one of embodiments 96-100, wherein the penalties for additional residues in a gap is −0.5 (minus point five).

102. The derivative of any one of embodiments 1-101, wherein the analogue comprises no K residues other than the first and the second K residue.

103. The derivative of any one of embodiments 1-102, wherein the amino acid modification(s) is (are) at one or more positions corresponding to the following positions in GLP-1 (7-37) (SEQ ID NO: 1): 7, 8, 9, 23, 30, 31, 34, 36, 37, and 38.

104. The derivative of any one of embodiments 1-103, wherein the analogue comprises, preferably has, a minimum of two amino acid modifications, as compared to GLP-1(7-37) (SEQ ID NO: 1); the minimum two amino acid modifications being preferably at each of the positions corresponding to position 34 and 37 of GLP-1(7-37) (SEQ ID NO: 1), and more preferably so that the amino acid at the position corresponding to position 37 is K, and the amino acid at the position corresponding to position 34 is not K.

105. The derivative of any one of embodiments 1-104, wherein the GLP-1 analogue has a C-terminal amide.

106. The derivative of embodiment 105, wherein the amino acid at the position corresponding to position 34 is R or Q.

107. The derivative of any one of embodiments 1-106, wherein the amino acid modifications are selected from the following: ($R^{34}$ or $Q^{34}$), $K^{37}$, ($Des^7$ or $Imp^7$), (D-$Ala^8$, $Des^8$, $Aib^8$, $G^8$, or $S^8$), ($Q^9$ or $G^9$), $R^{23}$, $E^{30}$, $H^{31}$, $G^{36}$, and/or ($E^{38}$ or $G^{38}$).

108. The derivative of any one of embodiments 1-107, wherein the amino acid modifications are selected from the following: ($R^{34}$ or $Q^{34}$), $K^{37}$, ($Des^7$ or $Imp^7$), ($Des^8$ or $Aib^8$), ($Q^9$ or $G^9$), $R^{23}$, $E^{30}$, $H^{31}$, $G^{36}$, and/or ($E^{38}$ or $G^{38}$).

109. The derivative of any one of embodiments 1-108, wherein the analogue comprises ($R^{34}$ or $Q^{34}$), and $K^{37}$.

110. The derivative of any one of embodiments 1-109, wherein the analogue comprises $Imp^7$, and/or ($Aib^8$ or $S^8$); preferably $Imp^7$, and/or $Aib^8$; more preferably $Imp^7$; or most preferably $Aib^8$.

111. The derivative of any one of embodiments 1-110, wherein the analogue comprises $G^{38}$ or $E^{38}$, preferably $E^{38}$.

112. The derivative of any one of embodiments 1-111, wherein the analogue comprises $Q^9$ or $G^9$.

113. The derivative of any one of embodiments 1-112, wherein the analogue comprises $G^{36}$.

114. The derivative of any one of embodiments 1-113, wherein the analogue comprises $H^{31}$.

115. The derivative of any one of embodiments 1-114, wherein the analogue comprises $R^{23}$.

116. The derivative of any one of embodiments 1-115, wherein the analogue comprises $des^7$ and/or $des^8$, preferably both.

117. The derivative of any one of embodiments 1-116, wherein one amino acid has been deleted at a position corresponding to position 7 of GLP-1(7-37) (SEQ ID NO: 1).

118. The derivative of any one of embodiments 1-117, wherein one amino aicd has been deleted at a position corresponding to position 8 of GLP-1(7-37) (SEQ ID NO: 1).

119. The derivative of any one of embodiments 1-118, wherein two amino acids have been deleted at positions corresponding to position 7 and 8 of GLP-1(7-37) (SEQ ID NO: 1).

120. The derivative of any one of embodiments 1-119, which is an analogue of GLP-1(8-37) (amino acids 2-31 of SEQ ID NO: 1), having up to ten, nine, eight, or six amino acid modifications as compared to GLP-1(7-37) (SEQ ID NO: 1).

121. The derivative of any one of embodiments 1-120, which is an analogue of GLP-1(9-37) (amino acids 3-31 respectively, of SEQ ID NO: 1), having up to ten, nine, eight, or six amino acid modifications as compared to GLP-1(7-37) (SEQ ID NO: 1). 122. The derivative of any one of embodiments 1-121, wherein the GLP-1 analogue corresponds to (a) $K^{37}$-GLP-1(7-37), (b) $K^{37}$-GLP-1(8-37), (c) $K^{37}$-GLP-1(9-37), or (d) an analogue of any one of (a)-(c) having up to ten, nine, eight, or six amino acid modifications as compared to GLP-1(7-37) (SEQ ID NO: 1).

123. The derivative of any one of embodiments 1-122, wherein a His-mimetic other than His is at a position corresponding to position 2 of GLP-1(7-37) (SEQ ID NO: 1).

124. The derivative of any one of embodiments 1-123, wherein a His-Ala-mimetic other than His-Ala is at the positions corresponding to position 7 and 8 of GLP-1(7-37) (SEQ ID NO: 1).

125. The derivative of any one of embodiments 123-124, wherein the His-mimetic, or the His-Ala mimetic, comprises a) imidazole; or b) pyridine.

126. The derivative of embodiment 125, wherein the imidazole is a derivative of an imidazole which comprises a *—CO end, for covalent coupling to *—NH of the N-terminal amino acid of the analogue, via formation of an amide bond.

127. The derivative of embodiment 125, wherein the pyridine is a derivative of pyridine which comprises a *—CO end, for covalent coupling to *—NH of the N-terminal amino acid of the analogue, via formation of an amide bond.

128. The derivative of any one of embodiments 125-127, wherein the imidazole derivative is mono-substituted.

129. The derivative of any one of embodiments 125-127, wherein the pyridine derivative is mono-substituted.

130. The derivative of any one of embodiments 125-129, wherein the imidazole derivative is substituted with a group comprising a carboxylic acid radical of a lower alkyl having from one to six carbon atoms.

131. The derivative of any one of embodiments 125-129, wherein the pyridine derivative is substituted with a group comprising a carboxylic acid radical of a lower alkyl having from one to six carbon atoms.

132. The derivative of any one of embodiments 130-131, wherein the carboxylic acid radical is selected from acetyl; and straight or branched propionyl, butyryl, pentanoyl; preferably acetyl.

133. The derivative of any one of embodiments 1-132, wherein the amino acid residue at the position corresponding to position 8 of GLP-1(7-37) (SEQ ID NO: 1) has 3H-Imidazol-4-yl-acetyl attached to its N-atom.

134. The derivative of any one of embodiments 1-133, wherein the amino acid residue at the position corresponding to position 8 of SEQ ID NO: 1 is alanine.

135. The derivative of any one of embodiments 125-134, wherein the imidazole is substituted with (methylcarbamoyl)-2-methyl-propionyl, (ethylcarbamoyl)-2-methyl-propionyl, (propylcarbamoyl)-2-methyl-propionyl, or (butylcarbamoyl)-2-methyl-propionyl; preferably with (ethylcarbamoyl)-2-methyl-propionyl.

136. The derivative of any one of embodiments 1-135, wherein the amino acid residue at the position corresponding to position 9 of GLP-1(7-37) (SEQ ID NO: 1) has {2-[2-(1H-Imidazol-4-yl)-ethylcarbamoyl]-2-methyl-propionyl} attached to its N-atom.

137. The derivative of any one of embodiments 125-136, wherein the pyridine is substituted with (methylcarbamoyl)-2-methyl-propionyl, (ethylcarbamoyl)-2-methyl-propionyl, (propylcarbamoyl)-2-methyl-propionyl, or (butylcarbamoyl)-2-methyl-propionyl; preferably with (methylcarbamoyl)-2-methyl-propionyl.

138. The derivative of any one of embodiments 1-137, wherein the amino acid residue at the position corresponding to position 9 of GLP-1(7-37) (SEQ ID NO: 1) has [2,2-dimethyl-3-oxo-3-(pyridin-2-ylmethylamino)propanoyl] attached to its N-atom.

139. The derivative of any one of embodiments 1-138, wherein the amino acid residue at the position corresponding to position 9 of the GLP-1 analogue is glutamic acid.

140. The derivative of any one of embodiments 1-139, wherein the analogue does not comprise ($H^{31}$ and $Q^{34}$).

141. The derivative of any one of embodiments 1-140, wherein the analogue does not comprise ($des^7$ and $des^8$); and/or does not comprise a His-mimetic, or a His-Ala mimetic as defined in any one of embodiments 116-140.

142. The derivative of any one of embodiments 1-141, wherein the analogue is an analogue of GLP-1(7-37), or GLP-1(9-37).

143. The derivative of any one of embodiments 1-142, wherein the analogue comprises, preferably has, the following amino acid changes, or modifications, as compared to GLP-1(7-37) (SEQ ID NO: 1): i) (34R, 37K); ii) (8Aib, 34R, 37K); iii) (31H, 34Q, 37K); iv) (des7, des8, 34R, 37K), and optionally 38E; or v) (34R, 36G, 37K).

144. The derivative of any one of embodiments 1-143, wherein the analogue has a maximum of nine amino acid modifications.

145. The derivative of any one of embodiments 1-144, wherein the analogue has a maximum of eight amino acid modifications.

146. The derivative of any one of embodiments 1-145, wherein the analogue has a maximum of seven amino acid modifications.

147. The derivative of any one of embodiments 1-146, wherein the analogue has a maximum of six amino acid modifications.

148. The derivative of any one of embodiments 1-147, wherein the analogue has a maximum of five amino acid modifications.

149. The derivative of any one of embodiments 1-148, wherein the analogue has a maximum of four amino acid modifications.

150. The derivative of any one of embodiments 1-149, wherein the analogue has a maximum of three amino acid modifications.

151. The derivative of any one of embodiments 1-150, wherein the analogue has a maximum of two amino acid modifications.

152. The derivative of any one of embodiments 1-151, wherein the analogue has a minimum of two amino acid modifications.

153. The derivative of any one of embodiments 1-152, wherein the analogue has a minimum of three amino acid modifications.

154. The derivative of any one of embodiments 1-153, wherein the analogue has a minimum of four amino acid modifications.

155. The derivative of any one of embodiments 1-154, wherein the analogue has a minimum of five amino acid modifications.

156. The derivative of any one of embodiments 1-155, wherein the analogue has a minimum of six amino acid modifications.

157. The derivative of any one of embodiments 1-156, wherein the analogue has a minimum of seven amino acid modifications.

158. The derivative of any one of embodiments 1-157, wherein the analogue has a minimum of eight amino acid modifications.

159. The derivative of any one of embodiments 1-158, wherein the analogue has a minimum of nine amino acid modifications.

160. The derivative of any one of embodiments 1-159, wherein the analogue has a minimum of ten amino acid modifications.

161. The derivative of any one of embodiments 1-160, wherein the analogue has one amino acid modification.

162. The derivative of any one of embodiments 1-161, wherein the analogue has two amino acid modifications.

163. The derivative of any one of embodiments 1-162, wherein the analogue has three amino acid modifications.

164. The derivative of any one of embodiments 1-163, wherein the analogue has four amino acid modifications.

165. The derivative of any one of embodiments 1-164, wherein the analogue has five amino acid modifications.

166. The derivative of any one of embodiments 1-165, wherein the analogue has six amino acid modifications.

167. The derivative of any one of embodiments 1-166, wherein the analogue has seven amino acid modifications.

168. The derivative of any one of embodiments 1-167, wherein the analogue has eight amino acid modifications.

169. The derivative of any one of embodiments 1-169, wherein the analogue has nine amino acid modifications.

170. The derivative of any one of embodiments 1-170, wherein the analogue has ten amino acid modifications.

171. The derivative of any one of embodiments 1-171, wherein the modifications are, independently, substitutions, additions, and/or deletions.

172. The derivative of any one of embodiments 1-172, wherein the modifications are substitutions.

173. The derivative of any one of embodiments 1-173, wherein the modifications are deletions.

174. The derivative of any one of embodiments 1-174, wherein the modifications are additions.

175. The derivative of any one of embodiments 1-174, wherein
 a) the position corresponding to any of the indicated positions of GLP-1(7-37) (SEQ ID NO: 1), and/or
 b) the number of amino acid modifications as compared to GLP-1(7-37) (SEQ ID NO: 1)
is/are identified by handwriting and eyeballing.

176. The derivative of any one of embodiments 1-175, wherein
a) the position corresponding to any of the indicated positions of GLP-1(7-37) (SEQ ID NO: 1), and/or b) the number of amino acid modifications as compared to GLP-1(7-37) (SEQ ID NO: 1)
is/are identified as described in any one of embodiments 96-101.

177. A compound selected from the following: Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64, Chem. 65, Chem. 66, Chem. 67, and Chem. 68; or a pharmaceutically acceptable salt, amide, or ester thereof.

178. A compound characterised by its name, and selected from a listing of each of the names of the compounds of Examples 1-49 herein, or a pharmaceutically acceptable salt, amide, or ester thereof.

179. The compound of embodiment 178, which is a compound of embodiment 177.

180. The compound of any one of embodiments 178 and 179, which is a derivative according to any one of embodiments 1-176.

181. The derivative of any one of embodiments 1-180 which is selected from the following:

(i) $N^{\epsilon 26}$-[2-[2-[2-[[2-[2-[2-[[(4S)-4-carboxy-[10-(4-carboxyphenoxy)decanoylamino]butanoyl]amino]ethoxy] ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl] amino]ethoxy]ethoxy]acetyl]-[Arg$^{34}$,Gly$^{36}$,Lys$^{37}$]-GLP-1-(7-37)-peptide (SEQ ID NO: 6), Chem. 62:

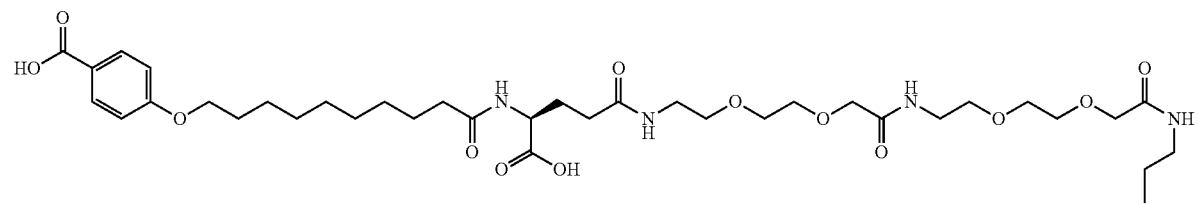

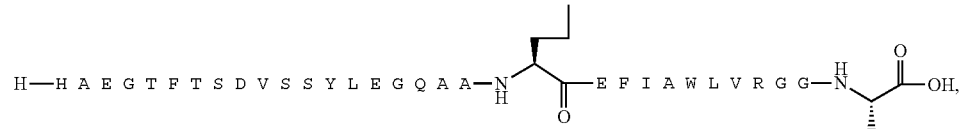

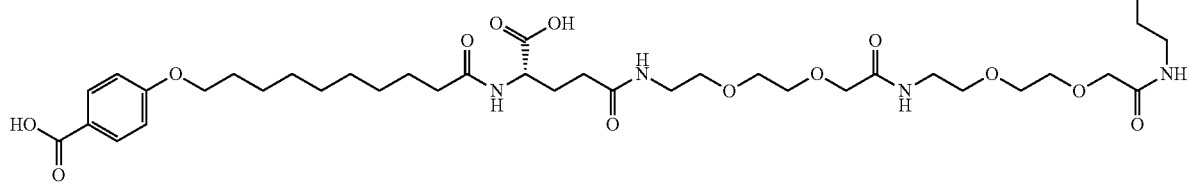

$N^{\epsilon 26}$-[2-[2-[2-[[2-[2-[2-[[(4S)-4-carboxy-4-[8-(4-carboxyphenoxy)octanoylamino]butanoyl]amino]ethoxy] ethoxy]acetyl]amino]ethoxy]ethoxy]acetyl], $N^{\epsilon 37}$-[2-[2-[2-[[2-[2-[2-[[(4S)-4-carboxy-4-[8-(4-carboxyphenoxy)octanoylamino]butanoyl]amino]ethoxy]ethoxy]acetyl] amino]ethoxy]ethoxy]acetyl]-[Aib$^8$,Arg$^{34}$,Lys$^{37}$]-GLP-1-(7-37)-peptide (SEQ ID NO: 7), Chem. 58:

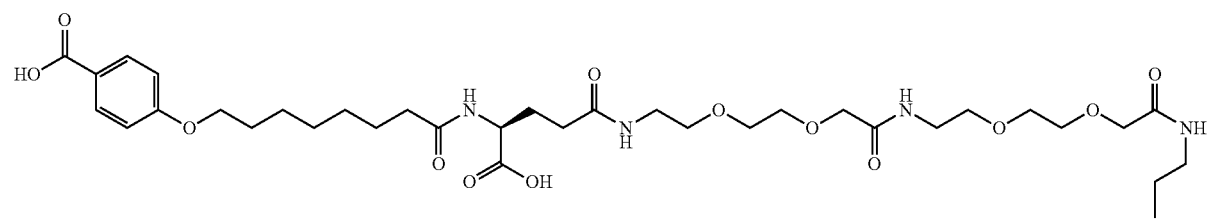

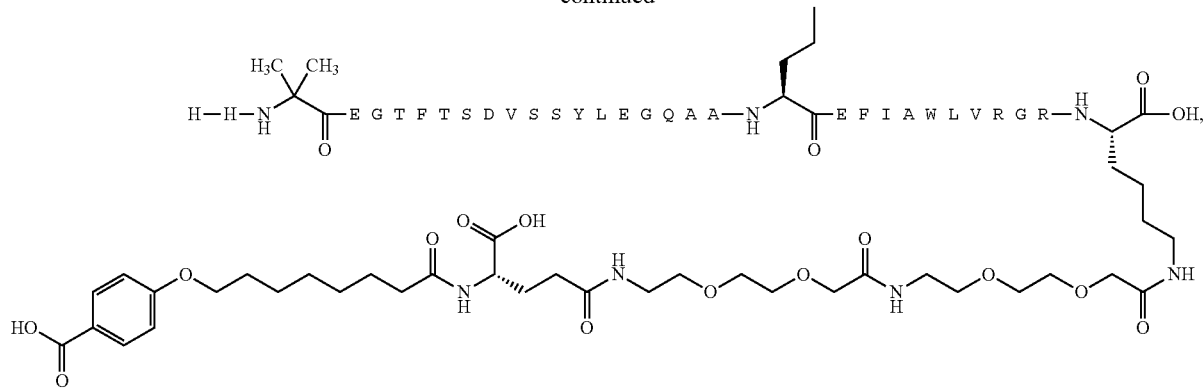

$N^{\epsilon 26}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], $N^{\epsilon 37}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl][Aib$^8$,His$^{31}$,Gln$^{34}$,Lys$^{37}$]GLP-1(7-37)-peptide (SEQ ID NO: 3), Chem. 40:

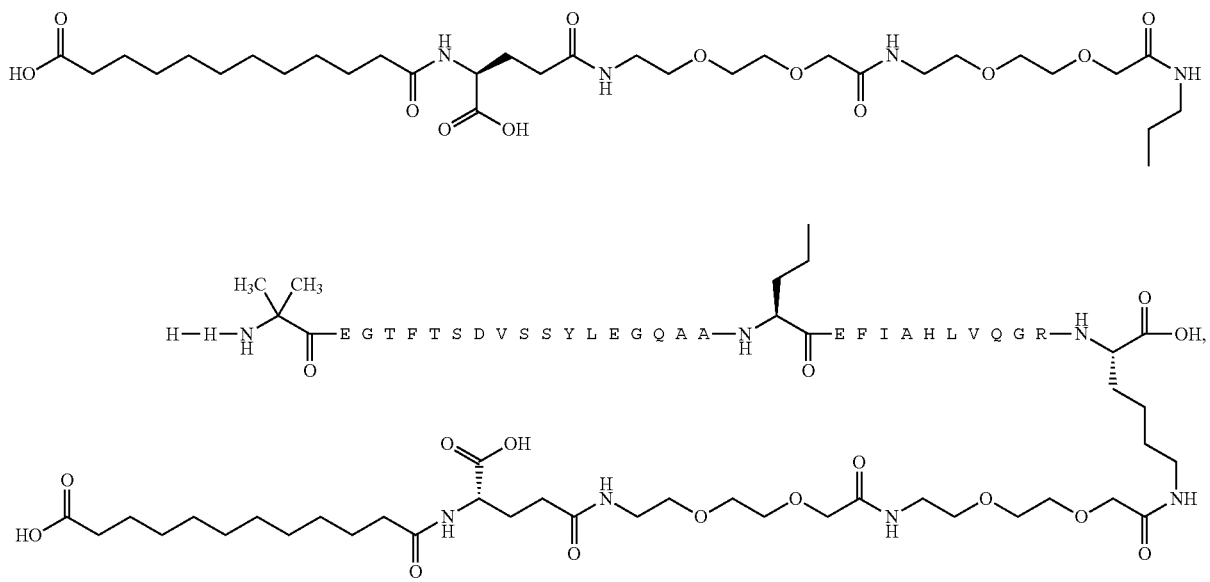

$N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Gln$^9$,Arg$^{34}$,Lys$^{37}$]-GLP-1-(7-37)-peptide (SEQ ID NO: 8), Chem. 56:

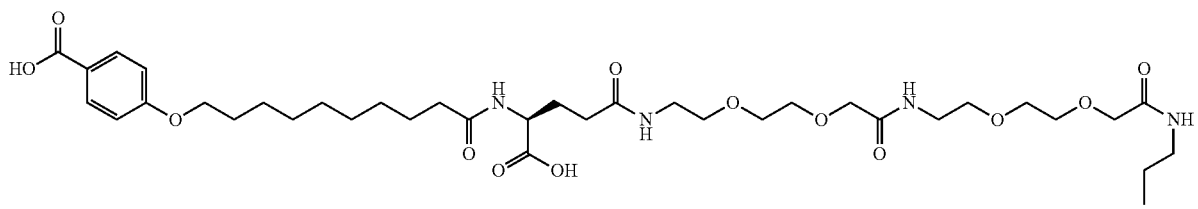

-continued

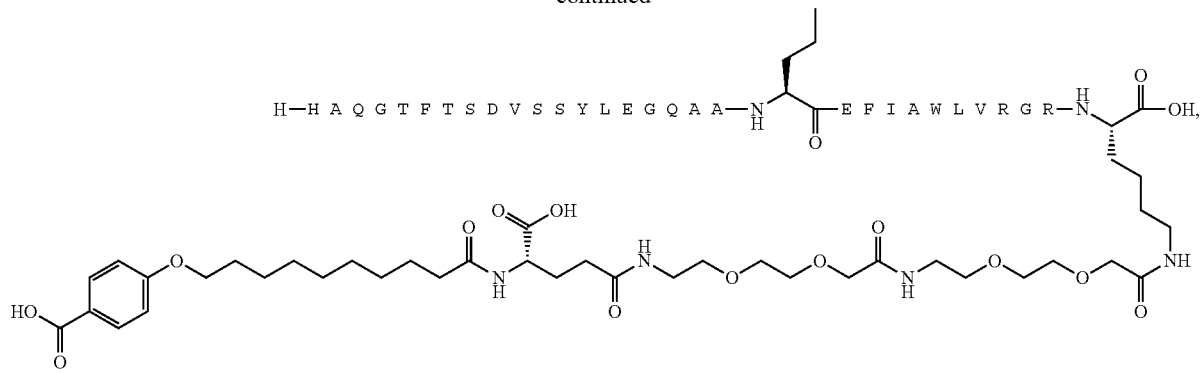

N^ε26{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy)acetyl}, N^ε37-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[Aib^8,Arg^34,Lys^37] GLP-1(7-37)-peptide (SEQ ID NO: 7), Chem. 21:

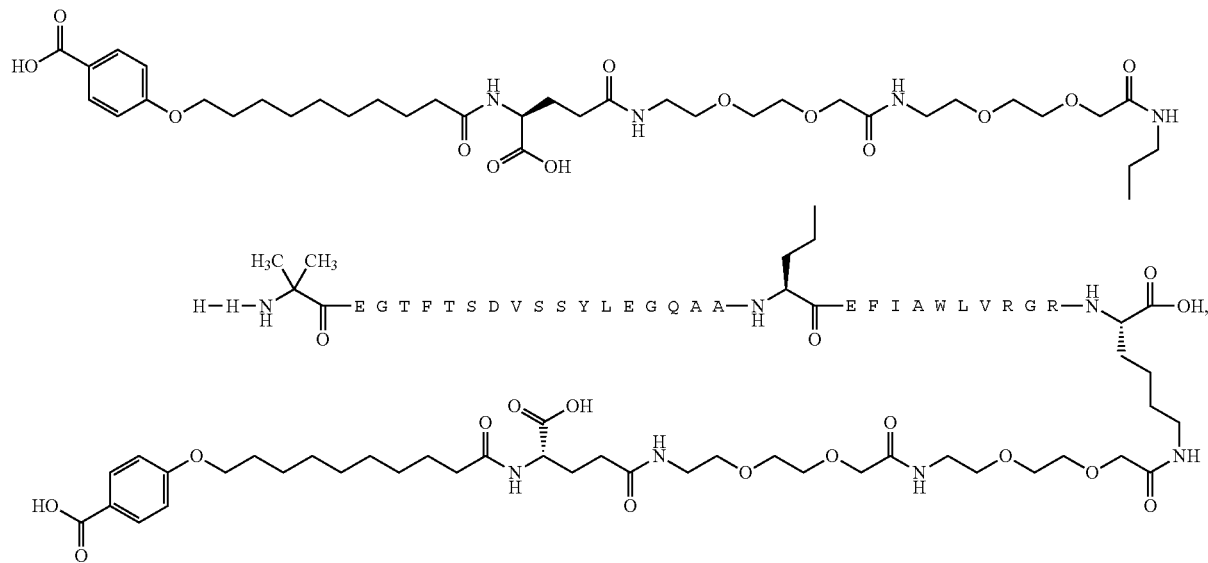

N^ε26-[2-[2-[2-[[2-[2-[2-[[(4S)-4-carboxy-4-[9-(4-carboxyphenoxy)nonanoylamino]butanoyl]amino]ethoxy]ethoxy]acetyl]amino]ethoxy]ethoxy]acetyl], N^ε37-[2-[2-[2-[[2-[2-[2-[[(4S)-4-carboxy-4-[9-(4-carboxyphenoxy)nonanoylamino]butanoyl]amino]ethoxy]ethoxy]acetyl]amino]ethoxy]ethoxy]acetyl]-[Arg^34,Lys^37]-GLP-1-(7-37)-peptide (SEQ ID NO: 9), Chem. 63:

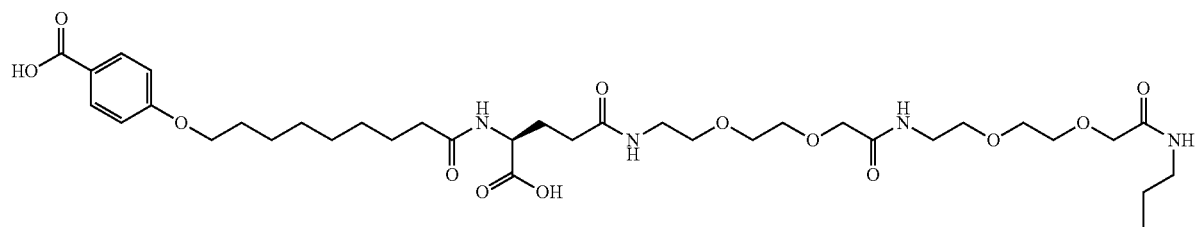

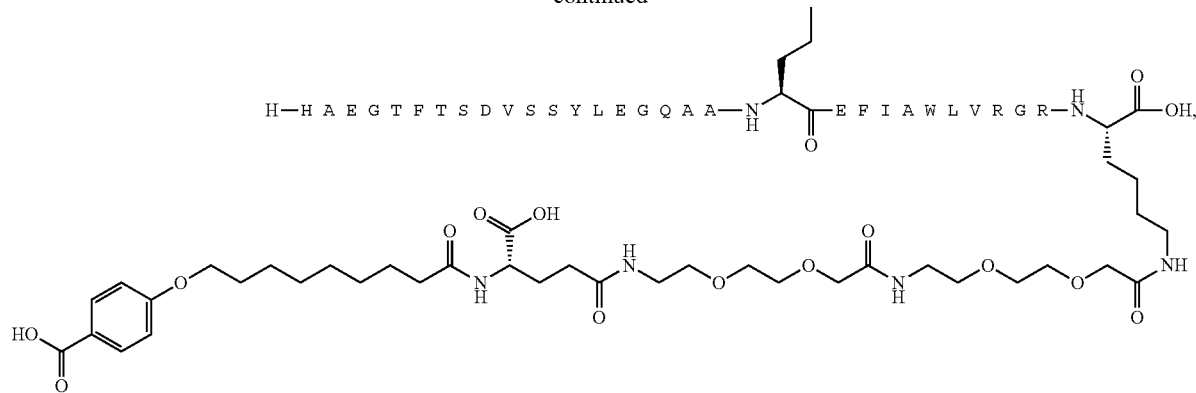

$N^{\epsilon 26}$-[2-(2-[2-(2-[2-(2-[4-(10-(4-Carboxyphenoxy)decanoylamino)-4(S)-carboxybutyrylamino]ethoxy)ethoxy]acetylamino)ethoxy]ethoxy)acetyl]-$N^{\epsilon 37}$-[2-(2-[2-(2-[2-(2-[4-(10-(4-Carboxyphenoxy)decanoylamino)-4(S)-carboxybutyrylamino]ethoxy)ethoxy]acetylamino)ethoxy]ethoxy)acetyl][Aib$^8$,His$^{31}$,Gln$^{34}$,Lys$^{37}$]GLP-1(7-37)-peptide (SEQ ID NO: 3), Chem. 36:

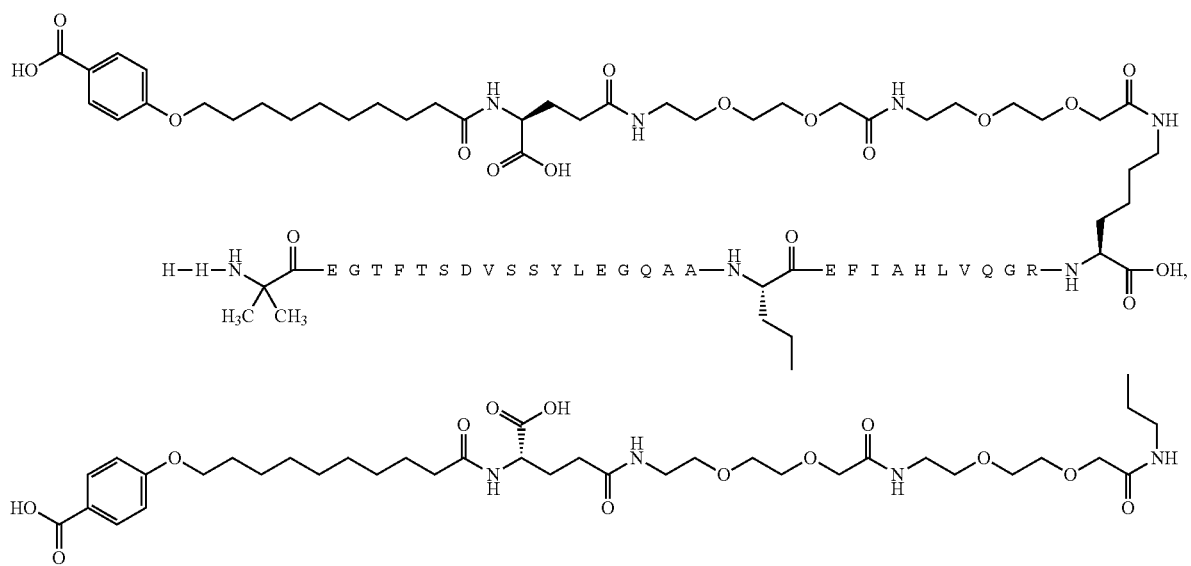

$N^{\epsilon 26}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl], $N^{\epsilon 37}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl][His$^{31}$,Gln$^{34}$,Lys$^{37}$]-GLP-1-(7-37)-peptide (SEQ ID NO: 10), Chem. 55:

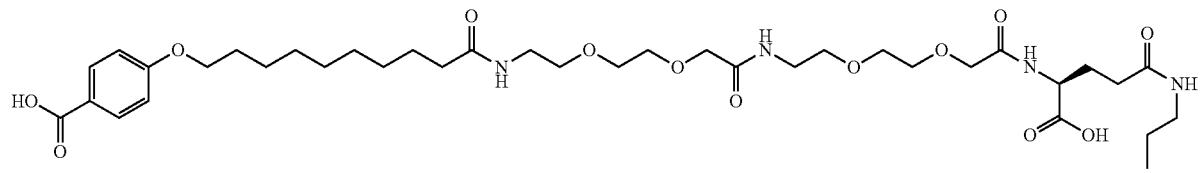

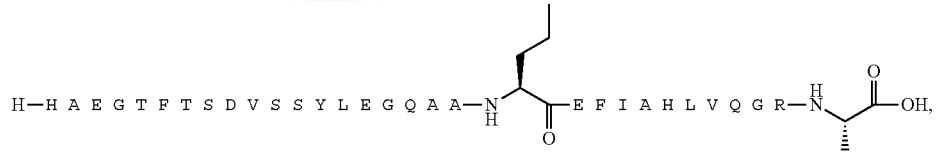

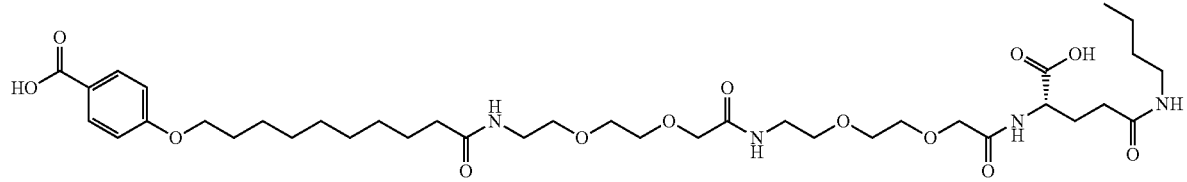

N$^{\epsilon26}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\epsilon37}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Arq34,Lys37]-GLP-1-(7-37)-peptide (SEQ ID NO: 9), Chem. 51:

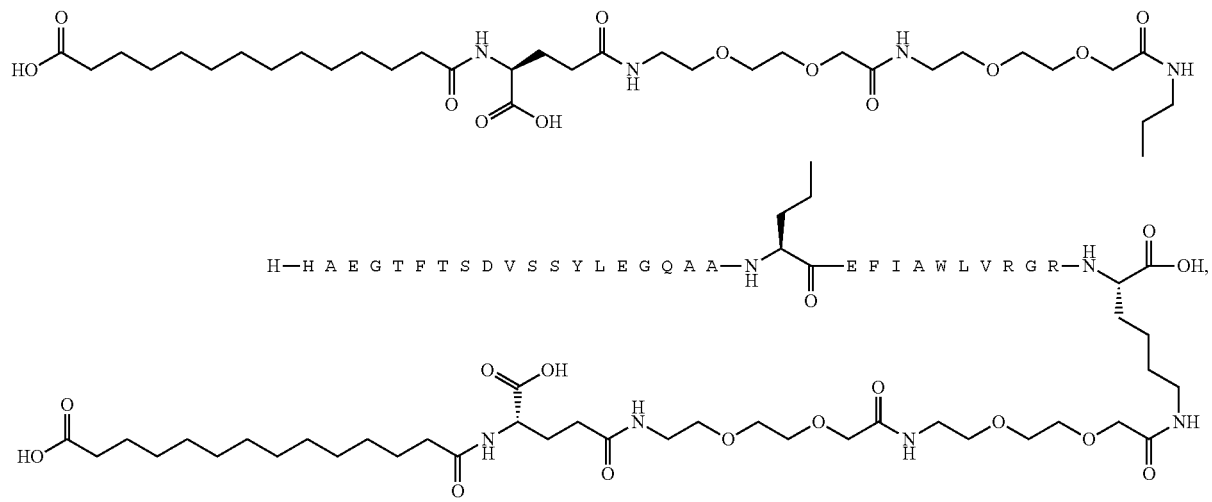

N$^{\epsilon26}$-[(S)-4-Carboxy-4-{2-[2-(2-[2-(2-{2-[(13-carboxytridecanoylamino)]ethoxy}ethoxy)ethoxy]acetylamino]ethoxy)ethoxy]acetylamino}butyryl], N$^{\epsilon37}$-[(S)-4-Carboxy-4-{2-[2-(2-[2-(2-{2-[(13-carboxytridecanoylamino)]ethoxy}ethoxy)acetylamino]ethoxy)ethoxy]acetylamino}butyryl][Aib$^8$,Arg$^{34}$,Lys$^{37}$]GLP-1(7-37)-peptide (SEQ ID NO: 7), Chem. 44:

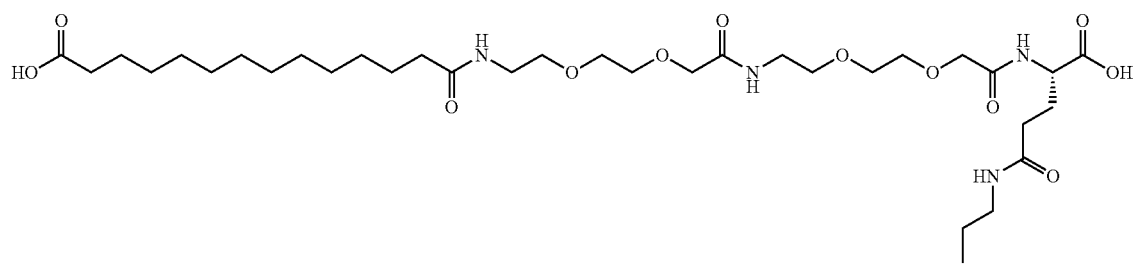

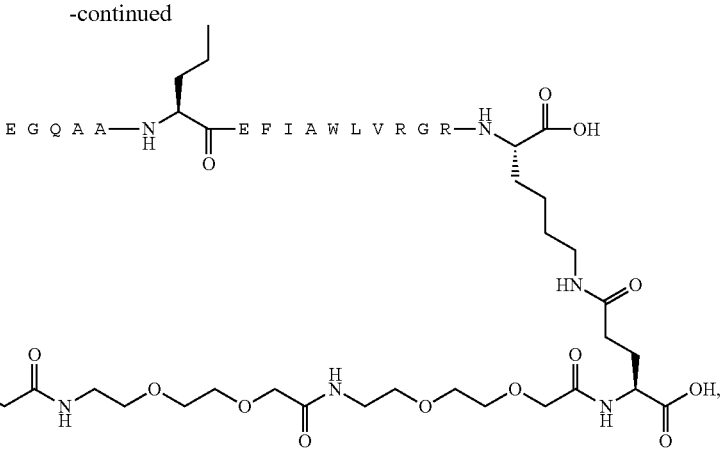

N^ε26-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N^ε37-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl][Arg^34,Lys^37]-GLP-1-(7-37)-peptidyl-Glu (SEQ ID NO: 9), and Chem. 64:

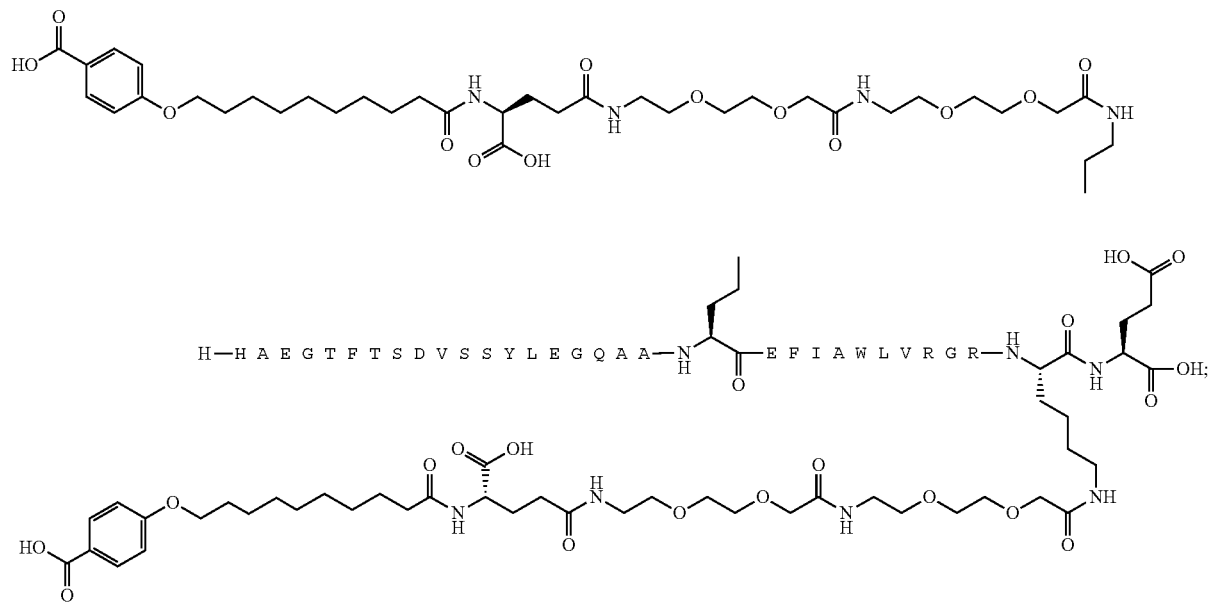

(ii) N^9-{2-[2-(1H-Imidazol-4-yl)-ethylcarbamoyl]-2-methylpropionyl}-N^ε26-{2-[2-(2-{2-[2-(2-{(S)-4-[4-(4-tert-Butylphenyl)butyrylamino]-4-carboxybutyrylamino}ethoxy)ethoxy]acetylamino}ethoxy)ethoxy]acetyl}, N^ε37-{2-[2-(2-{2-[2-(2-{(S)-4-[4-(4-tert-Butylphenyl)butyrylamino]-4-carboxybutyrylamino}ethoxy)ethoxy]acetylamino}ethoxy)ethoxy]acetyl}[Arg^34, Lys^37]GLP-1 (9-37)-peptide (SEQ ID NO: 9), Chem. 46:

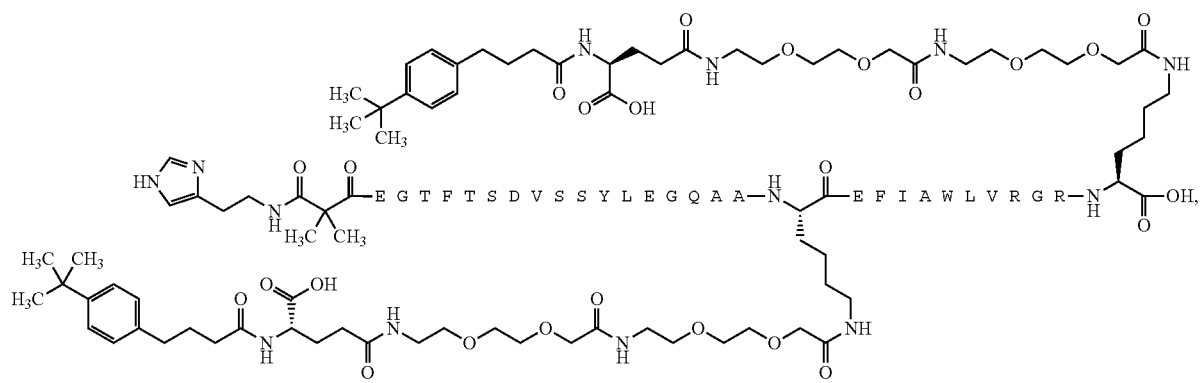

$N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Arg$^{23}$,Arg$^{34}$,Lys$^{37}$]-GLP-1-(7-37)-peptide (SEQ ID NO: 4), Chem. 50:

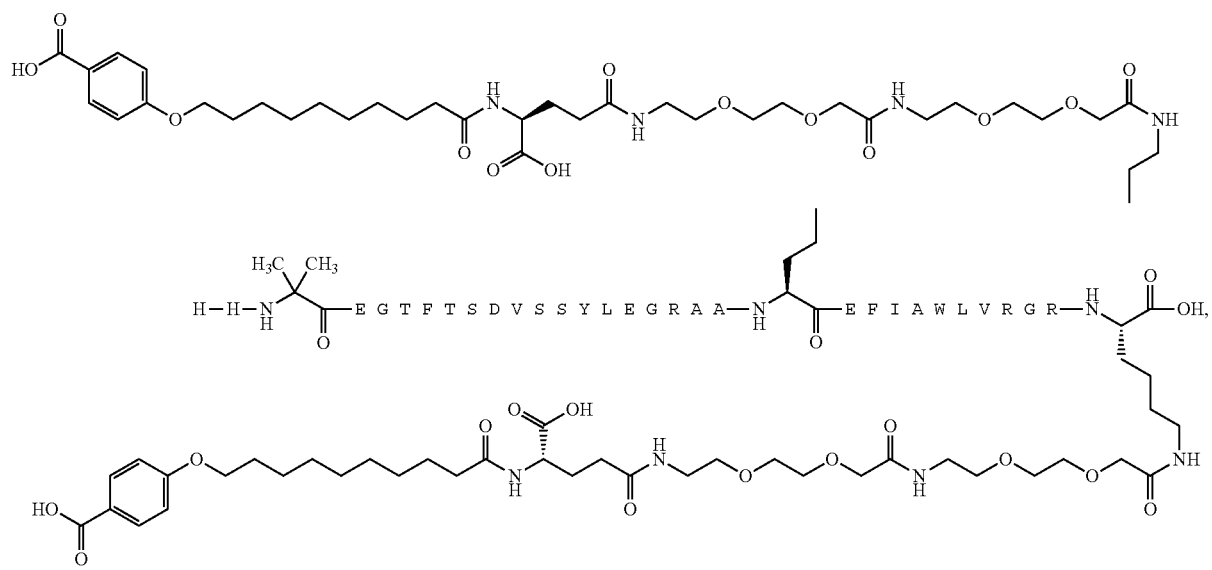

$N^{\epsilon 26}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], $N^{\epsilon 37}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl][Aib$^8$,Arg$^{34}$,Lys$^{37}$]GLP-1(7-37)-peptide (SEQ ID NO: 7), Chem. 24:

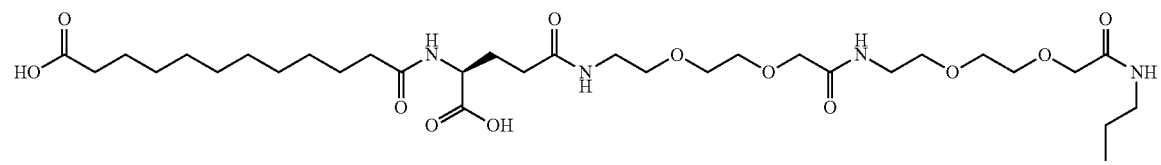

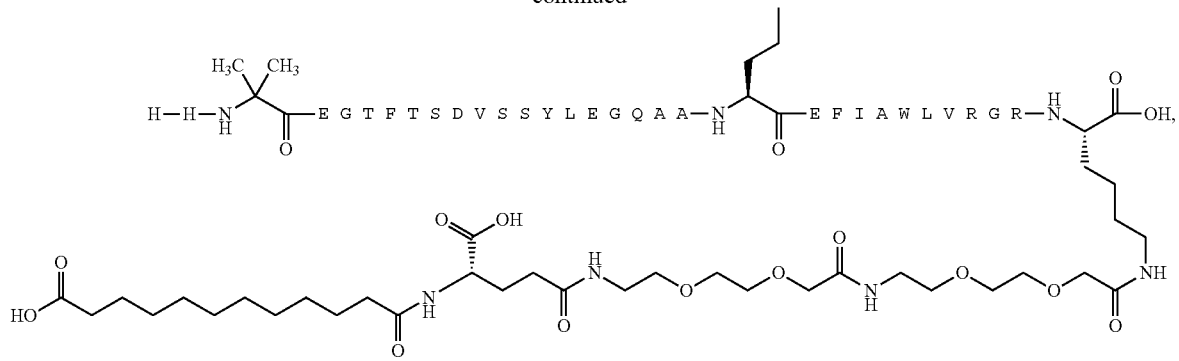

$N^{\epsilon 26}$-{2-[2-(2-{2-[2-(2-{(S)-4-Carboxy-4-[4-(4-iodo-phenyl)-butyrylamino]-butyrylamino}-ethoxy)-ethoxy]-acetylamino}-ethoxy)-ethoxy]acetyl}, $N^{\epsilon 37}$-{2-[2-(2-{2-[2-(2-{(S)-4-Carboxy-4-[4-(4-iodo-phenyl)-butyrylamino]-butyrylamino}-ethoxy)-ethoxy]-acetylamino}-ethoxy)-ethoxy]-acetyl}[Aib$^8$,Arg$^{34}$,Lys$^{37}$] GLP-1(7-37)-peptide (SEQ ID NO: 7), and Chem. 31:

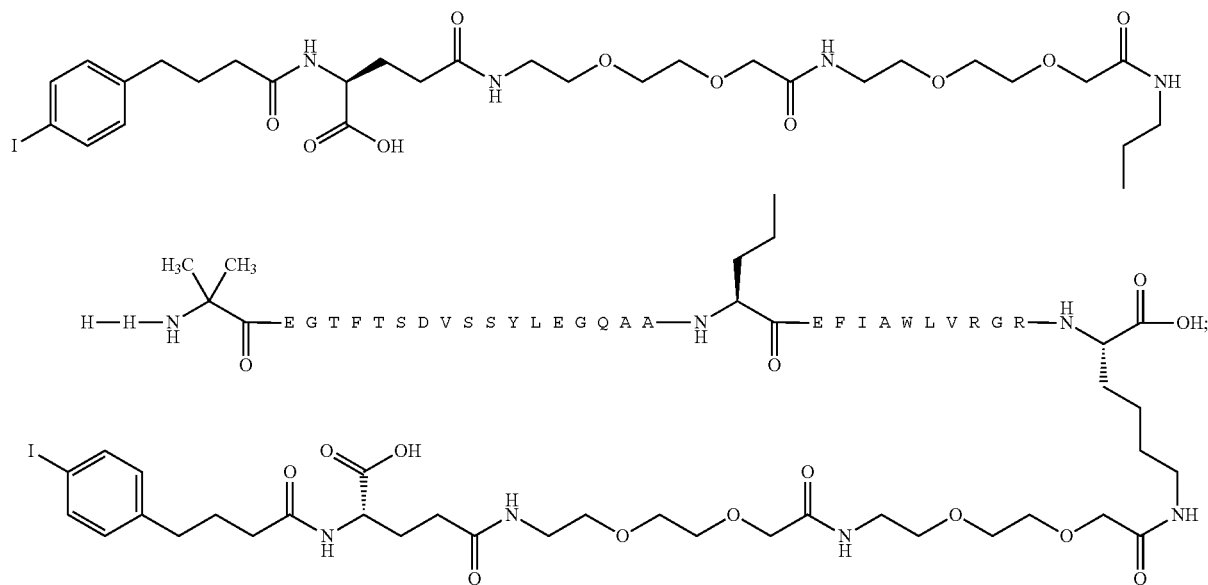

(iii)  $N^{\epsilon 26}$-{2-[2-(2-{2-[2-(2-{(S)-4-Carboxy-4-[12-(3-carboxyphenoxy)dodecanoylamino]butyrylamino}ethoxy)ethoxy]acetylamino}ethoxy)ethoxy]acetyl}, $N^{\epsilon 37}$-{2-[2-(2-{2-[2-(2-{(S)-4-Carboxy-4-[12-(3-carboxyphenoxy)dodecanoylamino]butyrylamino}ethoxy)ethoxy]acetylamino}ethoxy)ethoxy]acetyl}[Aib$^8$,Arg$^{34}$,Lys$^{37}$] GLP-1(7-37)-peptide (SEQ ID NO: 7), Chem. 35:

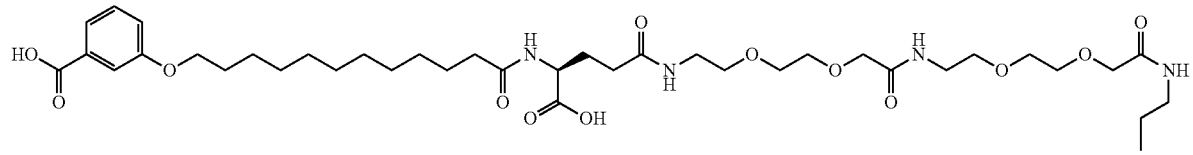

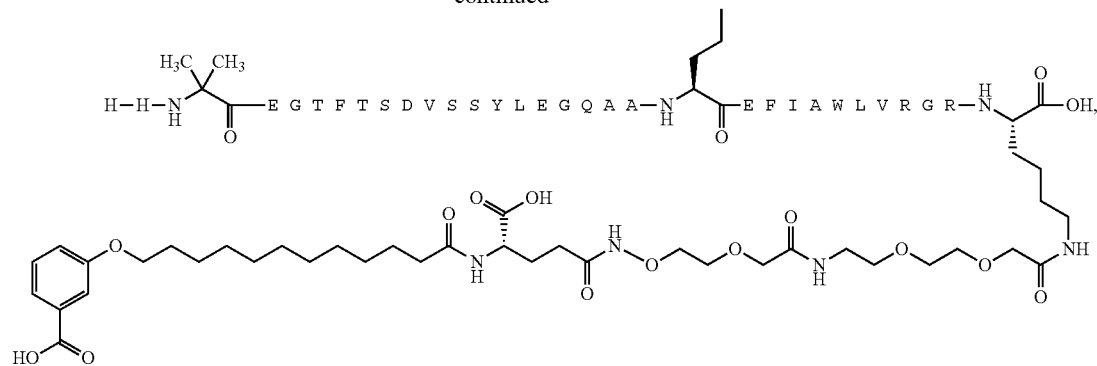

$N^{26}$-[2-(2-{2-[2-(2-{2-[(S)-4-Carboxy-4-(13-carboxytridecanoylamino)butyrylamino]ethoxy}ethoxy)acetylamino]ethoxy}ethoxy)acetyl], $N^{\epsilon 37}$-[2-(2-{2-[2-(2-{2-RS)-4-Carboxy-4-(13-carboxytridecanoylamino)butyrylamino]ethoxy}ethoxy)acetylamino]ethoxy}ethoxy)acetyl][Aib$^8$, Arg$^{34}$, Lys$^{37}$]GLP-1(7-37)-peptide (SEQ ID NO: 7), Chem. 23:

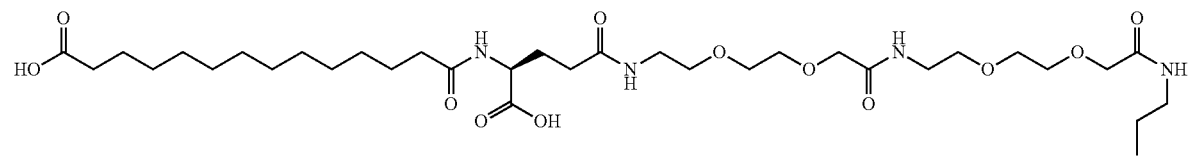

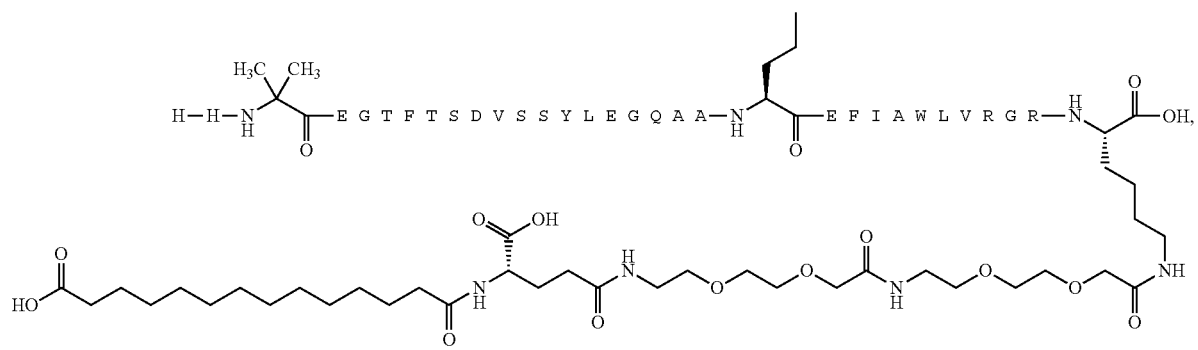

$N^{\epsilon 26}$-[(S)-4-Carboxy-4-{2-[2-(2-[2-(2-{2-[(13-carboxytridecanoylamino)]ethoxy}ethoxy)acetylamino]ethoxy)ethoxy]acetylamino}butyryl], $N^{\epsilon 37}$-[(S)-4-Carboxy-4-{2-[2-(2-[2-(2-{2-[(13-carboxytridecanoylamino)]ethoxy}ethoxy)acetylamino]ethoxy)ethoxy]acetylamino}butyryl][Aib$^8$,Arg$^{34}$,Lys$^{37}$]GLP-1(7-37)-peptide (SEQ ID NO: 7), Chem. 44:

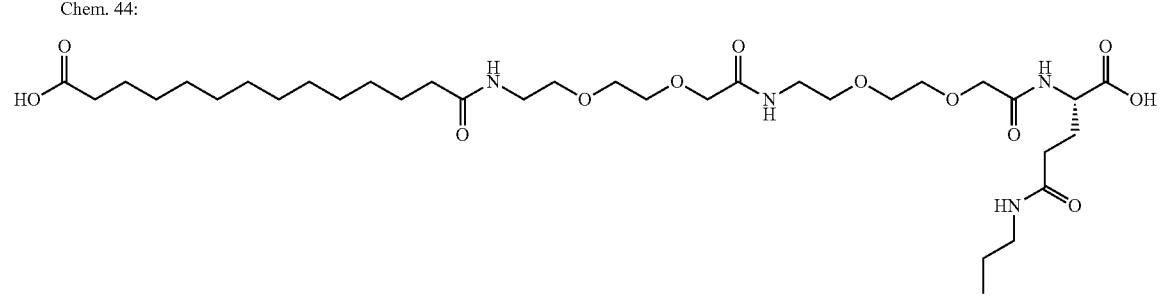

-continued

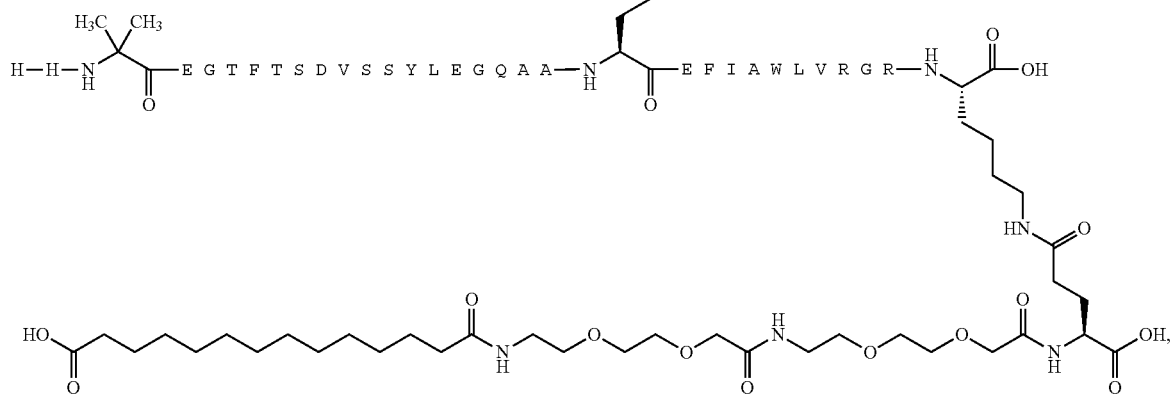

$N^{\epsilon26}${2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, $N^{\epsilon37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[Aib$^8$,Arg$^{34}$,Lys$^{37}$] GLP-1(7-37)-peptide (SEQ ID NO: 7), Chem. 21:

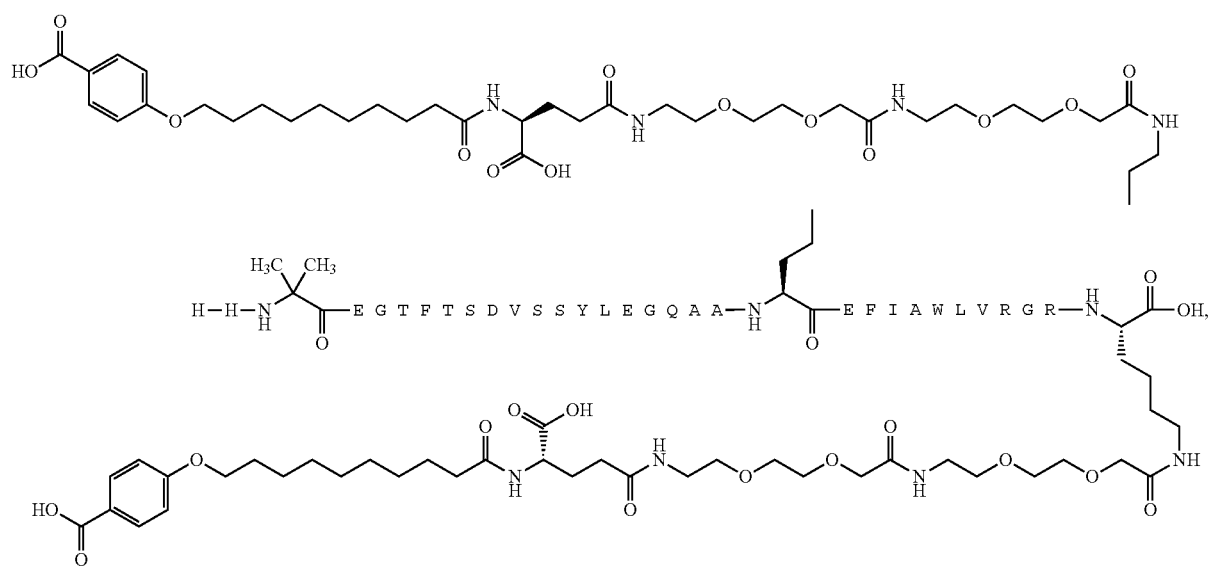

$N^{\epsilon26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Arg$^{34}$,Lys$^{37}$]-GLP-1-(7-37)-peptide (SEQ ID NO: 9), and Chem. 48:

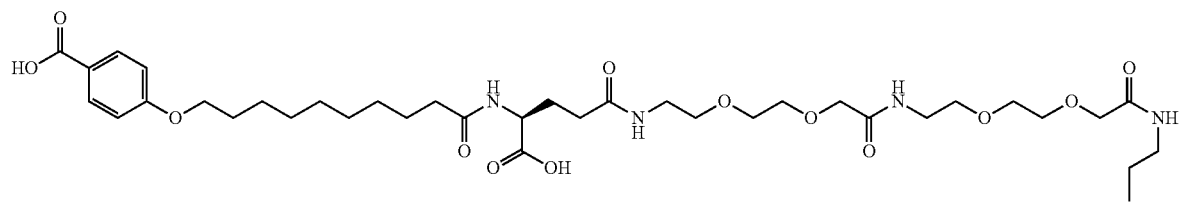

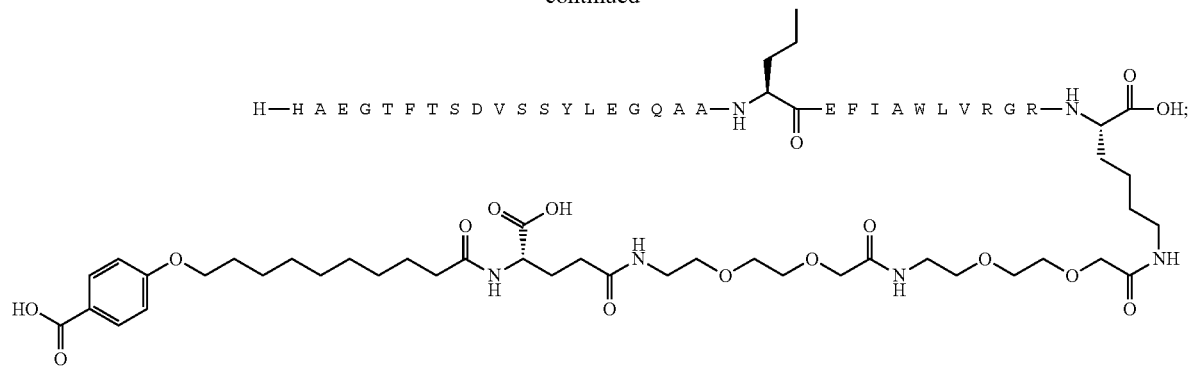

(iv) N^ε26-{2-[2-(2-{2-[2-(2-{(S)-4-Carboxy-4-[12-(3-carboxyphenoxy)dodecanoylamino]butyrylamino}ethoxy)ethoxy]acetylamino}ethoxy)ethoxy]acetyl}, N^ε37-{2-[2-(2-{2-[2-(2-{(S)-4-Carboxy-4-[12-(3-carboxyphenoxy)dodecanoylamino]butyrylamino}ethoxy)ethoxy]acetylamino}ethoxy)ethoxy]acetyl}[Aib^8,Arg^34,Lys^37]GLP-1(7-37)-peptide (SEQ ID NO: 7), Chem. 35:

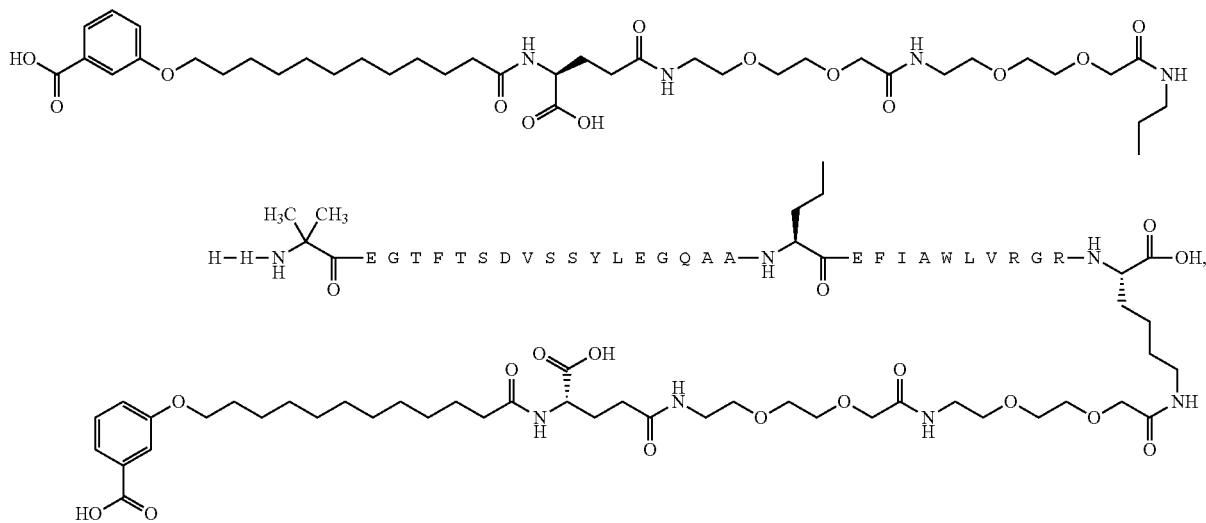

N^ε26{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, N^ε37-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[Aib^8,Arg^34,Lys^37]GLP-1(7-37)-peptide (SEQ ID NO: 7), Chem. 21:

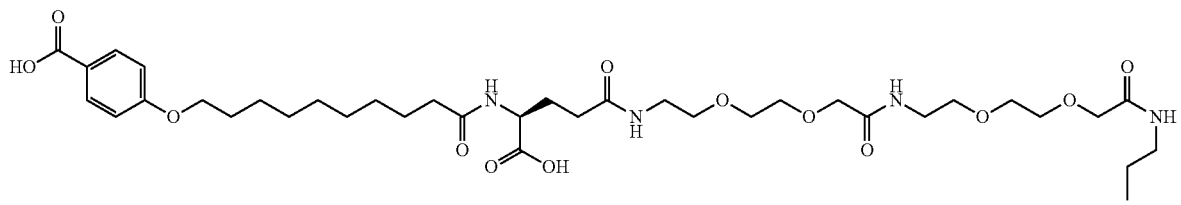

-continued

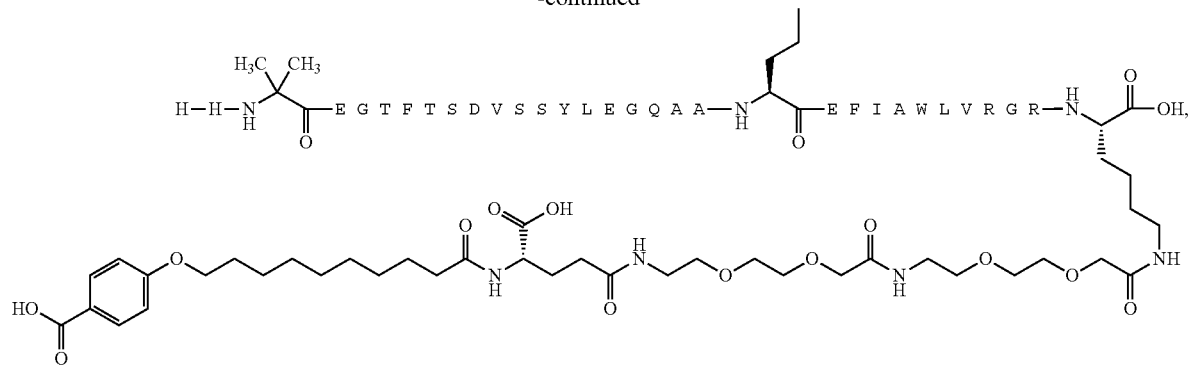

N^ε26-[2-{2-[(S)-4-Carboxy-4-(13-carboxytridecanoylamino)butyrylamino]], N^ε37-{2-[(S)-4-Carboxy-4-(13-carboxytridecanoylamino)butyrylamino]][Aib^8,Arg^34,Lys^37]GLP-1(7-37)-peptide amide (SEQ ID NO: 7), Chem. 29:

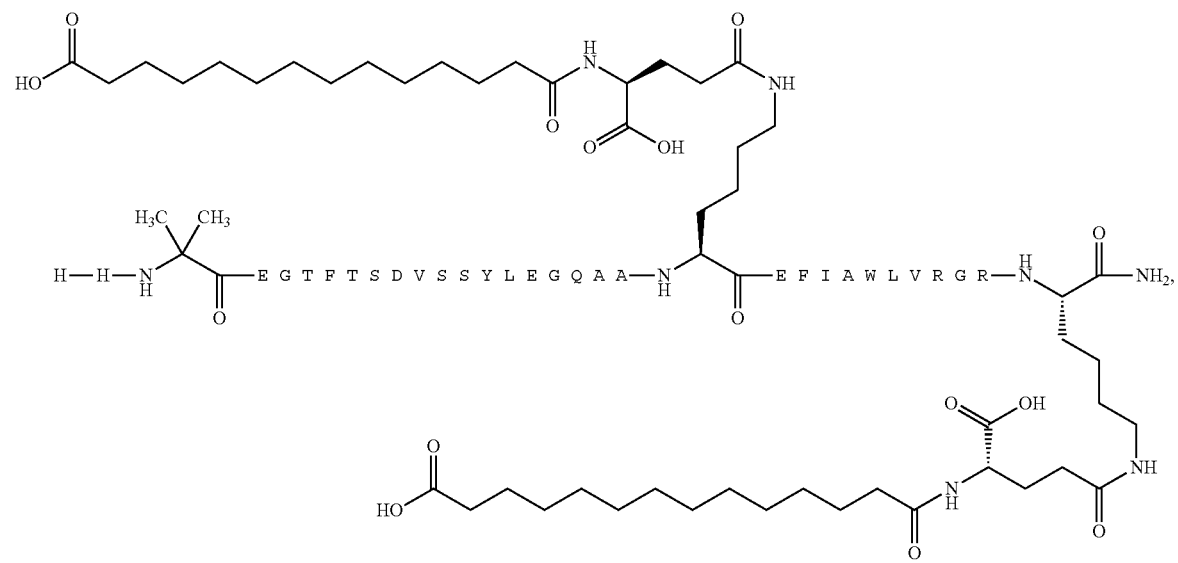

N^ε26-{2-[2-(2-{2-[2-(2-{(S)-4-Carboxy-4-[4-(4-iodo-phenyl)-butyrylamino]-butyrylamino}-ethoxy)-ethoxy]-acetylamino}-ethoxy)-ethoxy]-acetyl}, N^ε37-{2-[2-(2-{2-[2-(2-{(S)-4-Carboxy-4-[4-(4-iodo-phenyl)-butyrylamino]-butyrylamino}-ethoxy)-ethoxy]-acetylamino}-ethoxy)-ethoxy]-acetyl}[Aib^8,Arg^34,Lys^37]GLP-1(7-37)-peptide (SEQ ID NO: 7), and Chem. 31:

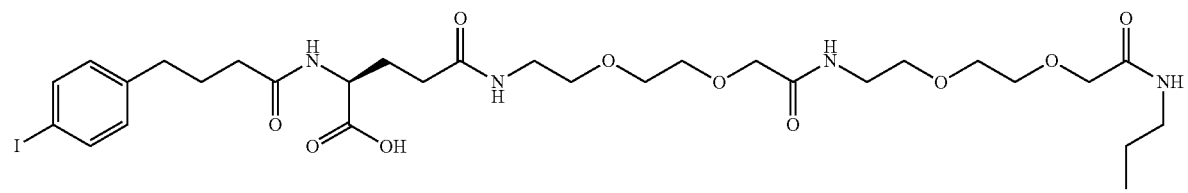

or a pharmaceutically acceptable salt, amide, or ester of any of these compounds.
182. The derivative of embodiment 181, which is Chem. 62, or a pharmaceutically acceptable salt, amide, or ester thereof.
183. The derivative of embodiment 181, which is Chem. 40, or a pharmaceutically acceptable salt, amide, or ester thereof.
184. The derivative of embodiment 181, which is Chem. 21, or a pharmaceutically acceptable salt, amide, or ester thereof.
185. The derivative of embodiment 181, which is Chem. 55, or a pharmaceutically acceptable salt, amide, or ester thereof.
186. The derivative of embodiment 181, which is Chem. 51, or a pharmaceutically acceptable salt, amide, or ester thereof.
187. The derivative of embodiment 181, which is Chem. 44, or a pharmaceutically acceptable salt, amide, or ester thereof.
188. The derivative of embodiment 181, which is Chem. 46, or a pharmaceutically acceptable salt, amide, or ester thereof.
189. The derivative of embodiment 181, which is Chem. 31, or a pharmaceutically acceptable salt, amide, or ester thereof.
190. The derivative of embodiment 181, which is Chem. 35, or a pharmaceutically acceptable salt, amide, or ester thereof.
191. The derivative of embodiment 181, which is Chem. 23, or a pharmaceutically acceptable salt, amide, or ester thereof.
192. The derivative of any one of embodiments 1-191, which has GLP-1 activity.
193. The derivative of embodiment 192, wherein GLP-1 activity refers to the capability of activating the human GLP-1 receptor.
194. The derivative of embodiment 193, wherein activation of the human GLP-1 receptor is measured in an in vitro assay, as the potency of cAMP production.
195. The derivative of any one of embodiments 1-194, which has a potency corresponding to an $EC_{50}$,
a) below 10000 μM, more preferably below 5000 μM, even more preferably below 4000 μM, or most preferably below 3000 μM;
b) at or below 3000 μM, preferably below 3000 μM, more preferably below 2500 μM, even more preferably below 2000 μM, or most preferably below 1500 μM;
c) below 2000 μM, preferably below 1000 μM, more preferably below 800 μM, even more preferably below 600 μM, or most preferably below 500 μM;
c) below 400 μM, preferably below 300 μM, more preferably below 200 μM, even more preferably below 150 μM, or most preferably below 100 μM;
d) below 80 μM, preferably below 60 μM, more preferably below 50 μM, even more preferably below 40 μM, or most preferably below 30 μM; or which has a potency corresponding to an $EC_{50}$,
e) which is less than 10 times the $EC_{50}$ of semaglutide, preferably less than 8 times the $EC_{50}$ of semaglutide, more preferably less than 6 times the $EC_{50}$ of semaglutide, even more preferably less than 4 times the $EC_{50}$ of semaglutide, or most preferably less than 2 times the $EC_{50}$, of semaglutide;
f) which is less than 10 times the $EC_{50}$ of liraglutide, preferably less than 8 times the $EC_{50}$ of liraglutide, more preferably less than 6 times the $EC_{50}$ of liraglutide, even more preferably less than 4 times the $EC_{50}$, of liraglutide, or most preferably less than 2 times the $EC_{50}$, of liraglutide; or
g) which is less than the $EC_{50}$ of liraglutide, preferably less than 0.8 times the $EC_{50}$ of liraglutide, more preferably less than 0.6 times the $EC_{50}$ of liraglutide, even more preferably less than 0.5 times the $EC_{50}$ of liraglutide, or most preferably less than or at 0.4 times the $EC_{50}$ of liraglutide.
196. The derivative of any one of embodiments 1-195, wherein the potency is determined as $EC_{50}$, for the dose-response curve showing dose-dependent formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 50.
197. The derivative of any one of embodiments 1-196, for which the ratio [GLP-1 receptor binding affinity ($IC_{50}$) in the presence of 2.0% HSA (high albumin), divided by GLP-1 receptor binding affinity ($IC_{50}$) in the presence of 0.005% HSA (low albumin)] is:
a) at least 0.5, preferably at least 1.0, more preferably at least 10, even more preferably at least 20, or most preferably at least 30;
b) at least 40, preferably at least 50, more preferably at least 60, even more preferably at least 70, or most preferably at least 80;
c) at least 90, preferably at least 100, more preferably at least 200, still more preferably at least 300, even more preferably at least 400, or most preferably at least 500;
d) at least 120, preferably at least 140, even more preferably at least 160, or most preferably at least 180;
e) at least 20% of the ratio of semaglutide, preferably at least 50% of the ratio of semaglutide, more preferably at least 75% of the ratio of semaglutide, or most preferably at least equal to the ratio of semaglutide; or f) at least equal to the ratio of liraglutide, preferably at least twice the ratio of liraglutide, more preferably at least three times the ratio of liraglutide, even more preferably at least 4 times the ratio of liraglutide, or most preferably at least 5 times the ratio of liraglutide.

198. The derivative of any one of embodiments 1-197, for which the GLP-1 receptor binding affinity ($IC_{50}$) in the presence of 0.005% HSA (low albumin) is a) below 1000.00 nM, preferably below 600.00 nM, more preferably below 100.00 nM, or most preferably below 50.00 nM; or b) below 20.00 nM, preferably below 10.00 nM, more preferably below 5.00 nM, even more preferably below 2.00 nM, or most preferably below 1.00 nM.

199. The derivative of any one of embodiments 1-198, for which the GLP-1 receptor binding affinity ($IC_{50}$) in the presence of 2.0% HSA (high albumin) is a) below 1100.00 nM, preferably at or below 1000.00 nM, more preferably below 800.00 nM, or most prefererably below 600 nM; or b) below 400.00 nM, preferably below 300.00 nM, more preferably below 200.00 nM, even more preferably below 100.00 nM, or most preferably below 50.00 nM.

200. The derivative of any one of embodiments 1-199, wherein the binding affinity to the GLP-1 receptor is measured by way of displacement of $^{125}$I-GLP-1 from the receptor, preferably using a SPA binding assay.

201. The derivative of any one of embodiments 1-200, wherein the GLP-1 receptor is prepared using a stable, transfected cell line, preferably a hamster cell line, more preferably a baby hamster kidney cell line, such as BHK tk-ts13.

202. The derivative of any one of embodiments 1-201, wherein the $IC_{50}$ value is determined as the concentration which displaces 50% of $^{125}$I-GLP-1 from the receptor.

203. The derivative of any one of embodiments 1-202, which has an oral bioavailability, preferably an absolute oral bioavailability, which is higher than that of semaglutide.

204. The derivative of embodiment 203, wherein oral bioavailability is measured in vivo in rats, as exposure in plasma after direct injection into the intestinal lumen.

205. The derivative of any one of embodiments 1-204, for which the plasma concentration (pM) of the derivative, determined 30 minutes after injection of a solution of the derivative in the jejunum of rat, divided by the concentration (µM) of the injected solution (dose-corrected exposure at 30 min) is at least 40, preferably at least 50, more preferably at least 60, still more preferably at least 70, even more preferably at least 80, or most preferably at least 100.

206. The derivative of any one of embodiments 1-205, for which the plasma concentration (pM) of the derivative, determined 30 minutes after injection of a solution of the derivative in the jejunum of rat, divided by the concentration (µM) of the injected solution (dose-corrected exposure at 30 min) is at least 110, preferably at least 120, more preferably at least 130, still more preferably at least 140, even more preferably at least 150, or most preferably at least 160.

207. The derivative of any one of embodiments 1-206, for which the plasma concentration (pM) of the derivative, determined 30 minutes after injection of a solution of the derivative in the jejunum of rat, divided by the concentration (µM) of the injected solution (dose-corrected exposure at 30 min) is at least 180, preferably at least 190, more preferably at least 200, or most preferably at least 210.

208. The derivative of any one of embodiments 1-207, wherein the GLP-1 derivative is tested in a concentration of 1000 uM in admixture with 55 mg/ml sodium caprate.

209. The derivative of any one of embodiments 1-208, wherein male Sprague Dawley rats are used, preferably with a body weight upon arrival of approximately 240 g.

210. The derivative of any one of embodiments 1-209, wherein the rats are fasted for approximately 18 hours before the experiment.

211. The derivative of any one of embodiments 1-210, wherein the rats are taken into general anaesthesia after having fasted and before the injection of the derivative in the jejunum.

212. The derivative of any one of embodiments 1-211, wherein the derivative is administered in the proximal part of the jejunum (10 cm distal for the duodenum) or in the mid-intestine (50 cm proximal for the cecum).

213. The derivative of any one of embodiments 1-212, wherein 100 µl of the derivative is injected into the jejunal lumen through a catheter with a 1 ml syringe, and subsequently 200 µl of air is pushed into the jejunal lumen with another syringe, which is then left connected to the catheter to prevent flow back into the catheter.

214. The derivative of any one of embodiments 1-213, wherein blood samples (200 ul) are collected into EDTA tubes from the tail vein at desired intervals, such as at times 0, 10, 30, 60, 120 and 240 min, and centrifuged 5 minutes, 10000G, at 4° C. within 20 minutes.

215. The derivative of any one of embodiments 1-214, wherein plasma (75u1) is separated, immediately frozen, and kept at −20° C. until analyzed for plasma concentration of the derivative.

216. The derivative of any one of embodiments 1-215, wherein LOCI (Luminescent Oxygen Channeling Immunoassay) is used for analyzing the plasma concentration of the derivative.

217. The derivative of any one of embodiments 1-216, wherein the derivative is effective at lowering blood glucose in vivo in db/db mice.

218. The derivative of any one of embodiments 1-217, wherein the derivative is effective at lowering body weight in vivo in db/db mice.

219. The derivative of any one of embodiments 1-218, wherein db/db mice are treated, s.c., with a suitable range of doses of the GLP-1 derivative, and blood glucose and/or bodyweight is/are determined at appropriate intervals.

220. The derivative of any one of embodiments 1-219, wherein the dose of the GLP-1 derivative is 0.3 nmol/kg, 1.0 nmol/kg, 3.0 nmol/kg, 10 nmol/kg, 30 nmol/kg, and 100 nmol/kg, wherein kg refers to the body weight of the mouse.

221. The derivative of any one of embodiments 1-220, wherein a control group is treated with vehicle, s.c., preferably the medium in which the GLP-1 derivative is dissolved, e.g. with the following composition: 50 mM sodium phosphate, 145 mM sodium chloride, 0.05% Tween™ 80, pH 7.4.

222. The derivative of any one of embodiments 1-221, wherein blood glucose is determined, and/or the mice are weighed, at time −½h (half an hour prior to dosing (t=0)), and at times 1, 2, 4, 8, 24, 48, 72, and 96 h.

223. The derivative of any one of embodiments 1-222, wherein the glucose concentration is measured using the glucose oxidase method.

224. The derivative of any one of embodiments 1-223, wherein (i) $ED_{50}$ (body weight (BW)) is calculated as the dose giving rise to half-maximum effect on delta (e.g., decrease) BW 24 hours following the subcutaneous administration of the derivative; and/or (ii) $ED_{50}$ (blood glucose (BG)) is calcualated as the dose giving rise to half-maximum effect on AUC (Area Under the Curve) delta (e.g., decrease) BG 8 hours following the subcutaneous administration of the derivative.
225. The derivative of any one of embodiments 1-224, wherein a sigmoidal dose-response relationship exists, preferably with a clear definition of the maximum response.
226. The derivative of any one of embodiments 1-225, which has a more protracted profile of action than liraglutide.
227. The derivative of embodiment 226, wherein protraction means half-life in vivo in a relevant animal species, such as db/db mice, rat, pig, and/or, preferably, minipig; wherein the derivative is administered i) s.c., and/or, preferably, ii) s.c.
228. The derivative of any one of embodiments 1-227, wherein the terminal half-life ($T_{1/2}$) after i.v. administration in minipigs is
a) at least 12 hours, preferably at least 24 hours, more preferably at least 36 hours, even more preferably at least 48 hours, or most preferably at least 60 hours;
b) at least 7 hours, preferably at least 16 hours, more preferably at least 24 hours, even more preferably at least 30 hours, or most preferably at least 40 hours;
c) at least 44 hours, preferably at least 55 hours, more preferably at least 66 hours, even more preferably at least 77 hours, or most preferably at least 88 hours; or
d) at least 0.2 times the half-life of semaglutide, preferably at least 0.4 times the half-life of semaglutide, more preferably at least 0.6 times the half-life of semaglutide, even more preferably at least 0.8 times the half-life of semaglutide, or most preferably at least the same as the half-life of semaglutide.
229. The derivative of embodiment 228, wherein the minipigs are male Göttingen minipigs.
230. The derivative of any one of embodiments 227-229, wherein the minipigs are 7-14 months of age, and preferably weighing from 16-35 kg.
231. The derivative of any one of embodiments 227-230, wherein the minipigs are housed individually, and fed once or twice daily, preferably with SDS minipig diet.
232. The derivative of any one of embodiments 227-231, wherein the derivative is dosed, i.v., after at least 2 weeks of acclimatisation.
233. The derivative of any one of embodiments 227-232, wherein the animals are fasted for approximately 18 h before dosing and for at least 4 h after dosing, and have ad libitum access to water during the whole period.
234. The derivative of any one of embodiments 227-233, wherein the GLP-1 derivative is dissolved in 50 mM sodium phosphate, 145 mM sodium chloride, 0.05% tween 80, pH 7.4 to a suitable concentration, preferably from 20-60 nmol/ml.
235. The derivative of any one of embodiments 227-234, wherein intravenous injections of the derivative are given in a volume corresponding to 1-2 nmol/kg.
236. The derivative of any one of embodiments 1-235, which increases the glucose stimulated insulin secretion in minipigs.
237. The derivative of embodiment 236, wherein the minipigs are male Göttingen minipigs.
238. The derivative of any one of embodiments 236-237, wherein the minipigs are 7-14 months of age.
239. The derivative of any one of embodiments 236-238, wherein the minipigs are housed in single pens, and fed once or twice daily, preferably with SDS minipig fodder.
240. The derivative of any one of embodiments 236-239, wherein a single dose, optionally after a period with dose escalation, is given i.v., or s.c., in the thin skin behind the ear.
2-[1. The derivative of any one of embodiments 236-240, wherein the animals are fasted for approximately 18 h before dosing.
242. The derivative of any one of embodiments 236-2-[1, wherein a baseline group and a number of derivative dose groups corresponding to 2-6 different plasma concentration levels are tested, wherein the baseline group is a) vehicle treated, or b) untreated.
243. The derivative of any one of embodiments 236-242, wherein the plasma concencctration level is 3000-80000 pM.
244. The derivative of any one of embodiments 236-243, wherein a 1 or 2 hour intravenous glucose tolerance test (IVGTT) is performed.
245. The derivative of any one of embodiments 236-244, wherein 0.3 g/kg glucose is given i.v. over a period of 30 seconds, and blood samples taken at suitable time points, such as the following time points (t=0 corresopnds to the glucose bolus): −10, −5,0,2, 5, 10, 15, 20, 25, 30, 40, 50, 60, 70, 80, 90, 100, 110, 120 minutes.
246. The derivative of any one of embodiments 236-245, wherein the concentration in plasma of the derivative, glucose, and insulin is determined.
247. The derivative of any one of embodiments 236-246, wherein the derivative concentration is measured at t=0 min, and, optionally, at the end of the test (t=60 min, or t=120 min).
248. The derivative of any one of embodiments 236-247, wherein glucose is analyzed using the glucose oxidase method.
249. The derivative of any one of embodiments 236-248, wherein the area under the insulin curve (AUCinsulin) is calculated and used as a measure of insulin secretion.
250. The derivative of any one of embodiments 236-249, wherein for at least one concentration thereof, the AUCinsulin is higher than the baseline AUCinsulin, preferably at least 110% thereof, more preferably at least 120% thereof, even more preferably at least 130% thereof or most preferably at least 140% thereof.
251. The derivative of any one of embodiments 1-250, which causes a reduced feed intake in pigs relative to a control (preferably vehicle-treated, or untreated);
optionally the feed intake (0-24 h) may be 90% or lower relative to the vehicle-treated control, preferably 80% or lower, more preferably 70% or lower, even more preferably 60% or lower, or most preferably 50% or lower;
wherein feed intake (0-24 h) refers to the first 24 hours after administration of the derivative or vehicle.
252. The derivative of embodiment 251, wherein the pigs are female Landrace Yorkshire Duroc (LYD) pigs.
253. The derivative of any one of embodiments 251-252, wherein the pigs are 3 months of age, and preferably have a weight of 30-35 kg.
254. The derivative of any one of embodiments 251-253, where the animals are housed in a group for 1-2 weeks for acclimatisation.
255. The derivative of any one of embodiments 251-254, wherein during the experimental period the animals are placed in individual pens from Monday morning to Friday afternoon for measurement of individual food intake.
256. The derivative of any one of embodiments 251-255, wherein the animals are fed ad libitum with pig fodder (such as Svinefoder, Antonio).
257. The derivative of any one of embodiments 251-256, wherein food intake is monitored on line by logging the weight of fodder every 15 minutes, preferably using the Mpigwin system.
258. The derivative of any one of embodiments 251-257, which is dosed 0.3, 1.0, 3.0, 10, or 30 nmol/kg, preferably dissolved in a phosphate buffer (50 mM phosphate, 0.05% Tween™ 80, pH 8), more preferably at concentrations of 12, 40, 120, 400, or 1200 nmol/ml.

259. The derivative of any one of embodiments 251-258, wherein the phosphate buffer serves as vehicle.

260. The derivative of any one of embodiments 251-259, wherein the animals are dosed with a single subcutaneous dose of the derivative, or vehicle (preferably with a dose volume of 0.025 ml/kg), on the morning of day 1, and food intake is measured for 4 days after dosing.

261. The derivative of any one of embodiments 1-260, which has an in vitro half-life ($T_{1/2}$) in an extract of rat small intestines, divided by the corresponding half-life ($T_{1/2}$) of GLP-1 (7-37), of at least 0.4, preferably above 0.5, more preferably above 1.0, even more preferably above 2.0, still more preferably above 3.0, or most preferably above 4.0.

262. The derivative of any one of embodiments 1-261, which has an in vitro half-life ($T_{1/2}$) in an extract of rat small intestines, divided by a corresponding half-life ($T_{1/2}$) of GLP-1(7-37), of above 5.0, preferably above 6.0, more preferably above 7.0, even more preferably above 8.0, still more preferably above 9.0, or most preferably above 10.0.

263. The derivative of any one of embodiments 261-262, wherein the rat small intestine extract is prepared as described in Example 57, the derivative is incubated for one hour at 37° C., the concentration of the extract is titrated so that the half-life of GLP-1(7-37) is in the range of 10-20 minutes, e.g. 1.4 ug/ml, the resulting samples are analysed by UPLC and/or MALDI-TOF, and/or the incubation and analysis is performed as described in Example 57.

264. The derivative of any one of embodiments 1-263, for which a ratio [half-life ($T_{1/2}$) in vitro in rat small intestine extract, divided by a half-life ($T_{1/2}$) in vitro in rat small intestine extract of GLP-1(7-37)] is at least 0.5 times the corresponding ratio of semaglutide, preferably at least 2 times the ratio of semaglutide, more preferably at least 3 times the ratio of semaglutide, even more preferably at least 5 times the ratio of semaglutide, or most preferably at least 7 times the ratio of semaglutide.

265. The derivative of any one of embodiments 1-264, for which a ratio [half-life ($T_{1/2}$) in rat small intestine extract, divided by a half-life ($T_{1/2}$) in rat small intestine extract of GLP-1(7-37)] is at least 0.1 times the corresponding ratio of liraglutide, preferably at least 0.4 times the ratio of liraglutide, more preferably at least 0.8 times the ratio of liraglutide, even more preferably at least 1.2 times the ratio of liraglutide, or most preferably at least 1.5 times the ratio of liraglutide.

266. The derivative of any one of embodiments 1-265, which has a half-life ($T_{1/2}$) in vivo in rats after i.v. administration of at least 4 hours, preferably at least 6 hours, even more preferably at least 8 hours, or most preferably at least 10 hours.

267. The derivative of any one of embodiments 1-266, which has a half-life ($T_{1/2}$) in vivo in rats after i.v. administration of at least 12 hours, preferably at least 15 hours, even more preferably at least 18 hours, or most preferably at least 20 hours.

268. The derivative of any one of embodiments 1-266, which has a half-life ($T_{1/2}$) in vivo in rats after i.v. administration of at least 24 hours, preferably at least 26 hours, or most preferably at least 30 hours.

269. The derivative of any one of embodiments 266-268, in which the rats are male Sprague Dawley rats with a body weight from 300 to 600 g.

270. The derivative of any one of embodiments 1-269, which has a half-life ($T_{1/2}$) in vivo in rats after i.v. administration which is at least the same as the half-life of semaglutide, preferably at least 2 times the half-life of semaglutide, more preferably at least 3 times the half-life of semaglutide, even more preferably at least 4 times the half-life of semaglutide, or most preferably at least 5 times the half-life of semaglutide.

271. The derivative of any one of embodiments 1-270, which is not the compound of Examples 17, 21, 33, 34, 35, and 36; preferably not Chem. 36, Chem. 40, Chem. 52, Chem. 53, Chem. 54, and Chem. 55.

272. The derivative of any one of embodiments 1-271, which is not the compound of Examples 22, 23, 27, and 41; preferably not Chem. 41, Chem. 42, Chem. 46, and Chem. 60.

273. The derivative of Example 19; preferably Chem. 38.

274. The derivative of Example 10; preferably Chem. 29.

275. An intermediate product in the form of a GLP-1 analogue which comprises the following modifications as compared to GLP-1(7-37) (SEQ ID NO: 1): (A) (i) (8Aib, 31H, 34Q, 37K); (ii) (des7-8, 34R, 37K, 38E); (iii) (des7-8, 34R, 37K); (iv) (8Aib, 9G, 34R, 37K); (v) (8Aib, 23R, 34R, 37K); (vi) (31H, 34Q, 37K); (vii) (9Q, 34R, 37K); (iix) (30E, 34R, 37K); (ix) (34R, 37K, 38G); (x) (34R, 36G, 37K); or (xi) (34R, 37K, 38E);

wherein the analogue is preferably selected from the following analogues of GLP-1(7-37) (SEQ ID NO: 1):

(B) (i-a) (8Aib, 31H, 34Q, 37K); (ii-a) (des7-8, 34R, 37K, 38E); (iii-a) (des7-8, 34R, 37K); (iv-a) (8Aib, 9G, 34R, 37K); (v-a) (8Aib, 23R, 34R, 37K); (vi-a) (31H, 34Q, 37K); (vii-a) (9Q, 34R, 37K); (iix-a) (30E, 34R, 37K); (ix-a) (34R, 37K, 38G); (x-a) (34R, 36G, 37K); (xi-a) (34R, 37K, 38E); (xii-a) (7Imp, 34R, 37K); (xiii-a) (8Aib, 34R, 37K); and (xiv-a) (34R, 37K);

or a pharmaceutically acceptable salt, amide, or ester of any of the analogues of (A) or (B).

276. The analogue of embodiment 275, wherein the comparison with GLP-1(7-37) (SEQ ID NO: 1) is made by handwriting and eyeballing.

277. The analogue of embodiment 275, wherein the comparison with GLP-1(7-37) (SEQ ID NO: 1) is made by use of a standard protein or peptide alignment program.

278. The analogue of embodiment 277, wherein the alignment program is a Needleman-Wunsch alignment.

279. The analogue of any one of embodiment 277-278, wherein the default scoring matrix and the default identity matrix is used.

280. The analogue of any one of embodiments 277-279, wherein the scoring matrix is BLOSUM62.

281. The analogue of any one of embodiments 277-280, wherein the penalty for the first residue in a gap is −10 (minus ten).

282. The analogue of any one of embodiments 277-281, wherein the penalties for additional residues in a gap is −0.5 (minus point five).

283. The analogue of any one of embodiments 277-282, which has GLP-1 activity.

284. The analogue of embodiment 283, wherein GLP-1 activity is defined as described in embodiments 192-196.

285. An intermediate product comprising a protracting moiety selected from Chem. 2c, Chem. 3b, and Chem. 4b:

| | |
|---|---|
| HOOC—$C_6H_4$—O—$(CH_2)_y$—CO—PG | Chem. 2c: |
| $R^1$—$C_6H_4$—$(CH_2)_z$—CO—PG | Chem. 3b: |
| HOOC—$C_4H_2$—$(CH_2)_w$—CO—PG | Chem. 4b: | in which y is an integer in the range of 3-17, z is an integer in the range of 1-5, $R^1$ is a group having a molar mass not higher than 150 Da, w is an integer in the range of 6-18, and *—PG is a protection group; wherein, optionally, the distal *—COOH group of the protracting moiety, if present, is also protected; or a pharmaceutically acceptable salt, amide or ester thereof.

286. The intermediate product of embodiment 285, wherein *—CO—PG is i)*—COOH, or ii) an activated ester.

287. The intermediate product of embodiment 286, wherein the activated ester is an ester of p-nitrophenol; 2,4,5-trichlorophenol; N-hydroxysuccinimide; N-hydroxysulfosuccinimide; 3,4-dihydro-3-hydroxy-1,2,3-benzotriazine-4-one; 5-chloro-8-hydroxyquinoline; N-hydroxy-5-norbornene-2,3-dicarboxylic acid imide; pentafluorophenol; p-sulfotetrafluorophenol; N-hydroxyphthalimide; 1-hydroxybenzotriazole; 1-hydroxy-7-azabenzotriazole; N-hydroxymaleimide; 4-hydroxy-3-nitrobenzene sulfonic acid; or any other activated ester known in the art.

288. The intermediate product of any one of embodiments 285-287, which comprises a) a protracting moiety selected from Chem. 2, Chem. 3, and Chem. 4:

HOOC—C$_6$H$_4$—O—(CH$_2$)$_y$—CO—*  Chem. 2:

R$^1$—C$_6$H$_4$—(CH$_2$)$_z$—CO—*  Chem. 3:

HOOC—C$_4$H$_2$—(CH$_2$)$_w$—CO—*  Chem. 4:

in which y is an integer in the range of 3-17, z is an integer in the range of 1-5, R$^1$ is a group having a molar mass not higher than 150 Da, and w is an integer in the range of 6-18; and
b) a linker selected from Chem. 5b, Chem. 6, and Chem. 7:

Chem. 5b:

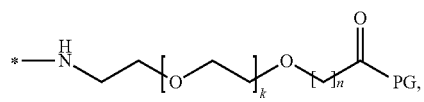

Chem. 6a:

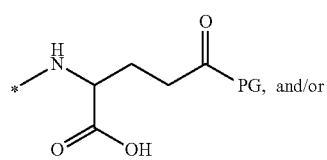
PG, and/or

Chem. 7a:

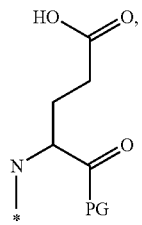

wherein k is an integer in the range of 1-5, and n is an integer in the range of 1-5; and PG is a protection group; wherein, optionally, the *—COOH group of the protracting moiety, if present, is preferably also protected as is known in the art, preferably functionalised as a non-reactive ester; or a pharmaceutically acceptable salt, amide, or ester thereof.

289. The intermediate product of any one of embodiments 285-288, wherein the linker is as defined in any one of embodiments 1-57.

290. The intermediate product of any one of embodiments 285-289, wherein the protracting moiety is as defined in any one of embodiments 1-87.

291. An intermediate product comprising, preferably consisting of, a) a protracting moiety selected from Chem. 2, Chem. 3, and Chem. 4:

HOOC—C$_6$H$_4$—O—(CH$_2$)$_y$—CO—*  Chem. 2:

R$^1$—C$_6$H$_4$—(CH$_2$)$_z$—CO—*  Chem. 3:

HOOC—C$_4$H$_2$—(CH$_2$)$_w$—CO—*  Chem. 4:

in which y is an integer in the range of 3-17, z is an integer in the range of 1-5, R$^1$ is a group having a molar mass not higher than 150 Da, and w is an integer in the range of 6-18; and b) a linker comprising Chem. 5b:

Chem. 5b:

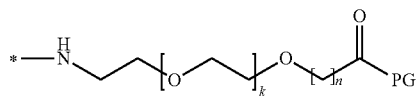

wherein k is an integer in the range of 1-5, and n is an integer in the range of 1-5; and PG is a protection group;

wherein, optionally, the distal *—COOH group of the protracting moiety, if any, is also protected as is known in the art; preferably under the formation of a non-reactive ester; more preferably i) an ester of an alcohol with a bulky side chain, such as an ester of a phenol, optionally substituted; or ii) an ester of branched alkyl, preferably lower alkyl; most preferably protected as OtBu, OBz, and the like; or a pharmaceutically acceptable salt, amide, or ester thereof.

292. An intermediate product, preferably according to any one of embodiments 285-291, selected from the following:

Chem. 69:

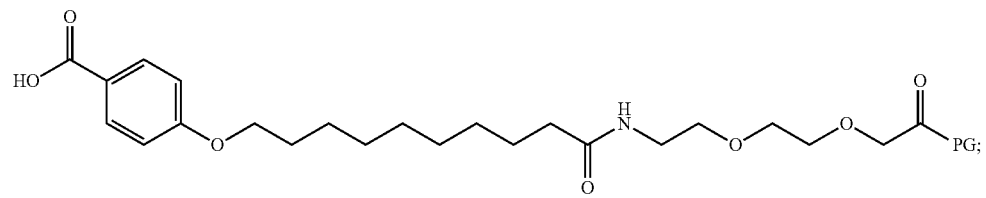

Chem. 70:
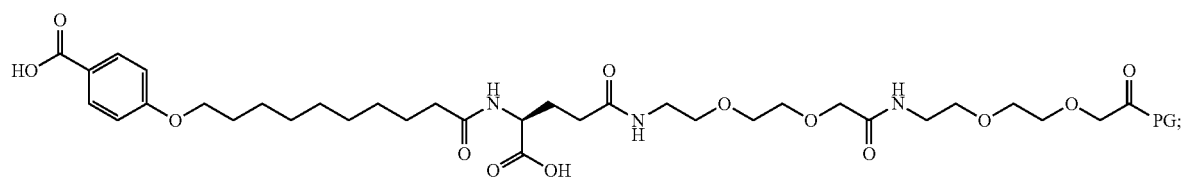
Chem. 71:
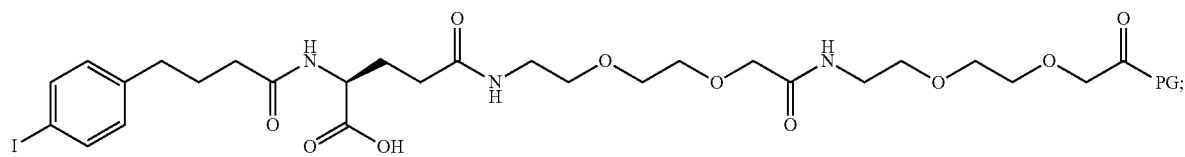
Chem. 72:
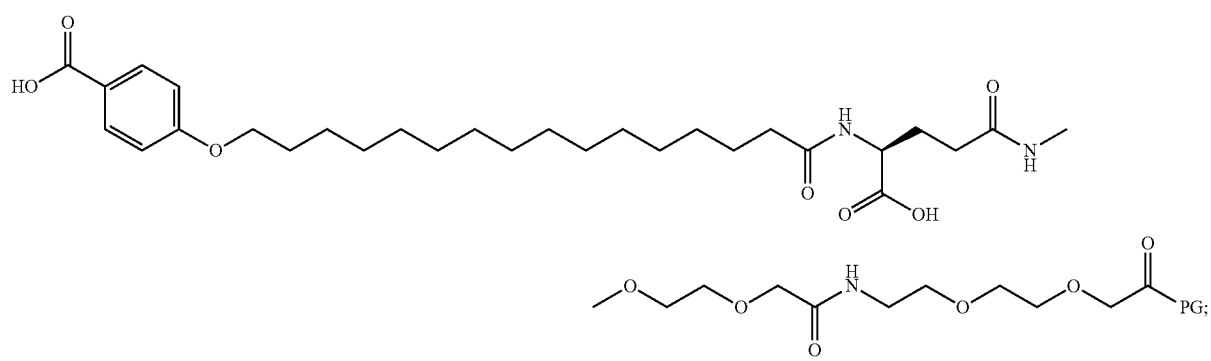
Chem. 73:
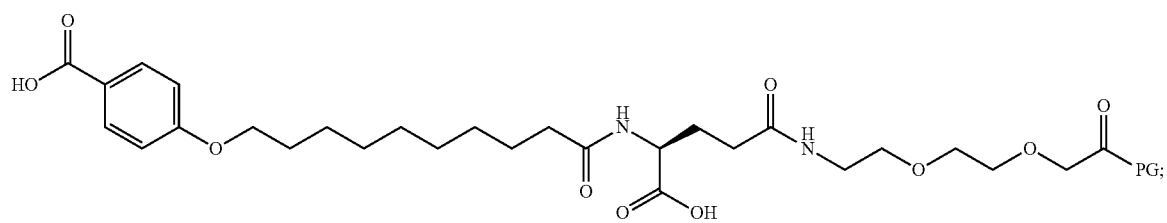
Chem. 74:
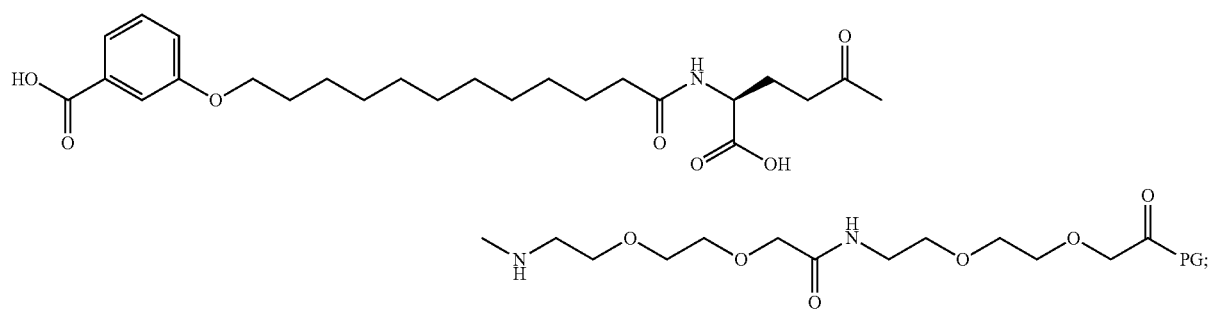
Chem. 75:
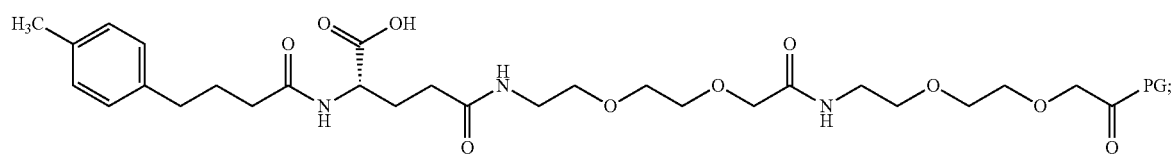

Chem. 76:
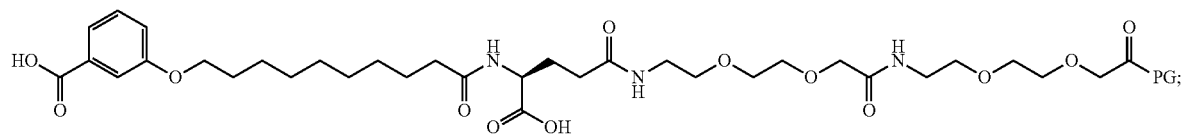
Chem. 77:
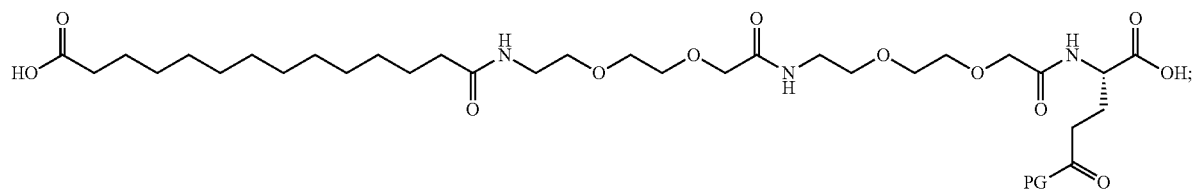
Chem. 78:
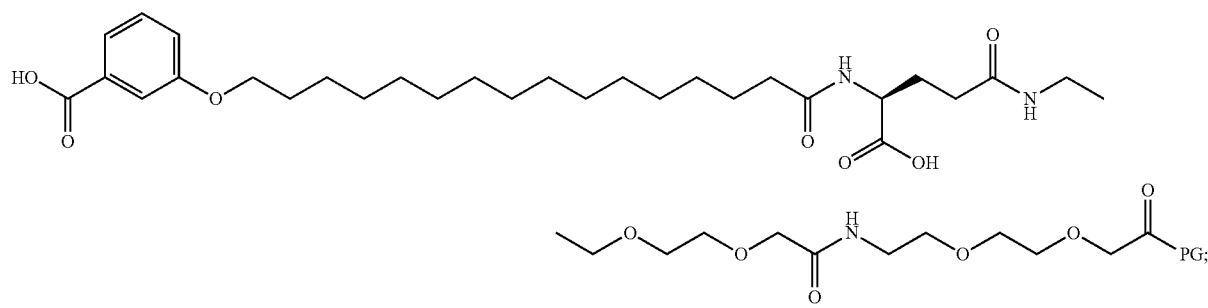
Chem. 79:
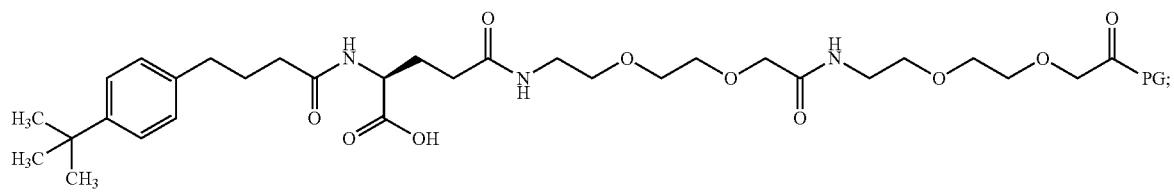
Chem. 80:
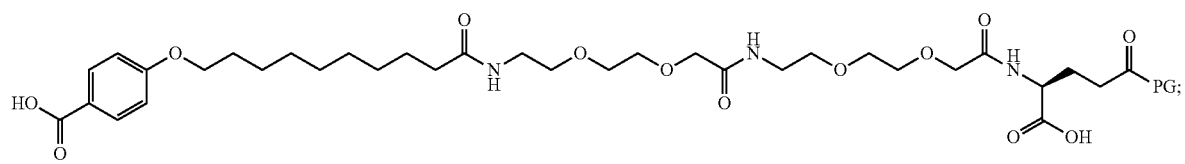
Chem. 81:
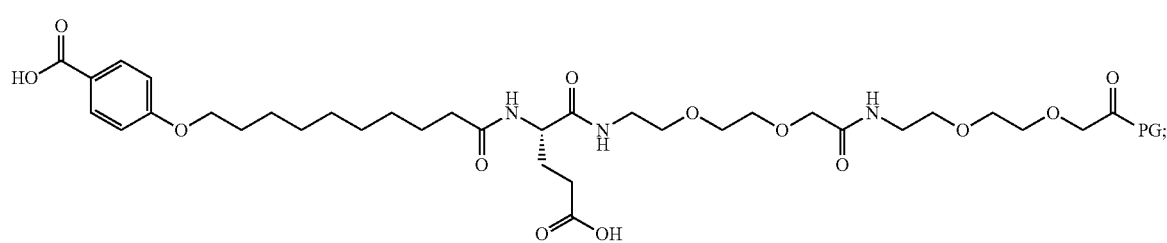
Chem. 82:
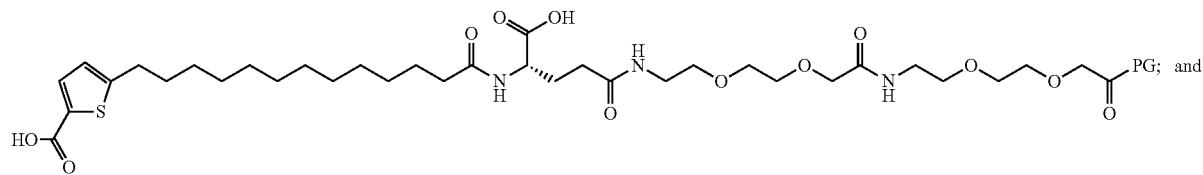

Chem. 83:

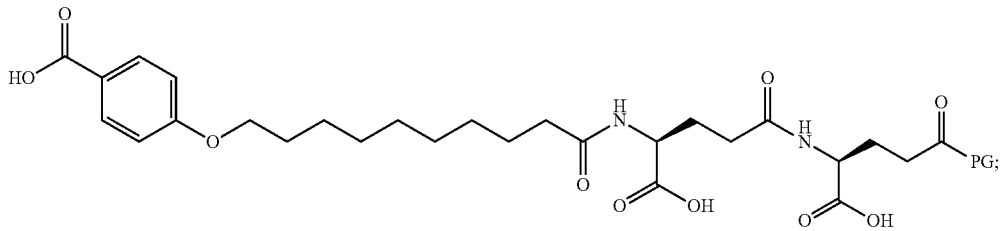

wherein, optionally, one or more of the *—COOH group(s), preferably the distal *—COOH group of the protracting moiety is also protected.

293. A derivative according to any one of embodiments 1-274, for use as a medicament.

294. A derivative according to any one of embodiments 1-274, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving n-cell function, and/or for delaying or preventing diabetic disease progression.

295. Use of a derivative according to any one of embodiments 1-274 in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

296. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any one of embodiments 1-274.

297. A derivative of a GLP-1 analogue, which comprises a protracting moiety selected from Chem. 2, Chem. 3, and Chem. 4:

HOOC—C$_6$H$_4$—O—(CH$_2$)$_y$—CO—*   Chem. 2:

R$^1$—C$_6$H$_4$—(CH$_2$)$_z$—CO—*   Chem. 3:

HOOC—C$_4$H$_2$—(CH$_2$)$_w$—CO—*   Chem. 4:

in which x is an integer in the range of 6-18, y is an integer in the range of 3-17, z is an integer in the range of 1-5, R$^1$ is a group having a molar mass not higher than 150 Da, and w is an integer in the range of 6-18;

or a pharmaceutically acceptable salt, amide, or ester thereof.

298. The derivative of embodiment 297, wherein the GLP-1 analogue is as defined in any one of embodiments 1-296.

299. The derivative of any one of embodiments 297-298, wherein the protracting moiety is as defined in any one of embodiments 1-296.

300. The derivative of any one of embodiments 297-299, which further comprises a linker, preferably as defined in any one of embodiments 1-296.

ADDITIONAL PARTICULAR EMBODIMENTS

The following are additional particular embodiments of the invention:

1. A derivative of a GLP-1 analogue, wherein the GLP-1 analogue is K$^{37}$-GLP-1(7-37) or an analogue thereof having up to six amino acid residues changed as compared to GLP-1(7-37) (SEQ ID NO: 1), which derivative has two albumin binding moieties attached to K$^{26}$ and K$^{37}$, respectively, wherein the albumin binding moiety comprises a protracting moiety selected from HOOC—(CH$_2$)$_n$—CO—, HOOC—C$_6$H$_4$—O—(CH$_2$)$_m$—CO—, and R$^1$—C$_6$H$_4$—(CH$_2$)$_p$—CO—, in which n is an integer in the range of 8-16, m is an integer in the range of 7-17, p is an integer in the range of 1-5, and R$^1$ is a group having a molar mass not higher than 150 Da; or a pharmaceutically acceptable salt, amide, or ester thereof.

2. The derivative of embodiment 1, in which n is an even number.

3. The derivative of embodiment 2, in which n is 8, 10, 12, 14, or 16; preferably 10, 12, or 14.

4. The derivative of embodiment 1, in which m is an odd number.

5. The derivative of embodiment 4, in which m is 7, 9, 11, 13, 15, or 17; preferably 9, 11, or 15; most preferably 9.

6. The derivative of embodiment 1, in which p is an odd number.

7. The derivative of embodiment 6, in which p is 1, 3, or 5, preferably 3.

8. The derivative of any one of embodiments 1 and 4-5, in which the COOH group is in the meta- or para-position, preferably in the para-position.

9. The derivative of any one of embodiments 1-8, in which R$^1$ has a molar mass not higher than 130 Da, preferably not higher than 100 Da, more preferably not higher than 75 Da, even more preferably not higher than 60 Da, or most preferably not higher than 50 Da.

10. The derivative of any one of embodiments 1-9, in which R$^1$ has a molar mass not higher than 40 Da, preferably not higher than 30 Da, more preferably not higher than 20 Da, or most preferably not higher than 15 Da.

11. The derivative of any one of embodiments 1-10, wherein R$^1$ is selected from halogen, and straight-chain or branched alkyl having from 1-5 C-atoms.

12. The derivative of any one of embodiments 1 and 6-7, in which R$^1$ is methyl or tert-butyl.

13. The derivative of embodiment 12, in which R$^1$ is in the para-position.

14. The derivative of any one of embodiments 1 and 6-7, in which R$^1$ is —I.

15. The derivative of embodiment 14, in which R$^1$ is in the para-position.

16. The derivative of any one of embodiments 1-15, in which the GLP-1 analogue has a maximum of five, preferably a maximum of four, more preferably a maximum of three, or most preferably a maximum of two amino acid changes, as compared to GLP-1(7-37) (SEQ ID NO: 1).
17. The derivative of any one of embodiments 1-16, in which the GLP-1 analogue has a C-terminal amide.
18. The derivative of any one of embodiments 1-16, in which the GLP-1 analogue has a C-terminal —COOH group, or a pharmaceutically acceptable salt thereof.
19. The derivative of any one of embodiments 1-18, in which the GLP-1 analogue comprises at least one deletion, as compared to GLP-1(7-37) (SEQ ID NO: 1).
20. The derivative of any one of embodiments 1-19, in which one or two amino acids have been deleted at the N-terminus of the GLP-1 analogue, so that the analogue preferably comprises des7, des8, or (des7+des8); more preferably des7, or (des7+des8).
21. The derivative of any one of embodiments 1-20, wherein the GLP-1 analogue is an analogue of GLP-1(8-37) or GLP-1(9-37) having up to six amino acid residues changed as compared to GLP-1(7-37) (SEQ ID NO: 1).
22. The derivative of any one of embodiments 1-21, wherein the GLP-1 analogue is selected from the following: (i) $K^{37}$-GLP-1(7-37), (ii) $K^{37}$-GLP-1(8-37), (iii) $K^{37}$-GLP-1(9-37), or (iv) an analogue of any one of (i)-(iii) having up to six amino acid residue changes as compared to GLP-1(7-37) (SEQ ID NO: 1).
23. The derivative of any one of embodiments 20-21 or 22(ii)-(iv), wherein a His-mimetic or a His-Ala-mimetic has been added to the new N-terminal amino acid.
24. The derivative of any one of embodiments 20-23, wherein a derivative of an imidazole with a free carboxylic acid group has been covalently coupled to the N-terminus, preferably via formation of an amide bond between the free carboxylic acid group and the N-terminal amino group.
25. The derivative of embodiment 24, wherein the imidazole derivative is a mono-substituted imidazole.
26. The derivative of embodiment 25, wherein the imidazole is substituted with a carboxylic acid radical of a lower alkyl having from one to six carbon atoms.
27. The derivative of embodiment 26, wherein the carboxylic acid radical is selected from acetyl; and straight or branched propionyl, butyryl, pentanoyl; preferably acetyl.
28. The derivative of any one of embodiments 1-27, wherein the amino acid residue at position 8 of the GLP-1 analogue has 3H-Imidazol-4-yl-acetyl attached to its N-atom.
29. The derivative of any one of embodiments 1-28, wherein the amino acid residue at position 8 of the GLP-1 analogue is alanine.
30. The derivative of embodiment 25, wherein the imidazole is substituted with (methylcarbamoyl)-2-methyl-propionyl, (ethylcarbamoyl)-2-methyl-propionyl, (propylcarbamoyl)-2-methyl-propionyl, or (butylcarbamoyl)-2-methyl-propionyl.
31. The derivative of embodiment 30, wherein the imidazole is substituted with (methylcarbamoyl)-2-methyl-propionyl, (ethylcarbamoyl)-2-methyl-propionyl, or (propylcarbamoyl)-2-methyl-propionyl, preferably with (ethylcarbamoyl)-2-methyl-propionyl.
32. The derivative of any one of embodiments 1-31, wherein the amino acid residue at position 9 of the GLP-1 analogue has {2-[2-(1H-Imidazol-4-yl)-ethylcarbamoyl]-2-methyl-propionyl} attached to its N-atom.
33. The derivative of any one of embodiments 1-32, wherein the amino acid residue at position 9 of the GLP-1 analogue is glutamic acid.
34. The derivative of any one of embodiments 1-33, which, in addition to 37K, comprises at least one of the following substitutions: 8Aib; 31H; 34E,Q,R; and/or 38E.
35. The derivative of embodiment 34 which comprises 8Aib.
36. The derivative of embodiment 34, which comprises 34E, 34Q, or 34R; preferably 34R.
37. The derivative of embodiment 35, which further comprises 34R.
38. The derivative of embodiment 34, which comprises 31H.
39. The derivative of embodiment 35, which further comprises 31H and/or 34Q, preferably both.
40. The derivative of embodiment 34, which comprises 34R.
41. The derivative of embodiment 34, which comprises 38E.
42. The derivative of embodiment 37, which further comprises 38E.
43. The derivative of any one of embodiments 1-42 in which the two albumin binding moieites are similar; preferably substantially identical; or, most preferably, identical.
44. The derivative of any one of embodiments 1-43 in which the two protracting moieties are similar; preferably substantially identical; or, most preferably, identical.
45. The derivative of any one of embodiments 1-44 in which the two albumin binding moieties, and/or the two protracting moieties have a percentage of identity of at least 80%, preferably at least 85%, more preferably at least 90%, or even more preferably at least 95%, or most preferably at least 99%.
46. The derivative of embodiment 45, wherein the percentage of identity is determined using datamodelling with the Tanimoto similarity coefficient and the ECFP_6 extended connectivity fingerprints.
47. The derivative of any one of embodiments 1-46, in which the albumin binding moieties are attached to the epsilon amino group of the lysine residues at position 26 and 37, respectively, via amide bonds, optionally via a linker moiety.
48. The derivative of any one of embodiments 1-47 in which the albumin binding moiety comprises a linker moiety, which at one end is attached, via an amide bond, to the CO-group of the protracting moiety, and at the other end is attached, via an amide bond, to the epsilon amino group of the lysine residues at position 26 and 37, respectively.
49. The derivative of any one of embodiments 47-48 in which the linker moiety has from 5 to 30 C-atoms, preferably from 5 to 25 C-atoms, more preferably from 5 to 20 C-atoms, or most preferably from 5 to 17 C-atoms.
50. The derivative of any one of embodiments 47-49 in which the linker moiety has from 4 to 20 hetero atoms, preferably from 4 to 18 hetero atoms, more preferably from 4 to 14 hetero atoms, or most preferably from 4 to 12 hetero atoms.
51. The derivative of embodiment 50 in which the hetero atoms are N—, and/or O-atoms.
52. The derivative of any one of embodiments 47-51 in which the linker moiety is selected from the following:

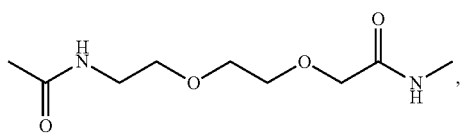

-continued

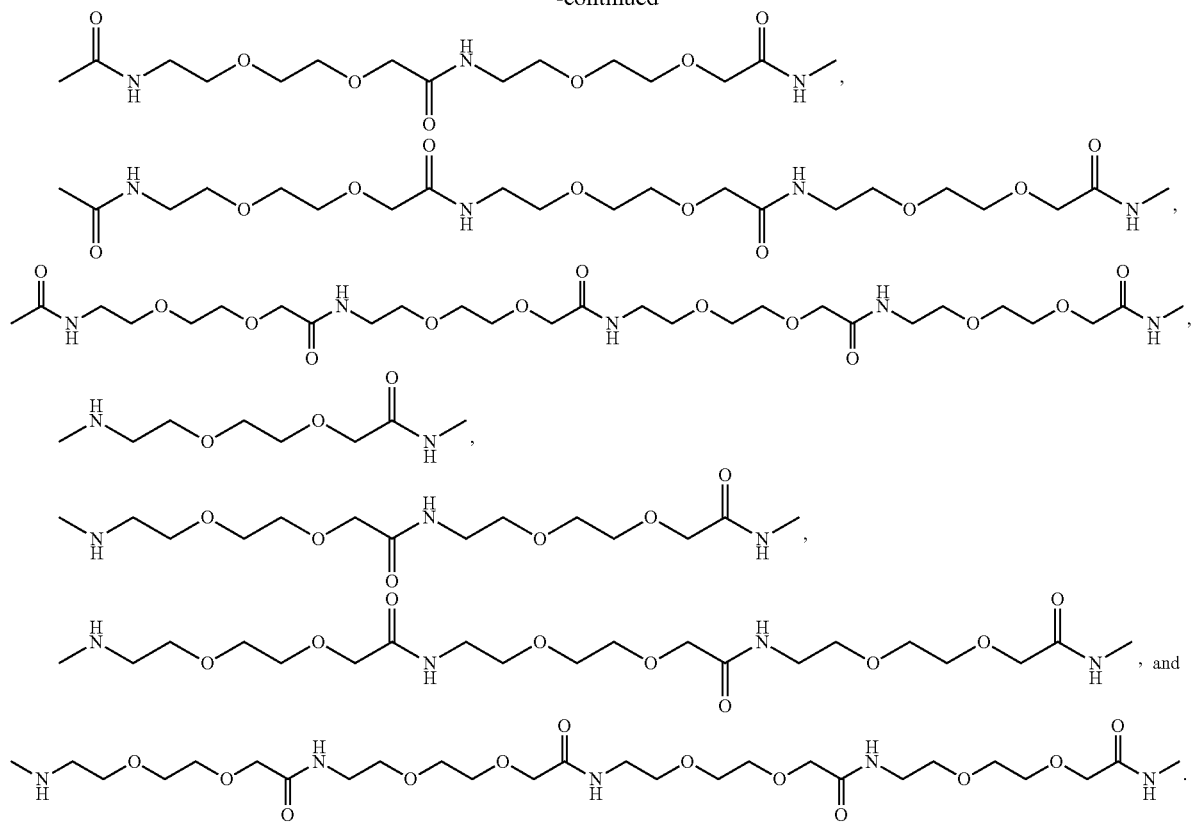

53. The derivative of any one of embodiments 47-52, in which the linker moiety comprises at least one OEG radical, and/or at least one Glu (glutamic acid) radical.
54. The derivative of embodiment 53, in which the linker consists of one OEG radical, or one Glu radical, the gamma-carboxylic acid group of which preferably forms an amide bond with the epsilon amino group of the lysine residue.
55. The derivative of embodiment 53, in which the linker consists of two OEG radicals, or two Glu radicals, the radicals being interconnected via amide bonds, and so that, preferably, in case of two Glu radicals, the gamma-carboxylic acid group of one Glu forms an amide bond with the epsilon amino group of the lysine residue, or—more preferably "and" —the gamma-carboxylic acid group of the other Glu forms an amide bond with the amino group of the first Glu.
56. The derivative of embodiment 53, in which the linker comprises at least one OEG radical and at least one Glu radical, preferably one of each, more preferably with the carboxy end of the OEG radical forming an amide bond with the epsilon amino group of the lysine residue, and the amino end of the OEG radical forming an amide bond with the gamma-carboxy group of the Glu radical.
57. The derivative of embodiment 56, in which the linker consists of one Glu radical and two OEG radicals, preferably selected from the following: -Glu-OEG-OEG-, —OEG-Glu-OEG-, and —OEG-OEG-Glu-, in which the amino group of the leftmost radical forms an amide bond with the protractor moiety, and the carboxy group of the rightmost radical forms an amide bond with the epsilon amino group of the lysine residue, preferably, in case of a Glu radical at the rightmost end, its gamma-carboxy group is used for the amide bond.
58. The derivative of any one of embodiments 1-57 which has a potency ($EC_{50}$) at or below 3000 pM, preferably below 3000 pM, more preferably below 2500 pM, even more preferably below 2000 pM, or most preferably below 1500 pM.
59. The derivative of any one of embodiments 1-58 which has a potency ($EC_{50}$) below 1000 pM, preferably below 800 pM, more preferably below 600 pM, even more preferably below 400 pM, or most preferably below 200 pM.
60. The derivative of any one of embodiments 1-59 which has a potency ($EC_{50}$) below 180 pM, preferably below 160 pM, more preferably below 140 pM, even more preferably below 120 pM, or most preferably below 100 pM.
61. The derivative of any one of embodiments 1-60 which has a potency ($EC_{50}$) below 80 pM, preferably below 60 pM, more preferably below 50 pM, even more preferably at or below 40 pM, or most preferably below 30 pM.
62. The derivative of any one of embodiments 58-61, wherein the potency is determined as stimulation of the formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 50.
63. The derivative of any one of embodiments 1-62, the potency ($EC_{50}$) of which is less than 10 times the potency of semaglutide, preferably less than 8 times the potency of semaglutide, more preferably less than 6 times the potency of semaglutide, even more preferably less than 4 times the potency of semaglutide, or most preferably less than 2 times the potency of semaglutide.

64. The derivative of any one of embodiments 1-63, the potency ($EC_{50}$) of which is less than 10 times the potency of liraglutide, preferably less than 8 times the potency of liraglutide, more preferably less than 6 times the potency of liraglutide, even more preferably less than 4 times the potency of liraglutide, or most preferably less than 2 times the potency of liraglutide.

65. The derivative of any one of embodiments 1-64, the potency ($EC_{50}$) of which is less than the potency of liraglutide, preferably less than 0.8 times the potency of liraglutide, more preferably less than 0.6 times the potency of liraglutide, even more preferably less than 0.5 times the potency of liraglutide, or most preferably less than or at 0.4 times the potency of liraglutide.

66. The derivative of any one of embodiments 1-65, for which the ratio [GLP-1 receptor binding affinity ($IC_{50}$) in the presence of 2.0% human serum albumin (HSA), divided by GLP-1 receptor binding affinity ($IC_{50}$) in the presence of 0.005% HSA] is at least 1, preferably at least 10, more preferably at least 20, even more preferably at least 30, or most preferably at least 40.

67. The derivative of any one of embodiments 1-66, for which the ratio [GLP-1 receptor binding affinity ($IC_{50}$) in the presence of 2.0% human serum albumin (HSA), divided by GLP-1 receptor binding affinity ($IC_{50}$) in the presence of 0.005% HSA] is at least 50, preferably at least 60, more preferably at least 70, even more preferably at least 80, or most preferably at least 90.

68. The derivative of any one of embodiments 1-67, for which the ratio [GLP-1 receptor binding affinity ($IC_{50}$) in the presence of 2.0% human serum albumin (HSA), divided by GLP-1 receptor binding affinity ($IC_{50}$) in the presence of 0.005% HSA], is at least 100, preferably at least 120, more preferably at least 140, still more preferably at least 160, even more preferably at least 180, or most preferably at least 200.

69. The derivative of any one of embodiments 1-68, the GLP-1 receptor binding affinity ($IC_{50}$) of which is measured by way of its ability to displace $^{125}$I-GLP-1 from the receptor, the receptor being preferably provided in the form of membranes from a stable cell-line such as BHK tk-ts13 transfected with the human GLP-1 receptor; and/or using a SPA binding assay, preferably employing SPA-particles such as Wheat germ agglutinin SPA beads, the binding assay being most preferably performed as described in Example 51.

70. The derivative of any one of embodiments 1-69, for which the ratio [GLP-1 receptor binding affinity ($IC_{50}$) in the presence of 2.0% human serum albumin (HSA), divided by GLP-1 receptor binding affinity ($IC_{50}$) in the presence of 0.005% HSA] is at least 20% of the ratio of semaglutide, preferably at least 50% of the ratio of semaglutide, more preferably at least 75% of the ratio of semaglutide, or most preferably at least equal to the ratio of semaglutide.

71. The derivative of any one of embodiments 1-70, for which the ratio [GLP-1 receptor binding affinity ($IC_{50}$) in the presence of 2.0% human serum albumin (HSA), divided by GLP-1 receptor binding affinity ($IC_{50}$) in the presence of 0.005% HSA] is at least equal to the ratio of liraglutide, preferably at least twice the ratio of liraglutide, more preferably at least three times the ratio of liraglutide, even more preferably at least 4 times the ratio of liraglutide, or most preferably at least 5 times the ratio of liraglutide.

72. The derivative of any one of embodiments 1-71, which has an in vitro half-life (TA in an extract of rat small intestines, divided by the corresponding half-life ($T_{1/2}$) of GLP-1(7-37), of above 0.5, preferably above 1.0, more preferably above 2.0, even more preferably above 3.0, or most preferably above 4.0.

73. The derivative of any one of embodiments 1-72, which has an in vitro half-life ($T_{1/2}$) in an extract of rat small intestines, divided by a corresponding half-life ($T_{1/2}$) of GLP-1(7-37), of above 5.0, preferably above 6.0, more preferably above 7.0, or most preferably above 8.0.

74. The derivative of any one of embodiments 72-73, wherein the rat small intestine extract is prepared as described in Example 57, the derivative is incubated for one hour at 37° C., the concentration of the extract is titrated so that the half-life of GLP-1(7-37) is in the range of 10-20 minutes, e.g. 1.4 ug/ml, the resulting samples are analysed by UPLC and/or MALDI-TOF, and/or the incubation and analysis is performed as described in Example 57.

75. The derivative of any one of embodiments 1-74, for which a ratio [half-life ($T_{1/2}$) in vitro in rat small intestine extract, divided by a half-life ($T_{1/2}$) in vitro in rat small intestine extract of GLP-1(7-37)] is at least 0.5 times the corresponding ratio of semaglutide, preferably at least 2 times the ratio of semaglutide, more preferably at least 3 times the ratio of semaglutide, even more preferably at least 5 times the ratio of semaglutide, or most preferably at least 7 times the ratio of semaglutide.

76. The derivative of any one of embodiments 1-75, for which a ratio [half-life ($T_{1/2}$) in rat small intestine extract, divided by a half-life ($T_{1/2}$) in rat small intestine extract of GLP-1(7-37)] is at least 0.1 times the corresponding ratio of liraglutide, preferably at least 0.4 times the ratio of liraglutide, more preferably at least 0.8 times the ratio of liraglutide, even more preferably at least 1.2 times the ratio of liraglutide, or most preferably at least 1.5 times the ratio of liraglutide.

76. The derivative of any one of embodiments 1-75, which has a half-life ($T_{1/2}$) in vivo in rats after i.v. administration of at least 4 hours, preferably at least 6 hours, even more preferably at least 8 hours, or most preferably at least 10 hours.

77. The derivative of any one of embodiments 1-76, which has a half-life ($T_{1/2}$) in vivo in rats after i.v. administration of at least 12 hours, preferably at least 15 hours, even more preferably at least 18 hours, or most preferably at least 20 hours.

78. The derivative of any one of embodiments 76-77, in which the rats are male Sprague Dawley rats with a body weight from 300 to 600 g.

79. The derivative of any one of embodiments 1-78, which has a half-life ($T_{1/2}$) in vivo in rats after i.v. administration which is at least the same as the half-life of semaglutide, preferably at least 2 times the half-life of semaglutide, more preferably at least 3 times the half-life of semaglutide, even more preferably at least 4 times the half-life of semaglutide, or most preferably at least 5 times the half-life of semaglutide.

80. The derivative of any one of embodiments 1-79 which has a half-life ($T_{1/2}$) in vivo in minipigs after i.v. administration of at least 12 hours, preferably at least 24 hours, more preferably at least 36 hours, even more preferably at least 48 hours, or most preferably at least 60 hours.

81. The derivative of embodiment 80, in which the minipigs are male Göttingen minipigs.

82. The derivative of any one of embodiments 1-81, which has a half-life ($T_{1/2}$) in vivo in minipigs after i.v. administration which is at least 0.2 times the half-life of semaglutide, preferably at least 0.4 times the half-life of semaglutide, more preferably at least 0.6 times the half-life of semaglutide, even more preferably at least 0.8 times the half-life of semaglutide, or most preferably at least the same as the half-life of semaglutide.

83. A GLP-1 derivative selected from the following:
(i) $N^{\epsilon 26}$-[2-(2-{2-[10-(4-Carboxyphenoxy)decanoylamino]ethoxy}ethoxy)acetyl], $N^{\epsilon 37}$-[2-(2-{2-[10-(4-Carboxyphenoxy)decanoylamino]ethoxy}ethoxy)acetyl]-[Aib$^8$, Arg$^{34}$,Lys$^{37}$]GLP-1(7-37)-peptide (SEQ ID NO: 7):

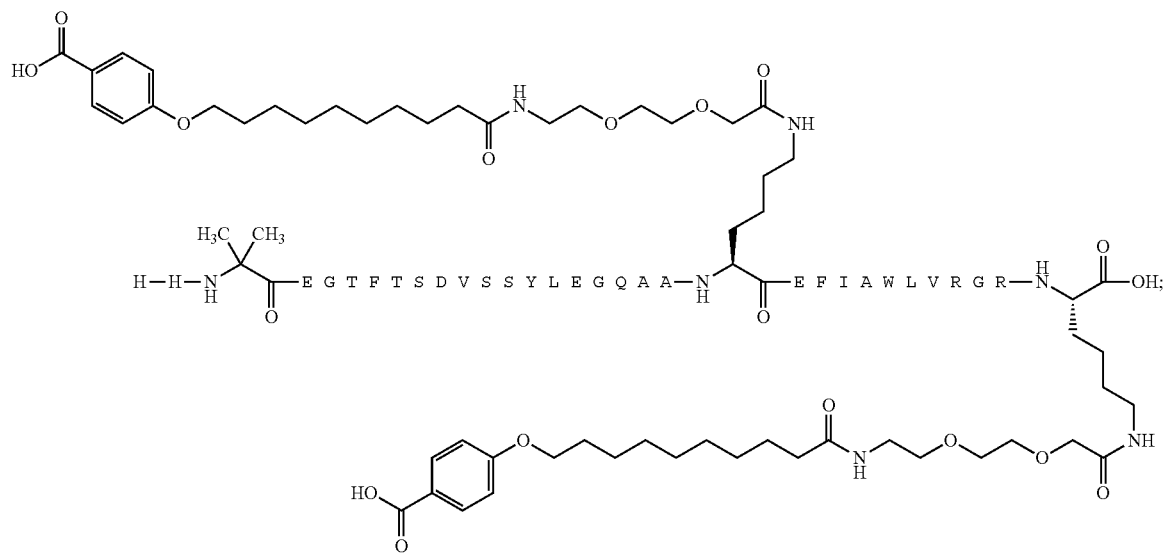

(ii) N^ε26{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, N^ε37-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}[Aib^8,Arg^34,Lys^37] GLP-1(7-37)-peptide (SEQ ID NO: 7):

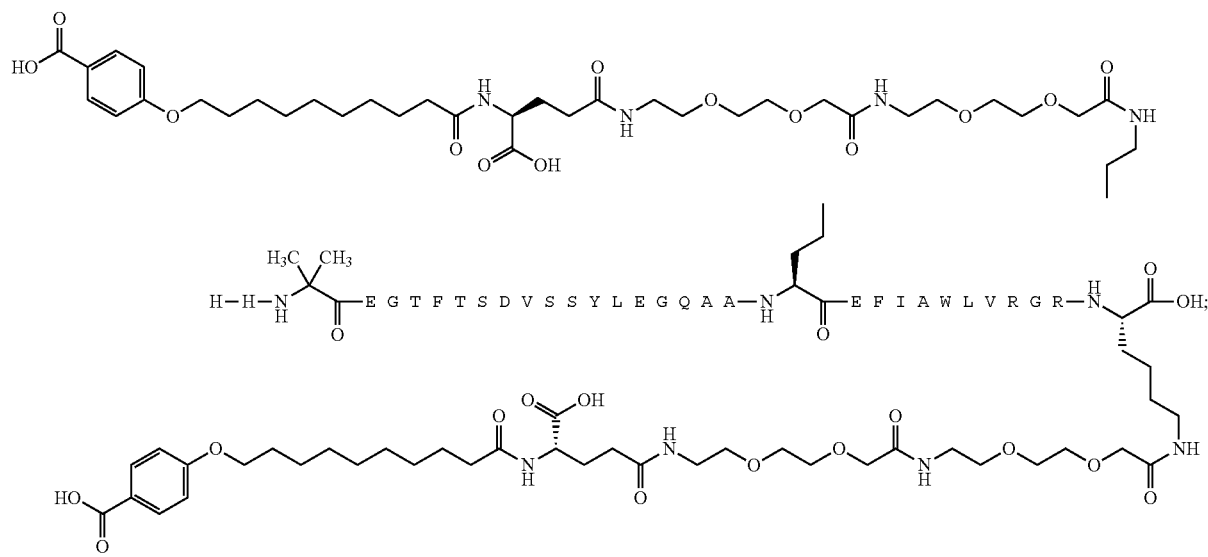

(iii) N^ε26-[2-(2-{2-[2-(2-{2-[(S)-4-Carboxy-4-(15-carboxypentadecanoylamino)butyrylamino]ethoxy}ethoxy)acetylamino]ethoxy}ethoxy)acetyl], N^ε37-[2-(2-{2-[2-(2-{2-[(S)-4-Carboxy-4-(15-carboxypentadecanoylamino)butyrylamino]ethoxy}ethoxy)acetylamino]ethoxy}ethoxy)acetyl][Aib^8,Arg^34,Lys^37]GLP-1(7-37)-peptide (SEQ ID NO: 7):

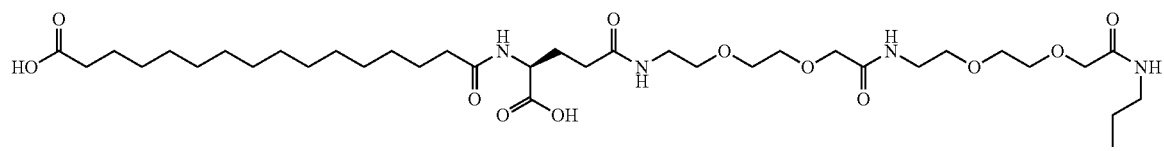

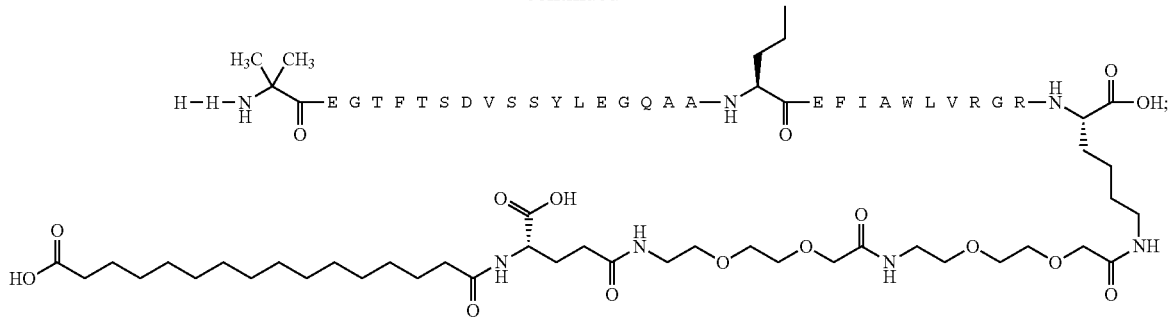

(iv) N^ε26-[2-(2-{2-[2-(2-{2-[(S)-4-Carboxy-4-(13-carboxytridecanoylamino)butyrylamino]ethoxy}ethoxy)acetylamino]ethoxy}ethoxy)acetyl], N^ε37-[2-(2-{2-[2-(2-{2-[(S)-4-Carboxy-4-(13-carboxytridecanoylamino)butyrylamino]ethoxy}ethoxy)acetylamino]ethoxy}ethoxy)acetyl][Aib^8,Arg^34,Lys^37]GLP-1(7-37)-peptide (SEQ ID NO: 7):

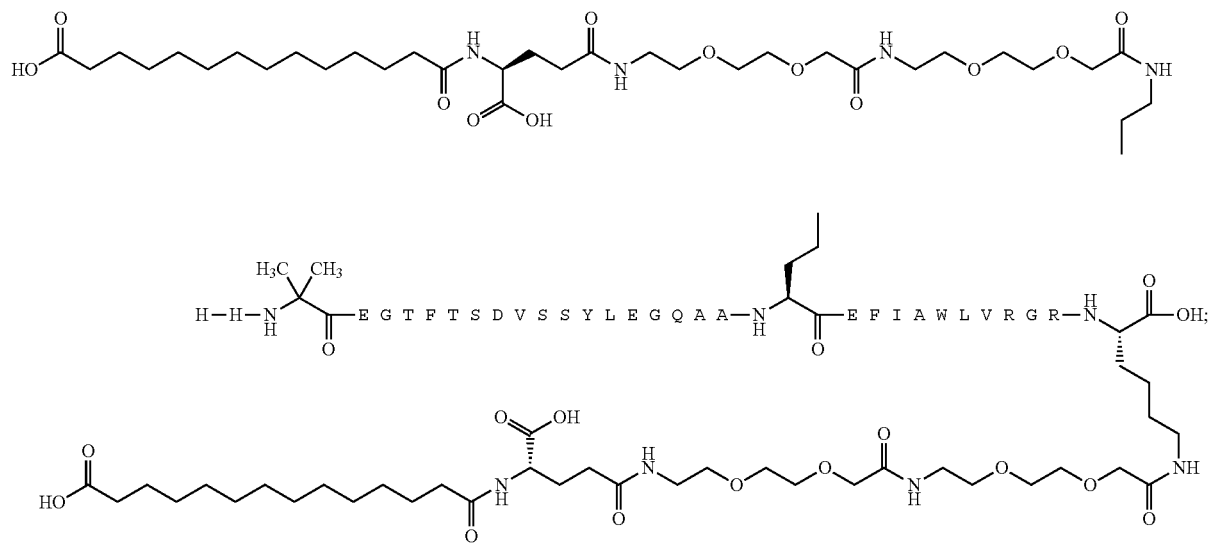

(v) N^ε26-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], N^ε37-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl][Aib^8,Arg^34,Lys^37]GLP-1(7-37)-peptide (SEQ ID NO: 7):

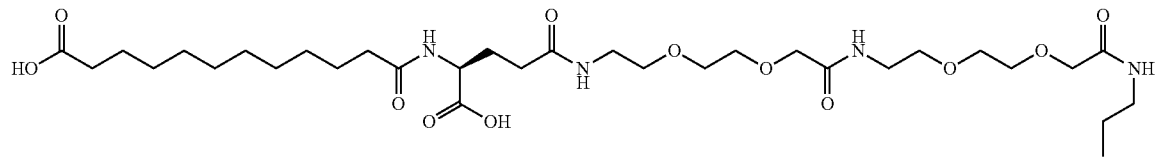

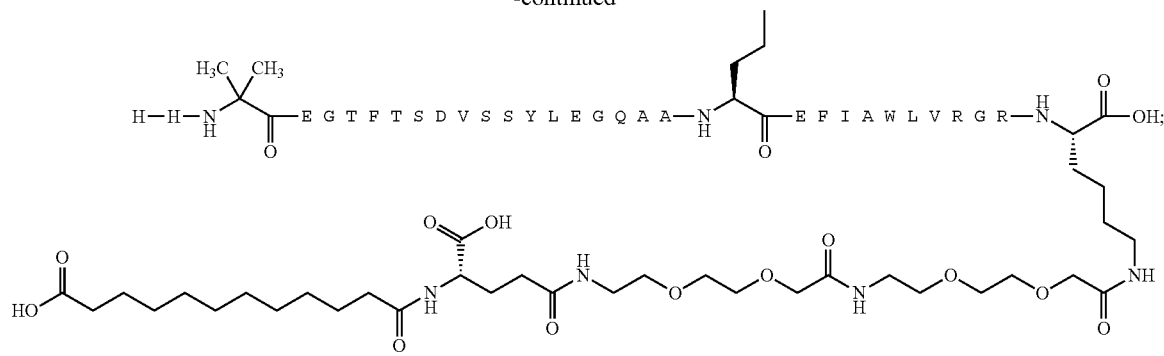

(vi) $N^{\epsilon 2}$-[2-(2-{2-[2-(2-{2-[(S)-4-Carboxy-4-(15-carboxy-pentadecanoylamino)butyrylamino]ethoxy}ethoxy)acetylamino]ethoxy}ethoxy)acetyl], $N^{\epsilon 37}$-[2-(2-{2-[2-(2-{2-[(S)-4-Carboxy-4-(15-carboxypentadecanoylamino)butyrylamino]ethoxy}ethoxy)acetylamino]ethoxy}ethoxy)acetyl][Aib$^8$,Arg$^{34}$,Lys$^{37}$]GLP-1(7-37)-peptide amide (SEQ ID NO: 7):

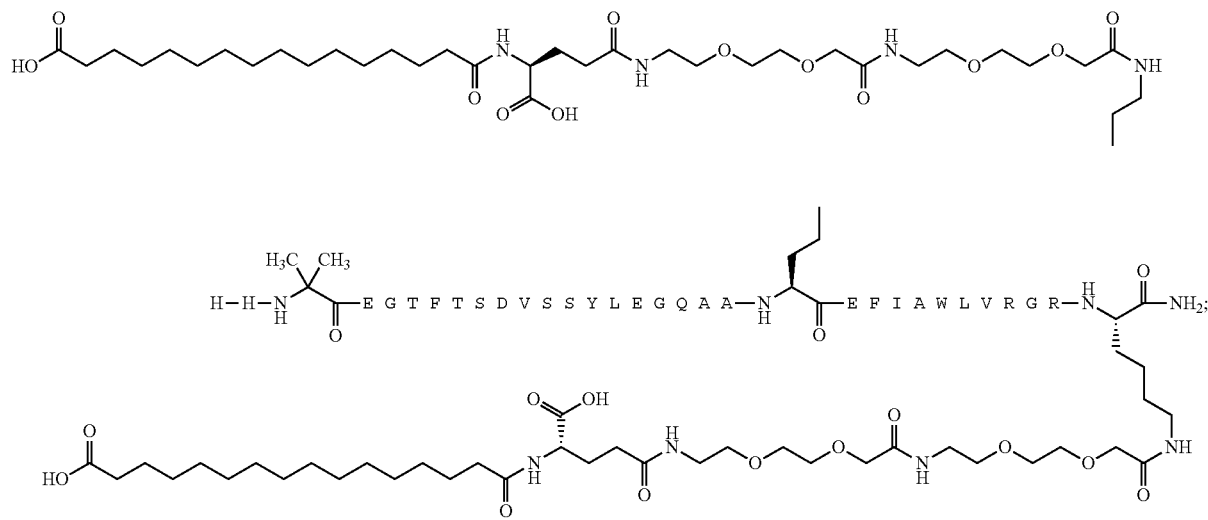

(vii) $N^{\epsilon 26}$-[2-(2-{2-[2-(2-{2-[(S)-4-Carboxy-4-(13-carboxytridecanoylamino)butyrylamino]ethoxy}ethoxy)acetylamino]ethoxy}ethoxy)acetyl], $N^{\epsilon 37}$-[2-(2-{2-[2-(2-{2-[(S)-4-Carboxy-4-(13-carboxytridecanoylamino)butyrylamino]ethoxy}ethoxy)acetylamino]ethoxy}ethoxy)acetyl][Aib$^8$,Arg$^{34}$,Lys$^{37}$]GLP-1(7-37)-peptide amide (SEQ ID NO: 7):

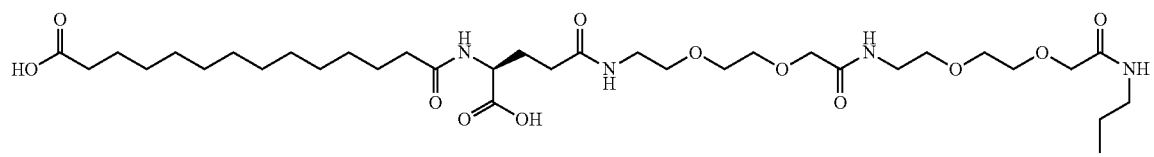

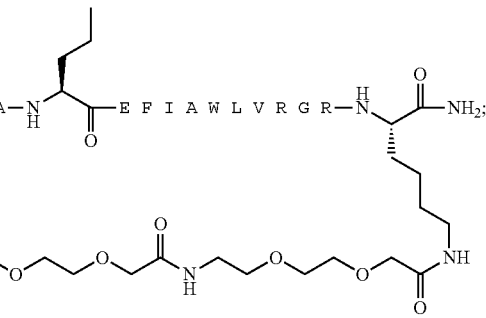

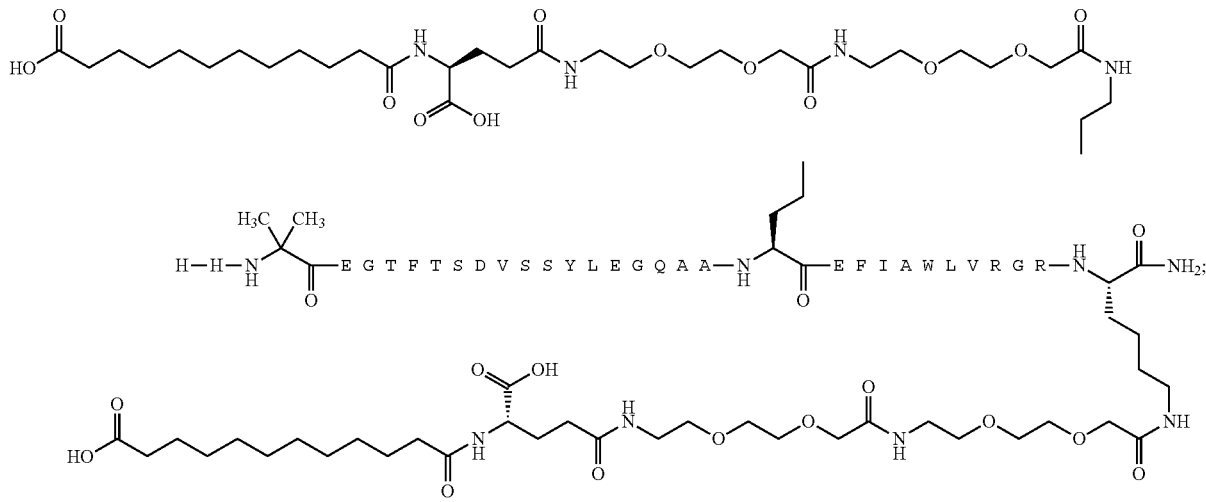

(iix) N^ε26-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], N^ε37-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl][Aib^8,Arg^34,Lys^37]GLP-1(7-37)-peptide amide (SEQ ID NO: 7):

(ix) N^ε26-[2-[2-(2-{2-[(S)-4-Carboxy-4-(13-carboxytridecanoylamino)butyrylamino]ethoxy}ethoxy)acetyl], N^ε37-[2-[2-(2-{2-[(S)-4-Carboxy-4-(13-carboxytridecanoylamino)butyrylamino]ethoxy}ethoxy)acetyl][Aib^8,Arg^34,Lys^37]GLP-1(7-37)-peptide amide (SEQ ID NO: 7):

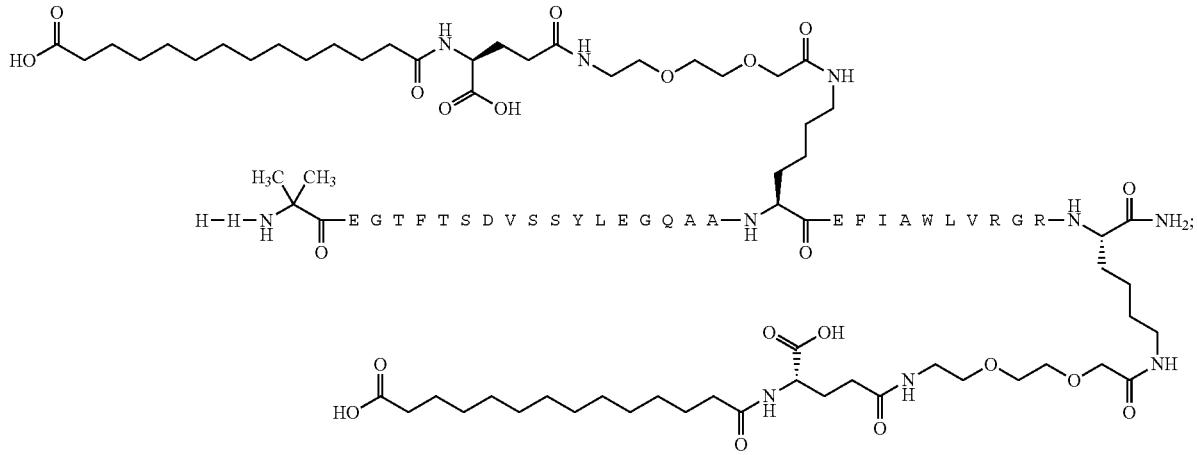

(x) N^{ε26}-[2-{2-[(S)-4-Carboxy-4-(13-carboxytridecanoylamino)butyrylamino] N^{ε37}-[2-{2-[(S)-4-Carboxy-4-(13-carboxytridecanoylamino)butyrylamino]][Aib^8,Arg^{34},Lys^{37}]GLP-1 (7-37)-peptide amide (SEQ ID NO: 7):

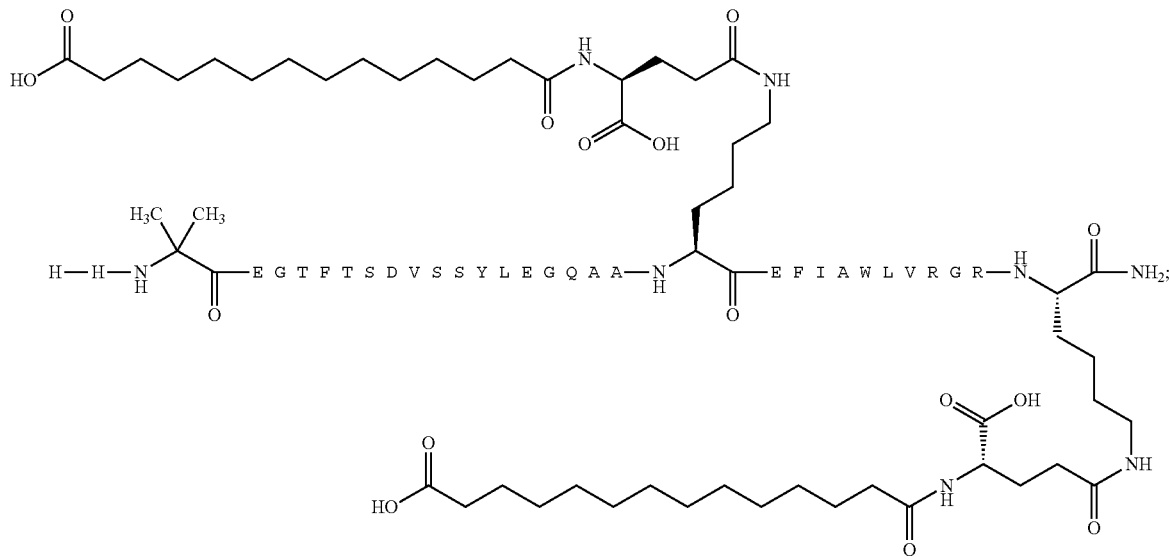

(xi) N^{ε26}-(2-{2-[2-(2-{2-[2-(13-Carboxy-tridecanoylamino)ethoxy]ethoxy}acetylamino)ethoxy]ethoxy}acetyl), N^{ε37}-(2-{2-[2-(2-{2-[2-(13-Carboxy-tridecanoylamino)ethoxy]ethoxy}acetylamino)ethoxy]ethoxy}acetyl)[Aib^8,Arg^{34},Lys^{37}]GLP-1(7-37)-peptide amide (SEQ ID NO: 7):

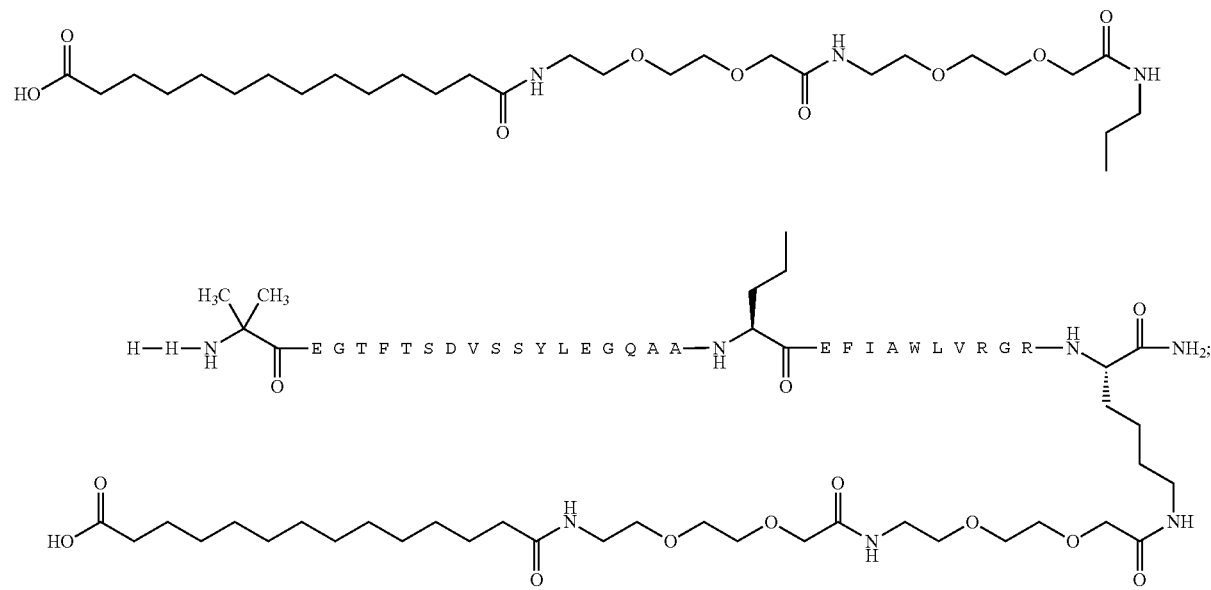

(xii) N^{ε26}-{2-[2-(2-{2-[2-(2-{(S)-4-Carboxy-4-[4-(4-iodo-phenyl)-butyrylamino]-butyrylamino}-ethoxy)-ethoxy]-acetylamino}-ethoxy)-ethoxy]-acetyl}, N^{ε37}-{2-[2-(2-{2-[2-(2-{(S)-4-Carboxy-4-[4-(4-iodo-phenyl]-butyrylamino]-butyrylamino}-ethoxy)-ethoxy]-acetylamino}-ethoxy)-ethoxy]-acetyl} [Aib^8,Arg^{34},Lys^{37}]GLP-1(7-37)-peptide (SEQ ID NO: 7):

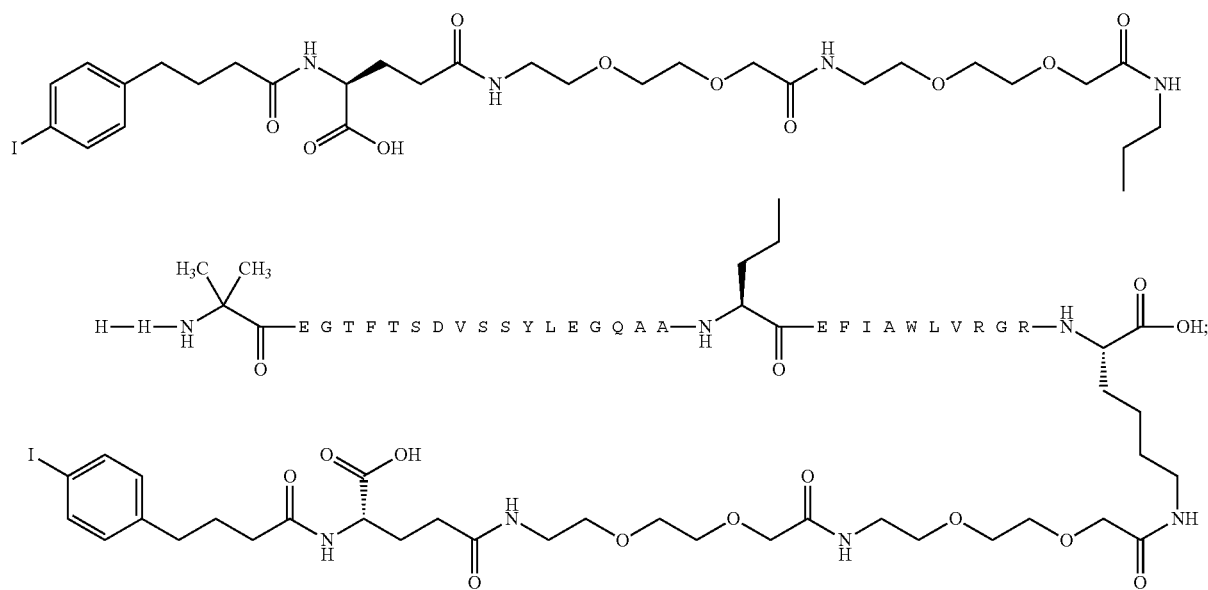

(xiii) AV²⁶-{2-[2-(2-{2-[2-(2-{(S)-4-Carboxy-4-[16-(4-carboxyphenoxy)hexadecanoylamino]butyrylamino}ethoxy)ethoxy]acetylamino}ethoxy)ethoxy]acetyl}, N^{ε37}-{2-[2-(2-{2-[2-(2-{(S)-4-Carboxy-4-[16-(4-carboxyphenoxy)hexadecanoylamino]butyrylamino}ethoxy)ethoxy]acetylamino}ethoxy)ethoxy]acetyl}-[Aib⁸,Arg³⁴,Lys³⁷] GLP-1(7-37)-peptide (SEQ ID NO: 7):

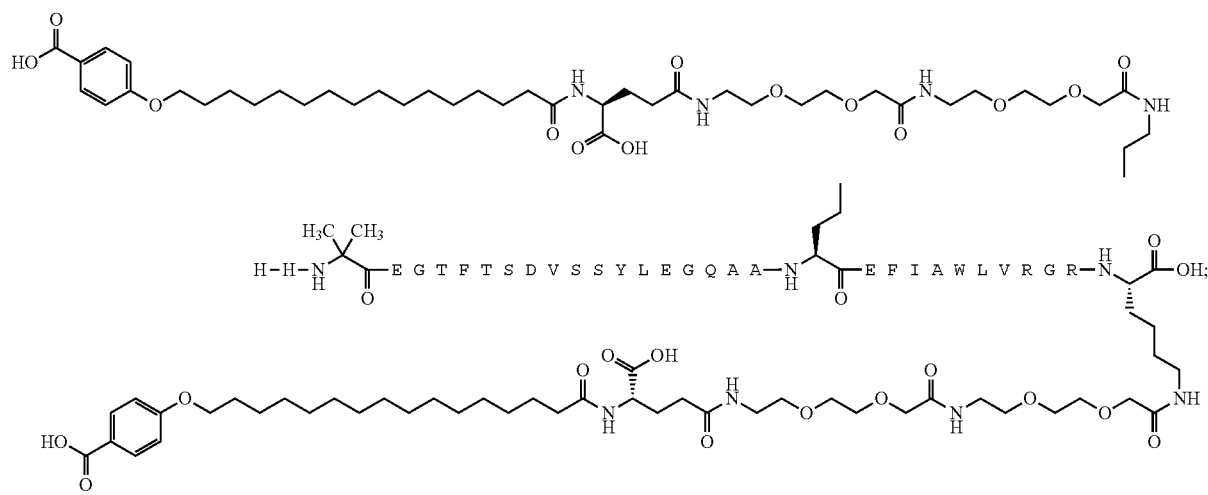

(xiv) N^{ε26}-{2-[2-(2-{2-[2-(2-{(S)-4-Carboxy-4-[16-(3-carboxyphenoxy)hexadecanoylamino]butyrylamino}ethoxy)ethoxy]acetylamino}ethoxy)ethoxy]acetyl}, N^{ε37}-{2-[2-(2-{2-[2-(2-{(S)-4-Carboxy-4-[16-(3-carboxyphenoxy)hexadecanoylamino]butyrylamino}ethoxy)ethoxy]acetylamino}ethoxy)ethoxy]acetyl}-[Aib⁸,Arg³⁴,Lys³⁷] GLP-1(7-37)-peptide (SEQ ID NO: 7):

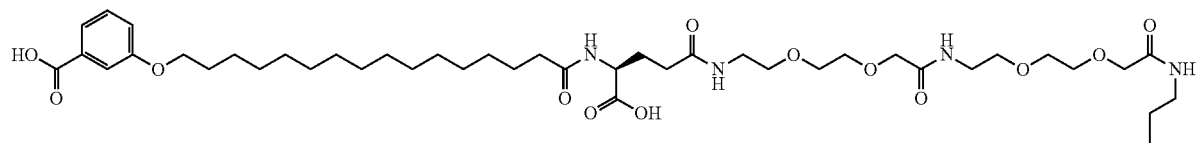

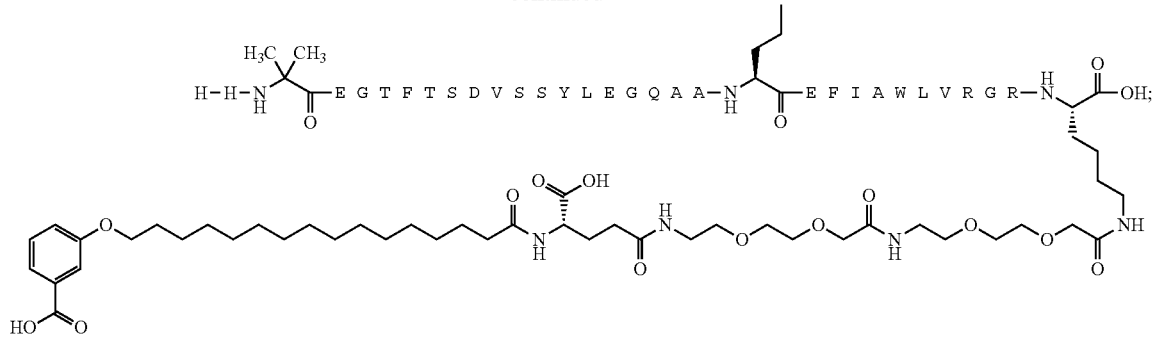

(xv) N^{ε26}-{2-[2-(2-{(S)-4-Carboxy-4-[10-(4-carboxyphenoxy)decanoylamino]butyrylamino}ethoxy)-ethoxy]acetyl}, N^{ε37}-{2-[2-(2-{(S)-4-Carboxy-4-[10-(4-carboxyphenoxy)decanoylamino]-butyrylamino}ethoxy)ethoxy]acetyl}[Aib⁸,Arg³⁴,Lys³⁷]GLP-1(7-37)-peptide (SEQ ID NO: 7):

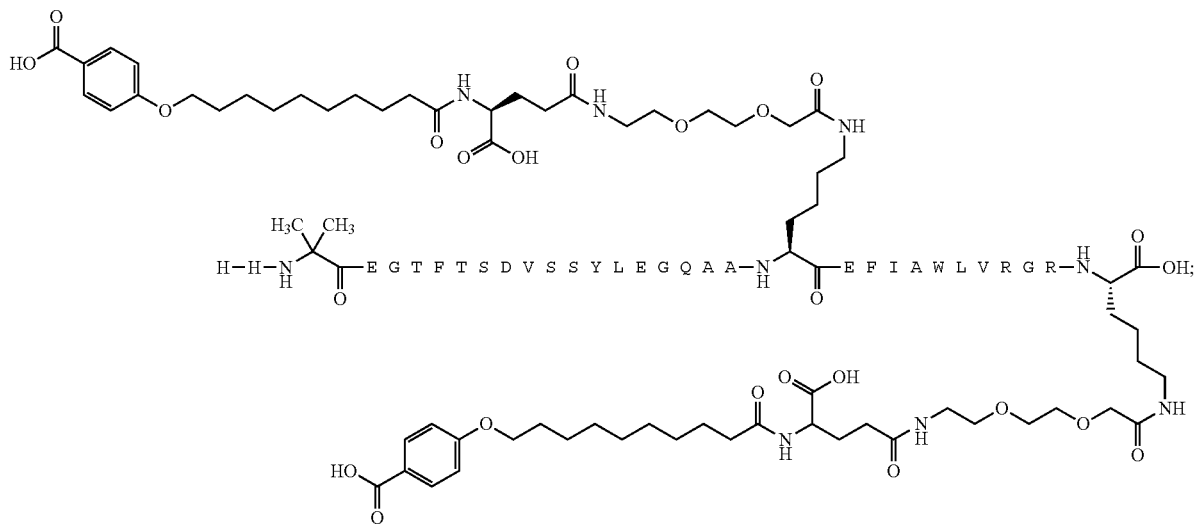

(xvi) N^{ε26}-{2-[2-(2-{2-[2-(2-{(S)-4-Carboxy-4-[12-(3-carboxyphenoxy)dodecanoylamino]butyrylamino}ethoxy)ethoxy]acetylamino}ethoxy)ethoxy]acetyl}, N^{ε37}-{2-[2-(2-{2-[2-(2-{(S)-4-Carboxy-4-[12-(3-carboxyphenoxy)dodecanoylamino]butyrylamino}ethoxy)ethoxy]acetylamino}ethoxy)ethoxy]acetyl}[Aib⁸,Arg³⁴,Lys³⁷]GLP-1(7-37)-peptide (SEQ ID NO: 7):

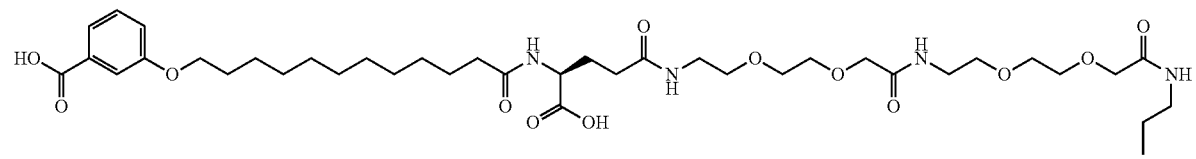

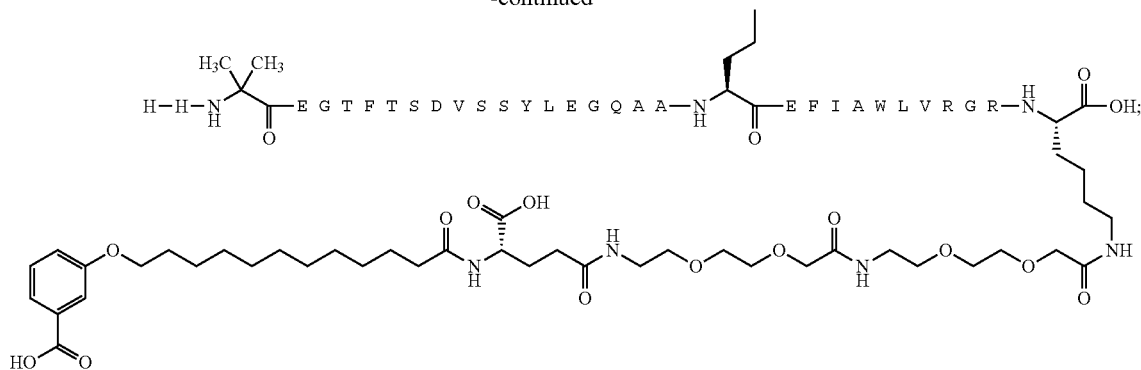

(xvii) N^ε26-[2-(2-[2-(2-[2-(2-[4-(10-(4-Carboxyphenoxy)decanoylamino)-4(S)-carboxybutyrylamino]ethoxy)ethoxy]acetylamino)ethoxy]ethoxy)acetyl]-N^ε37-[2-[2-(2-[2-(2-[4-(10-(4-Carboxyphenoxy)decanoylamino)-4(S)-carboxybutyrylamino]ethoxy)ethoxy]acetylamino)ethoxy]ethoxy)acetyl][Aib^8,His^31,Gln^34,Lys^37]GLP-1(7-37)-peptide (SEQ ID NO: 3):

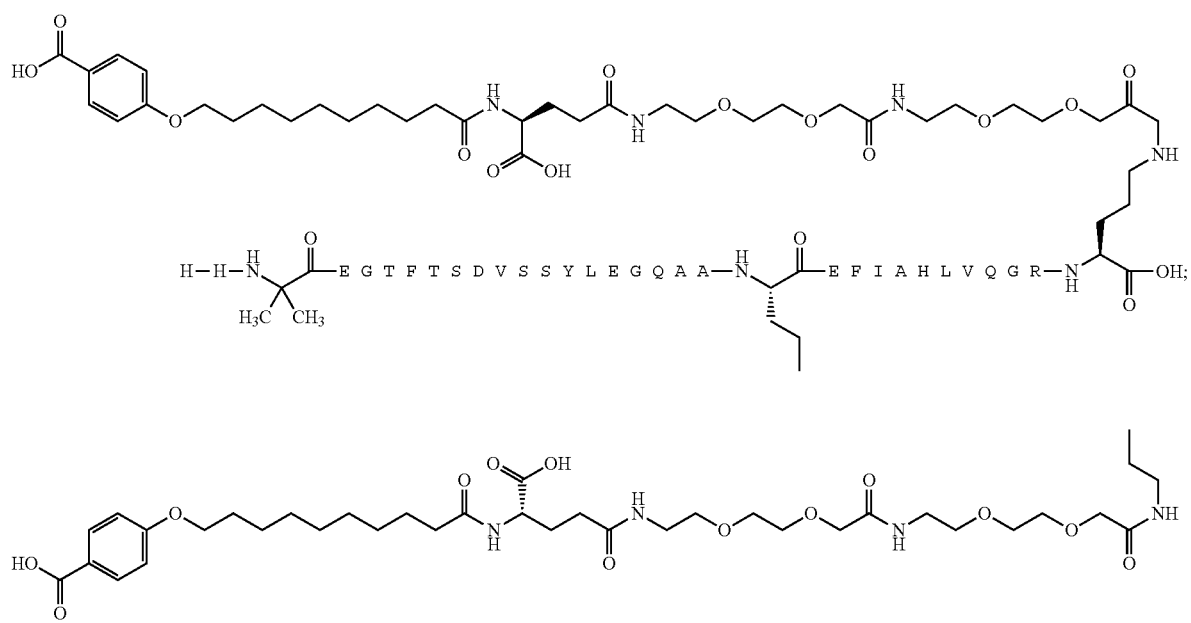

(iixx) N^ε26-{2-[2-(2-{2-[2-(2-{(S)-4-Carboxy-4-[4-(4-methylphenyl)butyrylamino]butyrylamino}ethoxy)ethoxy]acetylamino}ethoxy)ethoxy]acetyl}, N^ε37-{2-[2-(2-{2-[2-(2-{(S)-4-Carboxy-4-[4-(4-methylphenyl)butyrylamino]butyrylamino}ethoxy)ethoxy]-acetylamino}ethoxy)ethoxy]acetyl}[Aib^8,Arg^34,Lys^37]GLP-1(7-37)-peptide (SEQ ID NO: 7):

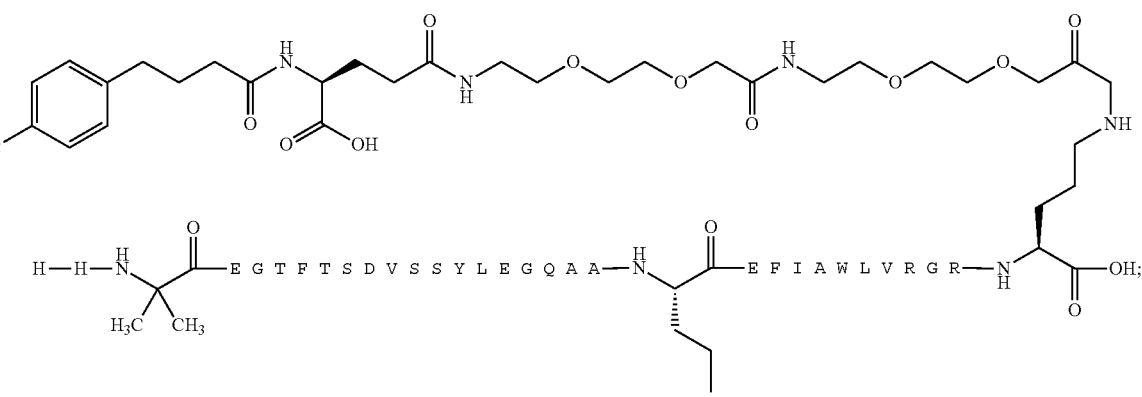

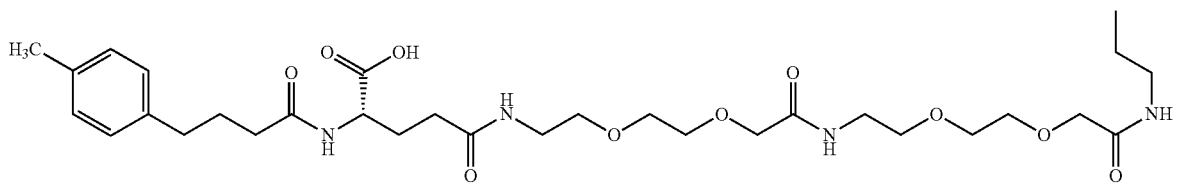

(ixx) N^ε26-((S)-4-Carboxy-4-{(S)-4-carboxy-4-[10-(4-carboxyphenoxy)-decanoylamino]butyrylamino}butyryl), N^ε37-((S)-4-Carboxy-4-{(S)-4-carboxy-4-[10-(4-carboxyphenoxy)-decanoylamino]butyrylamino}butyryl)[Aib8, Arg34,Lys37]GLP-1(7-37)-peptide (SEQ ID NO: 7):

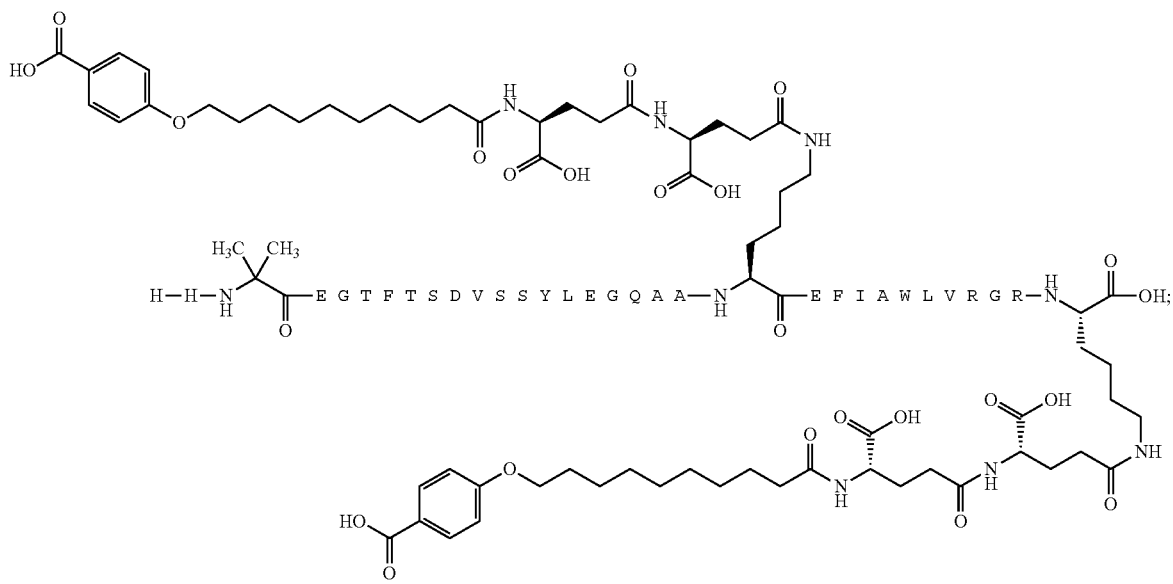

(xx) N^ε26-{2-[2-(2-{2-[2-(2-{4-Carboxy-4-[10-(3-carboxyphenoxy)decanoylamino]butyrylamino}ethoxy)ethoxy]acetylamino}ethoxy)ethoxy]acetyl}, N^ε37-{2-[2-(2-{2-[2-(2-{4-Carboxy-4-[10-(3-carboxyphenoxy)decanoylamino]butyrylamino}ethoxy)ethoxy]acetylamino}ethoxy)ethoxy]acetyl}[Aib8,Arg34,Lys37]GLP-1(7-37)-peptide (SEQ ID NO: 7):

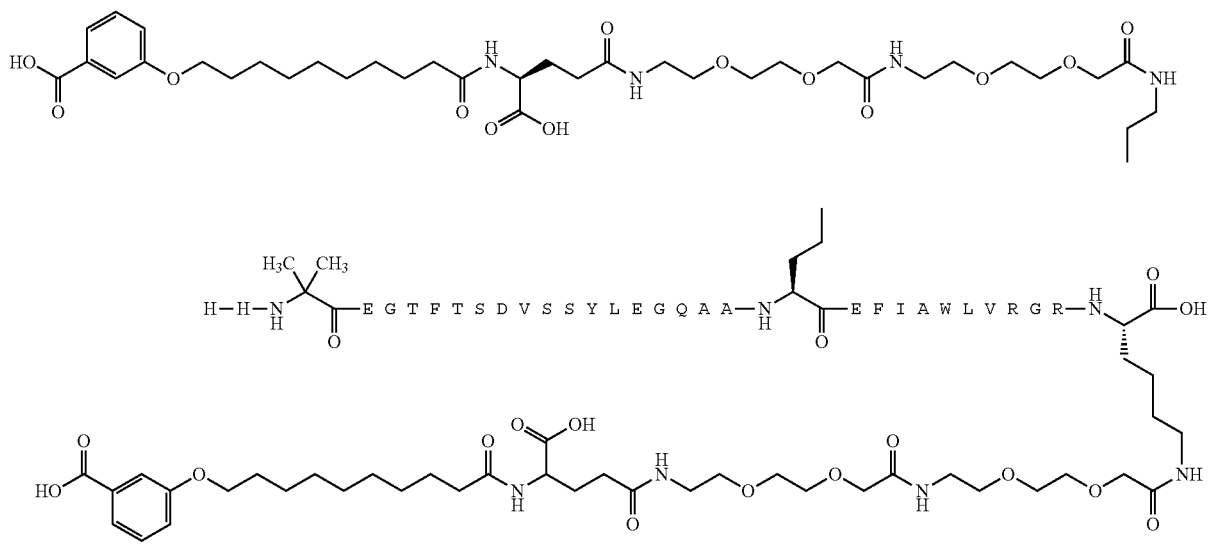

(xxi) $N^{\epsilon 26}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], $N^{\epsilon 37}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl][Aib$^8$,His$^{31}$,Gln$^{34}$,Lys$^{37}$]GLP-1(7-37)-peptide (SEQ ID NO: 3):

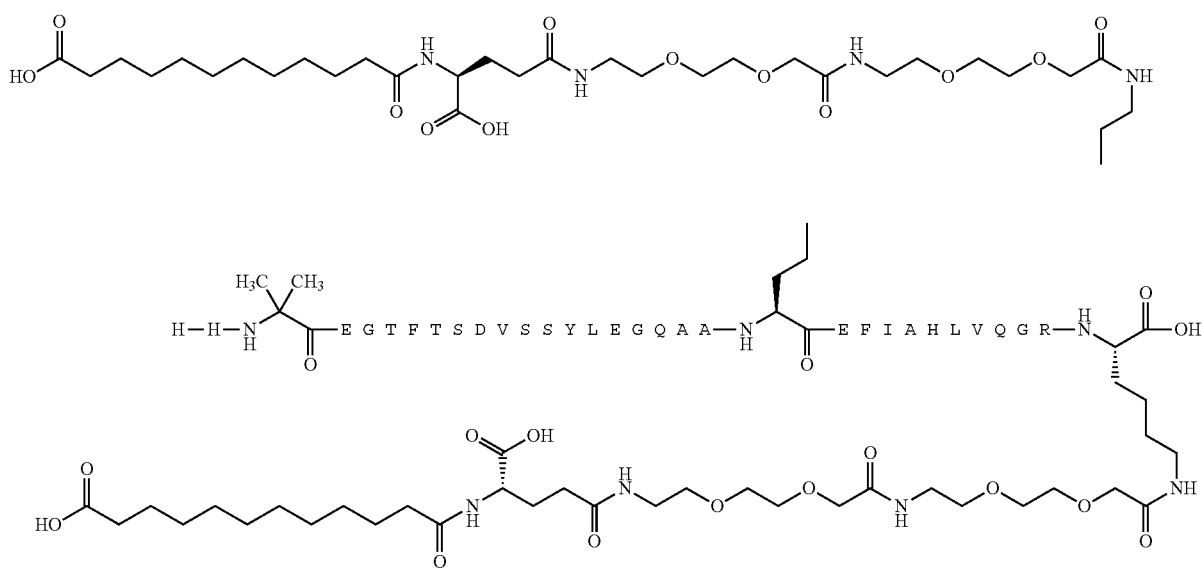

(xxii) $N^9$-{2-[2-(1H-Imidazol-4-yl)ethylcarbamoyl]-2-methylpropionyl}, $N^{\epsilon 26}$-{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, $N^{\epsilon 37}$-{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl} [Arg$^{34}$, Lys$^{31}$GLP-1(9-37)Glu$^{38}$-peptide (SEQ ID NO: 2):

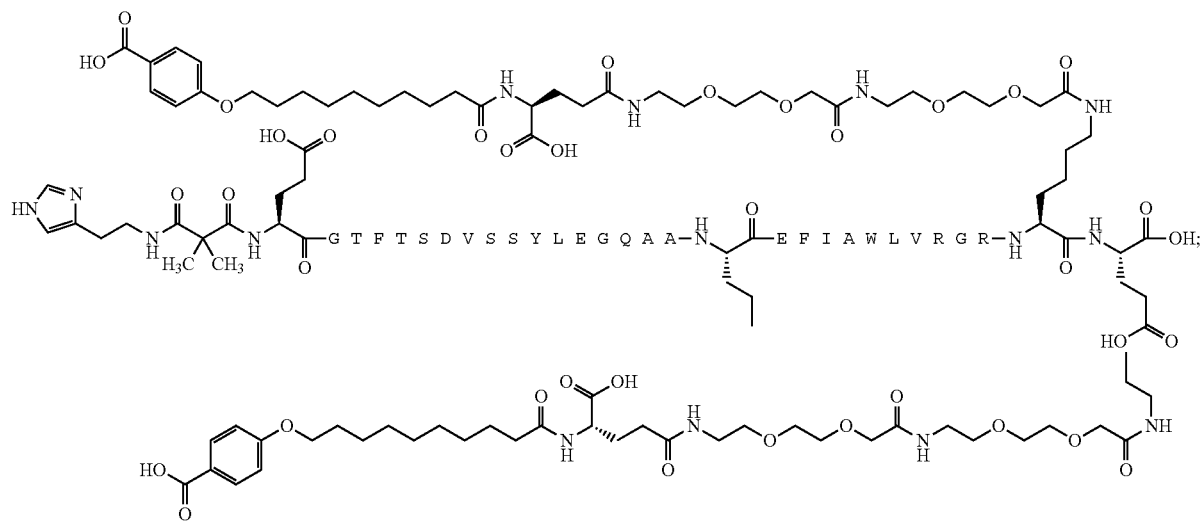

(xxiii) N⁹-{2-[2-(1H-Imidazol-4-yl)ethylcarbamoyl]-2-methylpropionyl]-N^{ε26}-{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, N^{ε37}-{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl} [Arg³⁴, Lys³⁷]GLP-1(9-37)-peptide (SEQ ID NO: 11):

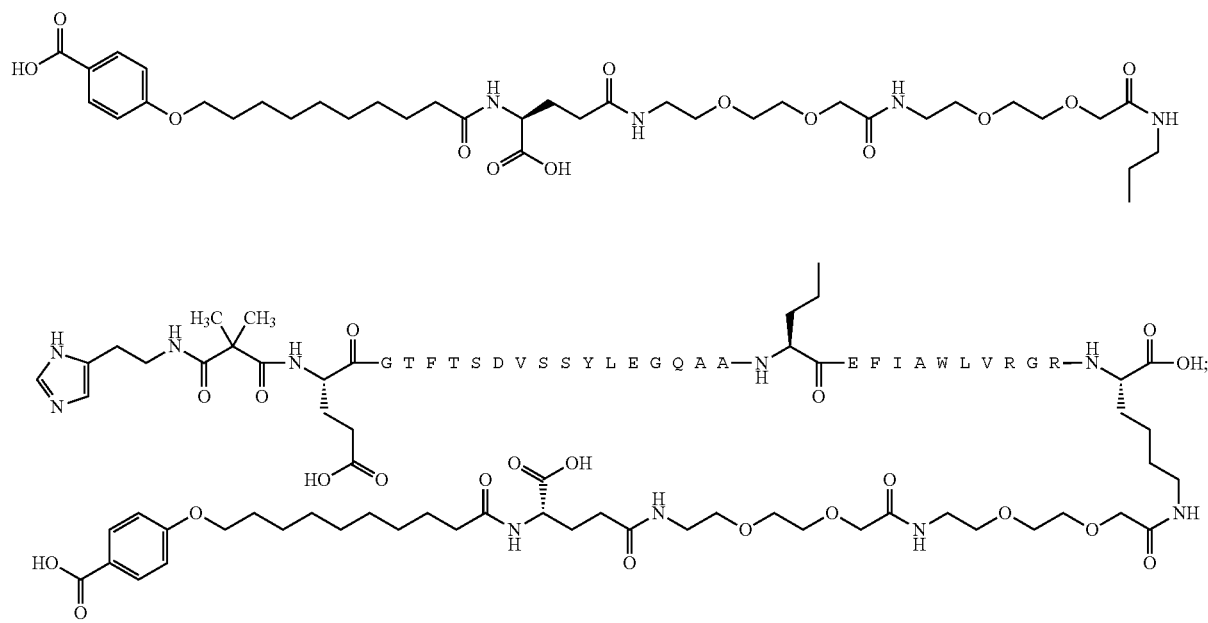

(xxiv) N^{ε26}-{2-[2-(2-{(S)-4-Carboxy-4-[2-(2-{2-[(13-carboxytridecanoylamino)]ethoxy}ethoxy)acetylamino]butyrylamino}ethoxy)ethoxy]acetyl}, N^{ε37}-{2-[2-(2-{(S)-4-Carboxy-4-[2-(2-{2-[(13-carboxytridecanoylamino)]ethoxy}ethoxy)acetylamino]butyrylamino}ethoxy)ethoxy]acetyl}-[Aib⁸,Arg³⁴,Lys³⁷]GLP-1(7-37)-peptide (SEQ ID NO: 7):

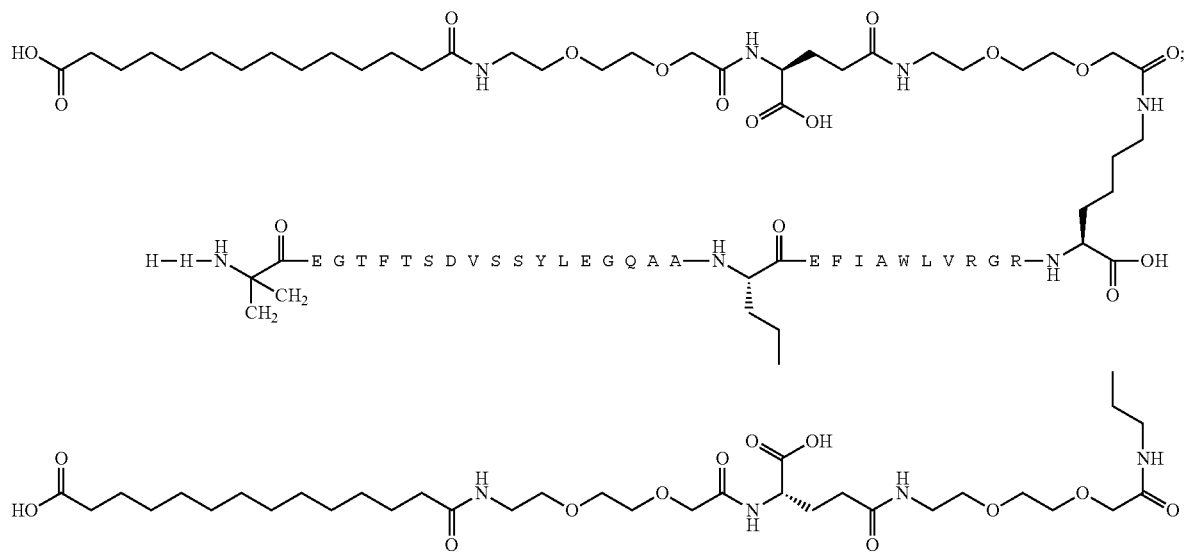

(xxv) N^ε2-[(S)-4-Carboxy-4-{2-[2-(2-[2-(2-{2-[(13-carboxytridecanoylamino)]ethoxy}ethoxy)acetylamino]ethoxy)ethoxy]acetylamino}butyryl], N^ε37-[(S)-4-Carboxy-4-{2-[2-(2-[2-(2-{2-[(13-carboxytridecanoylamino)]ethoxy}ethoxy)acetylamino]ethoxy)ethoxy]acetylamino}butyryl][Aib⁸,Arg³⁴,Lys³⁷]GLP-1(7-37)-peptide (SEQ ID NO: 7):

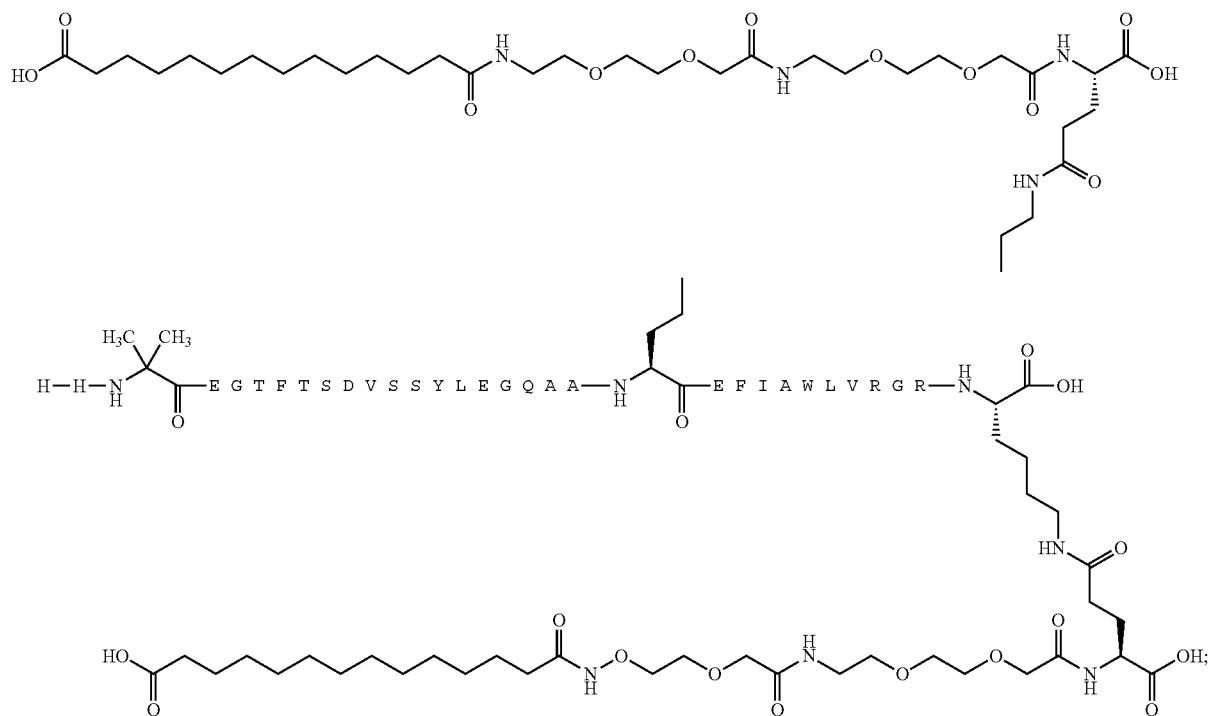

(xxvi) N^ε26-{2-[2-(2-{2-[2-(2-{(S)-4-[4-(4-tert-Butyl-phenyl)-butyrylamino]-4-carboxy-butyrylamino}ethoxy)ethoxy]acetylamino}ethoxy)ethoxy]acetyl}, N^ε37-{2-[2-(2-{2-[2-(2-{(S)-4-[4-(4-tert-Butyl-phenyl)-butyrylamino]-4-carboxy-butyrylaminoyethoxy}-ethoxy)-acetylamino}-ethoxy)-ethoxy]-acetyl} [Aib⁸, Arg³⁴,Lys³⁷]GLP-1(7-37)-peptide (SEQ ID NO: 7):

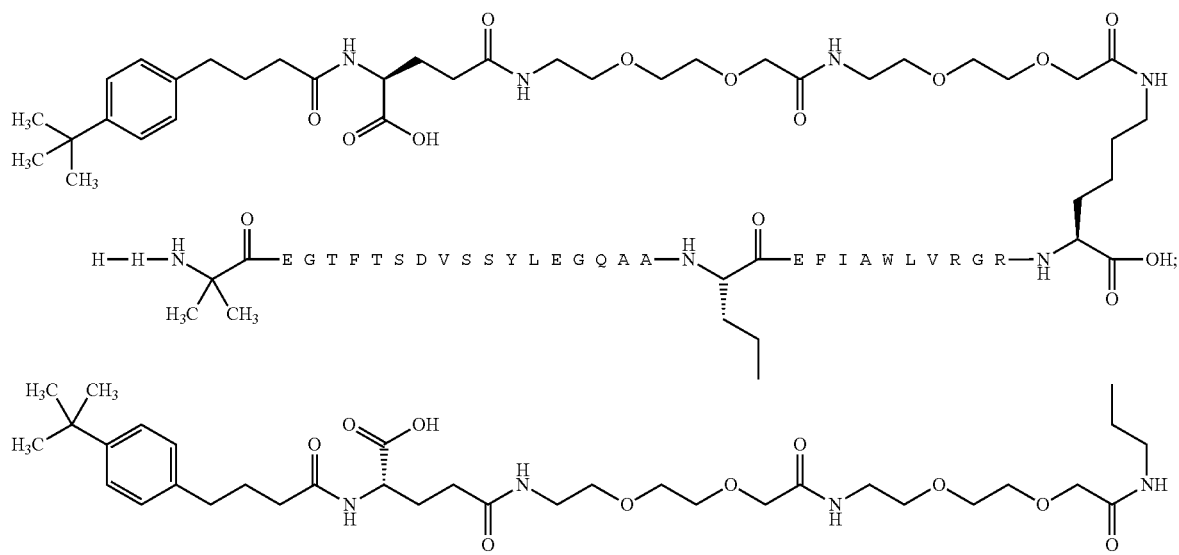

and (xxvii) N⁹-{2-[2-(1H-Imidazol-4-yl)-ethylcarbamoyl]-2-methylpropionyl}-N^{ε26}-{2-[2-(2-{2-[2-(2-{(S)-4-[4-(4-tert-Butylphenyl)butyrylamino]-4-carboxybutyrylamino}ethoxy)ethoxy]acetylamino}ethoxy)ethoxy]acetyl}, N^{ε37}-{2-[2-(2-{2-[2-(2-{(S)-4-[4-(4-tert-Butylphenyl)butyrylamino]-4-carboxybutyrylamino}ethoxy)ethoxy]acetylamino}ethoxy)ethoxy]acetyl}[Arg³⁴, Lys³⁷]GLP-1 (9-37)-peptide (SEQ ID NO: 11):

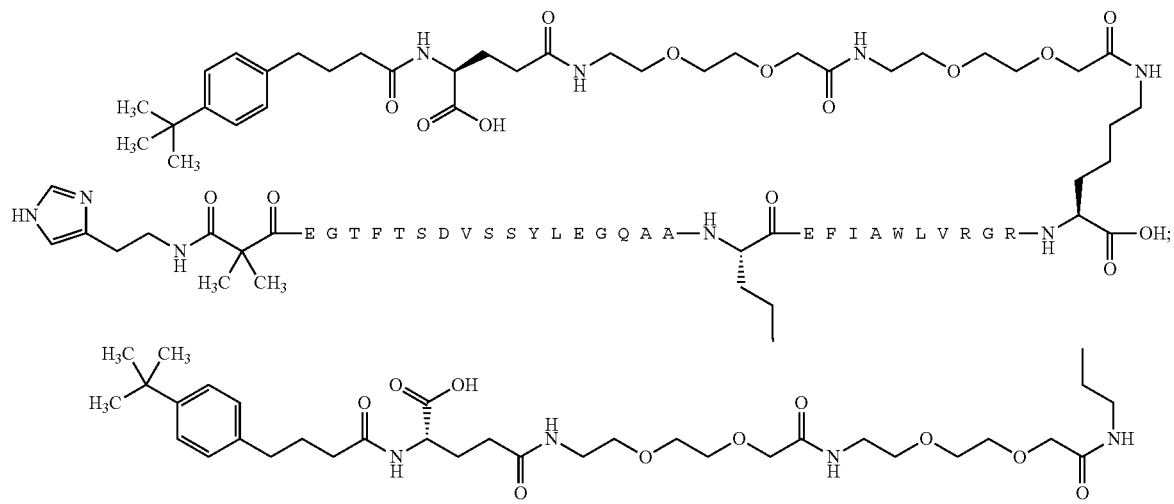

or a pharmaceutically acceptable salt, amide, or ester of any of the derivatives (i)-(xxvii).

84. A derivative according to any one of embodiments 1-83 for use as a medicament.

85. A derivative according to any one of embodiments 1-83, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

86. Use of a derivative according to any one of embodiments 1-83, in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

87. A method of treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression, by administering a pharmaceutically active amount of a derivative according to any one of embodiments 1-83.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

Abbreviations

The following abbreviations are used in the following, in alphabetical order:

Aib: aminoisobutyric acid (α-aminoisobutyric acid)
API: Active Pharmaceutical Ingredient
AUC: Area Under the Curve
BG: Blood Glucose
BHK Baby Hamster Kidney
BW: Body Weight
Bom: benzyloxymethyl
Boc: t-butyloxycarbonyl
BSA: Bovine serum albumin
Bzl: benzyl
Clt: 2-chlorotrityl
collidine: 2,4,6-trimethylpyridine
DCM: dichloromethane
Dde: 1-(4,4-dimethyl-2,6-dioxocyclohexylidene)ethyl
DIC: diisopropylcarbodiimide
DIPEA: diisopropylethylamine
DMAP: 4-dimethylaminopyridine
DMEM: Dulbecco's Modified Eagle's Medium (DMEM)
EDTA: ethylenediaminetetraacetic acid
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexafluoro-phosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid (also referred to as des-amino histidine, DesH)
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectro-scopy
MeOH: methanol
Mmt: 4-methoxytrityl
Mtt: 4-methyltrityl
NMP: N-methylpyrrolidone
OBz: benzoyl ester
OEG: 8-amino-3,6-dioxaoctanic acid
OPfp: pentafluorophenoxy
OPnp: para-nitrophenoxy
OSu: O-succinimidyl esters (hydroxysuccinimide esters)
OSuc: 2,5-dioxo-pyrrolidin-1-yl
OtBu: tert butyl ester
Pbf: 2,2,4,6,7-pentamethyldihydrobenzofuran-5-sulfonyl
PBS: Phosphate Buffered Saline
PD: Pharmacodynamic
Pen/Strep: Pencillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl or trityl
Trx: tranexamic acid
UPLC: Ultra Performance Liquid Chromatography Methods of Preparation

A. General Methods

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The protected amino acid derivatives used were standard Fmoc-amino acids (supplied from e.g. Anaspec, IRIS, or Novabiochem). The N-terminal amino acid was Boc protected at the alpha amino group (e.g. Boc-His(Boc)-OH, or Boc-His(Trt)-OH for peptides with H is at the N-terminus). The epsilon amino group of lysines in the sequence were either protected with Mtt, Mmt, Dde, ivDde, or Boc, depending on the route for attachment of the albumin binding moiety and spacer. The albumin binding moiety and/or linker can be attached to the peptide either by acylation of the resin bound peptide or by acylation in solution of the unprotected peptide. In case of attachment of the albumin binding moiety and/or linker to the protected peptidyl resin, the attachment can be modular using SPPS and suitably protected building blocks such as but not limited to Fmoc-Oeg-OH (Fmoc-8-amino-3, 6-dioxaoctanoic acid), Fmoc-Trx-OH (Fmoc-tranexamic acid), Fmoc-Glu-OtBu, octadecanedioic acid mono-tert-butyl ester, nonadecanedioic acid mono-tert-butyl ester, or 4-(9-carboxynonyloxy)benzoic acid tert-butyl ester.

1. Synthesis of Resin Bound Peptide
SPPS Method A

SPPS method A refers to the synthesis of a protected peptidyl resin using Fmoc chemistry on an Applied Biosystems 433 peptide synthesiser (also designated AB1433A synthesiser) in 0.25 mmol or 1.0 mmol scale using the manufacturers FastMoc UV protocols which employ HBTU or HATU mediated couplings in NMP, and UV monitoring of the deprotection of the Fmoc protection group.

The starting resin used for the synthesis of peptide amides was a suitable Rink-Amide resin (for peptide amides), or (for peptides with a carboxy C-terminus) either a suitable Wang resin or a suitable chlorotrityl resin. Suitable resins are commercially available from, e.g., Novabiochem.

SPPS Method B

SPPS method B refers to the synthesis of a protected peptidyl resin using Fmoc chemistry on a microwave-based Liberty peptide synthesiser (CEM Corp., North Carolina). A suitable resin is a pre-loaded, low-load Wang resin available from Novabiochem (e.g. low load Fmoc-Lys(Mtt)-Wang resin, 0.35 mmol/g). Fmoc-deprotection was with 5% piperidine in NMP at up to 70 or 75° C. The coupling chemistry was DIC/HOAt in NMP. Amino acid/HOAt solutions (0.3 M in NMP at a molar excess of 3-10 fold) were added to the resin followed by the same molar equivalent of DIC (0.75M in NMP). For example, the following amounts of 0.3M amino acid/HOAt solution were used per coupling for the following scale reactions: Scale/ml, 0.10 mmol/2.5 ml, 0.25 mmol/5 ml, 1 mmol/15 ml. Coupling times and temperatures were generally 5 minutes at up to 70 or 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 min then heated to 70 or 75° C. for 5 min. Some amino acids such as but not limited to Aib, were "double coupled", meaning that after the first coupling (e.g. 5 min at 75° C.), the resin is drained and more reagents are added (amino acid, HOAt and DIC), and the mixture in heated again (e.g. 5 min at 75° C.). When a chemical modification of a lysine side chain was desired, the lysine was incorporated as Lys(Mtt). The Mtt group was removed by washing the resin with DCM and suspending the resin in neat (undiluted) hexafluoroisopropanol for 20 minutes followed by washing with DCM and NMP. The chemical modification of the lysine was performed either by manual synthesis (see SPPS method D) or by one or more automated steps on the Liberty peptide synthesiser as described above, using suitably protected building blocks (see General methods), optionally including a manual coupling.

SPPS Method D

SPPS method D refers to synthesis of the protected peptidyl resin using manual Fmoc chemistry. This was typically used for the attachment of the linkers and side chains to the peptide backbone. The following conditions were employed at 0.25 mmol synthesis scale. The coupling chemistry was DIC/HOAt/collidine in NMP at a 4-10 fold molar excess. Coupling conditions were 1-6 h at room temperature. Fmoc-deprotection was performed with 20-25% piperidine in NMP (3×20 ml, each 10 min) followed by NMP washings (4×20 mL). Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with neat hexafluoroisopropanol (5×20 ml, each 10 min) followed by washings as above. The albumin binding moiety and/or linker can be attached to the peptide either by acylation of the resin bound peptide or acylation in solution of the unprotected peptide (see the routes described below). In case of attachment of the albumin binding moiety and/or linker to the protected peptidyl resin the attachment can be modular using SPPS and suitably protected building blocks (see General methods).

Attachment to Resin Bound Peptide—Route I:

Activated (active ester or symmetric anhydride) albumin binding moiety or linker such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, DCM, 2-propanol, methanol and diethyl ether.

Attachment to Resin Bound Peptide—Route II:

The albumin binding moiety was dissolved in NMP/DCM (1:1, 10 ml). The activating reagent such as HOBt (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed with NMP (2×20 ml), NMP/DCM (1:1, 2×20 ml) and DCM (2×20 ml).

Attachment to Peptide in Solution—Route III:

Activated (active ester or symmetric anhydride) albumin binding moiety or linker such as octadecanedioic acid mono-(2,5-dioxo-pyrrolidin-1-yl) ester (Ebashi et al. EP511600) 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the albumin binding residue such as tert-butyl, the reaction mixture was lyophilised overnight and the isolated crude peptide deprotected afterwards. In case of tert-butyl protection groups the deprotection was performed by dissolving the peptide in a mixture of trifluoroacetic acid, water and triisopropylsilane (90:5:5). After for 30 min the mixture was evaporated in vacuo and the crude peptide purified by preparative HPLC as described later.

SPPS Method E

SPPS method E refers to peptide synthesis by Fmoc chemistry on a Prelude Solid Phase Peptide Synthesiser from Protein Technologies (Tucson, Ariz. 85714 U.S.A.). A suitable resin is a pre-loaded, low-load Wang resin available from Novabiochem (e.g. low load fmoc-Lys(Mtt)-Wang resin, 0.35 mmol/g). Fmoc-deprotection was with 25% piperidine in NMP for 2×10 min. The coupling chemistry was DIC/HOAt/collidine in NMP. Amino acid/HOAt solutions (0.3 M in NMP at a molar excess of 3-10 fold) were added to the resin followed by the same molar equivalent of DIC (3 M in NMP) and collidine (3 M in NMP). For example, the following amounts of 0.3M amino acid/HOAt solution were used per coupling for the following scale reactions: Scale/ml, 0.10 mmol/2.5 ml, 0.25 mmol/5 ml. Coupling times were generally 60 minutes. Some amino acids including, but not limited to arginine, Aib or histidine were "double coupled", meaning that after the first coupling (e.g. 60 min), the resin is drained and more reagents are added (amino acid, HOAt, DIC, and collidine), and the mixture allowed to react gain (e.g. 60 min). Some amino acids and fatty acid derivatives including but not limited to Fmoc-Oeg-OH, Fmoc-Trx-OH, Fmoc-Glu-OtBu, octadecanedioic acid mono-tert-butyl ester, nonadecanedioic acid mono-tert-butyl ester, or 4-(9-carboxynonyloxy)benzoic acid tert-butyl ester were coupled for prolonged time, for example 6 hours. When a chemical modification of a lysine side chain was desired, the lysine was incorporated as Lys (Mtt). The Mtt group was removed by washing the resin with DCM and suspending the resin in hexafluoroisopropanol/DCM (75:25) for 3×10 minutes followed by washings with DCM, 20% piperidine and NMP. The chemical modification of the lysine was performed either by manual synthesis (see SPPS method D) or by one or more automated steps on the Prelude peptide synthesiser as described above using suitably protected building blocks (see General methods).

2. Cleavage of Peptide from the Resin and Purification

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 μM column, using acetonitrile/water/TFA. The fractions were analysed by a combination of UPLC, MALDI and LCMS methods, and the appropriate fractions were pooled and lyophilised.

3. Methods for Detection and Characterisation

LCMS Methods

LCMS Method 1 (LCMS1)

An Agilent Technologies LC/MSD TOF (G1969A) mass spectrometer was used to identify the mass of the sample after elution from an Agilent 1200 series HPLC system. The deconvolution of the protein spectra was calculated with Agilent's protein confirmation software.

Eluents:
A: 0.1% Trifluoro acetic acid in water
B: 0.1% Trifluoro acetic acid in acetonitrile
Column: Zorbax 5u, 300SB—C3, 4.8×50 mm
Gradient: 25%-95% acetonitrile over 15 min LCMS Method 2 (LCMS2)

A Perkin Elmer Sciex API 3000 mass spectrometer was used to identify the mass of the sample after elution from a Perkin Elmer Series 200 HPLC system.

Eluents:
A: 0.05% Trifluoro acetic acid in water
B: 0.05% Trifluoro acetic acid in acetonitrile
Column: Waters Xterra MS C-18×3 mm id 5 pm
Gradient: 5%-90% acetonitrile over 7.5 min at 1.5 ml/min LCMS Method 3 (LCMS3)

A Waters Micromass ZQ mass spectrometer was used to identify the mass of the sample after elution from a Waters Alliance HT HPLC system.

Eluents:
A: 0.1% Trifluoro acetic acid in water
B: 0.1% Trifluoro acetic acid in acetonitrile
Column: Phenomenex, Jupiter C4 50 X 4.60 mm id 5 pm
Gradient: 10%-90% B over 7.5 min at 1.0 ml/min LCMS Method 4 (LCMS4)

LCMS4 was performed on a setup consisting of Waters Acquity UPLC system and LCT Premier XE mass spectrometer from Micromass. The UPLC pump was connected to two eluent reservoirs containing:
A: 0.1% Formic acid in water
B: 0.1% Formic acid in acetonitrile The analysis was performed at RT by injecting an appropriate volume of the sample (preferably 2-10 μl) onto the column which was eluted with a gradient of A and B. The UPLC conditions, detector settings and mass spectrometer settings were:
Column: Waters Acquity UPLC BEH, C-18, 1.7 pm, 2.1 mm×50 mm
Gradient: Linear 5%-95% acetonitrile during 4.0 min (alternatively 8.0 min) at 0.4 ml/min
Detection: 214 nm (analogue output from TUV (Tunable UV detector))
MS ionisation mode: API-ES
Scan: 100-2000 amu (alternatively 500-2000 amu), step 0.1 amu UPLC and HPLC methods Method 05_B5_1

UPLC (method 05_B5_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$
The following linear gradient was used: 60% A, 40% B to 30% A, 70% B over 8 minutes at a flow-rate of 0.40 ml/min.

Method 05_B7_1

UPLC (method 05_B7_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$
The following linear gradient was used: 80% A, 20% B to 40% A, 60% B over 8 minutes at a flow-rate of 0.40 ml/min.

Method 04_A2_1

UPLC (method 04_A2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 90% A, 10% B to 60% A, 40% B over 16 minutes at a flow-rate of 0.40 ml/min.

Method 04_A3_1

UPLC (method 04_A3_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 75% A, 25% B to 45% A, 55% B over 16 minutes at a flow-rate of 0.40 ml/min.

Method 04_A4_1

UPLC (method 04_A4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 65% A, 35% B to 25% A, 65% B over 16 minutes at a flow-rate of 0.40 ml/min.

Method 08_B2_1

UPLC (method 08_B2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 99.95% $H_2O$, 0.05% TFA
B: 99.95% $CH_3CN$, 0.05% TFA
The following linear gradient was used: 95% A, 5% B to 40% A, 60% B over 16 minutes at a flow-rate of 0.40 ml/min.
Method 08_B4_1

UPLC (method 08_B4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 99.95% $H_2O$, 0.05% TFA
B: 99.95% $CH_3CN$, 0.05% TFA
The following linear gradient was used: 95% A, 5% B to 95% A, 5% B over 16 minutes at a flow-rate of 0.40 ml/min.
Method 05_B10_1

UPLC (Method 05_B10_1): The RP-analyses was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$
The following linear gradient was used: 40% A, 60% B to 20% A, 80% B over 8 minutes at a flow-rate of 0.40 ml/min.
Method 01_A4_2

UPLC (Method 01_A4_2): The RP-analysis was performed using a Waters 600S system fitted with a waters 996 diode array detector. UV detections at 214 nm and 254 nm were collected using a Symmetry300 C18, 5 um, 3.9 mm×150 mm column, 42° C. The HPLC system was connected to three eluent reservoirs containing: A: 100% $H_2O$, B: 100% $CH_3CN$, C: 1% trifluoroacetic acid in $H_2O$. The following linear gradient was used: 90% A, 5% B, 5% C to 0% A, 95% B, 5% C over 15 minutes at a flow-rate of 1.0 ml/min.
Method 09_B2_1

UPLC (Method 09_B2_1): The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 40% A, 60% B over 16 minutes at a flow-rate of 0.40 ml/min.
Method 09_B4_1

UPLC (Method 09_B4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 5% A, 95% B over 16 minutes at a flow-rate of 0.40 ml/min.
Method 05_B8_1

UPLC (Method 05_B8_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 50% A, 50% B to 20% A, 80% B over 8 minutes at a flow-rate of 0.40 ml/min.
Method 10_B14_1

UPLC (Method 10_B14_1): The RP-analysis was performed using a Waters UPLC system fitted with a dual band detector. UV detections at 214 nm and 254 nm were collected using an ACQUITY UPLC BEH ShieldRP18, 1.7 um, 2.1 mm×150 mm column, 50° C. The UPLC system was connected to two eluent reservoirs containing: A: 99.95% $H_2O$, 0.05% TFA; B: 99.95% $CH_3CN$, 0.05% TFA. The following linear gradient was used: 70% A, 30% B to 40% A, 60% B over 12 minutes at a flow-rate of 0.40 ml/min.
Method 04_A6_1

UPLC (Method 04_A6_1): The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 10 mM TRIS, 15 mM ammonium sulphate, 80% $H_2O$, 20%, pH 7.3; B: 80% $CH_3CN$, 20% $H_2O$. The following linear gradient was used: 95% A, 5% B to 10% A, 90% B over 16 minutes at a flow-rate of 0.35 ml/min.
Method 01_B4_1

HPLC (Method 01_B4_1): The RP-analysis was performed using a Waters 600S system fitted with a Waters 996 diode array detector. UV detections were collected using a Waters 3 mm×150 mm 3.5 um C-18 Symmetry column. The column was heated to 42° C. and eluted with a linear gradient of 5-95% acetonitrile, 90-0% water, and 5% trifluoroacetic acid (1.0%) in water over 15 minutes at a flow-rate of 1 ml/min.
MALDI-MS Method Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.
NMR Method Proton NMR spectra were recorded using a Brucker Avance DPX 300 (300 MHz) with tetramethylsilane as an internal standard. Chemical shifts (δ) are given in ppm and splitting patterns are designated as follows: s, singlet; d, doublet; dd, double doublet; dt, double triplet t, triplet, tt, triplet of triplets; q, quartet; quint, quintet; sext, sextet; m, multiplet, and br=broad.

B. Synthesis of Intermediates

1. Synthesis of Mono Esters of Fatty Diacids

Overnight reflux of the C12, C14, C16 and C18 diacids with Boc-anhydride, DMAP, and t-butanol in toluene gives predominately the t-butyl mono ester. Obtained is after workup a mixture of mono acid, diacid and diester. Purification is carried out by washing, short plug silica filtration and crystallisation.

2. Synthesis of 2-(1-Trityl-1H-imidazol-4-yl)-ethyl amine

Chem. 13:

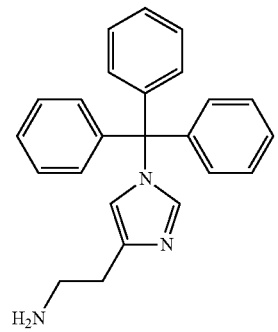

Histamine dihydrochloride (20.47 g; 0.111 mol) and triethylamine (48 mL; 0.345 mol) in absolute methanol (400 mL) were stirred at room temperature for 10 min. Trifluoroacetic acid ethyl ester (14.6 mL; 0.122 mol) in methanol (30 mL) was added dropwise over 30 min at 0° C. Reaction mixture was stirred for 3.5 hrs at room temperature and then it was evaporated to dryness in vacuo. The residue was dissolved in dichlormethane (450 mL) and triethylamine (31 mL; 0.222 mol) was added. Then trityl chloride (34.1 g; 0.122 mol) was added piecewise and mixture was stirred over night at room temperature. Chloroform (400 mL) and water (600 mL) were poured into reaction mixture. Aqueous layer was separated and extracted with chloroform (3×400 mL). The combined organic layers were dried over anhydrous magnesium sulfate. Solvent was removed and the beige solid was triturated with hexanes (1000 mL). Suspension was filtered to yield 2,2,2-trifluoro-N-[2-(1-trityl-1H-imidazol-4-yl)-ethyl]-acetamide as white solid.

Yield: 45.54 g (91%).

$^1$H NMR spectrum (300 MHz, CDCl$_3$, $\delta_H$): 8.44 (bs, 1H); 7.43 (s, 1H); 7.41-7.33 (m, 9H); 7.19-7.10 (m, 6H); 6.65 (s, 1H); 3.66 (q, J=5.9 Hz, 2H); 2.79 (t, J=5.9 Hz, 2H).

The above amide (45.54 g; 0.101 mmol) was dissolved in tetrahydrofuran (1000 mL) and methanol (1200 mL). A solution of sodium hydroxide (20.26 g; 0.507 mol) in water (500 mL) was added. Mixture was stirred for 2 hrs at room temperature and then it was concentrated in vacuo. The residue was separated between chloroform (1200 mL) and water (800 mL). Aqueous layer was extracted with chloroform (3×400 mL). Organic layers were combined and dried over anhydrous magnesium sulfate. Evaporation of the solvent yielded brown oil, which was dried for 3 days in vacuo to give the title product as beige solid.

Yield: 32.23 g (90%).
Overall yield: 82%.
M.p.: 111-113° C.

$^1$H NMR spectrum (300 MHz, CDCl$_3$, $\delta_H$): 7.39 (d, J=1.3, 1H); 7.38-7.32 (m, 9H); 7.20-7.12 (m, 6H); 6.61 (s, 1H); 3.00 (t, J=6.6 Hz, 2H); 2.70 (t, J=6.5 Hz, 2H); 1.93 (bs, 2H).

3. Synthesis of 2,2-Dimethyl-N-[2-(1-trityl-1H-imidazol-4-yl)-ethyl]-malonamic acid Chem. 14:

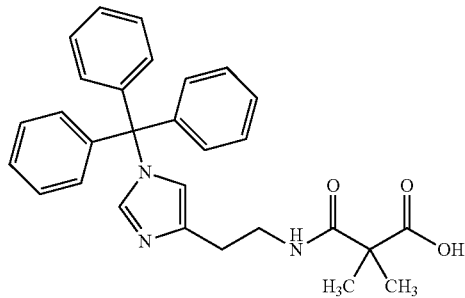

A mixture of Meldrum's acid (5.52 g, 38.3 mmol), potassium carbonate (26.5 g, 191 mmol) and methyl iodide (7.15 mL, 115 mmol) in acetonitrile (75 mL) was heated at 75° C. in a sealed tube for 7 hrs. The mixture was cooled to room temperature, diluted with dichloromethane (300 mL), filtered and the filtrate evaporated to dryness in vacuo. Ethyl acetate (75 mL), hexanes (75 mL) and water (50 mL) were added and phases were separated. The organic layer was washed with 10% aqueous solution of sodium thiosulfate (50 mL) and water (50 mL); dried over anhydrous magnesium sulfate and solvent removed in vacuo to give 2,2,5,5-tetramethyl-[1,3]dioxane-4,6-dione as white solid.

Yield: 6.59 g (79%).

R$_F$ (SiO$_2$, chloroform/ethyl acetate, 98:2): 0.60.

$^1$H NMR spectrum (300 MHz, CDCl$_3$, $\delta_H$): 1.76 (s, 6H); 1.65 (s, 6H).

A solution of 2-(1-Trityl-1H-imidazol-4-yl)-ethyl amine (5.00 g, 14.2 mmol) prepared as described above and triethylamine (9.86 mL, 70.7 mmol) in toluene (80 mL) was added dropwise over 50 min to a solution of the above dione compound (3.65 g, 21.2 mmol) in toluene (40 mL) at 75° C. The mixture was stirred at this temperature for additional 3 hrs (until the starting amine was detected on TLC), then it was evaporated to dryness. The residue was redissolved in chloroform (300 mL) and washed with 10% aqueous solution of citric acid (200 mL). The aqueous phase was extracted with chloroform (2×60 mL); the chloroform phases were combined, dried over anhydrous magnesium sulfate and solvent removed in vacuo. The residue was triturated with hot chloroform (140 mL); hexanes (70 mL) were added and the suspension was stirred at room temperature overnight. Solids were filtered off, washed with chloroform/hexanes mixture (1:1, 2×50 mL) and dried in vacuo to give the title product.

Yield: 6.73 g (88%).
M.p.: 161-162° C.
R$_F$ (SiO$_2$, chloroform/methanol, 85:15): 0.40.

$^1$H NMR spectrum (300 MHz, DMSO-d$_6$, $\delta_H$): 12.45 (bs, 1H); 7.66 (t, J=5.1Hz, 1H); 7.57-7.31 (m, 9H); 7.26 (s, 1H); 7.20-7.02 (m, 6H); 6.66 (s, 1H); 3.25 (m, 2H); 2.57 (t, J=7.3 Hz, 2H); 1.21 (s, 6H).

4. Synthesis of 4-(4-tert-Butyl-phenyl)-butyric acid

Chem. 15:

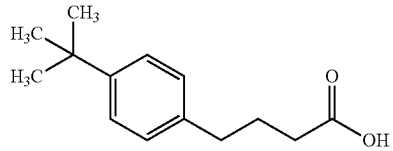

Aluminum chloride powder (80.0 g, 600 mmol) was added in portions to a stirred mixture of tert-butylbenzene (40.0 g, 300 mmol) and succinic anhydride (26.7 g, 267 mmol) and 1,1,2,2-tetrachloroethane (100 mL). After all the aluminum chloride had been added, the mixture was poured into a mixture of ice (500 mL) and concentrated hydrochloric acid (100 mL). The organic layer was separated, washed with water (500 mL) and the solvent distilled off. Solid residue was dissolved in hot 15% aqueous solution of sodium carbonate (1000 mL), filtered, cooled and the acid was precipitated with hydrochloric acid (acidified to pH=1). The crude acid was filtered, dried on air and recrystalised from benzene (500 mL) to give 4-(4-tert-butyl-phenyl)-4-oxo-butyric acid as colorless crystals.

Yield: 36.00 g (58%).
M.p.: 117-120° C.

$^1$H NMR spectrum (300 MHz, CDCl$_3$, $\delta_H$): 7.93 (dm, J=8.3 Hz, 2H); 7.48 (dm, J=8.3 Hz, 2H); 3.30 (t, J=6.6 Hz, 2H); 2.81 (t, J=6.6 Hz, 2H); 1.34 (s, 9H).

A mixture of the above acid (36.0 g, 154 mmol), potassium hydroxide (25.8 g, 462 mmol), hydrazine hydrate (20 mL, 400 mmol) and ethylene glycol (135 mL) was refluxed for 3 hrs, and then distilled until the temperature of the vapor had risen to 196-198° C. After a further 14 hrs reflux, the mixture was allowed to cool slightly, and was then poured into cold water (200 mL). The mixture was acidified with concentrated hydrochloric acid (to pH=1) and extracted with dichloromethane (2×400 mL). The organic extracts were combined, dried over anhydrous magnesium sulfate, solvent removed in vacuo and the residue was purified by column chromatography (Silicagel 60A, 0.060-0.200 mm; eluent: hexanes/ethyl acetate 10:1-6:1) to give the title product as off white solid.

Yield: 16.25 g (48%).
M.p.: 59-60° C.
$R_F$ (SiO$_2$, ethyl acetate): 0.60.
$^1$H NMR spectrum (300 MHz, CDCl$_3$, δ0: 7.31 (dm, J=8.1Hz, 2H); 7.12 (dm, J=8.1Hz, 2H); 2.64 (t, J=7.6 Hz, 2H); 2.38 (t, J=7.4 Hz, 2H); 1.96 (m, 2H); 1.31 (s, 9H).

5. Synthesis of 2,2-Dimethyl-N-(1-trityl-1H-imidazol-4-ylmethyl)-malonamic acid

Chem. 16:

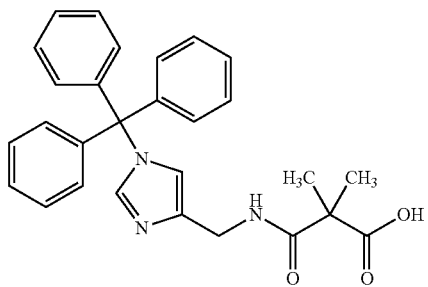

Hydroxylamine hydrochloride (15.9 g, 229 mmol) was added to a solution of 4(5)-imidazolecarboxaldehyde (20.0 g, 209 mmol) and sodium carbonate (12.1 g, 114 mmol) in water (400 mL) and the resulting solution was stirred at room temperature overnight. The mixture was evaporated to 100 mL and cooled in an ice bath. The solids were separated by filtration and the filtrate was concentrated to 40 mL. After cooling to 0° C., another portion of crystals was obtained. The solids (23 g) were combined and recrystallised from ethanol (approx. 160 mL) to afford imidazole-4(5)-carbaldehyde oxime as colorless crystals.

Yield: 15.98 g (69%).
$^1$H NMR spectrum (300 MHz, acetone-d$_3$+D$_2$O, δ$_H$): 7.78 (bs, 1H); 7.74 (d, J=0.9 Hz, 1H); 7.43 (s, 1H).

Acetyl chloride (51.0 mL, 718 mmol) was added dropwise to methanol (670 mL) at 0° C. under argon. After 30 min, the cooling bath was removed and the above oxime (16.0 g, 144 mmol) was added, followed by palladium on carbon (5 wt %, 6.1 g). The mixture was hydrogenated at atmospheric pressure for 17 hrs, then it was filtered through Celite and the solvent evaporated to give pure 4-(aminomethyl)-imidazole dihydrochloride as colorless crystals.

Yield: 23.92 g (98%).
$^1$H NMR spectrum (300 MHz, D$_2$O, δ$_H$): 8.72 (s, 1H); 7.60 (s, 1H); 4.33 (s, 2H). The above amine dihydrochloride (18.9 g; 111 mmol) and triethylamine (93 mL; 667 mmol) in methanol (1000 mL) were stirred at room temperature for 10 min. Trifluoroacetic acid ethyl ester (13.3 mL; 111 mmol) in methanol (30 mL) was added dropwise over 40 min at 0° C. Reaction mixture was stirred for 18 hrs at room temperature and then it was evaporated to dryness in vacuo. The residue was dissolved in dry dichlormethane (2000 mL) and triethylamine (31 mL; 222 mmol) was added. Then trityl chloride (31.6 g; 113 mmol) was added and the mixture was stirred overnight at room temperature. Chloroform (1000 mL) and water (1000 mL) were poured into the reaction mixture. Aqueous layer was separated and extracted with chloroform (2×300 mL). The combined organic layers were dried over anhydrous magnesium sulfate. Solvent was removed and the beige solid was triturated with hexanes (1000 mL). Suspension was filtered to yield 2,2,2-trifluoro-N-(1-trityl-1H-imidazol-4-ylmethyl)-acetamide as white solid.

Yield: 46.59 g (96%).
$R_F$ (SiO$_2$, dichloromethane/methanol 95:5): 0.35.
$^1$H NMR spectrum (300 MHz, DMSO-d$_6$, δ0: 9.77 (t, J=5.7 Hz, 1H); 7.47-7.34 (m, 9H); 7.33 (d, J=1.5 Hz, 1H); 7.13-7.03 (m, 6H); 6.80 (d, J=0.8 Hz, 1H); 4.25 (d, J=5.7 Hz, 2H).

The above amide (46.6 g; 107 mmol) was dissolved in tetrahydrofuran (600 mL) and ethanol (310 mL). A solution of sodium hydroxide (21.4 g; 535 mmol) in water (85 mL) was added. Mixture was stirred for 5 hrs at room temperature and then it was concentrated in vacuo. The residue was separated between chloroform (1600 mL) and water (800 mL). Aqueous layer was extracted with chloroform (4×200 mL). Organic layers were combined and dried over anhydrous magnesium sulfate. Evaporation of the solvent yielded (1-trityl-1H-imidazol-4-yl)-methylamine as off white solid.

Yield: 36.30 g (100%).
$^1$H NMR spectrum (300 MHz, CDCl$_3$, δ$_H$): 7.38 (d, J=1.3, 1H); 7.36-7.30 (m, 9H); 7.18-7.10 (m, 6H); 6.69 (m, 1H); 3.77 (s, 2H); 1.80 (bs, 2H).

A solution of the above amine (10.0 g, 29.5 mmol) and triethylamine (20.5 mL, 147 mmol) in toluene (220 mL) was added dropwise over 45 min to a solution of 2,2,5,5-tetramethyl-[1,3]dioxane-4,6-dione (3.65 g, 21.2 mmol) in toluene (80 mL) at 75° C. The mixture was stirred at this temperature for additional 3 hrs (until the starting amine was detected on TLC), then it was evaporated to dryness. The residue was redissolved in chloroform (500 mL) and washed with 10% aqueous solution of citric acid (300 mL). The aqueous phase was extracted with chloroform (100 mL); the chloroform phases were combined, washed with water (150 mL) dried over anhydrous magnesium sulfate and solvent removed in vacuo. The residue was purified by flash column chromatography (silica gel Fluka 60, dichloromethane/methanol 98:2 to 9:1) and crystallised from chloroform/hexanes mixture to give the title product as beige crystals.

Yield: 9.80 g (73%).
M.p.: 174-175° C.
$R_F$ (SiO$_2$, chloroform/methanol, 85:15): 0.35.
$^1$H NMR spectrum (300 MHz, CDCl$_3$, δ$_H$): 8.45 (t, J=5.8 Hz, 1H); 7.53 (s, 1H); 7.40-7.28 (m, 9H); 7.14-7.01 (m, 6H); 6.84 (s, 1H); 4.39 (d, J=5.8 Hz, 2H); 1.44 (s, 6H).

6. Synthesis of 3-(1-Trityl-1H-imidazol-4-yl)-propyl amine

Chem. 17:

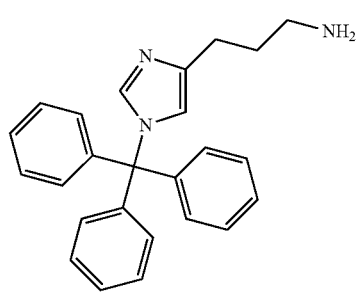

Ethyl 3-(1-trityl-4-imidazolyl)propionate (93.0 g, 223 mmol) in tetrahydrofuran/diethyl ether (1:1, 100 mL) was added dropwise to a suspension of lithium aluminium hydride (17.0 g, 446 mmol) during 1 hr. The mixture was refluxed for 3 hrs, then treated with water (100 mL), 20% sodium hydroxide (100 mL) and water (100 mL) under cooling with ice/water, filtered and the solid washed with tetrahydrofuran. The organic phase was dried over anhydrous potassium carbonate, filtered and evaporated to give 3-(1-trityl-4-imidazolyl)propanol as white solid.

Yield: 68.0 g (82%).

M.p.: 127-129° C.

$^1$H NMR spectrum (300 MHz, CDCl$_3$, $\delta_H$): 7.40-7.24 (m, 10H); 7.17-7.06 (m, 6H); 6.55 (s, 1H); 3.72 (t, J=5.3 Hz, 2H); 2.68 (t, J=6.6 Hz, 2H); 1.86 (m, 2H).

Methanesulfonyl chloride (8 mL, 104 mmol) was added dropwise to a solution of the above alcohol (32.0 g, 86.8 mmol) in dichloromethane (400 mL) and triethyl amine (15.5 mL) at 0° C. during 1 hr. The mixture was stirred without cooling for an additional 1 hr; then it was washed with 5% sodium bicarbonate and dried over anhydrous magnesium sulfate. Dichloromethane was evaporated at 30° C. in vacuo and the residual oily mesylate was used directly in the next step.

Yield: 31.2 g (80%).

$^1$H NMR spectrum (300 MHz, CDCl$_3$, $\delta_H$): 7.37-7.30 (m, 10H); 7.16-7.09 (m, 6H); 6.58 (s, 1H); 4.24 (t, J=6.3 Hz, 2H); 2.96 (s, 3H); 2.67 (m, 2H); 2.10 (m, 2H).

A mixture of the above mesylate (30.0 g, 67 mmol), potassium phtalimide (18.0 g, 100 mmol), sodium iodide (4.0 g, 26.7 mmol) and dimethylformamide (200 mL) was stirred overnight at ambient temperature and then treated with water (2 L) and benzene (2 L). The organic phase was dried over anhydrous magnesium sulfate, filtered and solvent evaporated giving a residue, which was recrystallised from benzene yielding 1-trityl-4-(3-phtalimidopropyl)imidazole as white solid.

Yield: 17.2 g (52%).

M.p.: 211-214° C.

$^1$H NMR spectrum (300 MHz, CDCl$_3$, $\delta_H$): 7.83 (m, 2H); 7.72 (m, 2H); 7.39-7.27 (m, 10H); 7.18-7.07 (m, 6H); 6.60 (d, J=0.9 Hz, 1H); 3.72 (t, J=7.4 Hz, 2H); 2.60 (t, J=7.5 Hz, 2H); 1.99 (m, 2H).

The above imidazole derivative (26.6 g, 53.5 mmol) was dissolved in ethanol (300 mL) and tetrahydrofuran (150 mL) at 60° C., hydrazine hydrate (50 g, 1 mol) was added and the solution was refluxed for 6 hrs and then heated at 70° C. overnight. The solid was removed by filtration and the filtrate was treated with 25% aqueous solution of ammonia (2.5 l) and dichloromethane (2.5 L). The organic layer was dried over anhydrous potassium carbonate and evaporated to give a residue, which was purified by column chromatography on silica gel (Fluka 60, chloroform saturated with ammonia/methanol) giving the title compound as white solid.

Yield: 14.2 g (72%).

M.p.: 112-113° C.

R$_F$ (SiO$_2$, chloroform saturated with ammonia/methanol 9:1): 0.30.

$^1$H NMR spectrum (300 MHz, CDCl$_3$, $\delta_H$): 7.37-7.28 (m, 10H); 7.18-7.09 (m, 6H); 6.53 (d, J=1.3 Hz, 1H); 2.74 (t, J=6.9 Hz, 2H); 2.59 (t, J=7.4 Hz, 2H); 1.95 (bs, 2H); 1.78 (m, 2H).

7. Synthesis of 2,2-Dimethyl-N-[3-(1-trityl-1H-imidazol-4-yl)-propyl]-malonamic acid Chem. 18:

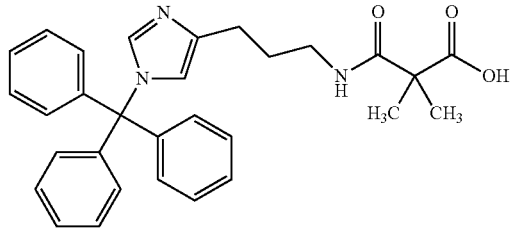

2-Chlorotrityl chloride resin (2.3 g, 3.0 mmol) was swelled in DCM for 20 mins and filtered. Dimethylmalonic acid (2 eq; 6.0 mmol; 793 mg) was dissolved i DCM:DMF 1:1 (10 mL) and added to the resin followed by DIPEA (6 eq; 18.0 mmol; 3.14 mL) and DCM (10 mL). The resin was shaken overnight at RT. The resin was filtered and washed with DCM:MeOH: DIPEA (17:2:1), DCM, NMP og DCM (2×25 mL of each). The resin was swelled in DMF for 20 mins and filtered. HOAt (3 eq; 9.0 mmol; 1.23 g), DIC (3 eq; 9.0 mmol; 1.40 mL) and DMF (25 mL) was added and the resin was shaken for 90 min at RT. The resin was filtrered and 3-(1-Trityl-1H-imidazol-4-yl)-propyl amine (1.8 eq; 5.40 mmol; 1.84 g), DIPEA (4 eq; 6.0 mmol; 2.09 mL), and DMF (10 mL) was added. The resin was shaken for 2 days. The resin was filtered and washed with NMP (5×20 mL) and DCM (10×20 mL). 2,2,2-Trifluoroethanol/dichlormethan 1:1 (20 mL) was added to the resin and it was shaked for 2 hrs. The resin was washed with 2,2,2-Trifluoroethanol/dichlormethan 1:1 (10 mL) and the combined filtrates were collected and concentrated in vacuo to yield the title compound.

Yield: 600 mg (41%).

LCMS4: m/z=482 (M+1)

UPLC (method 02_B4_4): Rt=8.07 min

1H NMR spectrum (300 MHz, DMSO-d$_s$, $\delta_H$): 7.36-7.44 (9H, m), 7.07-7.12 (6H, m), 6.62 (1H, s), 3.02-3.09 (2H, q), 2.38-2.43 (2H, t), 1.61-1.69 (2H, m), 1.26 (6H, s).

8. Synthesis of 2,2-Dimethyl-N-[3-(1-trityl-1H-imidazol-4-yl)-propyl]-malonamic acid Synthesis of 2,2-Dimethyl-N-pyridin-2-ylmethylmalonamic acid Chem. 19:

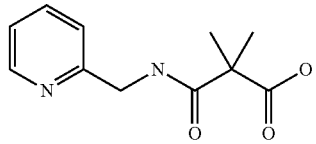

Chlorotrityl chloride resin (2.3 g, 3.0 mmol) was swelled in DCM for 20 mins and filtered. Dimethylmalonic acid (2 eq; 6.0 mmol; 793 mg) was dissolved i DCM:NMP 1:1 (10 mL) and added to the resin followed by DIPEA (6 eq; 18.0 mmol; 3.14 mL) and DCM (10 mL). The resin was shaken overnight at RT. The resin was filtered and washed with DCM:MeOH: DIPEA (17:2:1), DCM, NMP og DCM (2×25 mL of each). The resin was swelled in NMP for 20 mins and filtered. HOAt (3 eq; 9.0 mmol; 1.23 g), DIC (3 eq; 9.0 mmol; 1.40 mL) and NMP (25 mL) was added and the resin was shaken for 90 min at RT. The resin was filtrered and 2-(Aminomethyl)pyridine (2 eq; 6 mmol; 659 mg), DIPEA (4 eq; 6.0 mmol; 2.09 mL), and NMP (10 mL) was added. The resin was shaken for overnigth. The resin was filtered and washed with NMP (5×20 mL) and DCM (10×20 mL). TFA/TIS/water (95:2.5: 2.5; 30 mL) was added to the resin and it was shaked for 1 hr, filtered and concentrated in vacuo to yield the title compound.

Yield: 600 mg (41%).

LCMS4: m/z=223 (M+1)

UPLC (method 08_B4_1): Rt=1.79 min

B. Synthesis of Compounds of the Invention

Example 1

$N^{\epsilon 26}$-[2-(2-{2-[10-(4-Carboxyphenoxy)decanoylamino]ethoxy}ethoxy)acetyl], $N^{\epsilon 37}$-[2-(2-{2-[10-(4-Carboxyphenoxy)decanoylamino]ethoxy}ethoxy)acetyl]-[Aib$^8$,Arg$^{34}$,Lys$^{37}$]GLP-1(7-37) peptide (SEQ ID NO: 7), Chem. 20:

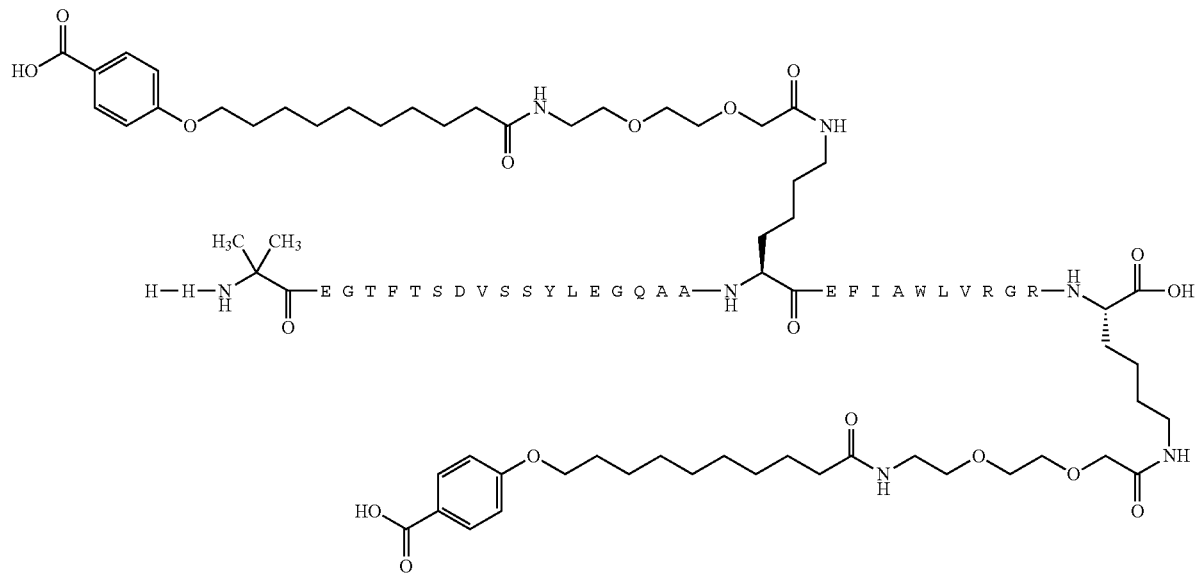

Preparation method: SPPS method B, starting with low-load Fmoc-Lys(Mtt)-Wang resin. Fmoc-Lys(Mtt)-OH was used in position 26, and Boc-His(trt)-OH was used in position 7. The Mtt was removed with HFIP, and 8-(9-fluorenylmethyloxy-carbonyl-amino)-3,6-dioxaoctanoic acid (commercially available from Iris Biotech) and 4-(9-carboxy-nonyloxy)-benzoic acid tert-butyl ester (prepared as described in Example 25, step 2 of WO 2006/082204) were coupled using a double coupling method on the Liberty Peptide synthesiser
UPLC (method 04_A3__1): 10.51 min
LCMS4: m/z=1085.2 (M+4H)$^{4+}$, 1447.3 (M+3H)$^{3+}$

Example 2

$N^{\epsilon 26}${2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, $N^{\epsilon 37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}[Aib$^8$,Arg$^{34}$,Lys$^{37}$]GLP-1(7-37)-peptide (SEQ ID NO: 7), Chem. 21:

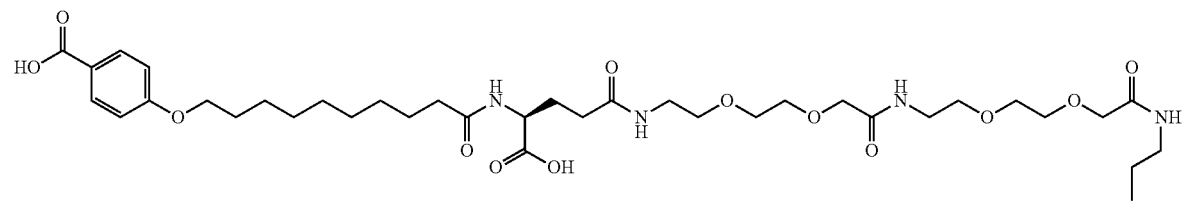

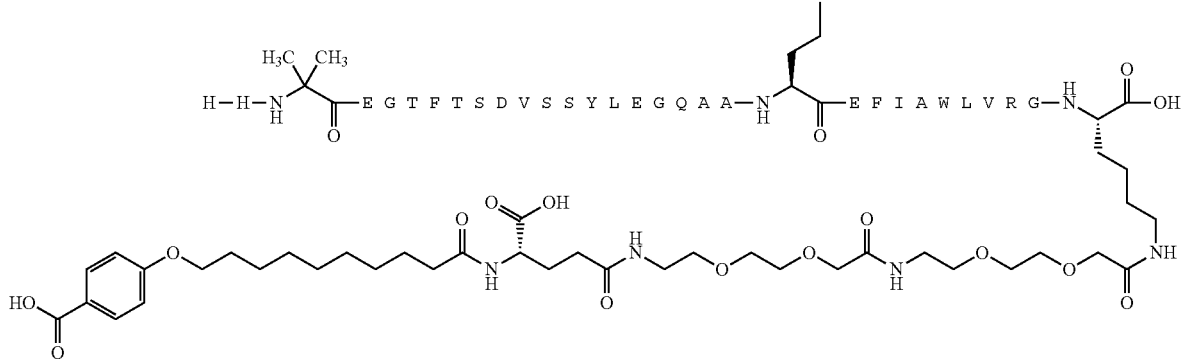

Preparation method: SPPS method B, starting with low-load Fmoc-Lys(Mtt)-Wang resin. Fmoc-Lys(Mtt)-OH was used in position 26, and Boc-His(Trt)-OH was used in position 7. The Mtt was removed with HFIP, and 8-(9-fluorenylmethyloxy-carbonyl-amino)-3,6-dioxaoctanoic acid (commercially available from Iris Biotech), Fmoc-Glu-OtBu, and 4-(9-carboxy-nonyloxy)-benzoic acid tert-butyl ester (prepared as described in Example 25, step 2 of WO 2006/082204) were coupled using a double coupling method on the Liberty Peptide synthesiser.

UPLC (method 04_A3__1): 7.19 min
LCMS4: m/z=978.5 (M+5H)$^{5+}$, 1222.8 (M+4H)$^{4+}$1630.1 (M+3H)$^{3+}$ up to 70° C., except for histidine which was coupled for 20 minutes at up to 50° C. All amino acids were protected with standard protecting groups, except for lysines to be acylated (in this case Lys26) which was protected with Mtt. Deprotection was with 5% piperidine in NMP at 50° C. for 3 minutes. After the synthesis was completed, the N-terminus was blocked with 10 equivalents of Boc-carbonate and 10 equivalents of DIPEA for 30 minutes. The Mtt groups were removed by treatment with neat (undiluted) hexafluoroisopropanol for 20 minutes and the side chains were built stepwise on the Liberty using the same protocol as above using Fmoc-8-amino-3,6-dioxaoctanoic acid, Fmoc-Glu-OBut, and hexadecanedioic acid mono-t-butyl ester. The peptide was cleaved with TFA/water/TIS (95:2.5:2.5) for 2 hours and isolated by precipitation with diethylether. The crude peptide was purified by preparative HPLC on a 20 mm×250 mm column packed with either 5u or 7u C18 silica. The peptide was dissolved in 5 ml 50% acetic acid and diluted to 20 ml with H$_2$O and injected on the column which then was eluted with a gradient of 40-60% CH$_3$CN in 0.1% TFA 10 ml/min during 50 min at 40° C. The peptide containing fractions were collected and purity assessed by MALDI and UPLC. The purified peptide was lyophilised after dilution of the eluate with water.

Example 3

N$^{\epsilon 26}$-[2-(2-{2-[2-(2-{2-[(S)-4-Carboxy-4-(15-carboxypentadecanoylamino)butyrylamino]ethoxy}ethoxy)acetylamino]ethoxy}ethoxy)acetyl], N$^{\epsilon 37}$-[2-(2-{2-[2-(2-{2-[(S)-4-Carboxy-4-(15-carboxypentadecanoylamino)butyrylamino]ethoxy}ethoxy)acetylamino]ethoxy}ethoxy)acetyl] [Aib$^8$,Arg$^{34}$,Lys$^{37}$]GLP-1(7-37)-peptide (SEQ ID NO: 7), Chem. 22:

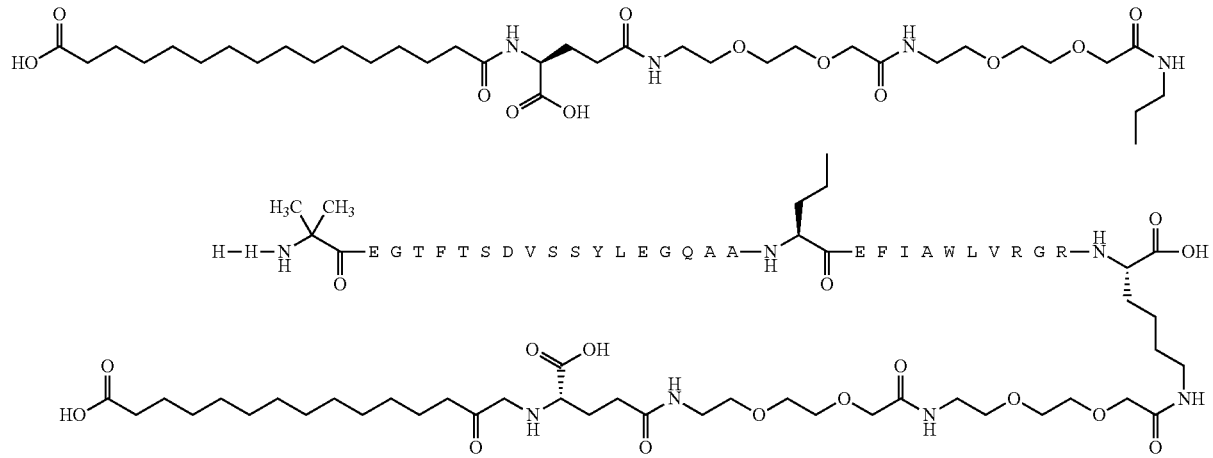

Preparation method: The peptide was synthesised on Lys(Mtt)-Wang resin with a loading of 0.35 mmol/g. The synthesis was performed on a Liberty synthesiser under microwave conditions using 5 minute single couplings with DIC/HOAt at The theoretical molecular mass of 4844.6 was confirmed by MALDI-MS.

UPLC (method 08_B4__1): Rt 9.50 min
UPLC (method 04_A3__1): Rt 11.23 min

Example 4

$N^{\epsilon 26}$-[2-(2-{2-[2-(2-{2-[(S)-4-Carboxy-4-(13-car-boxytridecanoylamino)butyrylamino]ethoxy}ethoxy)acetylamino]ethoxy}ethoxy)acetyl], $N^{\epsilon 37}$-[2-(2-{2-[2-(2-{2-[(S)-4-Carboxy-4-(13-carboxytridecanoylamino)butyrylamino]ethoxy}ethoxy)acetylamino]ethoxy}ethoxy)acetyl][Aib$^8$,Arg$^{34}$,Lys$^{37}$]GLP-1(7-37)-peptide (SEQ ID NO: 7), Chem. 23:

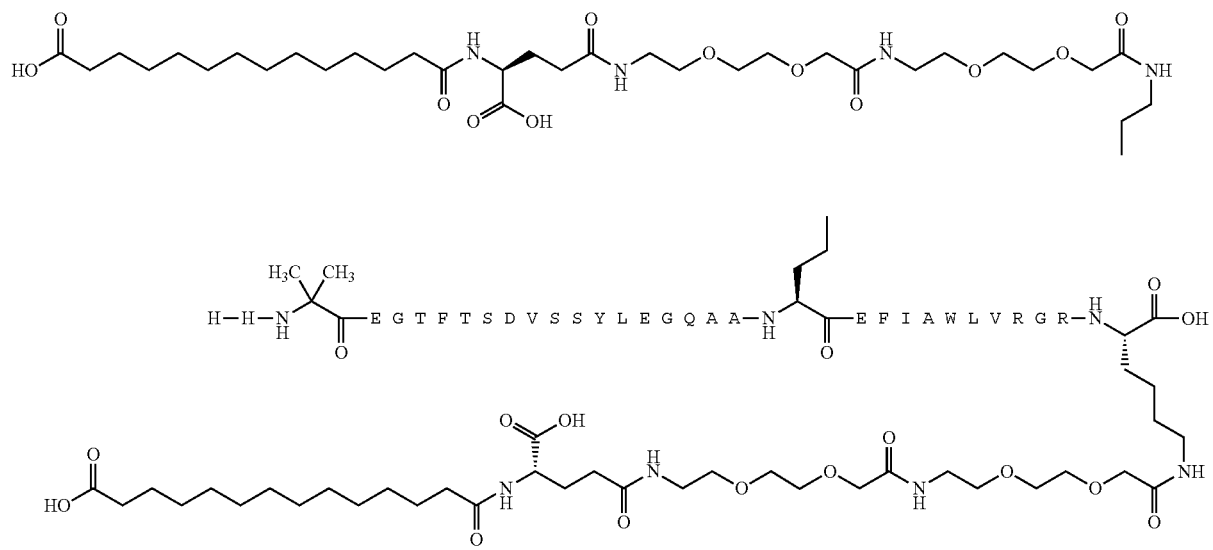

Preparation method: As in Example 3, except for the use of tetradecanedioic acid mono-t-butyl ester in the side chain. The theoretical molecular mass of 4788.5 was confirmed by MALDI-MS UPLC (method 08_B4__1): Rt 8.74 min
UPLC (method 04_A3__1): Rt 9.39 min

Example 5

$N^{\epsilon 26}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], $N^{\epsilon 37}$-(2-{2-[2-(2-{2-[(S)-4-Carboxy-4-(11-carboxyundecanoylamino)butyrylamino]ethoxy}ethoxy)acetylamino]ethoxy}ethoxy)acetyl][Aib$^8$,Arg$^{34}$,Lys$^{37}$]GLP-1(7-37)-peptide (SEQ ID NO: 7), Chem. 24:

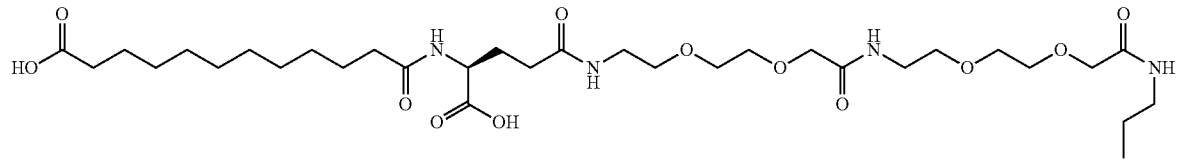

-continued

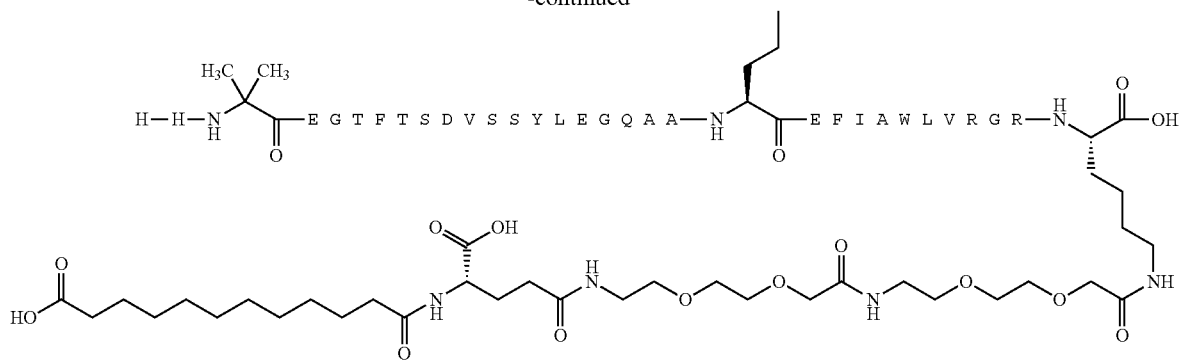

Preparation method: As in Example 3, except for the use of dodecanedioic acid mono-t-butyl ester in the side chain.
The theoretical molecular mass of 4732.4 was confirmed by MALDI-MS.
  UPLC (method 08_B4__1): Rt 8.19 min
  UPLC (method 04_A3__1): Rt 8.17 min

Example 6

$N^{\epsilon 26}$-[2-(2-{2-[2-(2-{2-[(S)-4-Carboxy-4-(15-carboxypentadecanoylamino)butyrylamino]ethoxy}ethoxy)acetylamino]ethoxy}ethoxy)acetyl],
$N^{\epsilon 37}$-[2-(2-{2-[2-(2-{2-[(S)-4-Carboxy-4-(15-carboxypentadecanoylamino)butyrylamino]ethoxy}ethoxy)acetylamino]ethoxy}ethoxy)acetyl][Aib$^8$,Arg$^{34}$,Lys$^{37}$]GLP-1(7-37)-peptide amide (SEQ ID NO: 7), Chem. 25:

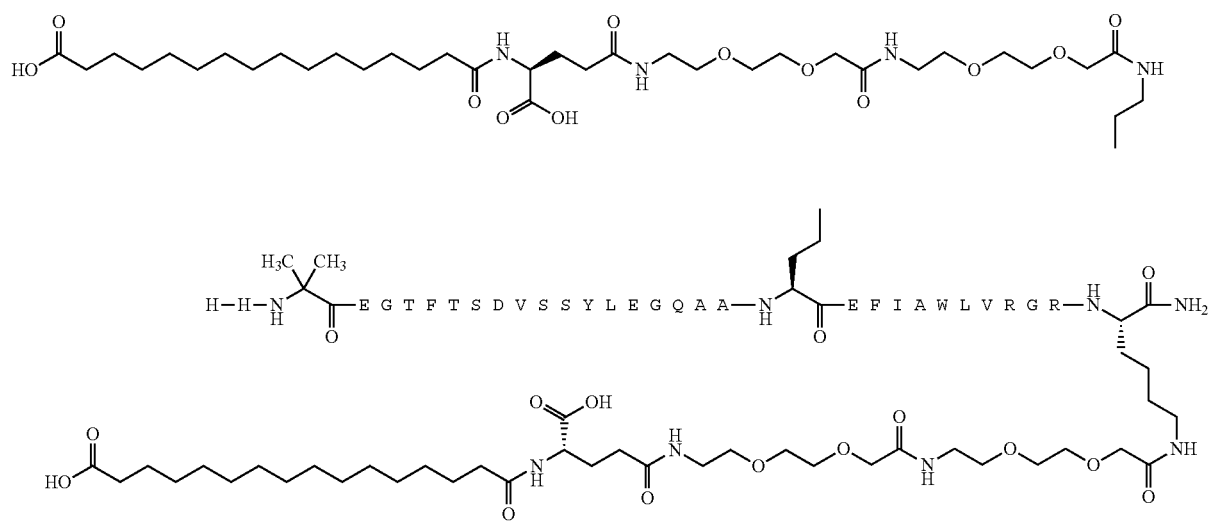

Preparation method: As in Example 3, except that the resin used was Tentagel S RAM with a loading of 0.24 mmol/g and the Fmoc-Lys(Mtt) was used both on positions 26 and 37.

The theoretical molecular mass of 4843.6 was confirmed by MALDI-MS.

UPLC (method 08_B4__1): Rt 9.43 min
  UPLC (method 04_A3__1): Rt 11.88 min

Example 7

$N^{\epsilon26}$-[2-(2-{2-[2-(2-{2-[(S)-4-Carboxy-4-(13-carboxytridecanoylamino)butyrylamino]ethoxy}ethoxy)acetylamino]ethoxy}ethoxy)acetyl], $N^{\epsilon37}$-[2-(2-{2-[2-(2-{2-[(S)-4-Carboxy-4-(13-carboxytridecanoylamino)butyrylamino]ethoxy}ethoxy)acetylamino]ethoxy}ethoxy)acetyl] [Aib$^8$,Arg$^{34}$,Lys$^{37}$]GLP-1(7-37)-peptide amide (SEQ ID NO: 7), Chem. 26:

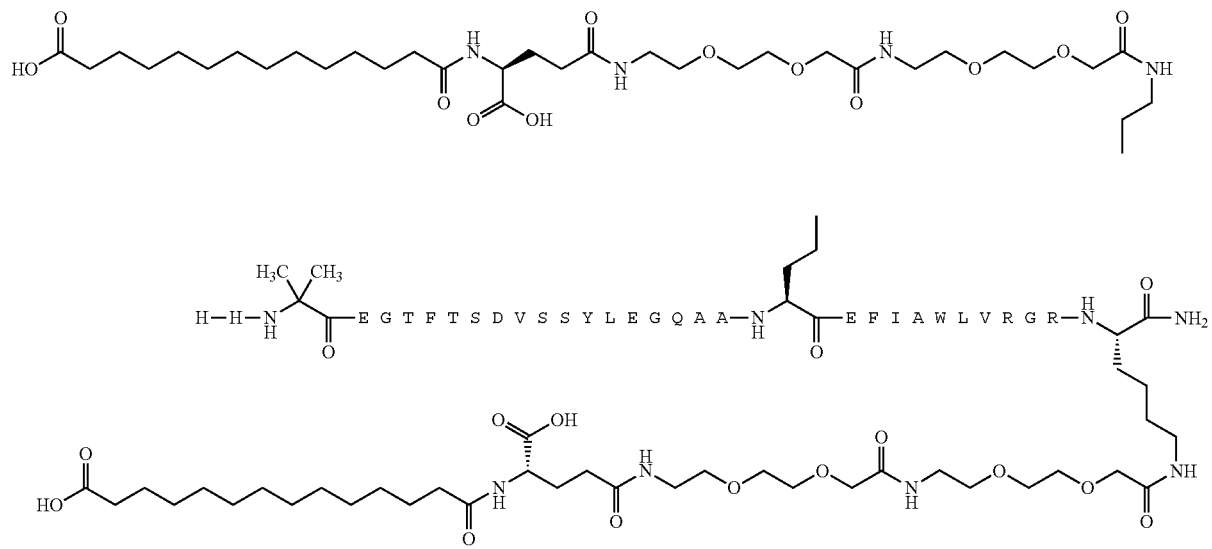

Preparation method: As in Example 6, except for the use of tetradecanedioic acid mono-t-butyl ester in the side chain. The theoretical molecular mass of 4787.5 was confirmed by MALDI-MS.

UPLC (method 08_B4_1): Rt 8.72 min
UPLC (method 04_A3_1): Rt 9.98 min

Example 8

$N^{\epsilon26}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], $N^{\epsilon37}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl] [Aib$^8$,Arg$^{34}$,Lys$^{37}$]GLP-1(7-37)-peptide amide (SEQ ID NO: 7), Chem. 27:

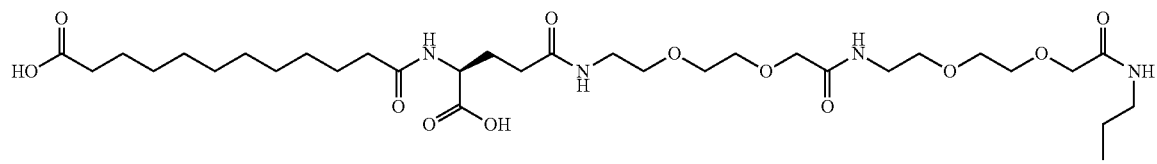

-continued

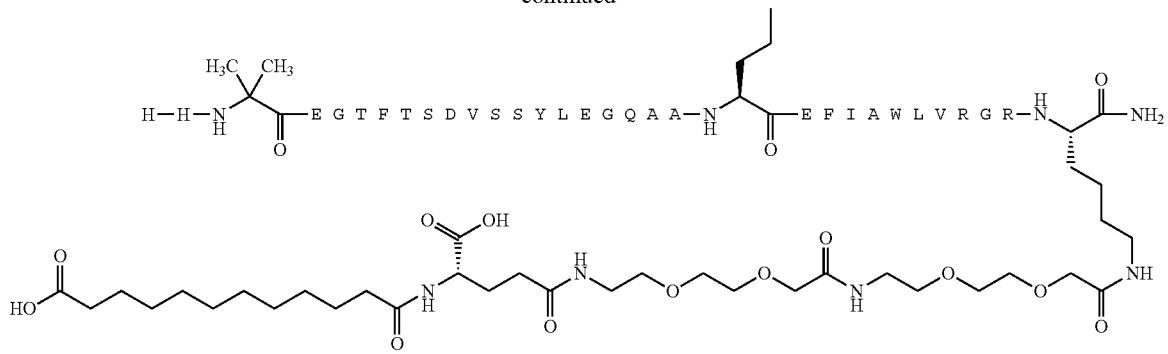

Preparation method: As in Example 6, except for the use of dodecanedioic acid mono-t-butyl ester in the side chain.
The theoretical molecular mass of 4731.4 was confirmed by MALDI-MS.
  UPLC (method 08_B4__1): Rt 8.16 min
  UPLC (method 04_A3__1): Rt 8.83 min Example 9

$N^{\epsilon 26}$-[2-[2-(2-{2-[(S)-4-Carboxy-4-(13-carboxytridecanoylamino)butyrylamino]ethoxy}ethoxy)acetyl], $N^{\epsilon 37}$-[2-[2-(2-{2-[(S)-4-Carboxy-4-(13-carboxytridecanoylamino)butyrylamino]ethoxy}ethoxy)acetyl][Aib$^8$,Arg$^{34}$,Lys$^{31}$GLP-1(7-37)-peptide amide (SEQ ID NO: 7), Chem. 28:

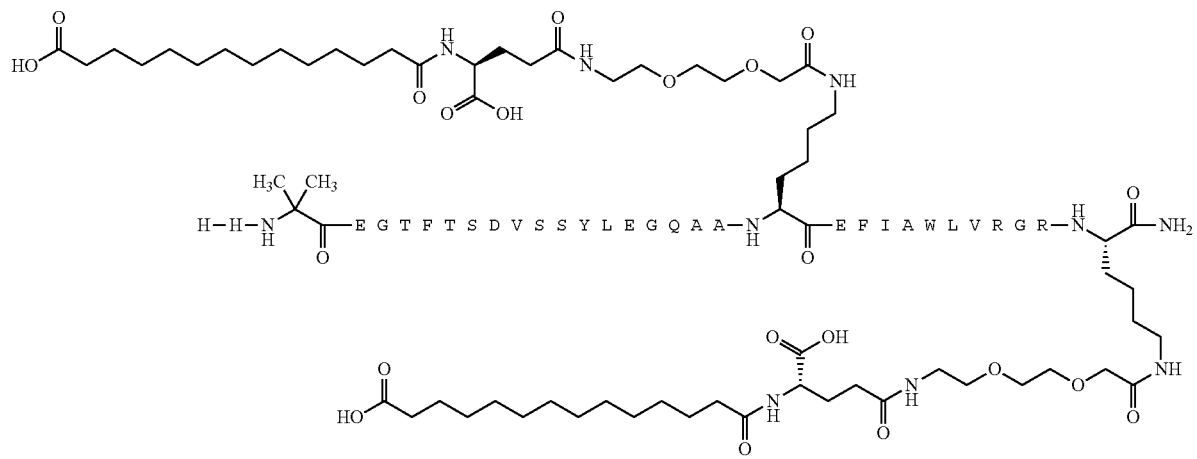

Preparation method: As in Example 7.
The theoretical molecular mass of 4497.2 was confirmed by MALDI-MS.
  UPLC (method 08_B4__1): Rt 8.85 min
  UPLC (method 04_A3__1): Rt 10.27 min

Example 10

$N^{\epsilon 26}$-[2-{2-[(S)-4-Carboxy-4-(13-carboxytridecanoylamino)butyrylamino]], $N^{\epsilon 37}$-[2-{2-[(S)-4-Carboxy-4-(13-carboxytridecanoylamino)butyrylamino]][Aib$^8$,Arg$^{34}$,Lys$^{37}$]GLP-1(7-37)-peptide amide (SEQ ID NO: 7), Chem. 29:

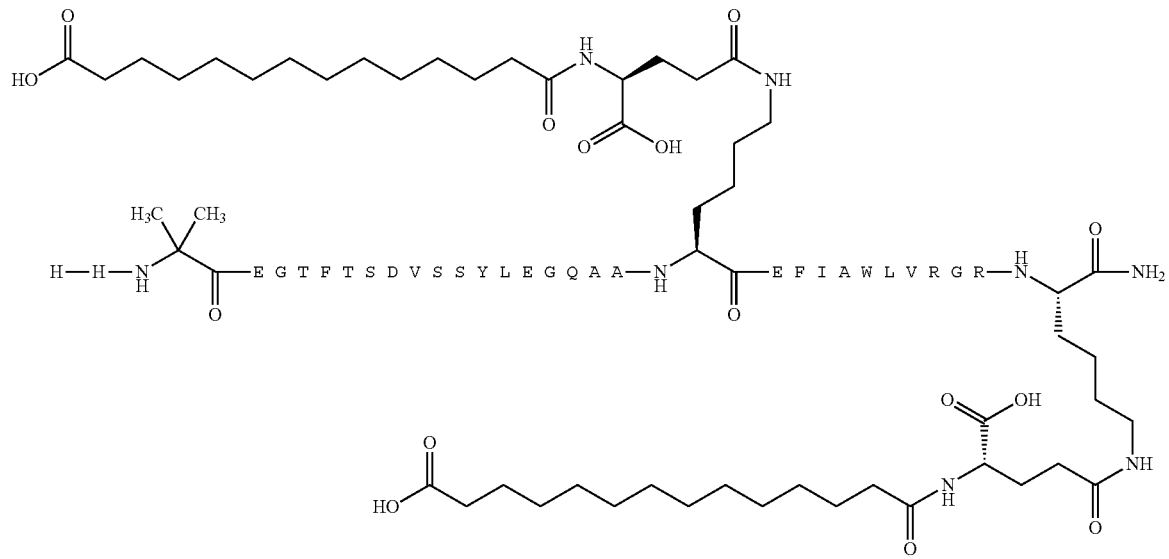

Preparation method: As in Example 7.
The theoretical molecular mass of 4206.8 was confirmed by MALDI-MS.
UPLC (method 08_B4__1): Rt 9.04 min
UPLC (method 04_A3__1): Rt 10.68 min

Example 11

$N^{\epsilon 26}$-(2-{2-[2-(2-{2-[2-(13-Carboxy-tridecanoylamino)ethoxy]ethoxy}acetylamino)ethoxy]ethoxy}acetyl), $N^{\epsilon 37}$-(2-{2-[2-(2-{2-[2-(13-Carboxy-tridecanoylamino)ethoxy]ethoxy}acetylamino)ethoxy]ethoxy}acetyl)[Aib$^8$,Arg$^{34}$, Lys$^{37}$]GLP-1(7-37)-peptide amide (SEQ ID NO: 7), Chem. 30:

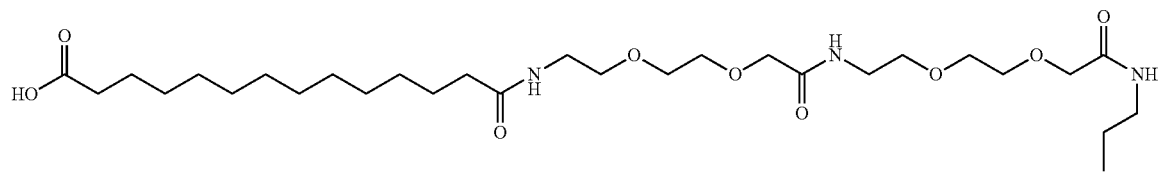

-continued

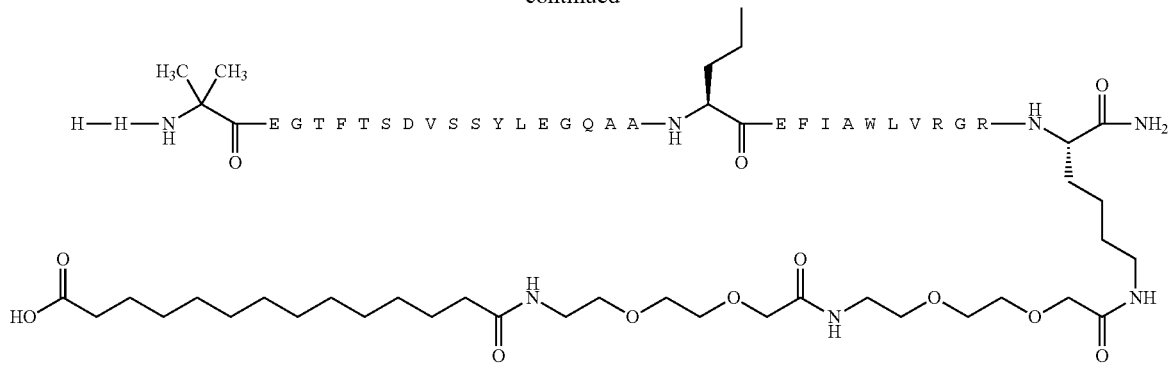

Preparation method: As in Example 7.
The theoretical molecular mass of 4529.2 was confirmed by MALDI-MS.
 UPLC (method 08_B4_1): Rt 9.07 min
 UPLC (method 04_A3_1): Rt 13.31 min Example 12

N$^{\epsilon 26}$-{2-[2-(2-{2-[2-(2-{(S)-4-Carboxy-4-[4-(4-iodo-phenyl)-butyrylamino]-butyrylamino}-ethoxy)-ethoxy]acetylamino}-ethoxy)-ethoxyFacetyll, N$^{\epsilon 37}$-{2-[2-(2-{2-[2-(2-{(S)-4-Carboxy-4-[4-(4-iodo-phenyl)-butyrylamino]-butyrylamino}-ethoxy)-ethoxy]-acetylamino}-ethoxy)-ethoxy]-acetyl}[Aib$^8$, Arg$^{34}$,Lys$^{37}$]GLP-1(7-37)-peptide (SEQ ID NO: 7)

Chem. 31:

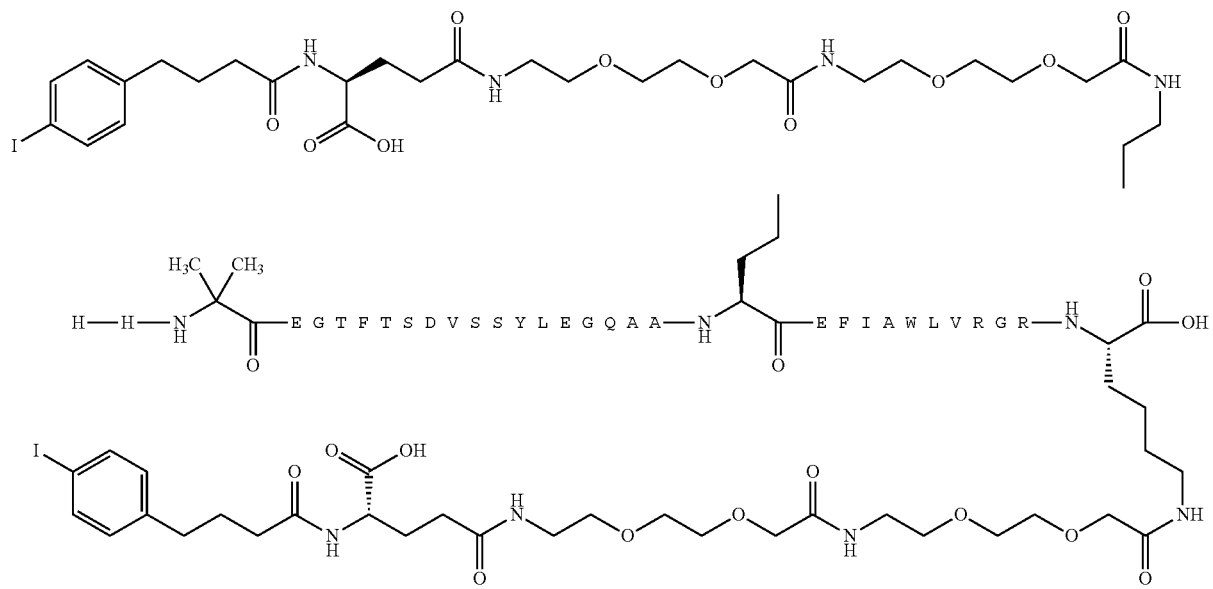

Preparation method: SPPS method B, 8-(9-fluorenylmethyloxycarbonyl-amino)-3,6-dioxaoctanoic acid (commercially available from Iris Biotech), 4-(4-iodophenyl)butyric acid (commercially available from Aldrich) and Fmoc-Glu-OtBu were coupled using SPPS method D.
 UPLC (method 04_A4_1): Rt=8.54 min
 UPLC (method 01_A4_2): Rt=10.23 min
 LCMS4: Rt=2.4 min, m/z=971(m/5) 1213 (m/44) 1617 (m/3)

Example 13

N^ε26-{2-[2-(2-{2-[2-(2-{(S)-4-Carboxy-4-[16-(4-carboxyphenoxy)hexadecanoylamino]butyrylamino}ethoxy)ethoxy]acetylamino}ethoxy)ethoxy]acetyl}, N^ε37-{2-[2-(2-{2-[2-(2-{(S)-4-Carboxy-4-[16-(4-carboxyphenoxy)hexadecanoylamino]butyrylamino}ethoxy)ethoxy]acetylamino}ethoxy)ethoxy]acetyl}-[Aib^8,Arg^34,Lys^37]GLP-1(7-37)-peptide (SEQ ID NO: 7)

Chem. 32:

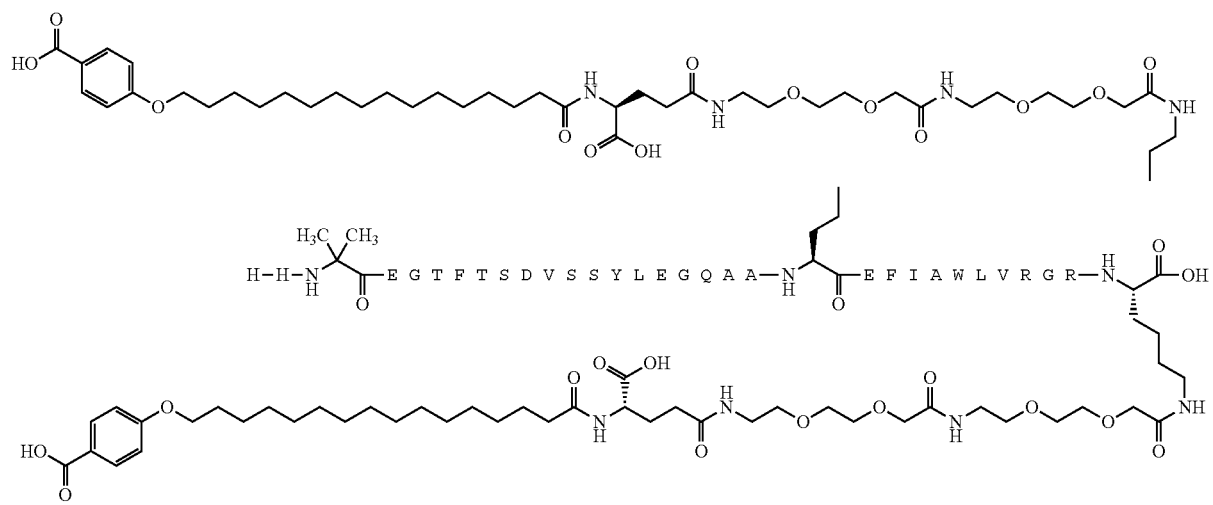

Preparation method: SPPS Method B. The final product was characterised by analytical UPLC and LC-MS with the exception that an acetic anhydride capping step was performed after the coupling of the following amino acids: Trp31, Ala25, Tyr19, Phe12 and Aib8 (2½ min, 65° C. with 1 N Acetic acid anhydride in NMP). The 4-(15-carboxy-pentadecyloxy)benzoic acid tert-butyl ester can be prepared as described in Example 17 in WO07128817.

UPLC (method 08_B4_1): Rt=11.272 min
UPLC (method 05_B10_1): Rt=7.319 min
LCMS4: Rt=2.37 min, m/z=5054.48 Calculated MW=5056.82

Example 14

N^ε26-{2-[2-(2-{2-[2-(2-{(S)-4-Carboxy-4-[16-(3-carboxyphenoxy)hexadecanoylamino]butyrylamino}ethoxy)ethoxy]acetylamino}ethoxy)ethoxy]acetyl}, N^ε37-{2-[2-(2-{2-[2-(2-{(S)-4-Carboxy-4-[16-(3-carboxyphenoxy)hexadecanoylamino]butyrylamino}ethoxy)ethoxy]acetylamino}ethoxy)ethoxy]acetyl}[Aib^8,Arg^34,Lys^37]GLP-1(7-37)-peptide (SEQ ID NO: 7)

Chem. 33:

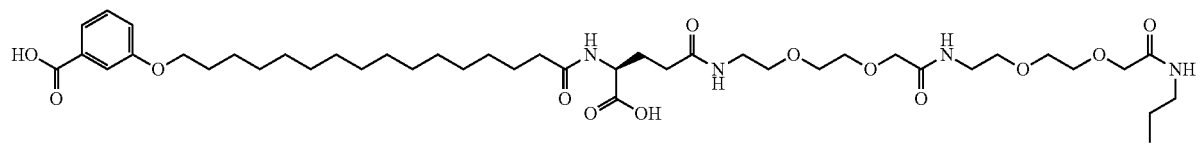

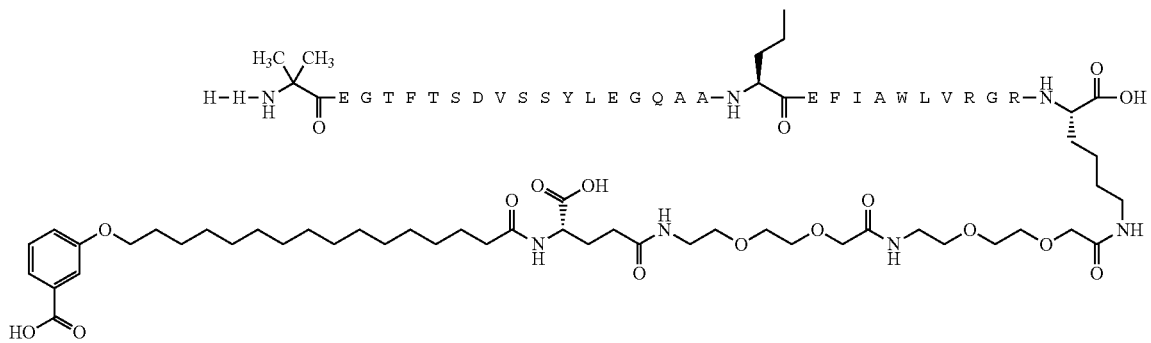

Preparation of 3-Hydroxy-benzoic acid tert-butyl ester

A mixture of 3-hydroxybenzoic acid (55.0 g, 400 mmol), di-tert-butyl dicarbonate (178 g, 820 mmol), magnesium perchlorate (0.89 g, 4.0 mmol) and dry nitromethane (750 mL) was stirred at 40° C. for 96 hrs. Ethyl acetate (800 mL) was added and the organic layer was washed with 5% aqueous solution of sodium bicarbonate (1500 mL). The organic solution was dried over anhydrous magnesium sulfate and then evaporated in vacuo. The residue was submitted to column chromatography (silica gel Fluke 60, hexanes/ethyl acetate 8:1) affording the title compound as white solid.

Yield: 9.07 g (12%)

M.p.: 94-96° C.

1H NMR spectrum (300 MHz, CDCl3, ♦$_H$ (dH)): 7.61-7.53 (m, 2H); 7.29 (t, J=8.1Hz, 1H); 7.05 (m, 1H); 6.06 (bs, 1H); 1.59 (s, 9H).

Preparation of 16-Bromo-hexadecanoic acid methyl ester

16-Bromo-hexadecanoic acid (6.0 g) was dissolved in MeOH (35 mL), toluene (100 mL) and trimethylorthoformate (20 mL), then Amberlyst 15 from Fluka (1.4 g) was added. The mixture was stirred at 55° C. for 16 h. The mixture was evaporated to dryness and dried under vacuum for 16 h to yield 7.7 g. The residue was suspended in MeOH (ca. 50 mL) and stirred for ca ½ h. The amberlyst 15 was filtered off after stirring with DCM (30 mL) for ½ h. The filtrate was concentrated to remove the DCM, and the clear solution was cooled and more MeOH (ca 20 mL, total ca 40 mL) was added. The flask was cooled and more crystals precipitated and after stirring for 30 min, the crystals were filtered off and washed with cold MeOH. The white crystals were dried under vacuum to yield 5.61 g.

Preparation of 3-(15-Methoxycarbonyl-pentadecyloxy)-benzoic acid tert-butyl ester 3-Hydroxy-benzoic acid tert-butyl ester (1.79 g) was dissolved in MeCN 75 ml, then bromo-hexadecanoic acid methyl ester (3.22 g) was added followed by K$_2$CO$_3$ (2.5 g). The reaction was stirred for 3 d at 80° C. The reaction mixture was filtered. The filtrate was evaporated, and the residue was dissolved in EtOAc 100 ml, and the EtOAc layer was washed twice with 100 ml brine. The organic layer was dried over MgSO$_4$ filtered and the solvent was removed by evaporation to give 4.165 g (98%).

Preparation of 3-(15-Carboxy-pentadecyloxy)-benzoic acid tert-butyl ester 3-(15-Methoxycarbonyl-pentadecyloxy)-benzoic acid tert-butyl ester (4.165 g) was dissolved in 50 ml THF and 50 ml MeOH. Water (10 mL) was added followed by LiOH (0.565 g, 13.5 mmol). The reaction was for 16 h at room temperature. The reaction mixture was evaporated and the residue was dissolved in EtOAC 150 ml, and water 80 and 20 ml of 1 N HCl was added. The layers were separated and the organic layer was dried over MgSO$_4$, filtered and the solvent was removed by evaporation to give a white solid compound (3.91 g, 97%).

Preparation method: SPPS Method B and using 3-(15-Carboxy-pentadecyloxy)-benzoic acid tert-butyl ester in similar fashion as in Example 1. The final product was characterised by analytical UPLC and LC-MS with the exception that an acetic anhydride capping step was performed after the coupling of the following amino acids: Trp31, Ala25, Tyr19, Phe12 and Aib8 (2½ min, 65° C. with 1 N Acetic acid anhydride in NMP).

UPLC (method 08_B4_1): Rt=11.201 min

UPLC (method 05_B10_1): Rt=8.622 min

LCMS4: Rt=2.37 min, m/z=1011.88 (m/5); 1664.32 (m/4); 5053.28

Calculated MW=5056.82

Example 15

$N^{\epsilon 26}$-{2-[2-(2-{(S)-4-Carboxy-4-[10-(4-carboxyphenoxy)decanoylamino]butyrylamino}ethoxy)-ethoxy]acetyl}, $N^{\epsilon 37}$-{2-[2-(2-{(S)-4-Carboxy-4-[10-(4-carboxyphenoxy)decanoylamino]-butyrylamino}ethoxy)ethoxy]acetyl}[Aib$^8$,Arg$^{34}$,Lys$^{37}$]GLP-1(7-37)-peptide (SEQ ID NO: 7)

Chem. 34:

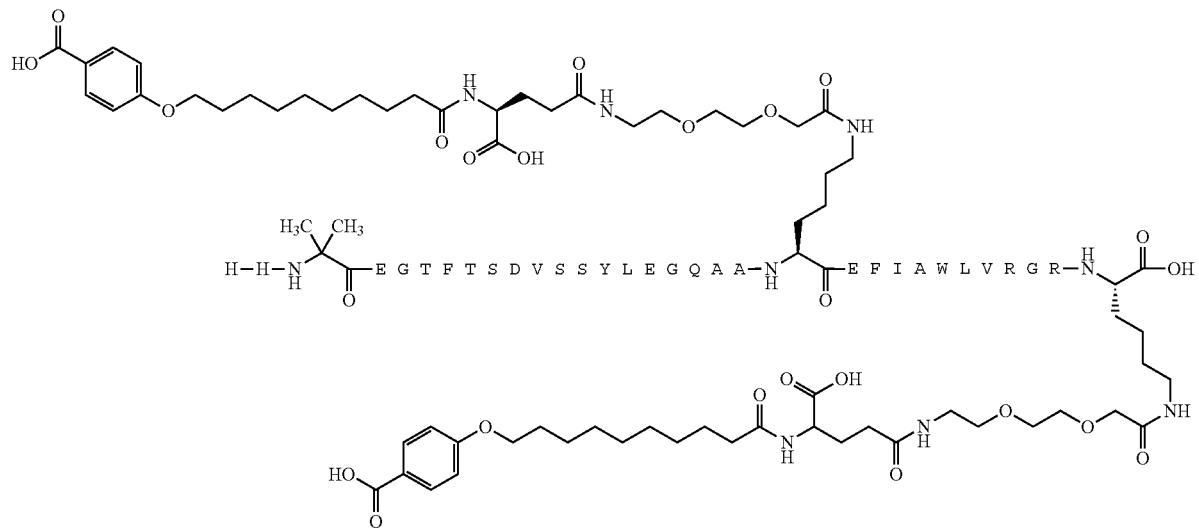

Preparation method: SPPS method B, starting with low-load Fmoc-Lys(Mtt)-Wang resin. Fmoc-Lys(Mtt)-OH was used in position 26, and Boc-His(Trt)-OH was used in position 7. The Mtt was removed with HFIP, and 8-(9-fluorenyl-methyloxycarbonyl-amino)-3,6-dioxaoctanoic acid (commercially available from Iris Biotech), Fmoc-Glu-OtBu and 4-(9-carboxy-nonyloxy)-benzoic acid tert-butyl ester (prepared as described in Example 25, step 2 of WO 2006/082204) were coupled using SPPS method D.

UPLC (method 08_B4__1): Rt=8.8 min
UPLC (method 04_A3__1): Rt=9.6 min
LCMS4: 4598.0
Calculated MW=4598.2

Example 16

$N^{\epsilon 26}$-{2-[2-(2-{2-[2-(2-{(S)-4-Carboxy-4-[12-(3-carboxyphenoxy)dodecanoylamino]butyrylamino}ethoxy)ethoxy]acetylamino}ethoxy)ethoxy]a cetyl}, $N^{\epsilon 37}$-{2-[2-(2-{2-[2-(2-{(S)-4-Carboxy-4-[12-(3-carboxyphenoxy)dodecanoylamino]butyrylamino}ethoxy)ethoxy]acetylamino}ethoxy)ethoxy]acetyl][Aib$^8$,Arg$^{34}$,Lys$^{37}$]GLP-1(7-37)-peptide (SEQ ID NO: 7)

Chem. 35:

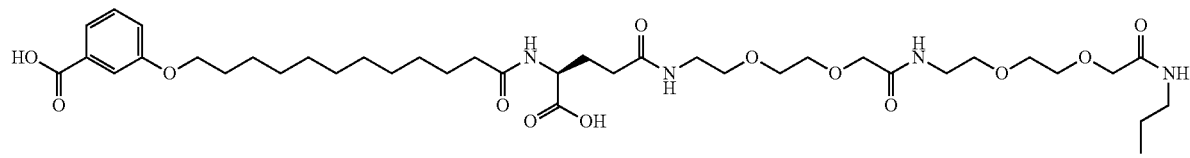

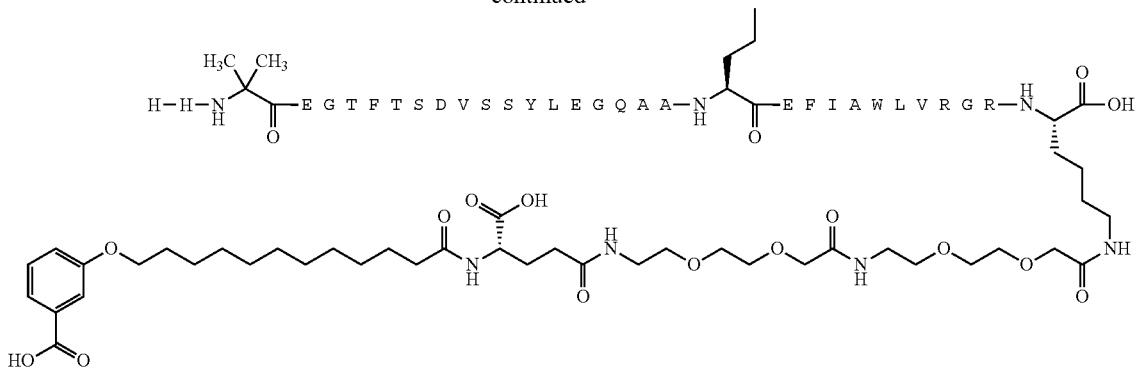

Preparation method: SPPS Method B. The 3-(11-carboxy-undecyloxy)-benzoic acid tert-butyl ester was prepared in similar fashion as described for 3-(15-carboxy-pentadecyloxy)-benzoic acid tert-butyl ester, empoying 12-bromo-dodecanoic acid. The final product was characterised by analytical UPLC and LC-MS with the exception that an acetic anhydride capping step was performed after the coupling of the following amino acids: Trp31, Ala25, Tyr19, Phe12 and Aib8 (2% min, 65° C. with 1 N Acetic acid anhydride in NMP)

UPLC (method 08_B4_1): Rt=9.449 min

LCMS4: Rt=2.37 min, m/z=m/z: 1011.88 (m/4); 1264.32 (m/3); 4942.24

Calculated MW=4944.608

Example 17

$N^{\epsilon 26}$-[2-(2-[2-(2-[2-(2-[4-(10-(4-Carboxyphenoxy)decanoylamino)-4(S)-carboxybutyrylamino]ethoxy)ethoxy]acetylamino)ethoxy]ethoxy)acetyl]-$N^{\epsilon 37}$-[2-(2-[2-(2-[2-(2-[4-(10-(4-Carboxyphenoxy)decanoylamino)-4(S)-carboxybutyrylamino]ethoxy)ethoxy]acetylamino) ethoxy]ethoxy)acetyl][Aib$^8$, His$^{31}$,Gln$^{34}$,Lys$^{37}$]GLP-1(7-37)-peptide (SEQ ID NO: 3)

Chem. 36:

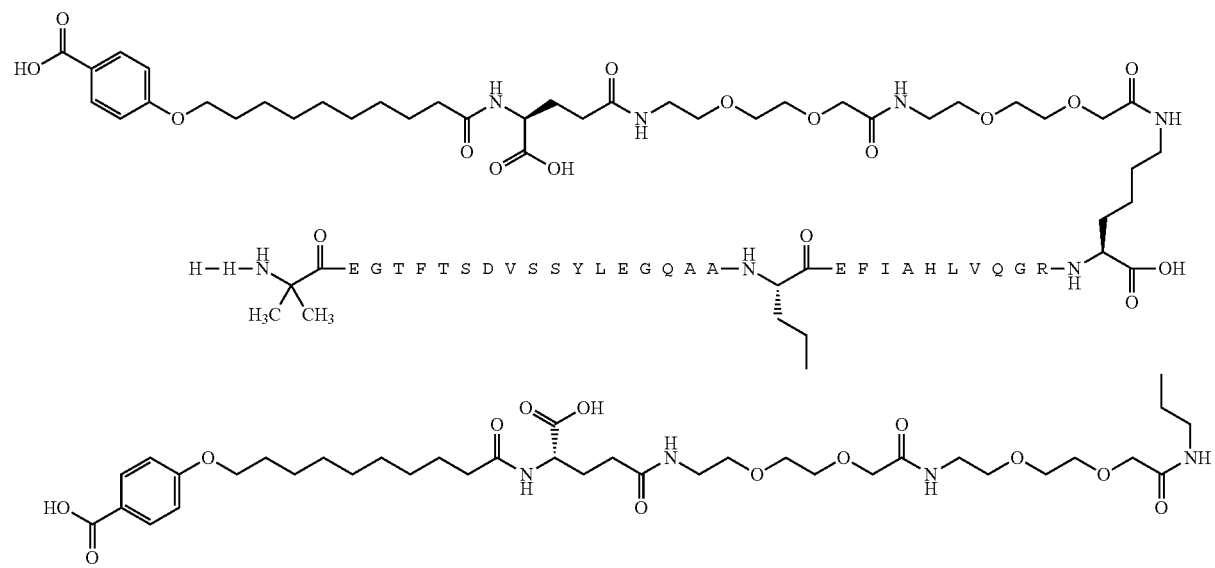

Preparation: SPPS method A, starting with low-load Fmoc-Lys(Mtt)-Wang resin. Fmoc-Lys(Mtt)-OH was used in position 26, and Boc-His(trt)-OH was used in position 7. The Mtt was removed with HFIP, and 8-(9-fluorenylmethyloxycarbonyl-amino)-3,6-dioxaoctanoic acid (commercially available from Iris Biotech) was coupled twice followed by Fmoc-Glu-OtBu and 4-(9-carboxy-nonyloxy)-benzoic acid tert-butyl ester (prepared as described in Example 25, step 2 of WO 2006/082204) were coupled using SPPS method A.

UPLC (method 05_B5_1): Rt=4.95 min (92%)

LCMS4: m/z=4011, calculated=4011

Example 18

N^ε26^-{2-[2-(2-{2-[2-(2-{(S)-4-Carboxy-4-[4-(4-methylphenyl)butyrylamino]butyrylamino}ethoxy)ethoxy]acetylamino}ethoxy)ethoxy]acetyl}, N^ε37^-{2-[2-(2-{2-[2-(2-{(S)-4-Carboxy-4-[4-(4-methylphenyl)butyrylamino]butyrylamino}ethoxy)ethoxy]-acetylamino}ethoxy)ethoxy]acetyl}[Aib^8^,Arg^34^,Lys^37^]GLP-1(7-37)-peptide (SEQ ID NO: 7)

Chem. 37:

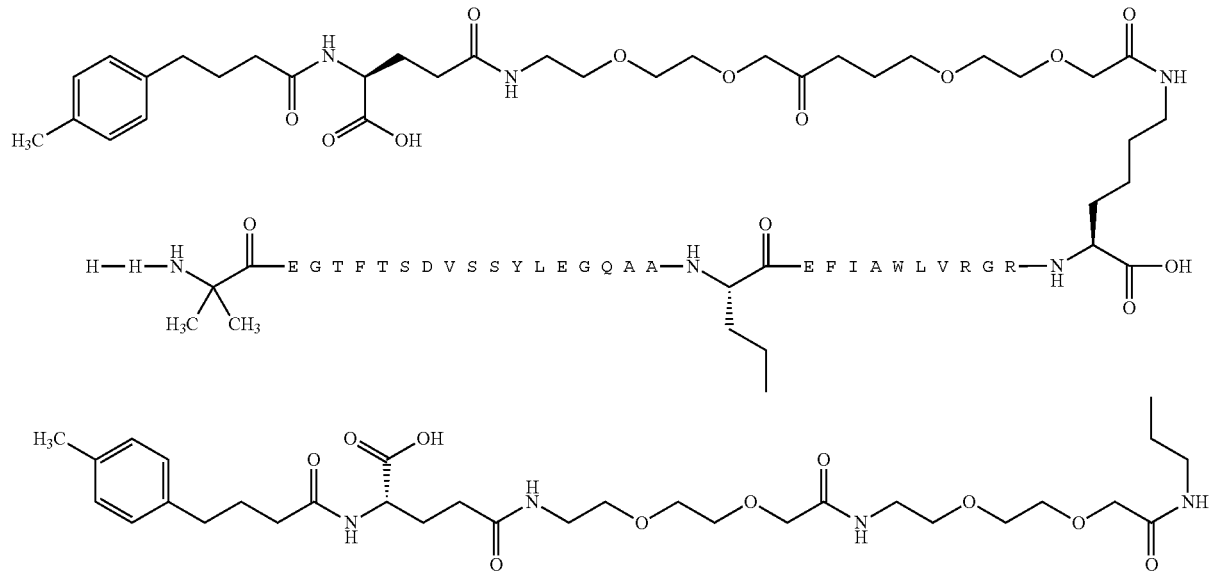

Preparation: SPPS method B, 8-(9-fluorenylmethyloxycarbonyl-amino)-3,6-dioxaoctanoic acid (commercially available from Iris Biotech), 4-(4-methylphenyl)butyric acid (commercially available from ABCR) and Fmoc-Glu-OtBu were coupled using SPPS method D.

UPLC (method 01_B4_1): Rt=9.93 min

LCMS4: Rt=2.44 min, m/z=926(m/5) 1157(m/4) 1543(m/3)

Example 19

N^ε26^-((S)-4-Carboxy-4-{(S)-4-carboxy-4-[10-(4-carboxyphenoxy)-decanoylamino]butyrylamino}butyryl), N^ε37^-((S)-4-Carboxy-4-{(S)-4-carboxy-4-[10-(4-carboxyphenoxy)-decanoylamino]butyrylamino}butyryl)[Aib^8^,Arg^34^,Lys^37^]GLP-1(7-37)-peptide (SEQ ID NO: 7)

Chem. 38:

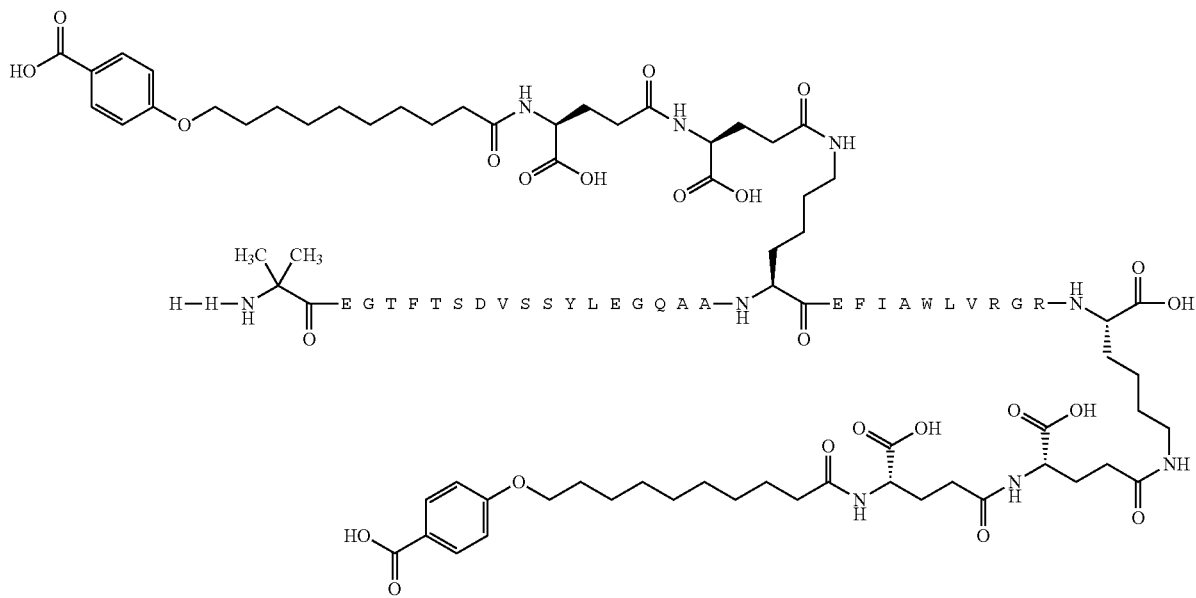

Preparation: SPPS method B, starting with low-load Fmoc-Lys(Mtt)-Wang resin. Fmoc-Lys(Mtt)-OH was used in position 26, and Boc-His(Trt)-OH was used in position 7. The Mtt was removed with HFIP, and Fmoc-Glu-OtBu and 4-(9-carboxy-nonyloxy)-benzoic acid tert-butyl ester (prepared as described in Example 25, step 2 of WO 2006/082204) were coupled using SPPS method D.

UPLC (method 08_B4__1): Rt=8.6 min
UPLC (method 04_A3__1): Rt=7.9 min
LCMS4: 4565.0
Calculated MW=4566.1

Example 20

$N^{\epsilon 26}$-{2-[2-(2-{2-[2-(2-{4-Carboxy-4-[10-(3-carboxyphenoxy)decanoylamino]butyrylamino}ethoxy)ethoxy]acetylamino}ethoxy)ethoxy]acetyl}, $N^{\epsilon 37}$-{2-[2-(2-{2-[2-(2-{4-Carboxy-4-[10-(3-carboxyphenoxy)decanoylamino]butyrylamino}ethoxy)ethoxy]acetylamino}ethoxy)ethoxy]acetyl}[Aib$^8$,Arg$^{34}$,Lys$^{37}$]GLP-1(7-37)-peptide (SEQ ID NO: 7)

Chem. 39:

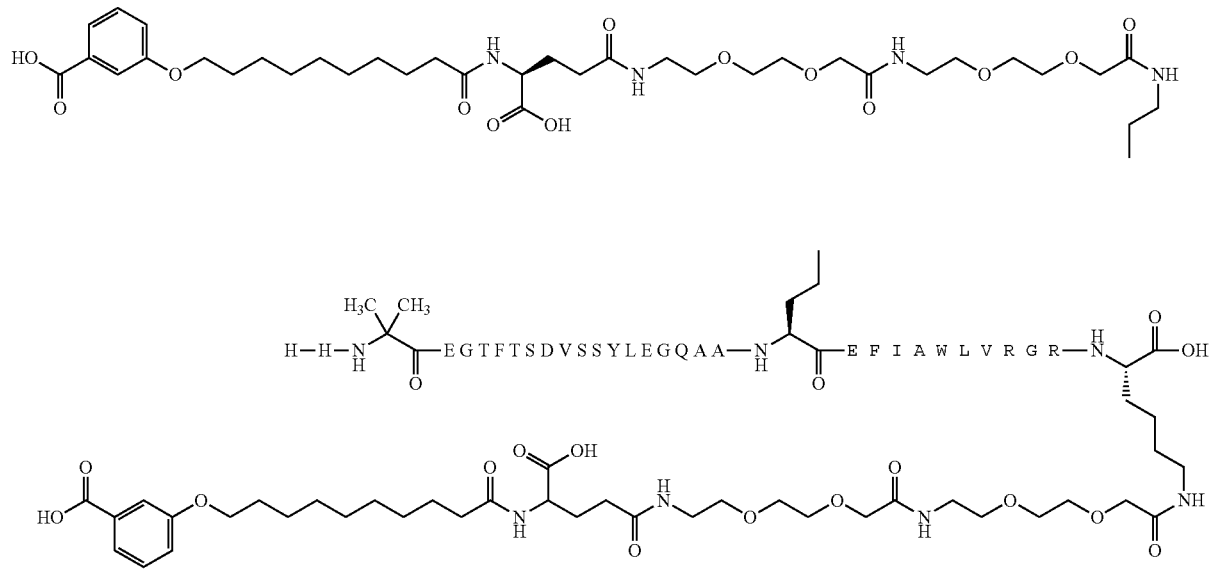

Preparation of 3-(9-Carboxy-nonyloxy)benzoic acid tert-butyl ester

3-Hydroxy-benzoic acid tert-butyl ester (3 g) was dissolved in acetonitrile (50 mL). 10-Bromo decanoic acid methyl ester from Aldrich (4.1 g) in acetonitrile (20 mL) was added and washing the vessel with acetonitrile (30 mL). Potassium carbonate was added and the mixture was refluxed under nitrogen for ca. 18 h. The reaction was cooled and evaporated to dryness. The residue was dissolved in AcOEt (80 mL) and water (30 mL) and extracted. The aqueous phase was washed with AcOEt (30 mL) and the combined organic phases were washed with water (50 mL), sat. NaCl (30 mL) and dried over MgSO$_4$ and the filtrate was concentrated under vacuum to yield a white solid (5.8 g). The residue was dissolved in DCM (15 mL) and heptane (ca 60 mL) was added, and the solution was concentrated to ca. 30 mL. After stirring for 30 min. crystals began to form, and the solution was ice-cooled. The crystals were filtered off and washed with cooled heptane and dried in under vacuum to yield 4.13 g (71%) of 3-(9-methoxycarbonyl-nonyloxy)-benzoic acid tert-butyl ester.

The crystals were dissolved in THF (30 mL) and 1N NaOH (11 mL) was added. The turbid solution was stirred for 16 h. The reaction mixture was concentrated to remove the majority of THF, and remaining aqueous solution was extracted with AcOEt (50 mL). The pH of the aqueous solution was adjusted to 1-2 with ca. 12 mL 1 N HCl, and the aqueous phase was extracted with AcOEt (25 mL). The combined organic phases were washed with water, dried over MgSO$_4$, filtered and concentrated to yield a white semi-crystalline solid (3.97 g). LCMS2: 401 (M+23), H-NMR (400 MHz, CDCl$_3$): 7.56 (d, 1H), 7.50 (m, 1H), 7.26-7.32 (m, 1H), 7.05 (dd, 1H), 3.99 (t, 2H), 2.35 (t, 2H), 1.75-1.82 (m, 2H), 1.62-1.65 (m, 2H), 1.59 (s, 9H), 1.42-1.47 (m, 2H), 1.33 (br, 8H).

Preparation method: SPPS Method B, starting with low-load Fmoc-Lys(Mtt)-Wang resin. Fmoc-Lys(Mtt)-OH was used in position 26, and Boc-His(trt)-OH was used in position 7. The Mtt was removed with HFIP, and 8-(9-fluorenylmethyloxycarbonyl-amino)-3,6-dioxaoctanoic acid (commercially available from Iris Biotech), Fmoc-Glu-OtBu, and 3-(9-carboxy-nonyloxy)-benzoic acid tert-butyl ester were coupled using a double coupling method on the Liberty Peptide synthesiser.

UPLC (method 04_A4__1): 10.01 min
UPLC (method 08_B4__1): 8.81 min
LCMS4: m/z=978.5 (M+5H)$^{5+}$, 1222.8 (M+4H)$^{4+}$, 1630.1 (M+3H)$^{3+}$

Example 21

$N^{\epsilon 26}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl], $N^{\epsilon 37}$-[2-(2-{2-[2-(2-{2-[(S)-4-Carboxy-4-(11-carboxyundecanoylamino)butyrylamino]ethoxy}ethoxy)acetylamino]ethoxy}ethoxy)acetyl] [Aib$^8$,His$^{31}$,Gln$^{34}$,Lys$^{37}$]GLP-1(7-37)-peptide (SEQ ID NO: 3)

Chem. 40:

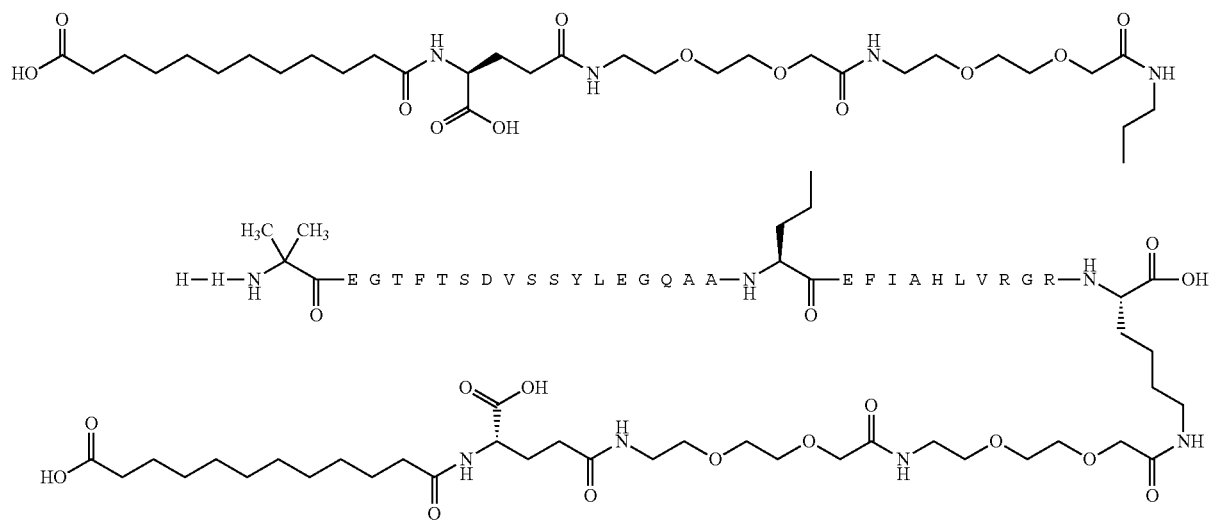

Preparation method: As in Example 5.
The theoretical molecular mass of 4655.2 was confirmed by MALDI
UPLC (method 08_B4__1): Rt=7.72 min
UPLC (method 04_A3__1): Rt=5.70 min

Example 22

$N^9$-{2-[2-(1H-Imidazol-4-yl)ethylcarbamoyl]-2-methylpropionyl}, $N^{\epsilon 26}$-{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, $N^{\epsilon 37}$-{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl} [Arg$^{34}$, Lys$^{37}$GLP-1(9-37)Glu$^{38}$-peptide (SEQ ID NO: 2)

Chem. 41:

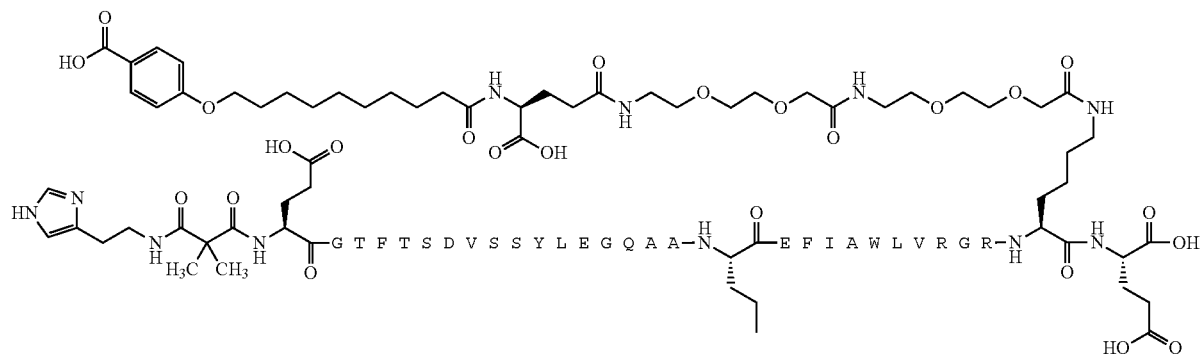

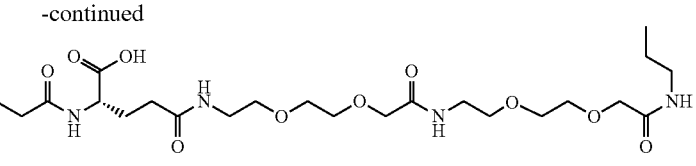

Preparation: SPPS method B. 2,2-Dimethyl-N-[2-(1-trityl-1H-imidazol-4-yl)-ethyl]-malonamic acid was coupled using the same coupling condition as an Aib amino acis. 8-(9-fluorenylmethyloxycarbonyl-amino)-3,6-dioxaoctanoic acid (commercially available from Iris Biotech), Fmoc-Glu-OtBu, and 4-(9-carboxy-nonyloxy)-benzoic acid tert-butyl ester (prepared as described in Example 25, step 2 of WO 2006/082204) were coupled using
SPPS method D.
UPLC (method 04_A3_1): Rt=9.32 min.
LCMS4: Rt=2.29 min., m/z=1669 (m/3), 1252 (m/4), 1001 (m/5)

Example 23

$N^9$-{2-[2-(1H-Imidazol-4-yl)ethylcarbamoyl]-2-methylpropionyl}-$N^{\epsilon 26}$-{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, $N^{\epsilon 37}$-{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl} [Arg$^{34}$, Lys$^{37}$]GLP-1(9-37)-peptide (SEQ ID NO: 11)

Chem. 42:

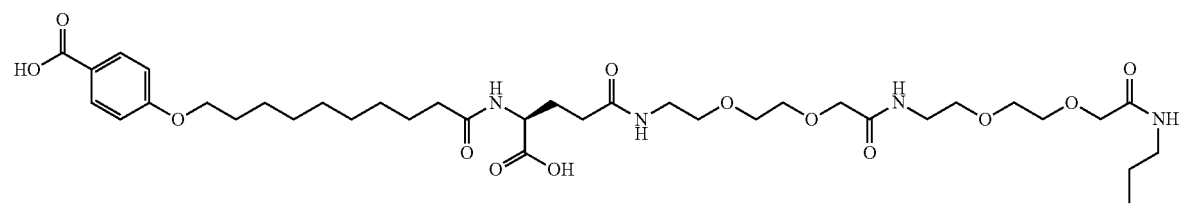

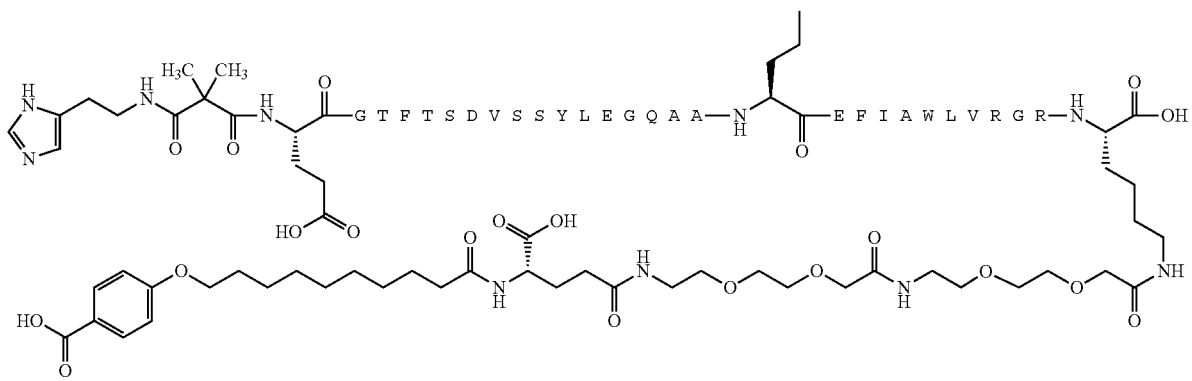

Preparation: SPPS method B, 2,2-Dimethyl-N-[2-(1-trityl-1H-imidazol-4-yl)-ethyl]-malonamic acid was coupled using the same coupling condition as an Aib amino acid. 8-(9-fluorenylmethyloxycarbonyl-amino)-3,6-dioxaoctanoic acid (commercially available from Iris Biotech), Fmoc-Glu-OtBu and 4-(9-carboxy-nonyloxy)-benzoic acid tert-butyl ester (prepared as described in Example 25, step 2 of WO 2006/082204) were coupled using SPPS method D.
UPLC (method 08_B4_1 (TFA)): Rt=8.81 min
LCMS4: Rt=2.29 min, m/z=1625 (m/3), 1219 (m/4), 975 (m/5)

Example 24

$N^{\epsilon 26}$-{2-[2-(2-{(S)-4-Carboxy-4-[2-(2-{2-[(13-carboxytridecanoylamino)]ethoxy}ethoxy)acetylamino]butyrylamino}ethoxy)ethoxy]acetyl}, $N^{\epsilon 37}$-{2-[2-(2-{(S)-4-Carboxy-4-[2-(2-{2-[(13-carboxytridecanoylamino)]ethoxy}ethoxy)acetylamino]butyrylamino}ethoxy)ethoxy]acetyl}-[Aib$^8$,Arg$^{34}$,Lys$^{37}$]GLP-1(7-37)-peptide (SEQ ID NO: 7)

Chem.43:

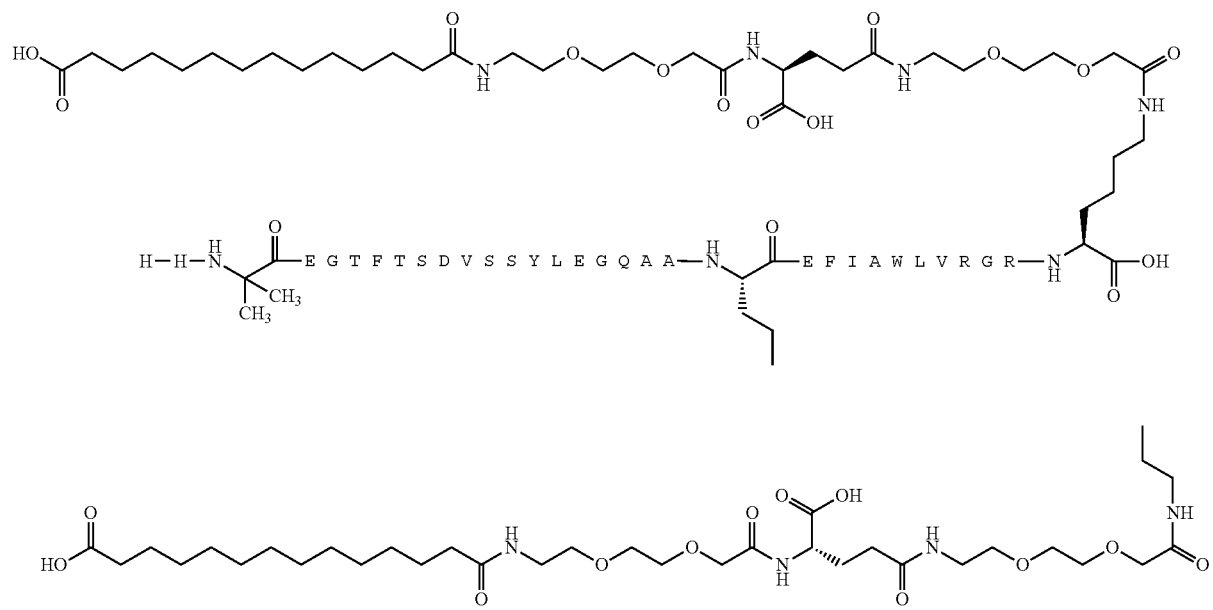

Preparation: SPPS method B, starting with low-load Fmoc-Lys(Mtt)-Wang resin. Fmoc-Lys(Mtt)-OH was used in position 26, and Boc-His(trt)-OH was used in position 7. The Mtt was removed with HFIP manually, and 8-(9-fluorenylmethyloxycarbonyl-amino)-3,6-dioxaoctanoic acid (commercially available from Iris Biotech), Fmoc-Glu-OtBu and tetradecanedioc were coupled using a double coupling method on the Liberty Peptide synthesiser. The theoretical molecular mass was confirmed by MALDI-MS.

UPLC (method 08_B4__1): Rt=8.6 min
UPLC (method 04_A3__1): Rt=9.7 min
MALDI-MS: 4788

Example 25

$N^{\epsilon 26}$-[(S)-4-Carboxy-4-{2-[2-(2-[2-(2-{2-[(13-carboxytridecanoylamino)]ethoxy}ethoxy)acetylamino]ethoxy)ethoxy]acetylamino}butyryl], $N^{\epsilon 37}$-[(S)-4-Carboxy-4-{2-[2-(2-[2-(2-{2-[(13-carboxytridecanoylamino)]ethoxy}ethoxy)acetylamino]ethoxy)ethoxy]acetylamino}butyryl][Aib$^8$,Arq$^{34}$,Lys$^{37}$]GLP-1(7-37)-peptide (SEQ ID NO: 7)

Chem. 44:

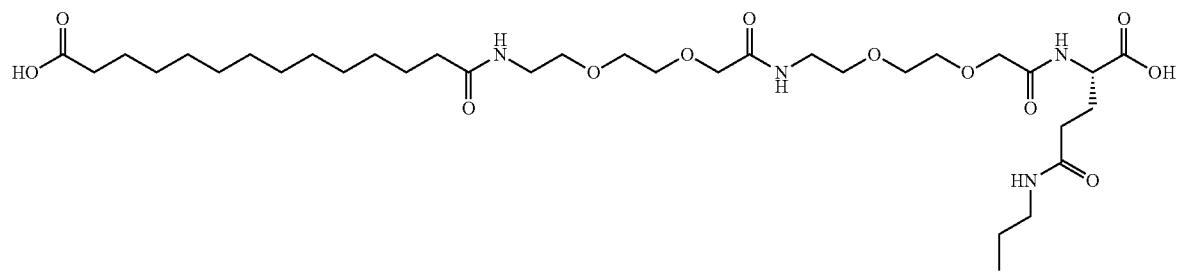

-continued

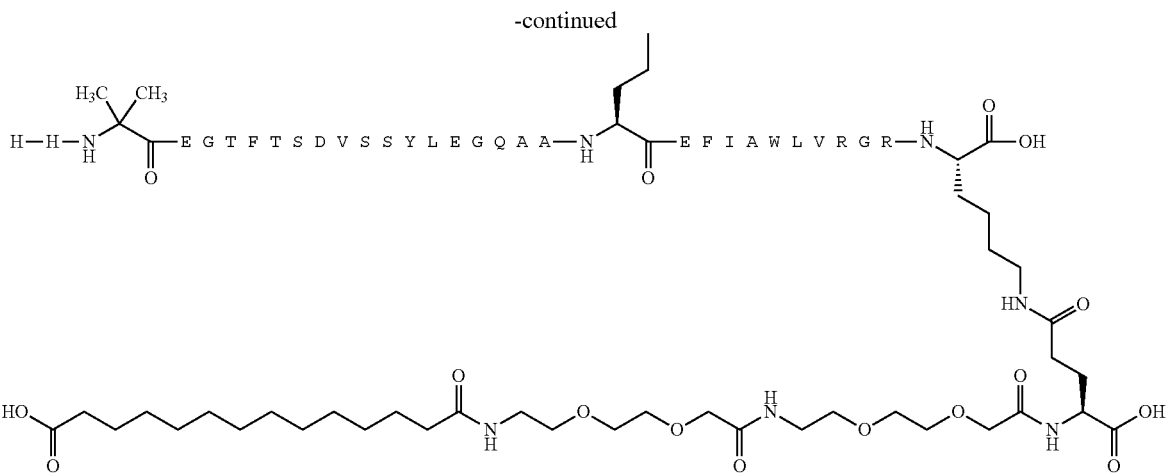

Preparation: SPPS method B, starting with low-load Fmoc-Lys(Mtt)-Wang resin. Fmoc-Lys(Mtt)-OH was used in position 26, and Boc-His(trt)-OH was used in position 7. The Mtt was removed with HFIP manually, and 8-(9-fluorenylmethyloxycarbonyl-amino)-3,6-dioxaoctanoic acid (commercially available from Iris Biotech), Fmoc-Glu-OtBu and tetradecanedioc were coupled using a double coupling method on the Liberty Peptide synthesiser. The theoretical molecular mass was confirmed by MALDI-MS.

UPLC (method 08_B4__1): Rt=8.8 min
UPLC (method 04_A3__1): Rt=10 min
MALDI-MS: 4787

Example 26

$N^{\epsilon 26}$-{2-[2-(2-{2-[2-(2-{(S)-4-[4-(4-tert-Butyl-phenyl)-butyrylamino]-4-carboxy-butyrylamino}ethoxy)ethoxy]acetylamino}ethoxy)ethoxy]acetyl}, $N^{\epsilon 37}$-{2-[2-(2-{2-[2-(2-{(S)-4-[4-(4-tert-Butyl-phenyl)-butyrylamino]-4-carboxy-butyrylamino}-ethoxy)-ethoxy]-acetylamino}-ethoxy)-ethoxy]-acetyl} [Aib$^8$,Arg$^{34}$,Lys$^{37}$]GLP-1(7-37)-peptide (SEQ ID NO: [[9]]7), Chem. 45

Chem. 45:

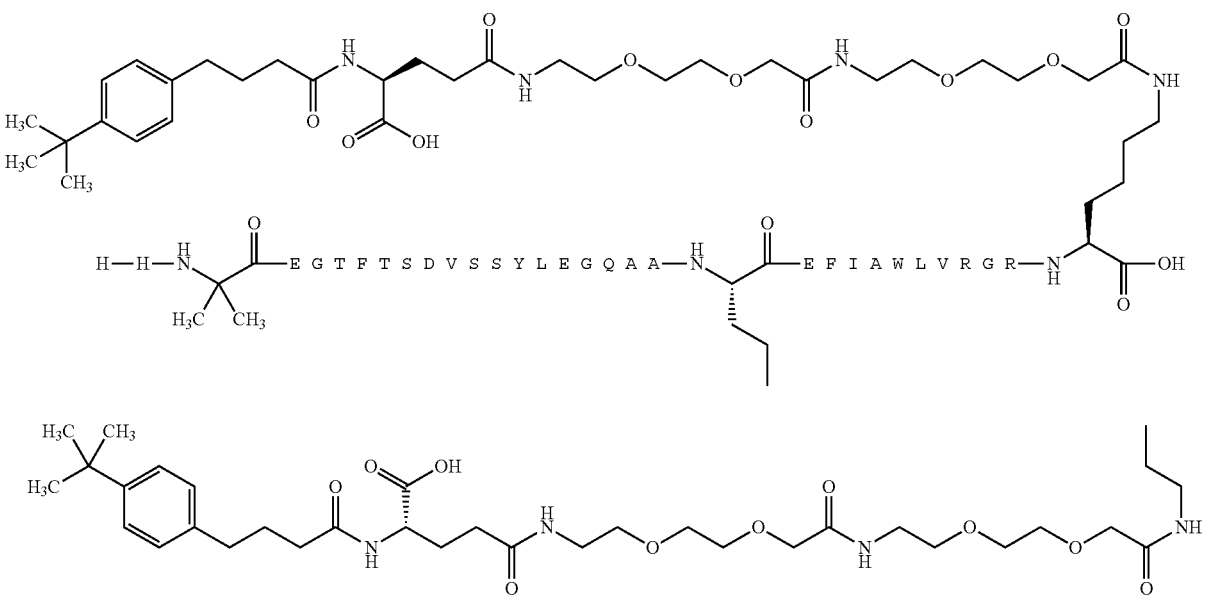

Preparation: SPPS method B, 8-(9-fluorenylmethyloxycarbonyl-amino)-3,6-dioxaoctanoic acid (commercially available from Iris Biotech), 4-(4-t-butylphenyl)butyric acid and Fmoc-Glu-OtBu were coupled using SPPS method D.

UPLC (method 08_B4__1): Rt=9.07 min
LCMS4: Rt=2.29 min, m/z=943 (m/5) 1179 (m/4) 1571 (m/3)

Example 27

N⁹-{2-[2-(1H-Imidazol-4-yl)-ethylcarbamoyl]-2-methylpropionyl}-N^(ε26)-{2-[2-(2-{2-[2-(2-{(S)-4-[4-(4-tert-Butylphenyl)butyrylamino]-4-carboxybutyrylamino}ethoxy)ethoxy]acetylamino}ethoxy)ethoxy]acetyl}, N^(ε37)-{2-[2-(2-{2-[2-(2-{(S)-4-[4-(4-tert-Butylphenyl)butyrylamino]-4-carboxybutyrylamino}ethoxy)ethoxy]acetylamino}ethoxy)ethoxy]acetyl][Arg³⁴,Lys³¹]GLP-1(9-37)-peptide (SEQ ID NO: 11)

Chem. 46:

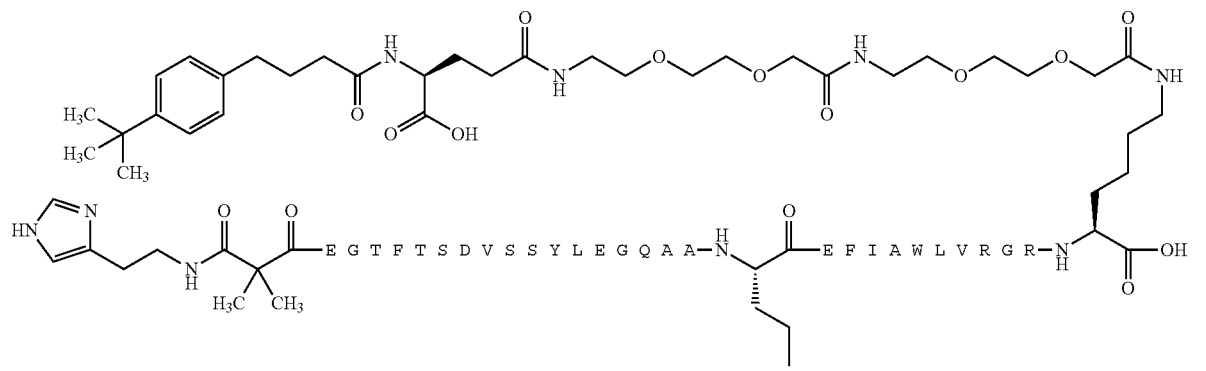

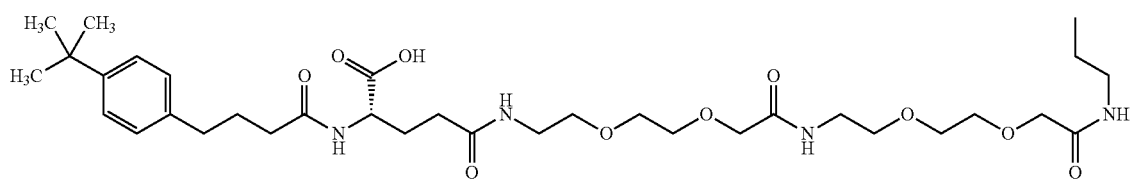

Preparation: SPPS method B, 2,2-Dimethyl-N-[2-(1-trityl-1H-imidazol-4-yl)-ethyl]-malonamic acid was coupled using the same coupling condition as Fmoc-Aib amino acid. 8-(9-fluorenylmethyloxycarbonyl-amino)-3,6-dioxaoctanoic acid (commercially available from Iris Biotech), Fmoc-Glu-OtBu and 4-(4-t-butylphenyl)butyric acid were coupled using SPPS method D.

UPLC (method 04_A4_1): Rt=10.56 min

LCMS4: Rt=2.40 min. m/z=940(m/5), 1174(m/4), 1565 (m/3)

Example 28

N^(ε26)-[2-[2-[2-[[2-[2-[2-[[(4S)-4-carboxy-4-[10-(4-carboxyphenoxy) decanoylamino]butanoyl]amino]ethoxy]ethoxy]acetyl]amino]ethoxy]ethoxy]acetyl], N^(ε37)-[2-[2-[2-[[2-[2-[2-[[(4S)-4-carboxy-4-[10-(4-carboxyphenoxy) decanoylamino]butanoyl]amino]ethoxy]ethoxy]acetyl]amino]ethoxy]ethoxy]acetyl]-[Imp⁷,Arg³⁴,Lys³⁷]-GLP-1-(7-37)-peptide (SEQ ID NO: 12)

Chem. 47:

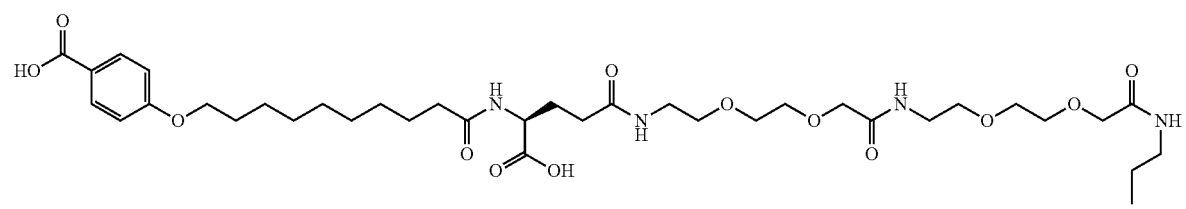

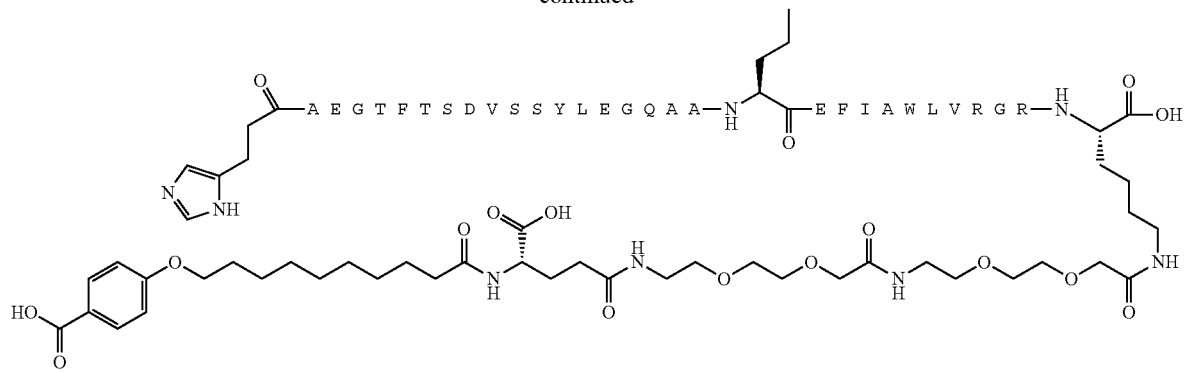

Preparation method: SPPS method B
LCMS4: Rt: 2.22 min, m/z: 4859.5; 1214.9 $(M+4H)^{4+}$; 1619.8 $(M+3H)^{3+}$
UPLC (method: 08_B4_1): Rt=8.88 min
UPLC (method: 04_A3_1): Rt=9.28 min Example 29

$N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Arg$^{34}$,Lys$^{37}$]-GLP-1-(7-37)-peptide (SEQ ID NO: 9)

Chem. 48:

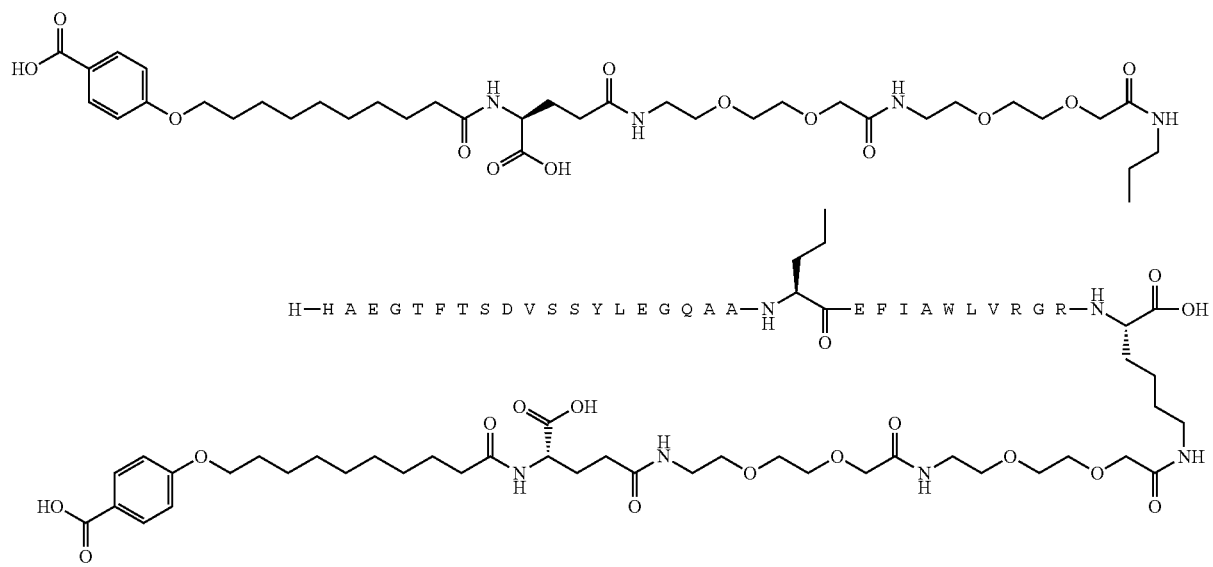

Preparation method: SPPS method B
UPLC (method 05_B5_1): Rt=5.75 min
UPLC (method 08_B2_1): Rt=13.09 min
LCMS4 (M/5)+1=976; (M/4)+1=1219; Exact mass=4874

Example 30

$N^{\varepsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\varepsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl] [Aib8,Gly9,Arg34,Lys37]-GLP-1-(7-37)-peptide
(SEQ ID NO: 5)

Chem. 49:

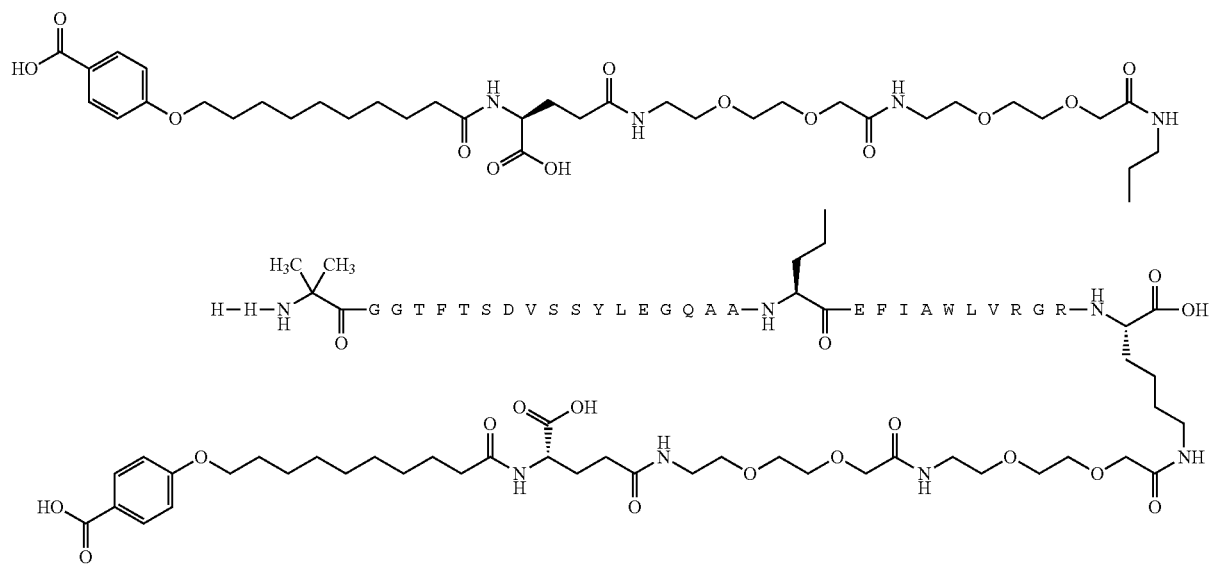

Preparation method: SPPS method A
UPLC (method 09_B2__1): Rt=13.20 min
UPLC (method 05_B5__1): Rt=6.05 min
LCMS4: (M/5)+1=964; (M/4)+1=1204; Exact mass=4816

Example 31

$N^{\varepsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl], $N^{\varepsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl] [Aib8,Arg23,Arg34,Lys37]-GLP-1-(7-37)-peptide
(SEQ ID NO: 4)

Chem. 50:

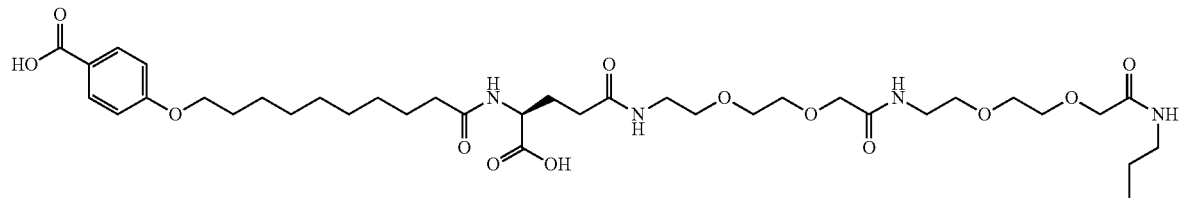

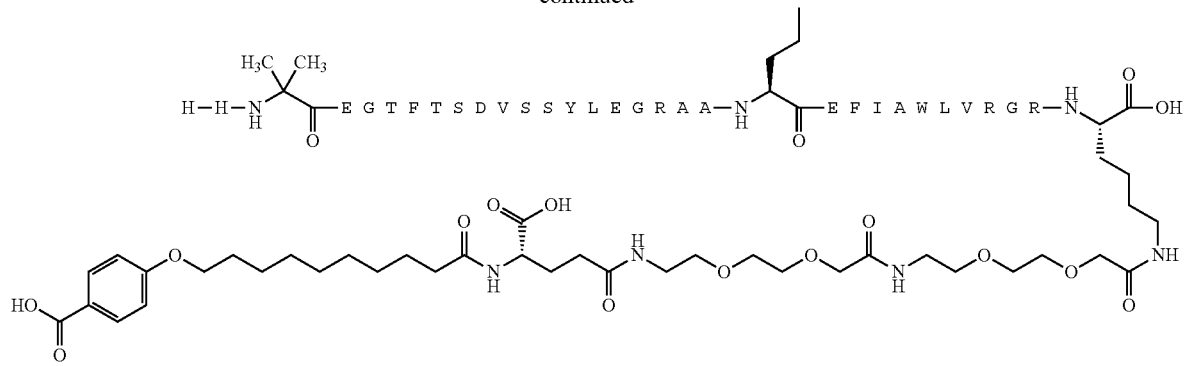

Preparation method: SPPS method B
LCMS4: Rt=2.12 min, m/z: 4916.0
UPLC (method: 08_B2__1): Rt=12.59 min
UPLC (method: 04_A3__1): Rt=10.57 min Example 32

$N^{\epsilon26}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon37}$-[2-[2-[2-[[2-[2-[2-[[(4S)-4-carboxy-4-(13-carboxytridecanoylamino)butanoyl]amino]ethoxy]ethoxy]acetyl]am no]ethoxy]ethoxy]acetyl]-[Arg34, Lys37]-GLP-1-(7-37)-peptide (SEQ ID NO: 9)

Chem. 51:

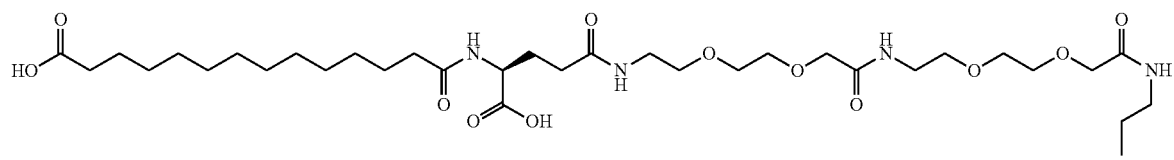

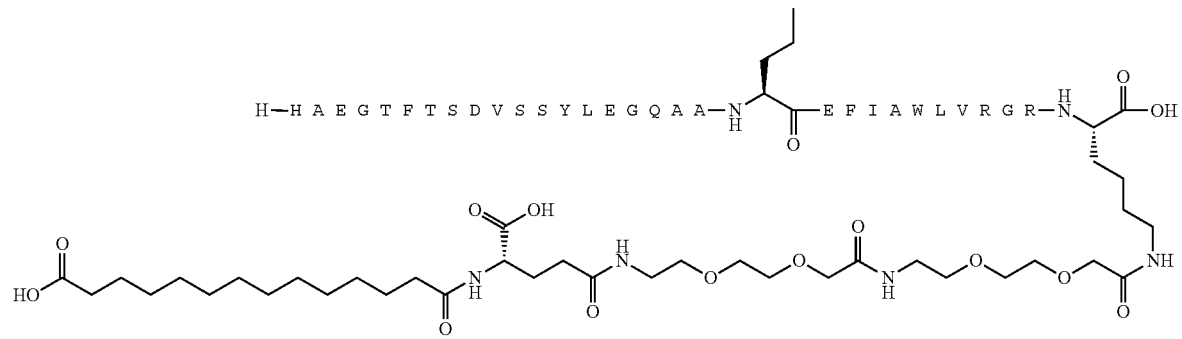

Preparation method: SPPS method B
LCMS4: Rt=2.12 min, m/z: 4774.4
UPLC (method: 09_B2__1): Rt=12.87 min
UPLC (method: 04_A3__1): Rt=8.86 min

Example 33

$N^{\epsilon26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl] [His$^{31}$,Gln$^{34}$,Lys$^{37}$]-GLP-1-(7-37)-peptide (SEQ ID NO: 10)

Chem. 52:

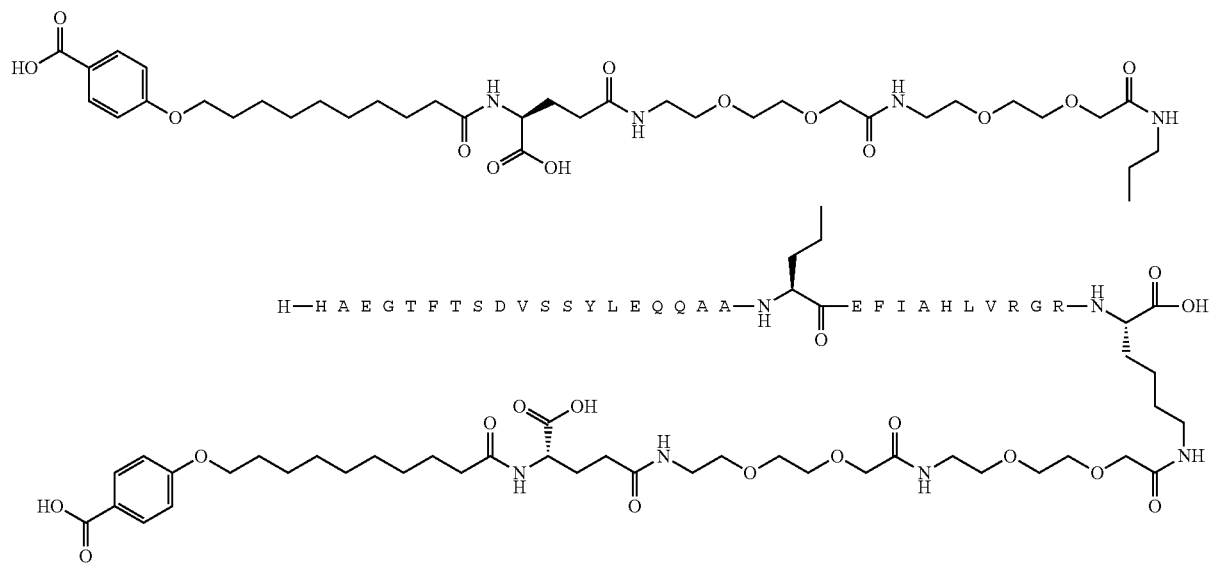

Preparation method: SPPS method B
LCMS4: Rt: =1.92 min, m/z: 4797.3; M/4: 1199.8; M/3: 1599.4
UPLC (method: 09_B4__1): Rt=8.12 min
UPLC (method: 05_B8__1): Rt=2.03 min

Example 34

$N^{\epsilon26}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon37}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[His$^{31}$, Gln$^{34}$,Lys$^{37}$]-GLP-1-(7-37)-peptide (SEQ ID NO: 10)

Chem. 53:

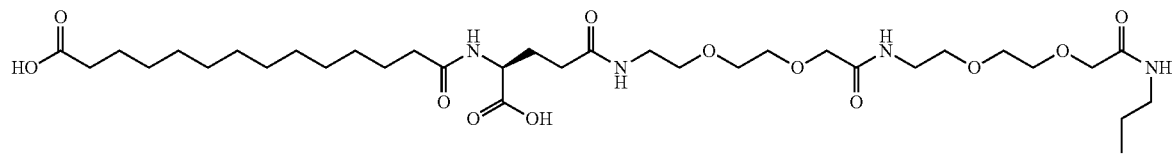

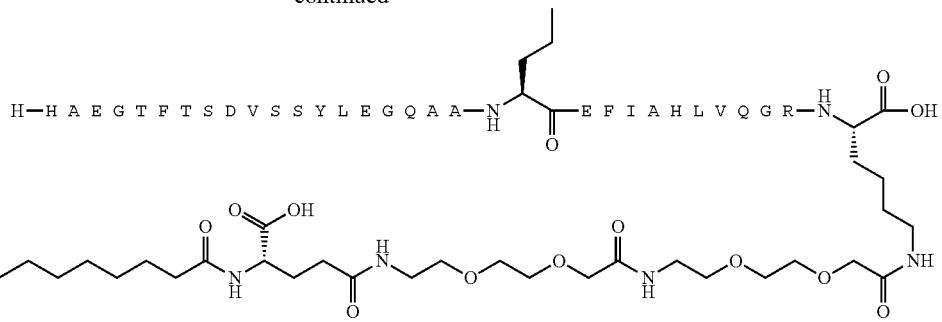

Preparation method: SPPS method B
LCMS4: Rt=1.99 min, m/z: 4697.0
UPLC (method: 09_B2__1) Rt=12.20 min
UPLC (method: 05_B5__1): Rt=5.31 min Example 35

N$^{\epsilon 26}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], N$^{\epsilon 37}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[His$^{31}$,Gln$^{34}$,Lys$^{37}$]-GLP-1-(7-37)-peptide (SEQ ID NO: 10)

Chem. 54:

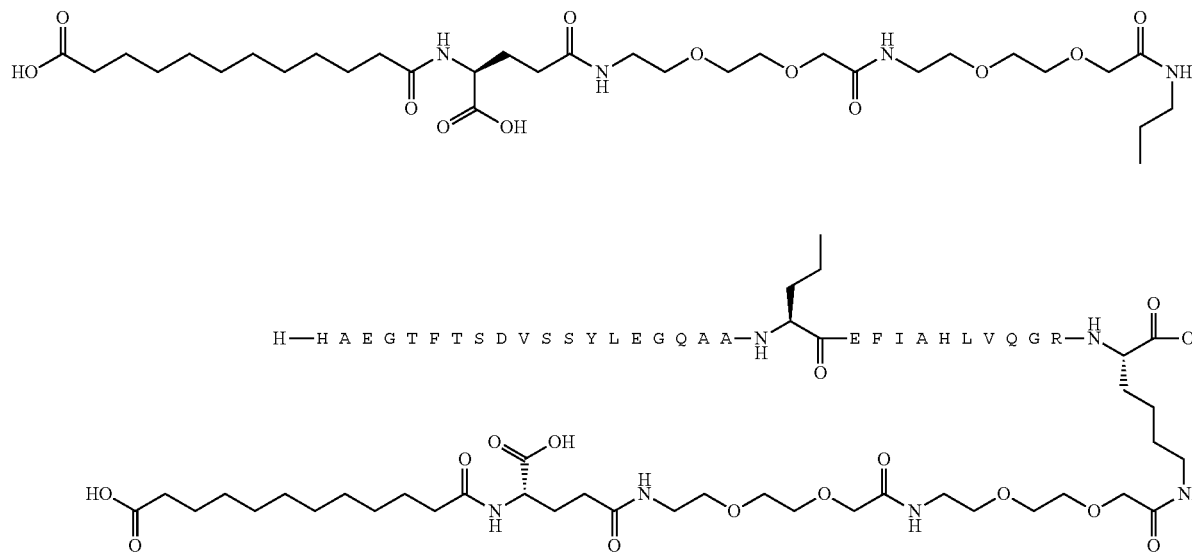

Preparation method: SPPS method B
LCMS4: Rt=1.89 min, m/z: 4641.2
UPLC (method: 09_B2__1): Rt=11.2 min
UPLC (method: 05_B5__1): Rt=4.00 min

Example 36

$N^{\epsilon 26}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl], $N^{\epsilon 37}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl] [His$^{31}$,Gln$^{34}$,Lys$^{37}$]-GLP-1-(7-37)-peptide (SEQ ID NO: 10)

Chem. 55:

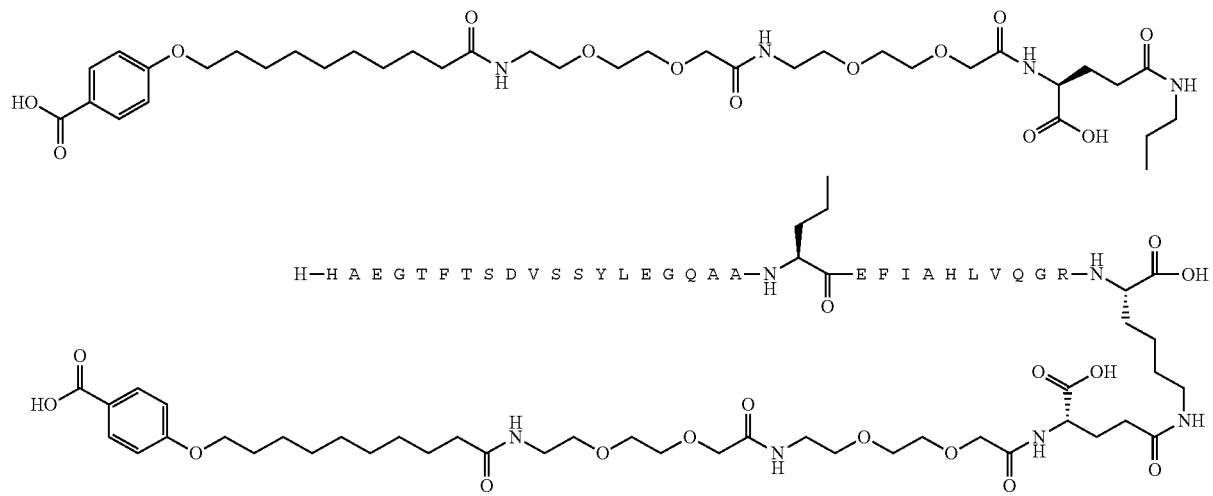

Preparation method: SPPS method B
LCMS4: Rt: 1.97 min, m/z: 4797.3; M/4: 1199.8; M/3: 1599.4
UPLC (method: 09_B4_1): Rt=8.24 min
UPLC (method: 05_B8_1): Rt=2.88 min

Example 37

$N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl] [Gln$^9$,Arg$^{34}$,Lys$^{37}$]-GLP-1-(7-37)-peptide (SEQ ID NO: 8)

Chem. 56:

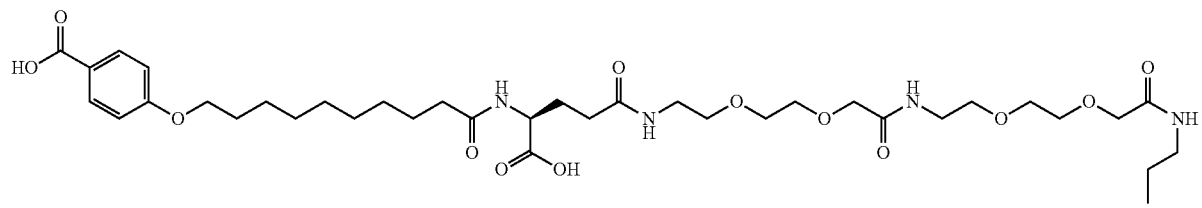

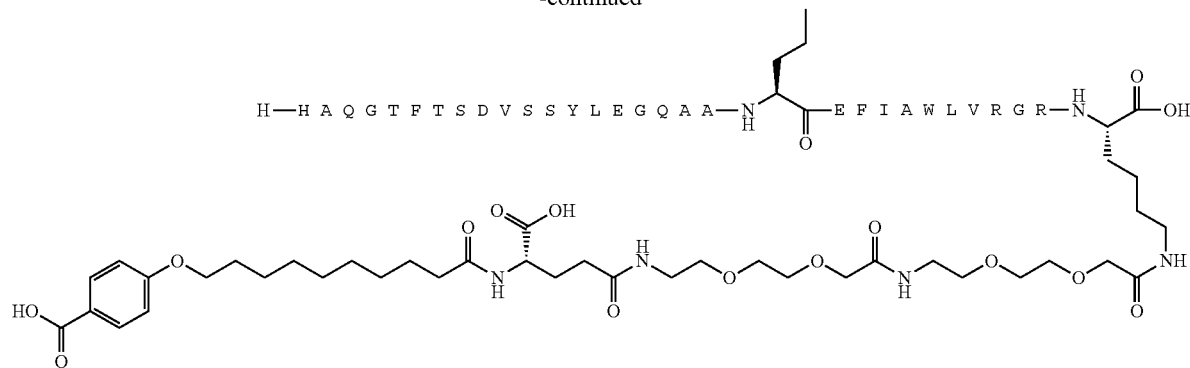

Preparation method: SPPS method B
LCMS4: Rt=1.06 min, m/z: 4873.3
UPLC (method: 09_B2_1): Rt=13.18 min
UPLC (method: 05_B5_1): Rt=6.40 min Example 38

$N^{\epsilon26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]a cetylF[Glu$^{30}$,Arg$^{34}$,Lys$^{37}$]-GLP-1-(7-37)-peptide (SEQ ID NO: 13), Chem. 57:

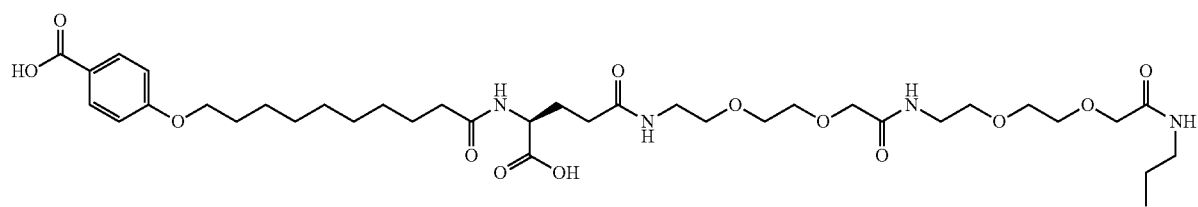

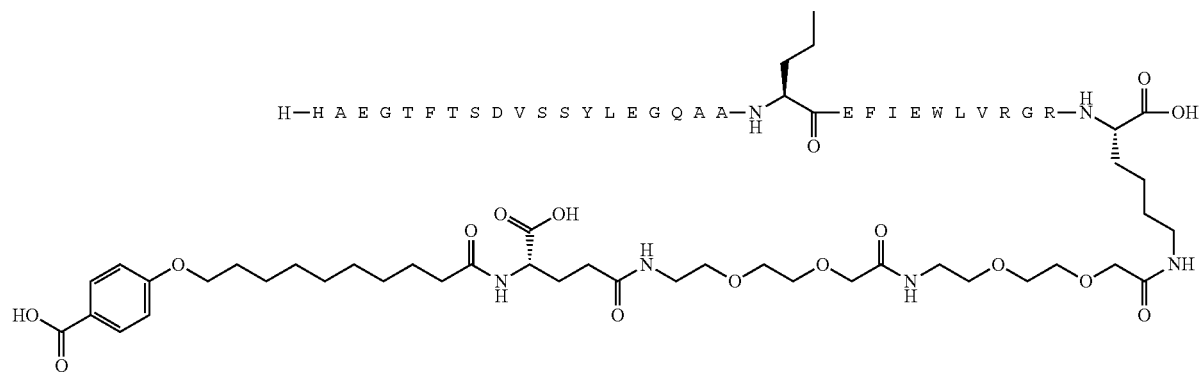

Preparation method: SPPS method B
LCMS4: Rt=2.13 min, m/z: 4932.7
UPLC (method: 09_B2_1): Rt=13.39 min
UPLC (method: 04_A3_1): Rt=8.20 min

Example 39

$N^{\epsilon 26}$-[2-[2-[2-[[2-[2-[2-[[(4S)-4-carboxy-4-[8-(4-carboxyphenoxy)octanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[8-(4-carboxyphenoxy)octanoylamino]butanoyl]amino]ethoxy]ethoxy]acetyl]amino]ethoxy]ethoxy]acetyl]-[Aib$^8$,Arg$^{34}$,Lys$^{37}$]-GLP-1-(7-37)-peptide (SEQ ID NO: 7)

Chem. 58:

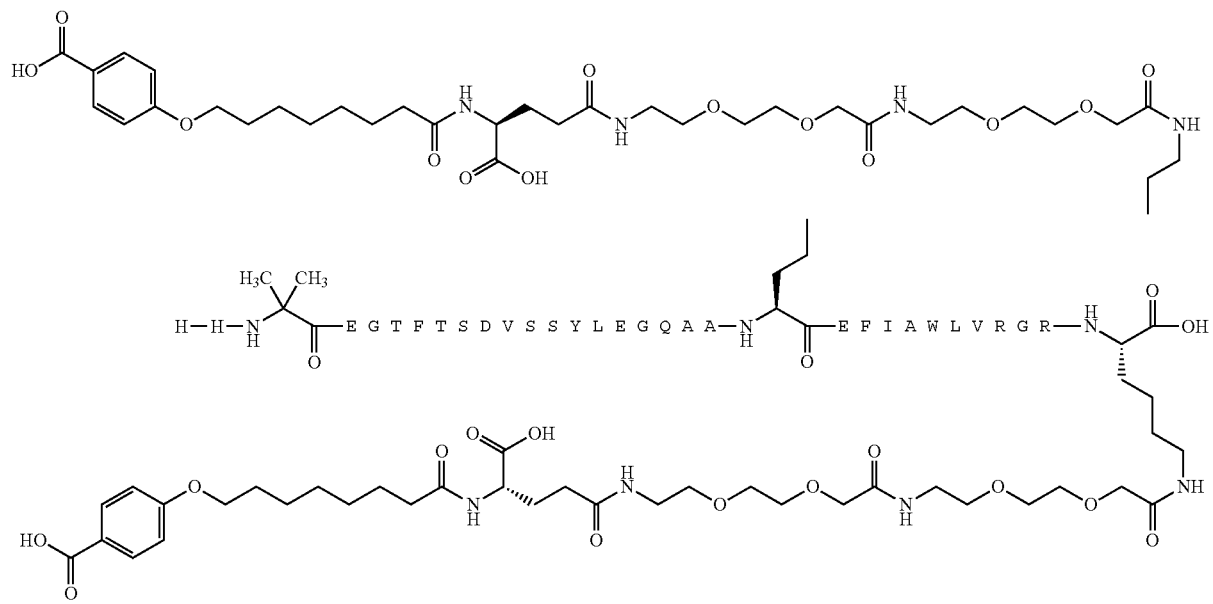

Preparation method: SPPS method B
LCMS4: Rt: 1.93 min, m/z: 4832.4; M/4: 1208.5; M/3: 1611.0
UPLC (method 09_B4_1): Rt=8.10 min
UPLC (method 04_A3_1): Rt=8.15 min
UPLC (method 05_B5_1): Rt=5.30 min

Example 40

$N^{\epsilon 26}$-[2-[2-[2-[[2-[2-[2-[[(4S)-4-carboxy-4-[8-(4-carboxyphenoxy)octanoylamino]butanoyl]amino]ethoxy]ethoxy]acetyl], $N^{\epsilon 37}$-[2-[2-[2-[[2-[2-[2-[[(4S)-4-carboxy-4-[8-(4-carboxyphenoxy)octanoylamino]butanoyl]amino]ethoxy]ethoxy]acetyl]amino]ethoxy]ethoxy]acetyl]-[Arg$^{34}$,Lys$^{37}$]-GLP-1-(7-37)-peptide (SEQ ID NO: 9)

Chem. 59:

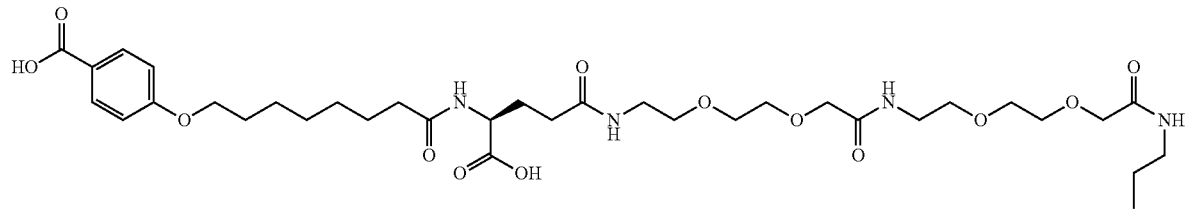

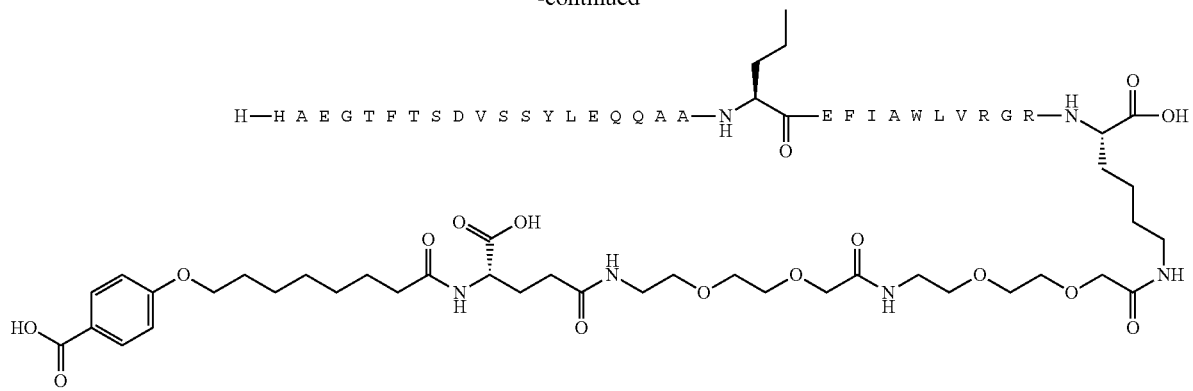

Preparation method: SPPS method B
LCMS4: Rt: 1.92 min, m/z: 4818.4; M/4: 1205.0; M/3: 1606.7
UPLC (method 09_B4_1): Rt=8.06 min
UPLC (method 04_A3_1): Rt=8.02 min Example 41

N{9}-[2,2-dimethyl-3-oxo-3-(pyridin-2-ylmethylamino)propanoyl], N$^{ε26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N$^{ε37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]a cetylF[Arg$^{34}$,Lys$^{37}$]-GLP-1-(9-37)-peptide (SEQ ID NO: 11)

Chem. 60:

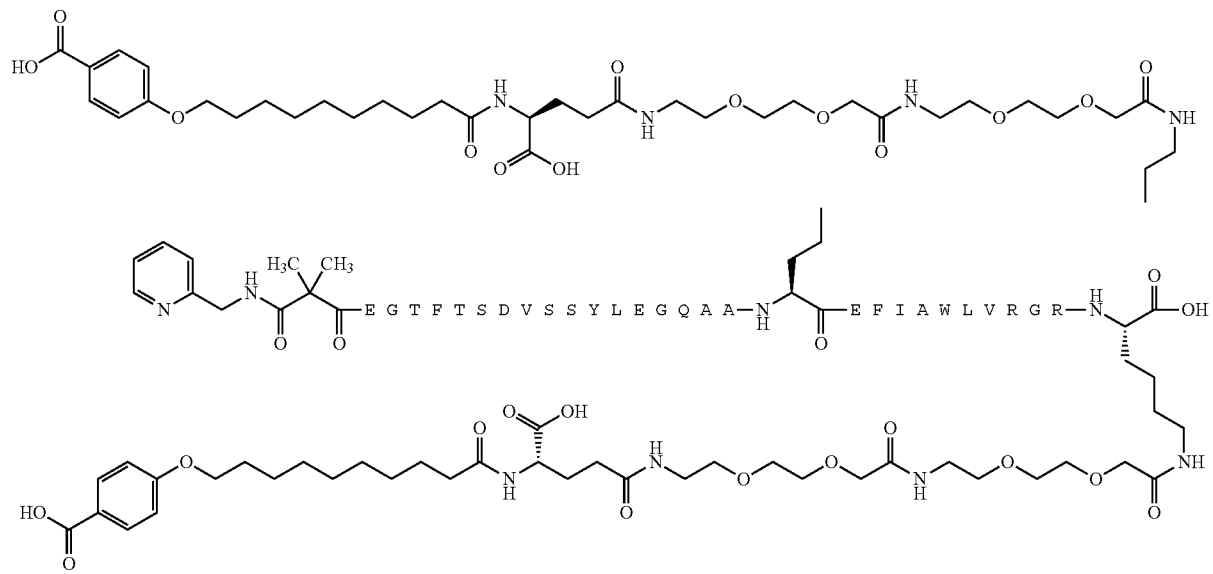

Preparation method: SSPS method B. 2,2-Dimethyl-N-pyridin-2-ylmethyl-malonamic acid was coupled using the same coupling condition as used for 2,2-Dimethyl-N-[2-(1-trityl-1H-imidazol-4-yl)-ethylFinalonamic acid in the previous examples. Fmoc-Glu-OtBu and 4-(9-carboxy-nonyloxy)-benzoic acid tert-butyl ester (prepared as described in Example 25, step 2 of WO 2006/082204) were coupled using SPPS method D.
UPLC (method 08_B4_1): Rt=8.98 min
LCMS4: Rt=2.23 min. m/z=1624(m/3), 1218 (m/4)

Example 42

$N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylam no] butanoyl]a m ino] ethoxy]ethoxy]acetyl]a mi no]ethoxy]ethoxy]acetyl]-[Arg$^{34}$,Lys$^{37}$]-GLP-1-(7-37)-peptidyl-Gly (SEQ ID NO: 9)

Chem. 61:

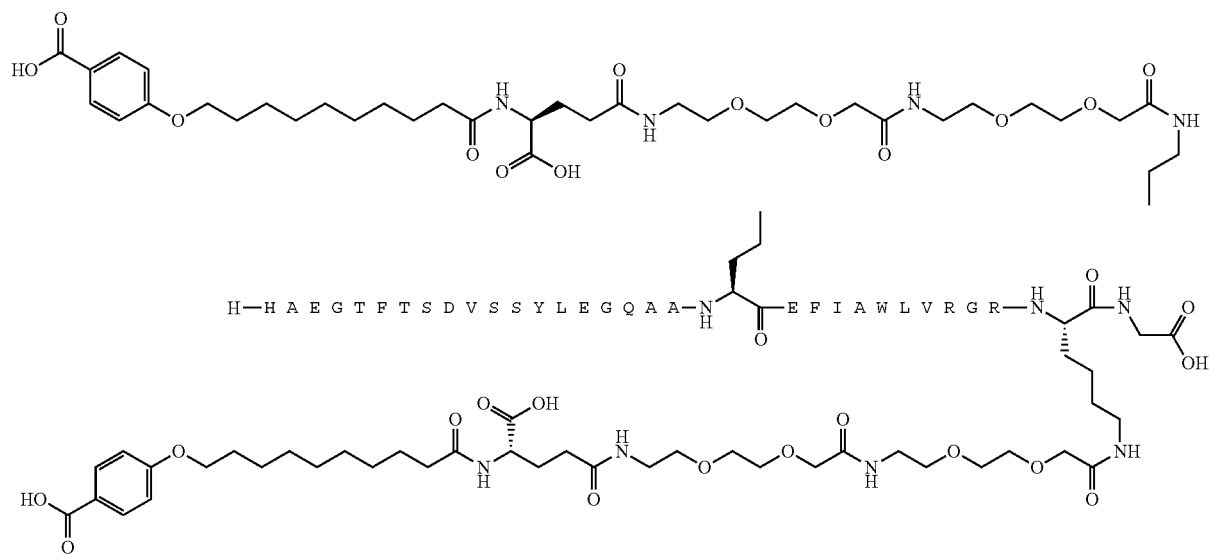

Preparation method: SSPS method B
LCMS4: Rt: 2.05 min, m/z: 4931.5; M/4: 1233.3; M/3: 1644.4
UPLC (method 09_B4_1): Rt=8.52 min
UPLC (method 05_B5_1): Rt=5.18 min
UPLC (method 04_A3_1): Rt=9.24 min

Example 43

$N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Arg$^{34}$,Gly$^{36}$,Lys$^{37}$]-GLP-1-(7-37)-peptide (SEQ ID NO: 6)

Chem. 62:

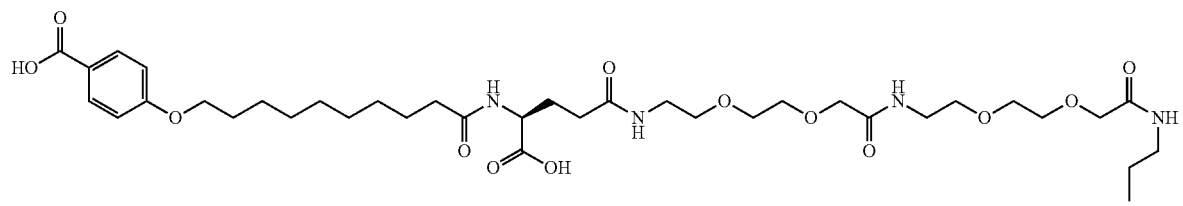

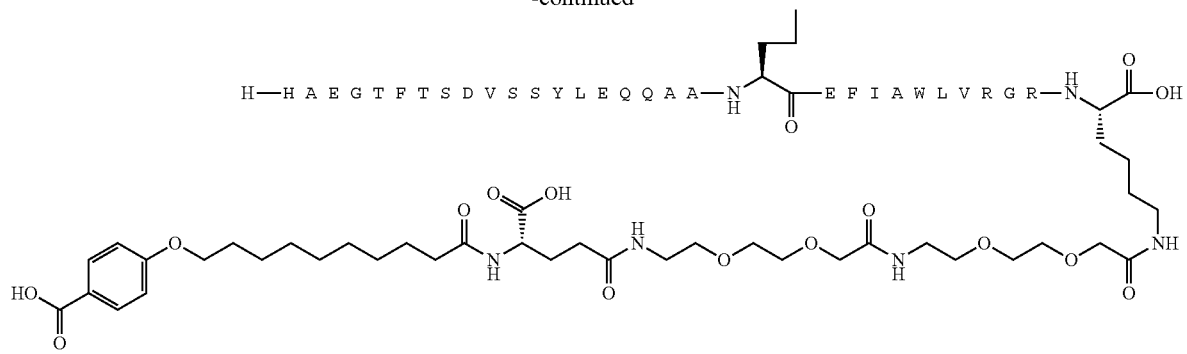

Preparation method: SSPS method B
LCMS4: Rt: 2.18 min, m/z: 4775.3; M/4: 1194.5; M/3: 1592.4
UPLC (method: 09_B4_1): Rt=9.01 min
UPLC (method: 04_A3_1): Rt=9.60 min
UPLC (method: 05_B5_1): Rt=5.88 min Example 44

$N^{\epsilon 26}$-[2-[2-[2-[[2-[2-[2-[[(4S)-4-carboxy-4-[9-(4-carboxyphenoxy)nonanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[9-(4-carboxyphenoxy)nonanoylamino]butanoyl]amino]ethoxy]ethoxy]acetyl]amino]ethoxy]ethoxy]acetyl]-[Arg$^{34}$,Lys$^{37}$]-GLP-1-(7-37)-peptide (SEQ ID NO: 9)

Chem. 63:

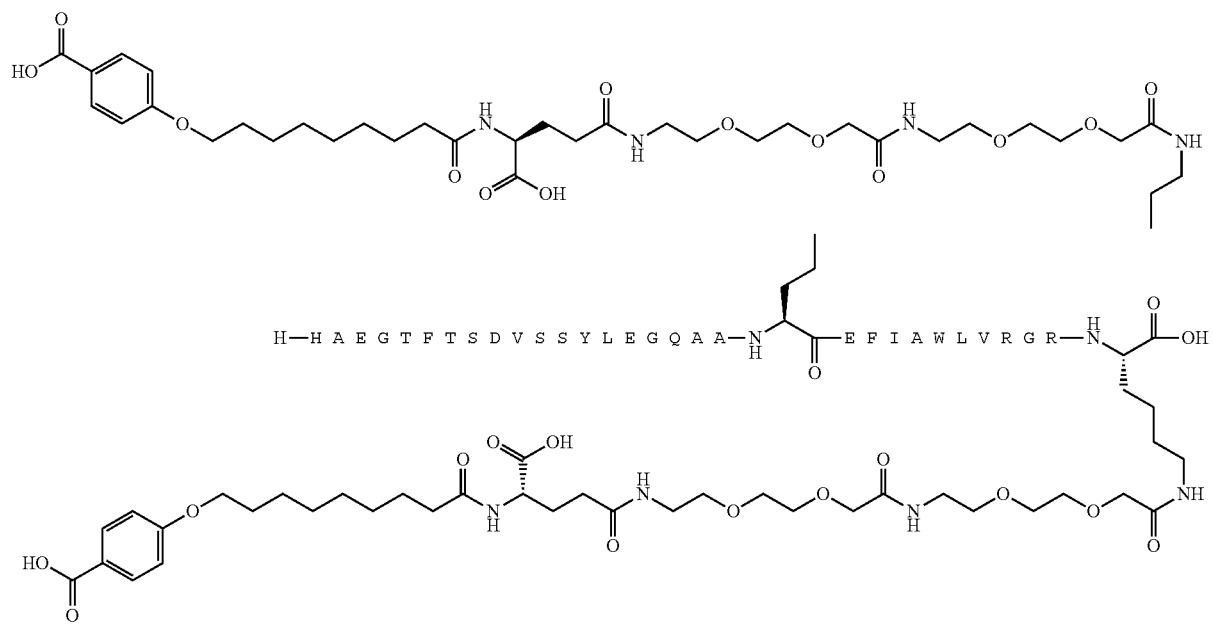

Preparation method: SSPS method B
LCMS4: Rt: 2.03 min, m/z: 4846.4; M/4: 1212.3; M/3: 1616.1
UPLC (method: 09_B4_1): Rt=8.27 min
UPLC (method: 05_B5_1): Rt=5.09 min

Example 45

N$^{\epsilon 26}$-[2-[2-[2-[[2-[2-[2-[[(4S)-4-carboxy-4-[13-(5-carboxythiophene-2-yl)tridecanoylamino]butanoyl]amino]ethoxy]ethoxy]acetyl]amino]ethoxy]ethoxy]acetyl], N$^{\epsilon 37}$-[2-[2-[2-[2-[2-[2-[[(4S)-4-carboxy-4-[13-(5-carboxythiophene-2-yl)tridecanoylamino]butanoyl]amino]ethoxy]ethoxy]acetyl]amino]ethoxy]ethoxy]acetyl]-[Aib$^8$,Arg$^{34}$,Lys$^{37}$]-GLP-1-(7-37)-peptide (SEQ ID NO: 7)

Chem. 64:

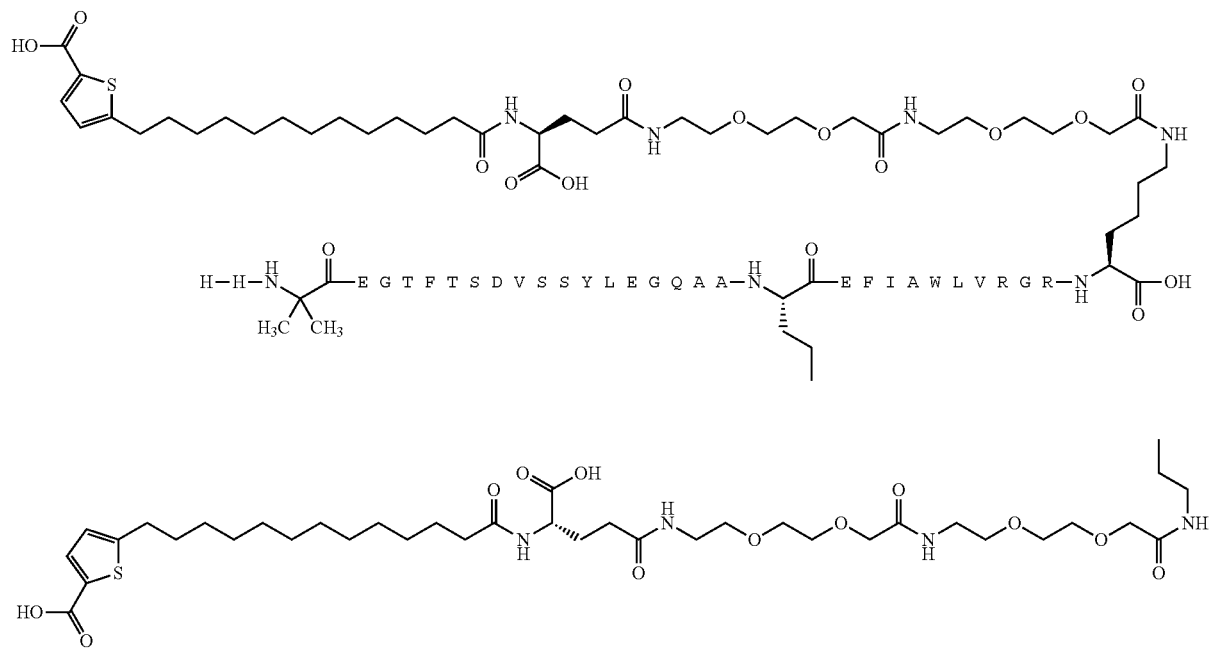

Preperation method: SSPS method B. 8-(9-fluorenylmethyloxycarbonyl-amino)-3,6-dioxaoctanoic acid (commercially available from Iris Biotech), Fmoc-Glu-OtBu, and 5-(12-Carboxy-dodecyl)-thiophene-2-carboxylic acid tert-butyl ester (prepared as described in Example 6 of WO07128815) were coupled using SSPS method D method on the Liberty synthesiser.

UPLC (method 08_B4__1): Rt=9.87 min

LCMS4: m/z=1651(m/3), 1239 (m/4), 991 (m/5)

Example 46

N$^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N$^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Arg$^{34}$,Lys$^{37}$]-GLP-1-(7-37)-peptidyl-Glu (SEQ ID NO: 14), Chem. 65

Chem. 65:

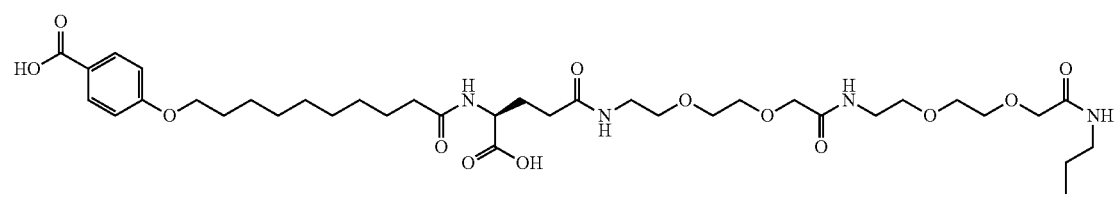

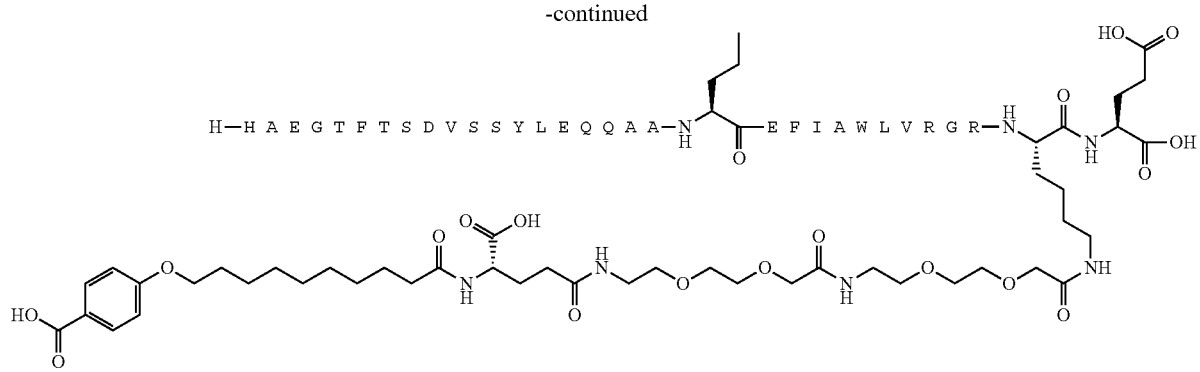

Preparation method: SPPS method A
UPLC (method 10_B14_1): Rt=6.54 min
LCMS4: (M/5)+1=1001; (M/4)+1=1251; Exact mass=5003.5

Example 47

$N^{\epsilon 26}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl], $N^{\epsilon 37}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoylF [Arg$^{34}$,Lys$^{37}$]-GLP-1-(7-37)-peptide (SEQ ID NO: 9)

Chem. 66:

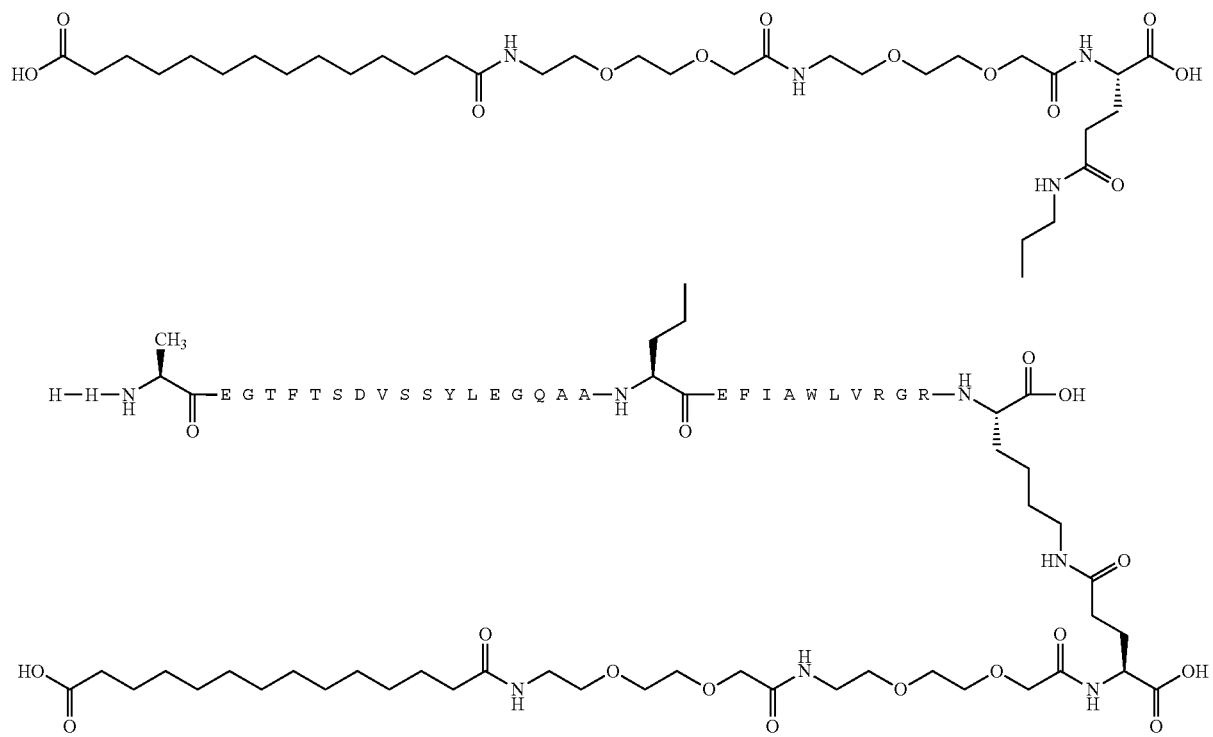

Preparation method: SSPS method B
UPLC (method: 09_B4_1): Rt=8.76 min.
UPLC (method: 04_A6_1): Rt=6.02 min.
LCMS4: Rt=2.12 min. m/z: 4775; M/4=1194; M/5=955

Example 48

$N^{\epsilon 26}$-[2-[2-[2-[[2-[2-[2-[[(2S)-4-carboxy-2-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(2S)-4-carboxy-2-[10-(4-carboxyphenoxy)decanoylamino]butanoyl]amino]ethoxy]ethoxy]acetyl]amino]ethoxy]ethoxy]acetyl]-[Aib$^8$,Arg$^{34}$,Lys$^{37}$]-GLP-1-(7-37)-peptide (SEQ ID NO: 7)

Chem. 67:

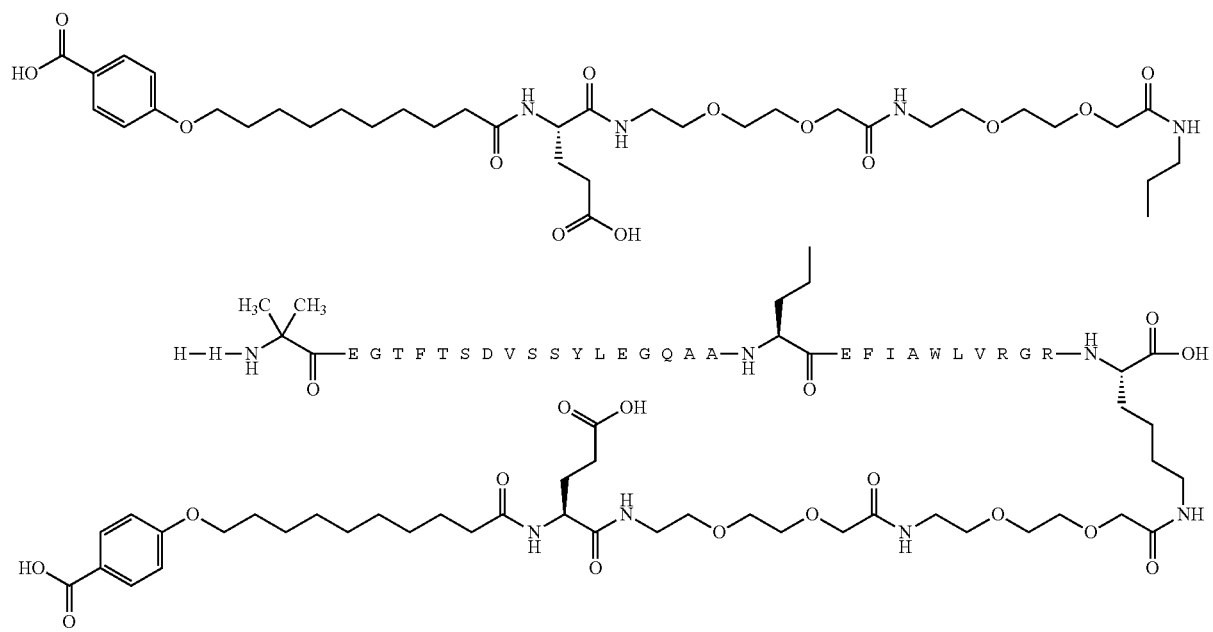

Preparation method: SSPS method B
UPLC (method:08_B2__1): Rt=13.193 min
UPLC (method:05_B5__1): Rt=6.685 min
LCMS4: m/z: 4887; m/3:1630; m/4:1222; m/5:978

Example 49

$N^{\epsilon 26}$-[2-[2-[2-[[2-[2-[2-[[(4S)-4-carboxy-4-[8-(4-carboxyphenoxy)octanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[8-(4-carboxyphenoxy)octanoylamino]butanoyl]amino]ethoxy]ethoxy]acetyl]amino]ethoxy]ethoxy]acetyl]-[Arg34,Gly36,Lys37]-GLP-1-(7-37)-peptide (SEQ ID NO: 6)

Chem. 68:

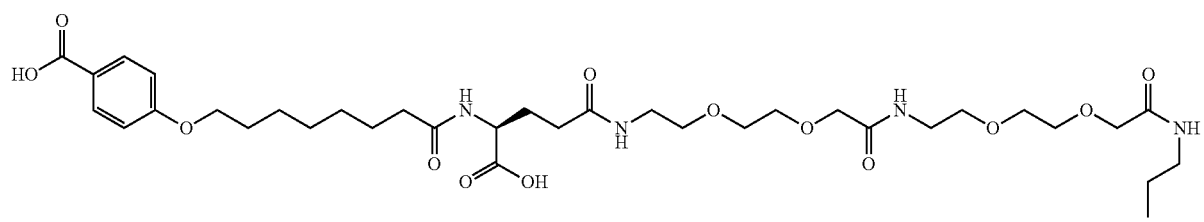

-continued

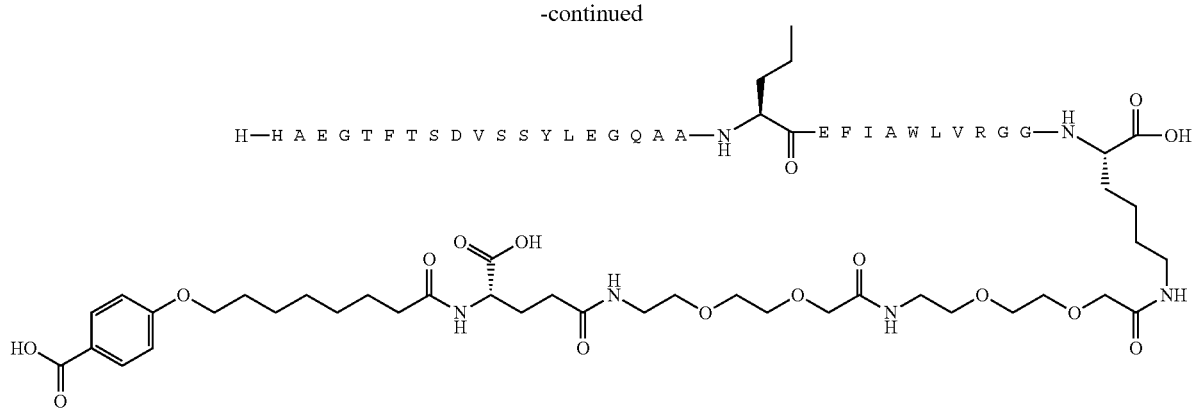

Preparation method: SSPS method B
LCMS4: Rt: 2.07 min, m/z: 4719.2; M/4: 1180.5; M/3: 1573.7
UPLC (method: 08_B4_1): Rt=8.45 min
UPLC (method: 05_B5_1): Rt=5.19 min Pharmacological Methods Example 50

In Vitro Potency

The purpose of this example is to test the activity, or potency, of the GLP-1 derivatives in vitro.

The potencies of theef GLP-1 derivatives of Examples 1-49 were determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor were stimulated with the GLP-1 analogue or derivative in question, and the potency of cAMP production was measured using the AlphaScreen™ cAMP Assay Kit from Perkin Elmer Life Sciences. The basic principle of The AlphaScreen Assay is a competition between endogenous cAMP and exogenously added biotin-cAMP. The capture of cAMP is achieved by using a specific antibody conjugated to acceptor beads.

Cell Culture and Preparation of Membranes

A stable transfected cell line and a high expressing clone were selected for screening. The cells were grown at 5% $CO_2$ in DMEM, 5% FCS, 1% Pen/Strep (Penicillin/Streptomycin) and 0.5 mg/ml of the selection marker G418.

Cells at approximate 80% confluence were washed 2× with PBS and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenised by the Ultrathurax for 20-30 sec. in 10 ml of Buffer 1 (20 mM Na-HEPES, 10 mM EDTA, pH=7.4), centrifuged 15 min at 20,000 rpm and the pellet resuspended in 10 ml of Buffer 2 (20 mM Na-HEPES, 0.1 mM EDTA, pH=7.4). The suspension was homogenised for 20-30 sec and centrifuged 15 min at 20,000 rpm. Suspension in Buffer 2, homogenisation and centrifugation was repeated once and the membranes were resuspended in Buffer 2. The protein concentration was determined and the membranes stored at −80° C. until use.

The assay was performed in ½-area 96-well plates, flat bottom (Costar cat. no: 3693). The final volume per well was 50 μl.

Solutions and Reagents

AlphaScreen cAMP Assay Kit from Perkin Elmer Life Sciences (cat. No: 6760625M); containing Anti-cAMP Acceptor beads (10 U/μl), Streptavidin Donor beads (10 U/μl) and Biotinylated-cAMP (133 U/μl).

AlphaScreen Buffer, pH=7.4: 50 mM TRIS-HCl (Sigma, cat. no: T3253); 5 mM HEPES (Sigma, cat. no: H3375); 10 mM $MgCl_2$, $6H_2O$ (Merck, cat. no: 5833); 150 mM NaCl (Sigma, cat. no: S9625); 0.01% Tween™ (Merck, cat. no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 uM.

cAMP standard (dilution factor in assay=5): cAMP Solution: 5 μL of a 5 mM cAMP-stock+495 μL AlphaScreen Buffer.

Suitable dilution series in AlphaScreen Buffer were prepared of the cAMP standard as well as the GLP-1 analogue or derivative to be tested, e.g. the following eight concentrations of the GLP-1 compound: $10^{-7}$, $10^{-8}$, $10^{-9}$, $10^{-10}$, $10^{-11}$, $10^{-12}$, $10^{-13}$ and $10^{-14}$M, and a series from, e.g., $10^{-6}$ to $3 \times 10^{-11}$ of cAMP.

Membrane/Acceptor Beads

Use hGLP-1/BHK 467-12A membranes; 6 μg/well corresponding to 0.6 mg/ml (the amount of membranes used pr. well may vary)

"No membranes": Acceptor Beads (15 μg/mlfinal) in AlphaScreen buffer

"6 μg/well membranes": membranes+Acceptor Beads (15 μg/mlfinal) in AlphaScreen buffer Add 10 μl "No membranes" to the cAMP standard (per well in duplicates) and the positive and negative controls Add 10 μl "6 μg/well membranes" to GLP-1 and analogues (per well in duplicates/triplicates)

Pos. Control: 10 μl "no membranes"+10 μl AlphaScreen Buffer

Neg. Control: 10 μl "no membranes"+10 μl cAMP Stock Solution (50 μM)

As the beads are sensitive to direct light, any handling was in the dark (as dark as possible), or in green light. All dilutions were made on ice.

Procedure
1. Make the AlphaScreen Buffer.
2. Dissolve and dilute the GLP-1/Analogues/cAMP standard in AlphaScreen Buffer.

3. Make the Donor Beads solution and incubate 30 min. at RT.
4. Add the cAMP/GLP-1/Analogues to the plate: 10 µl per well.
5. Prepare membrane/Acceptor Beads solution and add this to the plates: 10 µl per well.
6. Add the Donor Beads: 30 piper well.
7. Wrap the plate in aluminum foil and incubate on the shaker for 3 hours (very slowly) at RT.
8. Count on AlphaScreen—each plate pre incubates in the AlphaScreen for 3 minutes before counting.
Results The $EC_{50}$ [pM] values were calculated using the GraphPad Prism software (version 5).

The potency of all derivatives in vitro was confirmed. 43 derivatives had a good in vitro potency corresponding to an $EC_{50}$ of 2000 pM or below; 42 derivatives were even more potent having an $EC_{50}$ at 1000 pM or below; 35 derivatives had a still further improved potency corresponding to an $EC_{50}$ at 500 pM or below; 19 derivatives were very potent, corresponding to an $EC_{50}$ at 200 pM or below; and 10 derivatives had a very good potency corresponding to an $EC_{50}$ at 100 pM or below. For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had an in vitro potency corresponding to an $EC_{50}$ of 1200 pM.

If desired, the fold variation in relation to GLP-1 may be calculated as $EC_{50}$ (GLP-1)/$EC_{50}$ (analogue)–3693.2.

Example 51

GLP-1 Receptor Binding

The purpose of this experiment is to investigate the binding to the GLP-1 receptor of the GLP-1 derivatives, and how the binding is potentially influenced by the presence of albumin. This is done in an in vitro experiment as described below.

The binding affinity of the GLP-1 derivatives of Examples 1-49 to the human GLP-1 receptor was measured by way of their ability to displace of $^{125}$I-GLP-1 from the receptor. Liraglutide and semaglutide were included as comparative compounds. In order to test the binding of the derivatives to albumin, the assay was performed with a low concentration of albumin (0.005%—corresponding to the residual amount thereof in the tracer), as well as with a high concentration of albumin (2.0% added). A shift in the binding affinity, $IC_{50}$, is an indication that the peptide in question binds to albumin, and thereby a prediction of a potential protracted pharmacokinetic profile of the peptide in question in animal models.
Conditions
    Species (in vitro): Hamster
    Biological End Point: Receptor Binding
    Assay Method: SPA
    Receptor: GLP-1 receptor
    Cell Line: BHK tk-ts13
Cell Culture and Membrane Purification A stable transfected cell line and a high expressing clone were selected for screening. The cells were grown at 5% $CO_2$ in DMEM, 10% FCS, 1% Pen/Strep (Penicillin/Streptomycin) and 1.0 mg/ml of the selection marker G418.

The cells (approx. 80% confluence) were washed twice in PBS and harvested with Versene (aqueous solution of the tetrasodium salt of ethylenediaminetetraacetic acid), following which they were separated by centrifugation at 1000 rpm for 5 min. The cells/cell pellet must be kept on ice to the extent possible in the subsequent steps. The cell pellet was homogenised with Ultrathurrax for 20-30 seconds in a suitable amount of Buffer 1 (depending on the amount of cells, but e.g. 10 ml). The homogenate was centrifuged at 20000 rpm for 15 minutes. The pellet was resuspended (homogenised) in 10 ml Buffer 2 and re-centrifuged. This step was repeated once more. The resulting pellet was resuspended in Buffer 2, and the protein concentration was determined. The membranes were stored at minus 80° C.
    Buffer 1: 20 mM Na-HEPES+10 mM EDTA, pH 7.4
    Buffer 2: 20 mM Na-HEPES+0.1 mM EDTA, pH 7.4
Binding Assay:
    SPA:

Test compounds, membranes, SPA-particles and [$^{125}$I]]-GLP-1(7-36)$NH_2$ were diluted in assay buffer. 25 ul (micro liter) of test compounds were added to Optiplate. HSA ("high albumin" experiment containing 2% HSA), or buffer ("low albumin" experiment containing 0.005% HSA), was added (50 ul). 5-10 ug protein/sample was added (50 ul) corresponding to 0.1-0.2 mg protein/ml (to be preferably optimised for each membrane preparation). SPA-particles (Wheatgerm agglutinin SPA beads, Perkin Elmer, #RPNQ0001) were added in an amount of 0.5 mg/well (50 ul). The incubation was started with [$^{125}$I]-GLP-1]-(7-36)$NH_2$ (final concentration 0.06 nM corresponding to 49.880 DPM, 25 ul). The plates were sealed with PlateSealer and incubated for 120 minutes at 30° C. while shaking. The plates were centrifuged (1500 rpm, 10 min) and counted in Topcounter.
Assay Buffer:
    50 mM HEPES
    5 mM EGTA
    5 mM MgCl2
    0.005% Tween™ 20
    pH 7.4
    HSA was SIGMA A1653.
Calculations The $IC_{50}$ value was read from the curve as the concentration which displaces 50% of $^{125}$I-GLP-1 from the receptor, and the ratio of [($IC_{50}$/nM) high HSA]/[($IC_{50}$/nM) ultralow HSA] was determined.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$IC_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low).
Results The following results were obtained, where "ratio" refers to [($IC_{50}$/nM) high HSA]/[($IC_{50}$/nM) low HSA]):

All but two derivatives had a ratio above 1.0; 40 derivatives were above 10; 34 derivatives were above 25; 22 derivatives were above 50; 12 derivatives above 100; and 3 derivatives had a ratio above 250.

Furthermore as regards $IC_{50}$ (low albumin), all derivatives had an $IC_{50}$ (low albumin) below 600 nM; all but one were below 500 nM; 46 derivatives were below 100 nM; 44 derivatives were below 50.00 nM; 34 derivatives were below 10.00 nM; 23 derivatives were below 5.00 nM; and 7 derivatives were below 1.00 nM.

Finally as regards $IC_{50}$ (high albumin), all derivatives had an $IC_{50}$ (high albumin) at 1000.00 nM or below; 46 derivatives were below 1000.00 nM; 39 derivatives were below 500.00 nM; 7 derivatives were below 100.00 nM; and 4 derivatives were below 50.00 nM.

Example 52

Estimate of Oral Bioavailability

The purpose of this experiment is to estimate the oral bioavailability of the GLP-1 derivatives.

To this end, the exposure in plasma after direct injection into the intestinal lumen of the GLP-1 derivatives of Examples 2, 15-17, 21, 25, 32, 36-39, and 42-48 was studied in vivo in rats, as described in the following.

The GLP-1 derivatives were tested in a concentration of 1000 uM in a solution of 55 mg/ml sodium caprate.

32 male Sprague Dawley rats with a body weight upon arrival of approximately 240 g were obtained from Taconic (Denmark) and assigned to the different treatments by simple randomisation, 4 rats per group. The rats were fasted for approximately 18 hours before the experiment and taken into general anaesthesia (Hypnorm/Dormicum).

The GLP-1 derivatives were administered in the jejunum either in the proximal part (10 cm distal for the duodenum) or in the mid-intestine (50 cm proximal for the cecum). A PE50-catheter, 10 cm long was inserted into the jejunum, forwarded at least 1.5 cm into the jejunum, and secured before dosing by ligature around the gut and the catheter with 3/0 suture distal to tip to prevent leak or catheter displacement. Catheter was placed without syringe and needle and 2 ml saline was administered into abdomen before closing the incision with wound clips.

100 μl of the respective GLP-1 derivative was injected into the jejunal lumen through the catheter with a 1 ml syringe. Subsequently, 200 μl of air was pushed into the jejunal lumen with another syringe to "flush" the catheter. This syringe was leaved connected to the catheter to prevent flow back into the catheter.

Blood samples (200 ul) were collected at desired intervals (usually at times 0, 10, 30, 60, 120 and 240 min) into EDTA tubes from the tail vein and centrifuged 5 minutes, 10000 G, at 4° C. within 20 minutes. Plasma (75u1) was separated to Micronic tubes, immediately frozen, and kept at −20° C. until analyzed for plasma concentration of the respective GLP-1 derivative with LOCI (Luminescent Oxygen Channeling Immunoassay), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

After the blood sampling the rats were sacrificed under anaesthesia and the abdomen was opened to verify correct catheter placement.

The mean (n=4) plasma concentrations (pmol/l) were determined as a function of time. The ratio of plasma concentration (pmol/l) divided by the concentration of the dosing solution (pmol/l) was calculated for each treatment, and the results for t=30 min (30 minutes after the injection of the compound in the jejunum) were assessed (dose-corrected exposure at 30 min) as a surrogate measure of intestinal bioavailability. The dose-corrected exposure has been shown to correlate significantly with the actual bioavailability.

The following results were obtained, where dose-corrected exposure at 30 min refers to (the plasma concentration 30 minutes after injection of the compound in the jejunum (pM)), divided by (the concentration of the compound in the dosing solution (μM)):

All derivatives had a dose-corrected exposure at 30 min of above 40; 17 were above 50, 14 were above 70; 11 were above 100; 6 were above 125; and 2 derivatives were above 150.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had a dose-corrected exposure at 30 min of below 40, and the dose-corrected exposure at 30 min for semaglutide was in the same range of below 40.

Example 53

Effect on Blood Glucose and Body Weight

The purpose of the study is to verify the effect of the GLP-1 derivatives on blood glucose (BG) and body weight (BW) in a diabetic setting.

The GLP-1 derivatives of Examples 2, 4-5, 17, and 29 were tested in a dose-response study in an obese, diabetic mouse model (db/db mice) as described in the following.

Fifty db/db mice (Taconic, Denmark), fed from birth with the diet NIH31 (NIH 31M Rodent Diet, commercially available from Taconic Farms, Inc., US, see www.taconic.com), were enrolled for the study at the age of 7-9 weeks The mice were given free access to standard chow (e.g. Altromin 1324, Brogaarden, Gentofte, Denmark) and tap water and kept at 24° C. After 1-2 weeks of acclimatisation, the basal blood glucose was assessed twice on two consecutive days (i.e. at 9 am). The 8 mice with the lowest blood glucose values were excluded from the experiments. Based on the mean blood glucose values, the remaining 42 mice were selected for further experimentation and allocated to 7 groups (n=6) with matching blood glucose levels. The mice were used in experiments with duration of 5 days for up to 4 times. After the last experiment the mice were euthanised.

The seven groups received treatment as follows:
1: Vehicle, s.c.
2: GLP-1 derivative, 0.3 nmol/kg, s.c.
3: GLP-1 derivative, 1.0 nmol/kg, s.c.
4: GLP-1 derivative, 3.0 nmol/kg, s.c.
5: GLP-1 derivative, 10 nmol/kg, s.c.
6: GLP-1 derivative, 30 nmol/kg, s.c.
7: GLP-1 derivative, 100 nmol/kg, s.c.
Vehicle: 50 mM sodium phosphate, 145 mM sodium chloride, 0.05% Tween™ 80, pH 7.4.

The GLP-1 derivative was dissolved in the vehicle, to concentrations of 0.05, 0.17, 0.5, 1.7, 5.0 and 17.0 nmol/ml. Animals were dosed s.c. with a dose-volume of 6 ml/kg (i.e. 300 μl per 50 g mouse).

On the day of dosing, blood glucose was assessed at time -1/2 h (8.30 am), where after the mice were weighed. The GLP-1 derivative was dosed at approximately 9 am (time 0).

On the day of dosing, blood glucose was assessed at times 1, 2, 4 and 8 h (10 am, 11 am, 1 pm and 5 pm).

On the following days, the blood glucose was assessed at time 24, 48, 72, and 96 h after dosing (i.e. at 9 am on day 2, 3, 4, 5). On each day, the mice were weighed following blood glucose sampling.

The mice were weighed individually on a digital weight.

Samples for the measurement of blood glucose were obtained from the tail tip capillary of conscious mice. Blood, 10 μl, was collected into heparinised capillaries and transferred to 500 μl glucose buffer (EKF system solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

$ED_{50}$ is the dose giving rise to half-maximal effect in nmol/kg. This value is calculated on the basis of the ability of the derivatives to lower body weight as well as the ability to lower blood glucose, as explained below.

$ED_{50}$ for body weight is calculated as the dose giving rise to half-maximum effect on delta BW 24 hours following the subcutaneous administration of the derivative. For example, if the maximum decrease in body weight after 24 hours is 4.0 g, then $ED_{50}$ bodyweight would be that dose in nmol/kg which gives rise to a decrease in body weight after 24 hours of 2.0 g. This dose ($ED_{50}$ body weight) may be read from the dose-response curve.

$ED_{50}$ for blood glucose is calcualated as the dose giving rise to half-maximum effect on AUC delta BG 8 hours following the subcutaneous administration of the analogue.

The $ED_{50}$ value may only be calculated if a proper sigmoidal dose-response relationship exists with a clear definition of the maximum response. Thus, if this would not be the case the derivative in question is re-tested in a different range of doses until the sigmoidal dose-response relationship is obtained.

The following results were obtained:

The tested derivatives had the expected effect on blood glucose as well as on body weight (a lowering in both cases). Furthermore, a sigmoidal dose-response curve was obtained enabling the calculation of the $ED_{50}$ values for blood glucose and body weight, respectively, as explained above.

Example 54

Half-Life in Minipigs

The purpose of this study is to determine the protraction in vivo of the GLP-1 derivatives after i.v. administration to minipigs, i.e. the prolongation of their time of action. This is done in a pharmacokinetic (PK) study, where the terminal half-life of the derivative in question is determined. By terminal half-life is generally meant the period of time it takes to halve a certain plasma concentration, measured after the initial distribution phase. Male Göttingen minipigs were obtained from Ellegaard Göttingen Minipigs (Dalmose, Denmark) approximately 7-14 months of age and weighing from approximately 16-35 kg were used in the studies. The minipigs were housed individually and fed restrictedly once or twice daily with SDS minipig diet (Special Diets Services, Essex, UK). After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between dosings.

The animals were fasted for approximately 18 h before dosing and for at least 4 h after dosing, but had ad libitum access to water during the whole period. The GLP-1 derivatives of Examples 2, 4-5, 16-17, 25, 29, and 39 were dissolved in 50 mM sodium phosphate, 145 mM sodium chloride, 0.05% Tween™ 80, pH 7.4 to a concentration of usually from 20-60 nmol/ml. Intravenous injections (the volume corresponding to usually 1-2 nmol/kg, for example 0.033 ml/kg) of the compounds were given through one catheter, and blood was sampled at predefined time points for up till 13 days post dosing (preferably through the other catheter). Blood samples (for example 0.8 ml) were collected in EDTA buffer (8 mM) and then centrifuged at 4° C. and 1942G for 10 minutes. Plasma was pippetted into Micronic tubes on dry ice, and kept at −20° C. until analyzed for plasma concentration of the respective GLP-1 compound using ELISA or a similar antibody based assay or LC-MS. Individual plasma concentration-time profiles were analyzed by a non-compartmental model in WinNonlin v. 5.0 (Pharsight Inc., Mountain View, Calif., USA), and the resulting terminal half-lives (harmonic mean) determined.

Results

All but one of the tested derivatives had a half-life of at least 12 hours, six had a half-life of at least 24 hours, five had a half-life of at least 36 hours, three had a half-life of at least 48 hours, and two had a half-life of at least 60 hours.

Example 55

Effect on Glucose Mediated Insulin Secretion

The purpose of this example is to test the effect of GLP-1 derivatives on glucose mediated insulin secretion.

This is done in Göttingen minipigs using intravenous glucose tolerance test (IVGTT).

Male Göttingen minipigs (Ellegaard Göttingen minipigs NS, Dalmose, Denmark), 7-14 months of age are used in the studies. The animals are housed in single pens during acclimatisation and during experiments. After at least 2 weeks of acclimatisation two permanent central venous catheters are implanted in vena cava caudalis or cranialis in each animal. The animals are allowed 1 week recovery after the surgery, and are then used for repeated studies with a suitable washout period between dosings.

The pigs are fed restrictedly 1-2 times a day with SDS minipig fodder (Special Diets Services, Essex, UK) and are allowed ad libitum access to water.

The effect of the GLP-1 derivatives is tested after a single dose or after a period with dose escalation to avoid adverse effects from acute high doses. The GLP-1 derivatives are given either i.v. or s.c. in the thin skin behind the ear.

For each tested GLP-1 derivative there is a vehicle treated (or untreated) baseline group and 2-6 GLP-1 dose groups corresponding to 2-6 different plasma concentration levels, which are usually from around 3000-80000 pM (n=5-8).

For each GLP-1 derivative a 1 or 2 hour intravenous glucose tolerance test is performed. The pigs are fasted for approximately 18 h before the experiment. Patency of the central venous catheters is checked, and two baseline blood samples are taken. After the sample at 0 minutes 0.3 g/kg glucose (Glucose 500 g/L, SAD) is given i.v. over a period of 30 seconds and the catheter is flushed with 20 ml of sterile 0.9% NaCl. Blood samples are usually taken at the following time points in relation to the glucose bolus: −10, −5,0,2, 5, 10, 15, 20, 25, 30, 40, 50, 60, 70, 80, 90, 100, 110, 120 minutes, and after each blood sample the catheter is flushed with 4 ml of sterile 0.9% NaCl with 10 U/ml Heparin. Blood samples for insulin, glucose and plasma concentrations of the derivatives are transferred to tubes coated with EDTA. The tubes are stored on wet ice until centrifugation within 1 hour (4° C., 3000 rpm, 10 min), plasma is pipetted into Micronic tubes on dry ice and stored at −20° C. until analysis. Depending of the half life of the GLP-1 derivative plasma concentrations are measured at t=0 min, or at t=0 min and at the end of the test (t=60 min or t=120 min). Glucose is analyzed using the glucose oxidase method according to the manufacturer's instructions with 10 μL plasma in 500 μL buffer (EBIO plus autoanalyzer and solution, Eppendorf, Germany). Insulin is analyzed using a suitable immunometric assay (such as LOCI, see e.g. Journal of Biomolecular Screening 2007, vol. 12, p. 240-247). The plasma concentration of GLP-1 derivative is analyzed using ELISA or a similar antibody based assay or LC-MS.

For each study the area under the insulin curve (AUCinsulin) is calculated and used as a measure of insulin secretion. The different dose groups are compared to the respective vehicle/baseline group using one-way ANOVA or other appropriate statistical analysis. An EC50 for AUCinsulin may also be calculated.

Example 56

Effect on Feed Intake

The purpose of this experiment is to investigate the effect of GLP-1 derivatives on feed intake in pigs. This is done in a pharmacodynamic (PD) study as described below, in which feed intake is measured 1, 2, 3, and 4 days after administration of a single dose of the GLP-1 derivative, as compared to a vehicle-treated control group.

Female Landrace Yorkshire Duroc (LYD) pigs, approximately 3 months of age, weighing approximately 30-35 kg are used (n=3-4 per group). The animals are housed in a group for 1-2 weeks during acclimatisation to the animal facilities. During the experimental period the animals are placed in individual pens from Monday morning to Friday afternoon for measurement of individual food intake. The animals are fed ad libitum with pig fodder (Svinefoder, Antonio) at all times both during the acclimatisation and the experimental period. Food intake is monitored on line by logging the weight of fodder every 15 minutes. The system used is Mpigwin (Ellegaard Systems, Faaborg, Denmark).

The GLP-1 derivatives are dissolved in a phosphate buffer (50 mM phosphate, 0.05% Tween™ 80, pH 8) at concentrations of 12, 40, 120, 400 or 1200 nmol/ml corresponding to doses of 0.3, 1, 3, 10 or 30 nmol/kg. The phosphate buffer served as vehicle. Animals are dosed with a single subcutaneous dose of the GLP-1 derivative or vehicle (dose volume 0.025 ml/kg) on the morning of day 1, and feed intake is measured for 4 days after dosing. On the last day of each study, 4 days after dosing, a blood sample for measurement of plasma exposure of the GLP-1 derivative is taken from the heart in anaesthetised animals. The animals are thereafter euthanised with an intra-cardial overdose of pentobarbitone. Plasma content of the GLP-1 derivatives is analysed using ELISA or a similar antibody based assay.

Feed intake is calculated as mean±SEM 24 h food intake on the 4 days.

Statistical comparisons of the 24 hour feed intake in the vehicle vs. GLP-1 derivative group on the 4 days are done using one-way or two-way-ANOVA repeated measures, followed by Bonferroni post-test.

Example 57

Stability Against Degradation by Intestinal Enzymes

The purpose of this example is to test the stability against degradation by intestinal enzymes. GLP-1(7-37) was used in the assay as a kind of a standard.

All example compounds, except for the compounds of Examples 4, 6, 8, 34-35, and 49, were tested.

The strongest proteolytic activities in the intestine are of pancreatic origin and include the serine endopeptidases trypsin, chymotrypsin, and elastase as well as several types of carboxypeptidases.

An assay with small intestine extract from rats was developed and used as described in the following.

Extracts from Rat Small Intestine

Small intestines were prepared from rats and flushed with 8 ml of 150 mM NaCl, 20 mM Hepes pH 7.4. The solutions were centrifuged for 15 min at 4,600 rpm in a Heraeus Multifuge 3 S-R centrifuge with a 75006445 rotor. The supernatants were removed and filtered through a 0.22 pm Millipore Millex GV PVDF membrane. Filtrates of several animals were pooled to average out individual differences.

The protein content of the obtained extracts was determined by Bradford Assay (see e.g. Analytical Biochemistry (1976), vol. 72, p. 248-254, and Analytical Biochemistry (1996), vol. 236 p. 302-308).

Degradation Assay 2.5 nmol of the derivatives to be tested were incubated with the intestinal extract in a volume of 250 μl at 37° C. over a period of one hour. Intestinal samples were assayed in presence of 20 mM Hepes at pH 7.4. The concentration of the intestinal extract was titrated in pilot experiments so that the half-life (t½) of GLP-1(7-37) was in the range of 10-20 minutes. The small intestine extract was used at a concentration of 1.4 μg/ml. All components except for the intestinal extract were mixed and pre-warmed for ten minutes at 37° C. Immediately after addition of the intestinal extract a sample of 50 μl was taken and mixed with the same volume of 1% trifluoroacetic acid (TFA). Further samples were taken accordingly after 15, 30, and 60 minutes.

Sample Analysis

UPLC Analysis

10 μl of the samples were analysed by UPLC using a Waters Acquity system with a BEH C18 1.7 μm 2.1×50 mm column and a 30 to 65% gradient of 0.1% TFA and 0.07% TFA in acetonitrile over 5 minutes at a flow rate of 0.6 ml/min. After baseline subtraction the peak integrals of the intact compounds in the HPLC chromatogram recorded at a wavelength of 214 nm were determined.

MALDI-TOF Analysis

1 μl of each sample was transferred to a Bruker/Eppendorf PAC HCCA 384 MALDI target. Analysis was performed with a Bruker Autoflex matrix-assisted laser desorption and ionisation—time of flight (MALDI-TOF) mass spectrometer using the pre-defined method "PAC_measure" with an extended detection range of 500 to 5000 Da and the pre-defined calibration method "PAC_calibrate".

Data Analysis

The peak integrals of the HPLC chromatograms were plotted against time. The half-life of the respective compound was calculated by fitting the data using SigmaPlot 9.0 software and an equation for a 2-parameter exponential decay.

For each compound tested, the relative half-life (relative $T_{1/2}$) was calculated as the half-life ($T_{1/2}$) of the compound in question, divided by the half-life ($T_{1/2}$) of GLP-1(7-37), determined in the same way.

Results

The relative half-life of the known compounds liraglutide and semaglutide was 4.8 and 1.2, respectively.

Except for one compound, all GLP-1 derivatives of the invention that were tested had a relative half-life of at least 1; thirty-one had a relative half-life of at least 2; and ten had a half-life of at least 5.

Example 58

Pharmacokinetics in Rat

The purpose of this Example is to investigate half-life in vivo in rat.

In vivo pharmacokinetic studies in rats were performed withten GLP-1 derivatives (compounds of the present Examples 2, 4-5, 16-17, 25, 29, 36, 39, and 43) of the invention, as described in the following. Semaglutide was included for comparison. Male Sprague Dawley rats of same age with a body weight from 400 to 600 g were obtained from Taconic (Denmark) and assigned to the treatments by simple randomisation on body weight, approximately 3-6 rats per group, so that all animals in each group were of similar body weight.

The GLP-1 derivatives (approximately 6 nmole/ml) were dissolved in 50 mM sodium phosphate, 145 mM sodium chloride, 0.05% Tween™ 80, pH 7.4. Intravenous injections (1.0 ml/kg) of the compounds were given through a catheter implanted in the right jugular vein. Blood was sampled from vena sublingualis for 5 days post dosing. Blood samples (200 µl) were collected in EDTA buffer (8 mM) and then centrifuged at 4° C. and 10000G for 5 minutes. Plasma samples were kept at −20° C. until analyzed for plasma concentration of the respective GLP-1 compound.

The plasma concentrations of the GLP-1 compounds were determined using a Luminescence Oxygen Channeling Immunoasssay (LOCI), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

Plasma concentration-time profiles were analyzed using WinNonlin (ver. 5.0, Pharsight Inc., Mountain View, Calif., USA), and the half-life ($T_{1/2}$) calculated using individual plasma concentration-time profiles from each animal.

Results

The half-life of semaglutide was 4 hours.

All ten derivatives of the invention that were tested had a half-life of at least 4 hours, all but one had a half-life of at least 8 hours, seven had a half-life of at least 12 hours, six had a half-life of at least 16 hours, and three had a half-life of at least 24 hours.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 analogue, which analogue comprises a first K residue at a position corresponding to position 37 of GLP-1(7-37) (SEQ ID NO: 1), a second K residue at a position corresponding to position 26 of GLP-1(7-37), wherein the first K residue is designated $K^{37}$, and the second K residue is designated $K^{26}$, which analogue has a maximum of three amino acid modifications as compared to GLP-1(7-37), where two of the modifications are $K^{37}$ and a Q or an R at a position corresponding to position 34 of GLP-1(7-37);

which derivative comprises an albumin binding moiety attached to each of $K^{26}$ and $K^{37}$ respectively, wherein the albumin binding moiety comprises a protracting moiety of formula Chem. 2a:

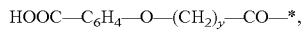
HOOC—C$_6$H$_4$—O—(CH$_2$)$_y$—CO—*, in which y is an integer in the range of 7-15;
or a pharmaceutically acceptable salt, amide, or ester thereof.

2. The derivative of claim 1, wherein the analogue has two amino acid modifications as compared to GLP-1(7-37).

3. The derivative of claim 1, wherein the analogue comprises Imp$^7$ or Aib$^8$.

4. The derivative of claim 3, wherein the analogue comprises Aib$^8$.

5. The derivative of claim 4, wherein the analogue comprises the following amino acid modifications, as compared to GLP-1(7-37) (SEQ ID NO: 1): (8Aib, 34R, 37K).

6. The derivative of claim 5, wherein the albumin binding moiety further comprises Chem. 6 and/or Chem. 5:

Chem. 6:

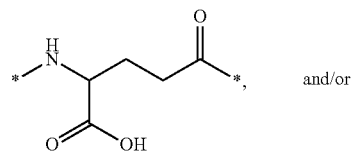

and/or

Chem. 5:

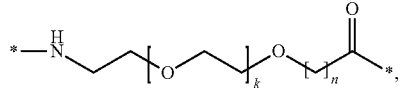

wherein k is an integer in the range of 1-5, and n is an integer in the range of 1-5.

7. The derivative of claim 1, wherein the albumin binding moiety further comprises Chem. 6 and/or Chem. 5:
Chem. 6:
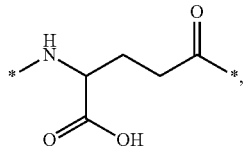
and/or
Chem. 5:
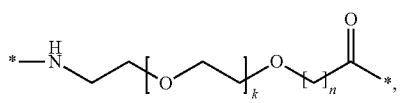
wherein k is an integer in the range of 1-5, and n is an integer in the range of 1-5.
8. The derivative of claim 7, wherein y is 9.
9. A compound selected from the following:
Chem. 20:
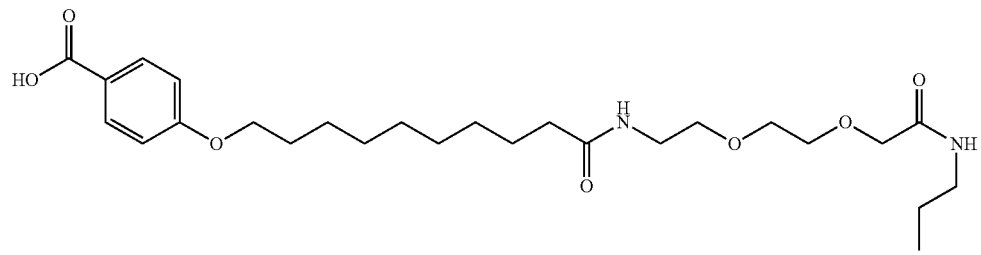
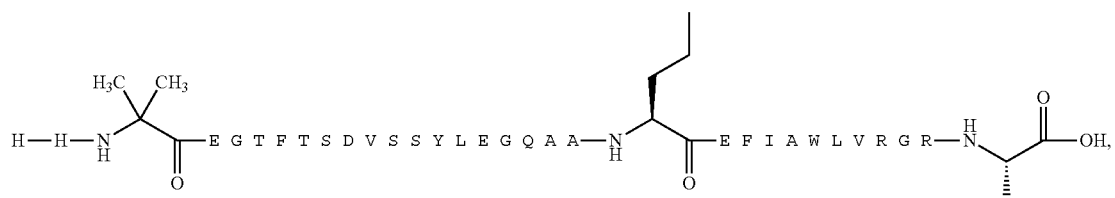
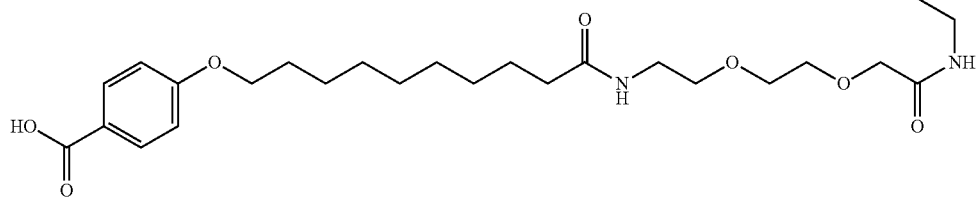
where the amino acid sequence is that of SEQ ID NO: 7,
Chem. 21:
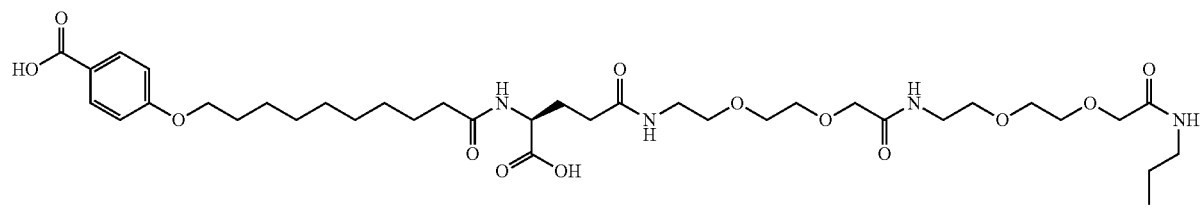

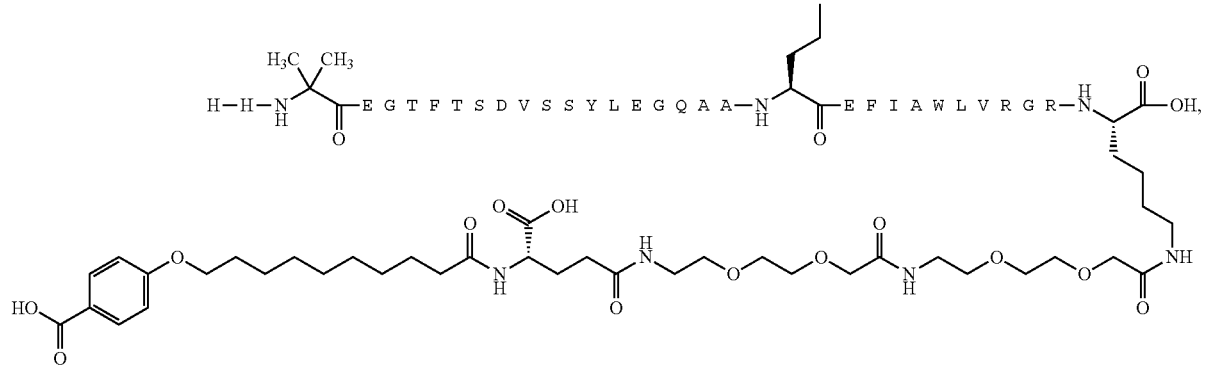
where the amino acid sequence is that of SEQ ID NO: 7,
Chem. 32:
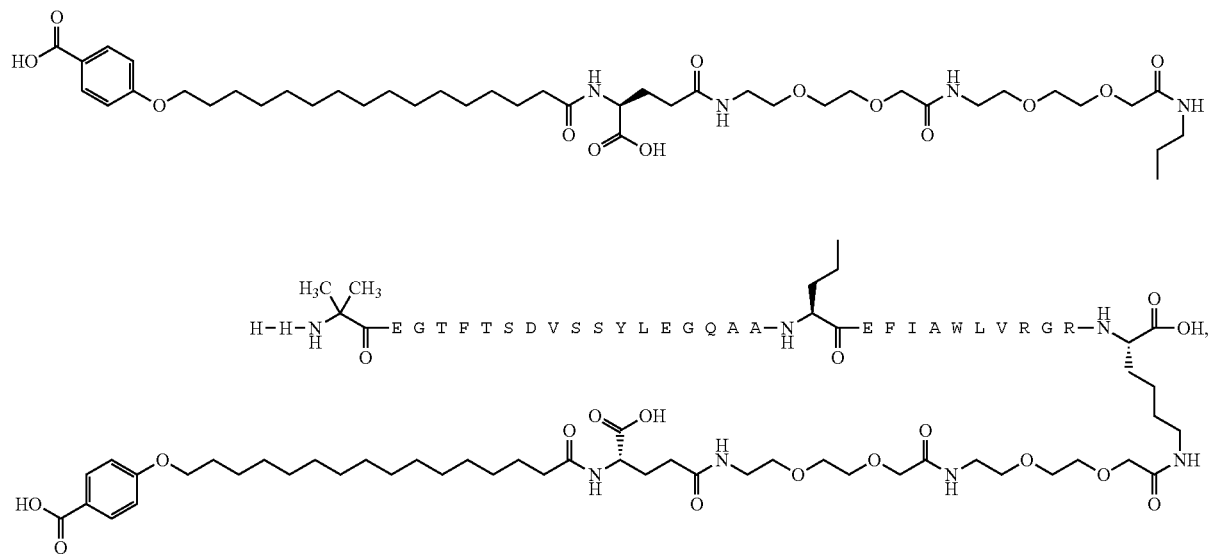
where the amino acid sequence is that of SEQ ID NO: 7,
Chem. 34:
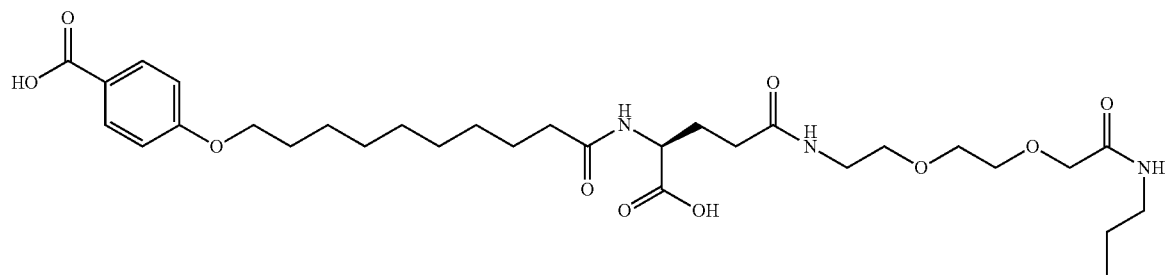

-continued
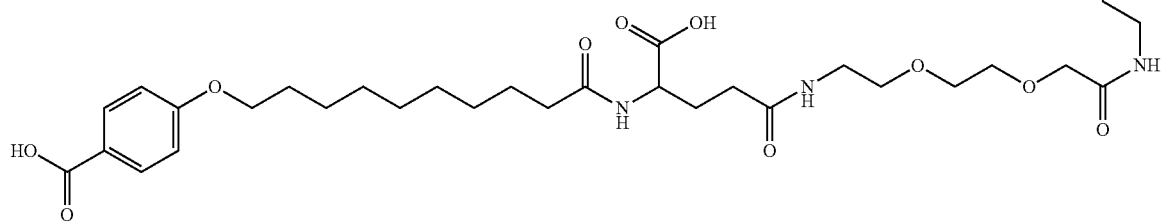
where the amino acid sequence is that of SEQ ID NO: 7,
Chem. 38:
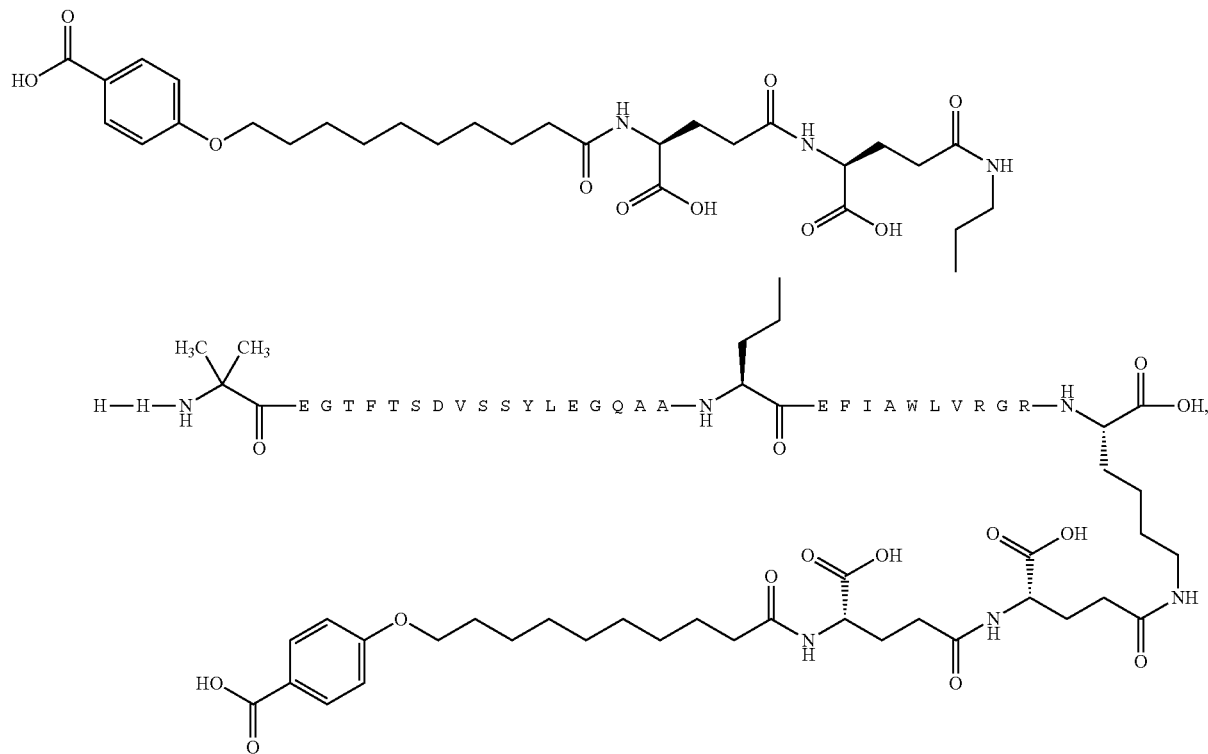
where the amino acid sequence is that of SEQ ID NO: 7,
Chem. 47:
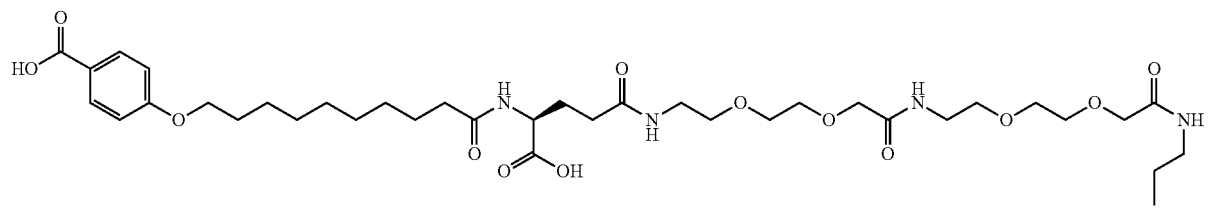

-continued
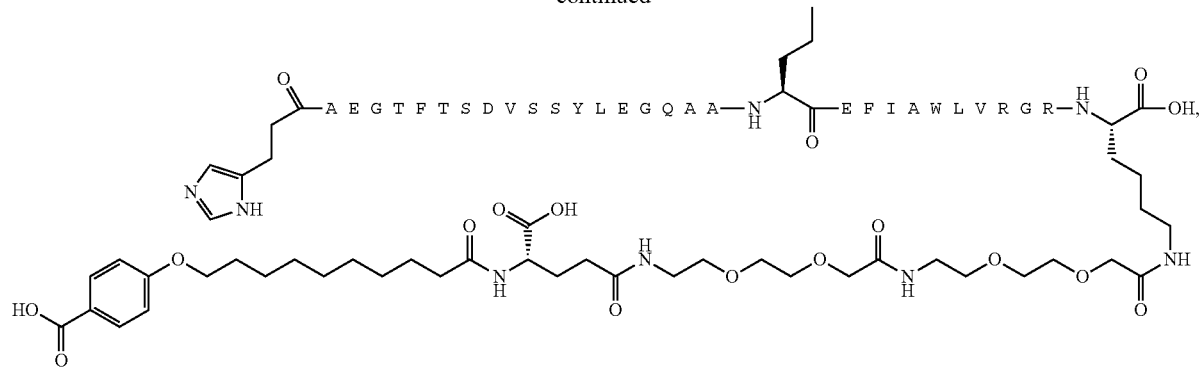
where the amino acid sequence is that of SEQ ID NO: 12,
Chem. 48:
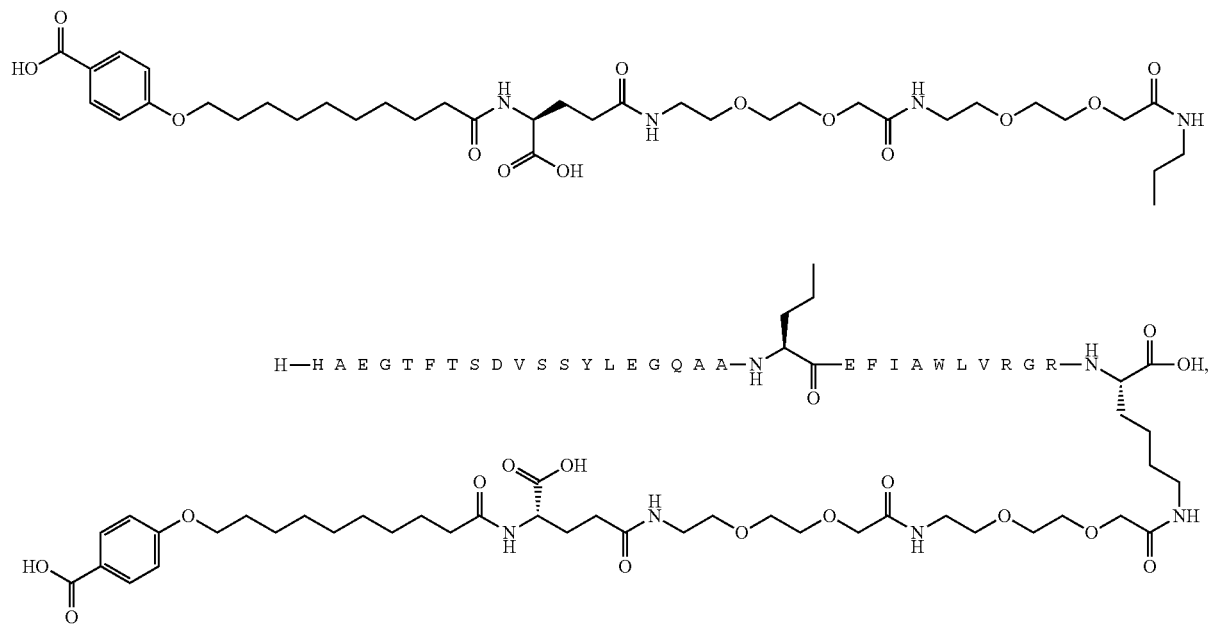
where the amino acid sequence is that of SEQ ID NO: 9,
Chem. 52:
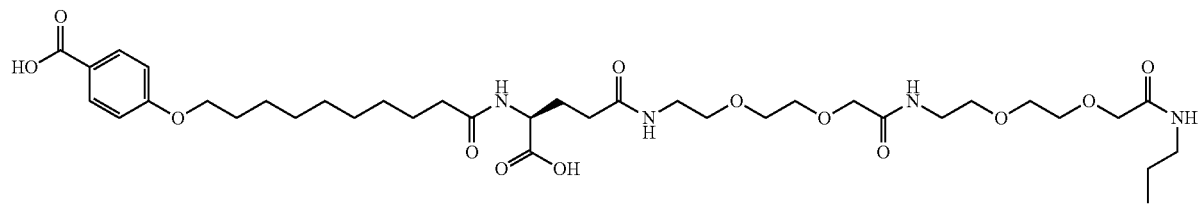

-continued
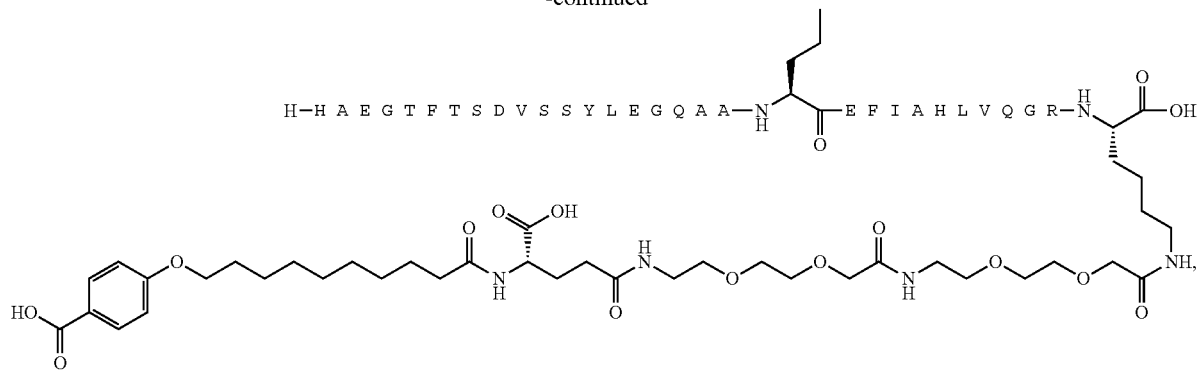
where the amino acid sequence is that of SEQ ID NO: 10,
Chem. 55:
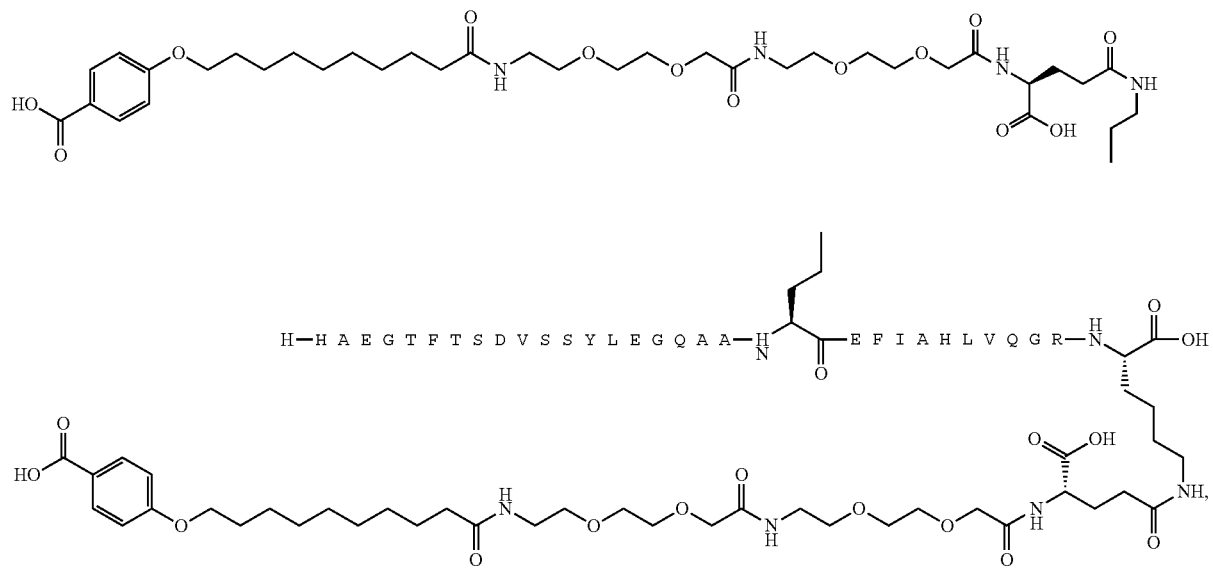
where the amino acid sequence is that of SEQ ID NO: 10,
Chem. 56:
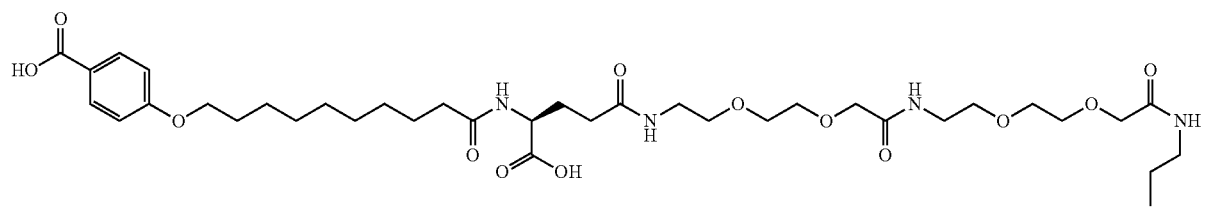

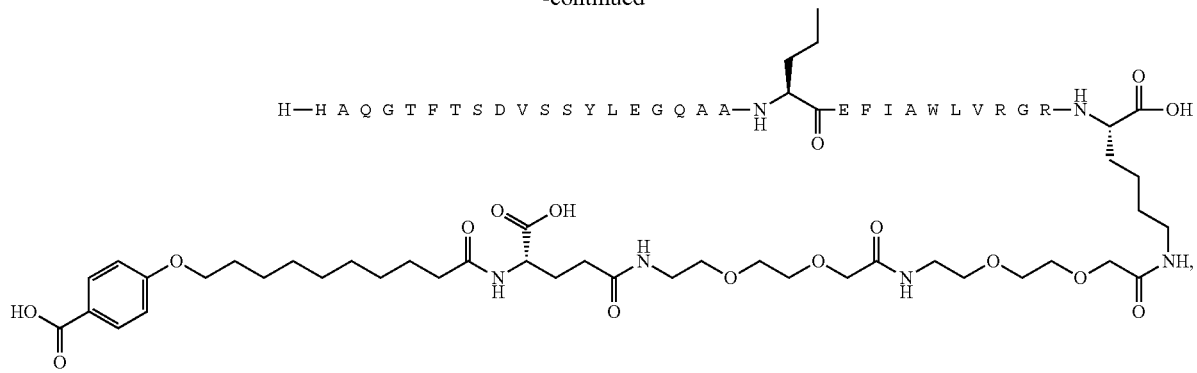
where the amino acid sequence is that of SEQ ID NO: 8,
Chem. 57:
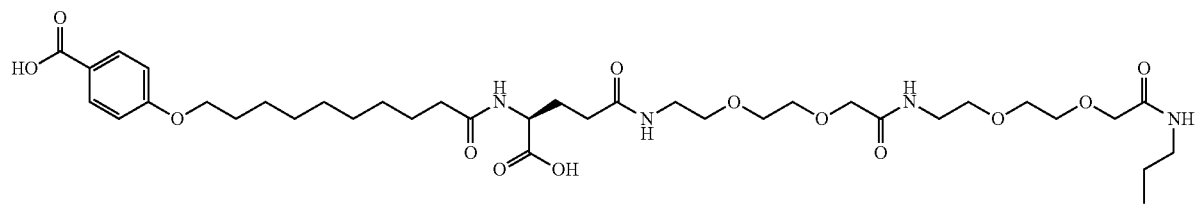
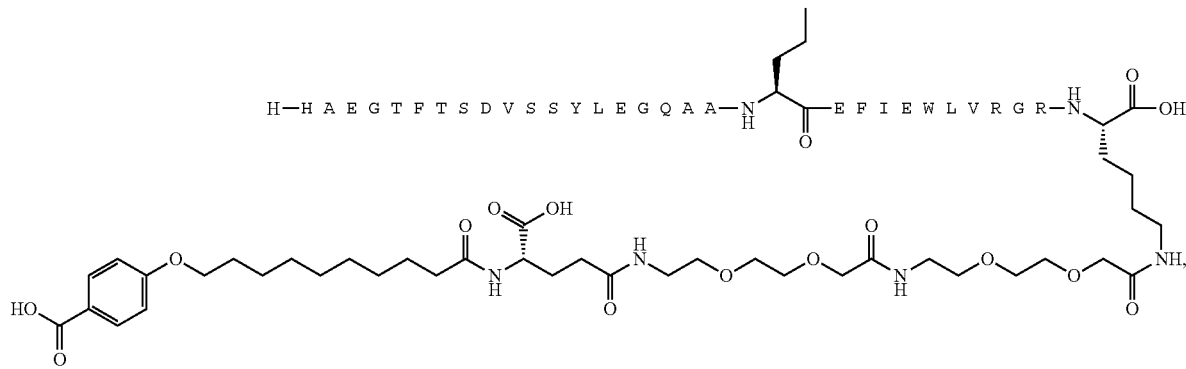
where the amino acid sequence is that of SEQ ID NO: 13,
Chem. 58:
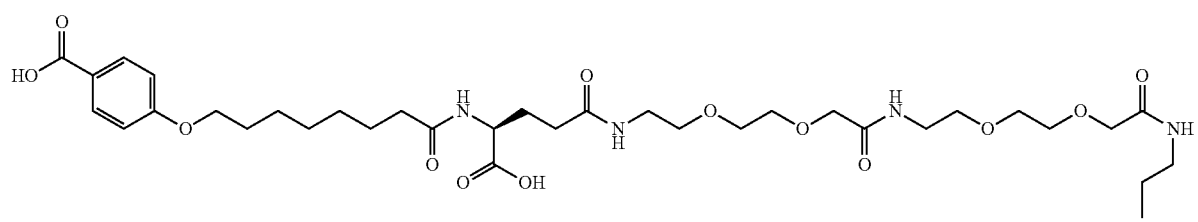

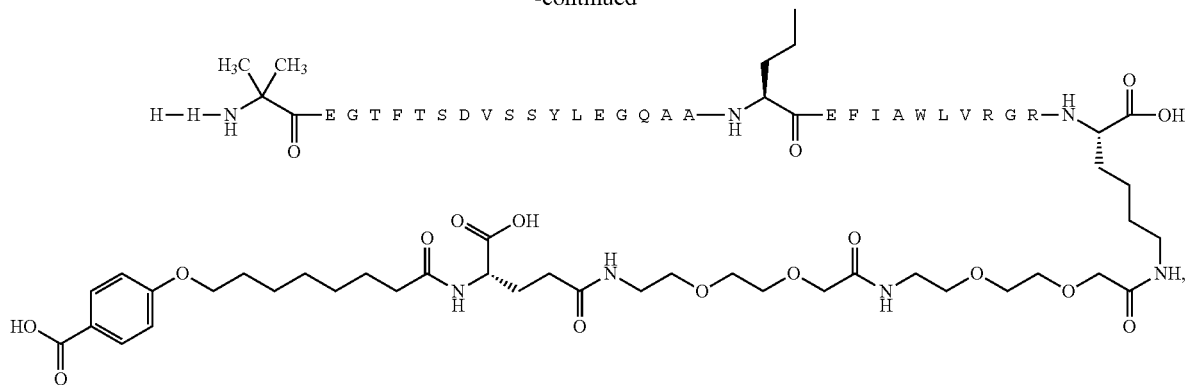
where the amino acid sequence is that of SEQ ID NO: 7,
Chem. 59:
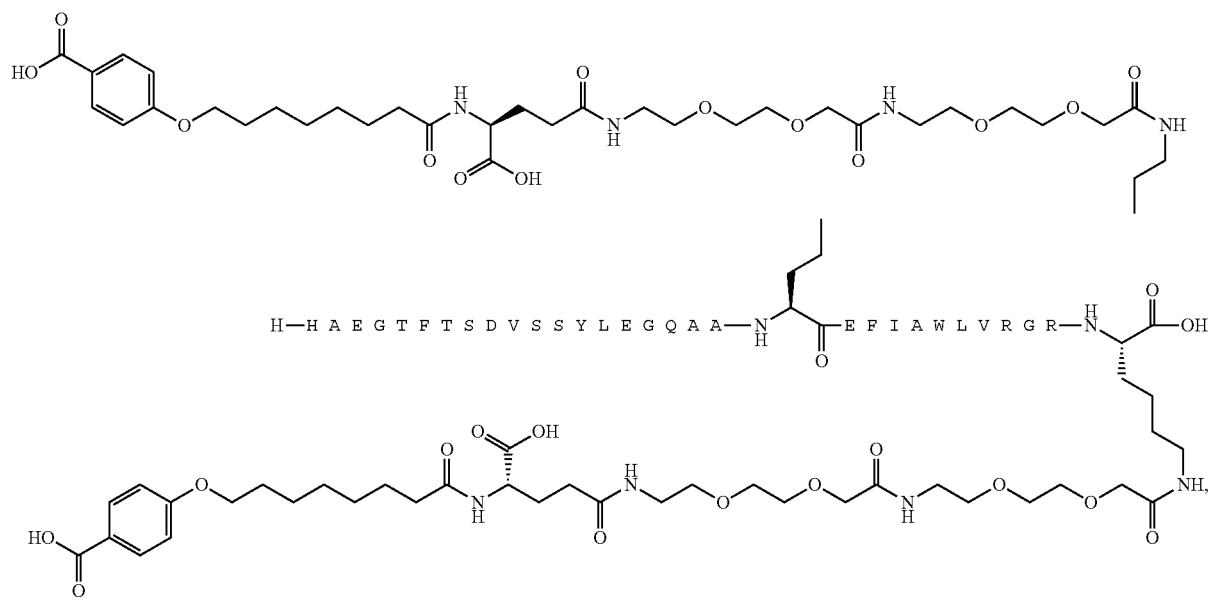
where the amino acid sequence is that of SEQ ID NO: 9,
Chem. 61:
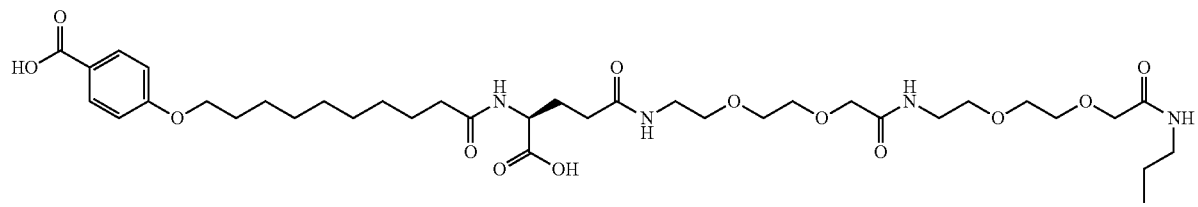

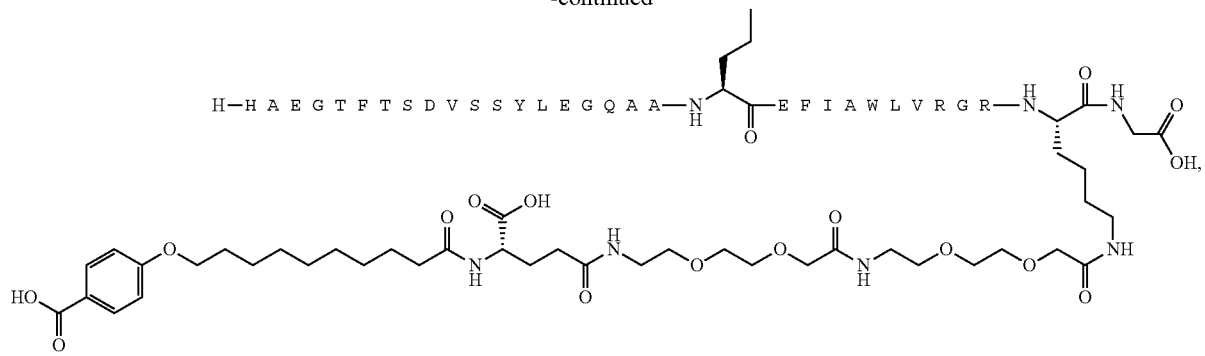
where the amino acid sequence is that of SEQ ID NO: 9,
Chem. 62:
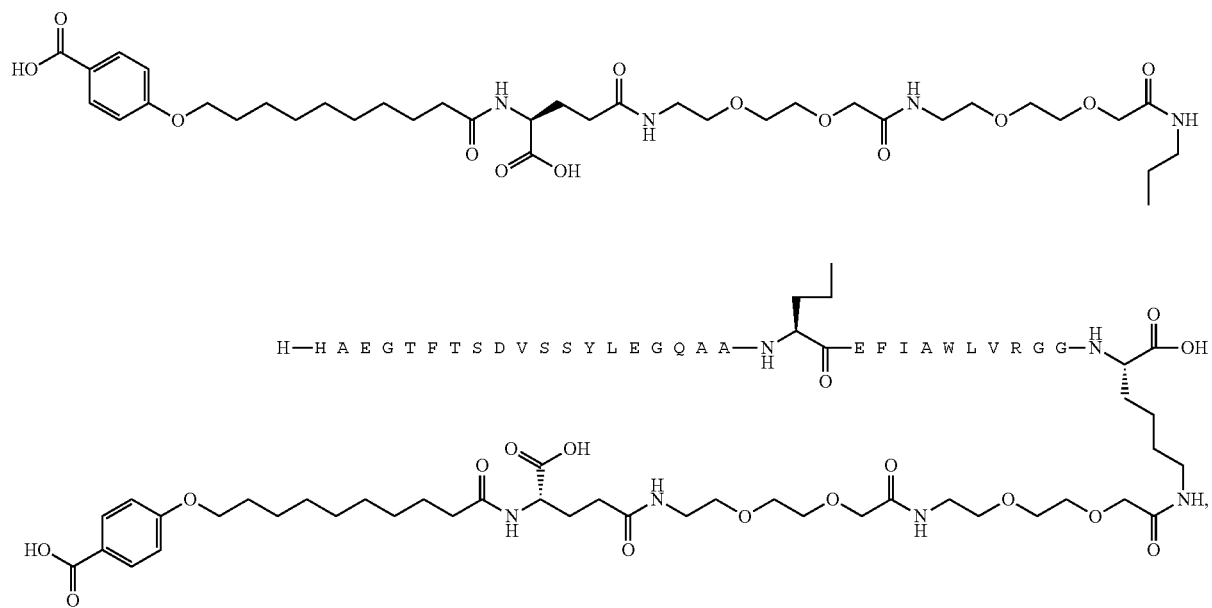
where the amino acid sequence is that of SEQ ID NO: 6,
Chem. 63:
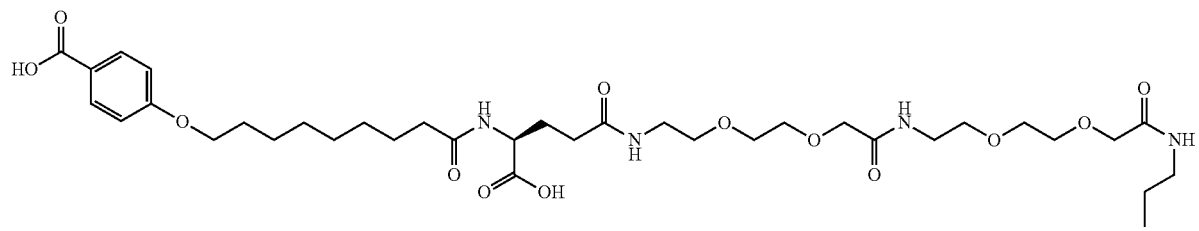

-continued
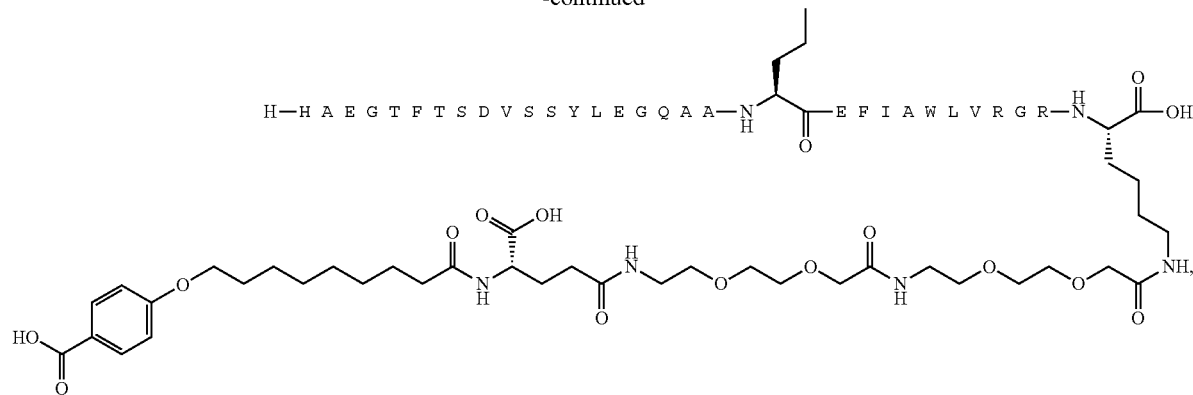
where the amino acid sequence is that of SEQ ID NO: 9,
Chem. 65:
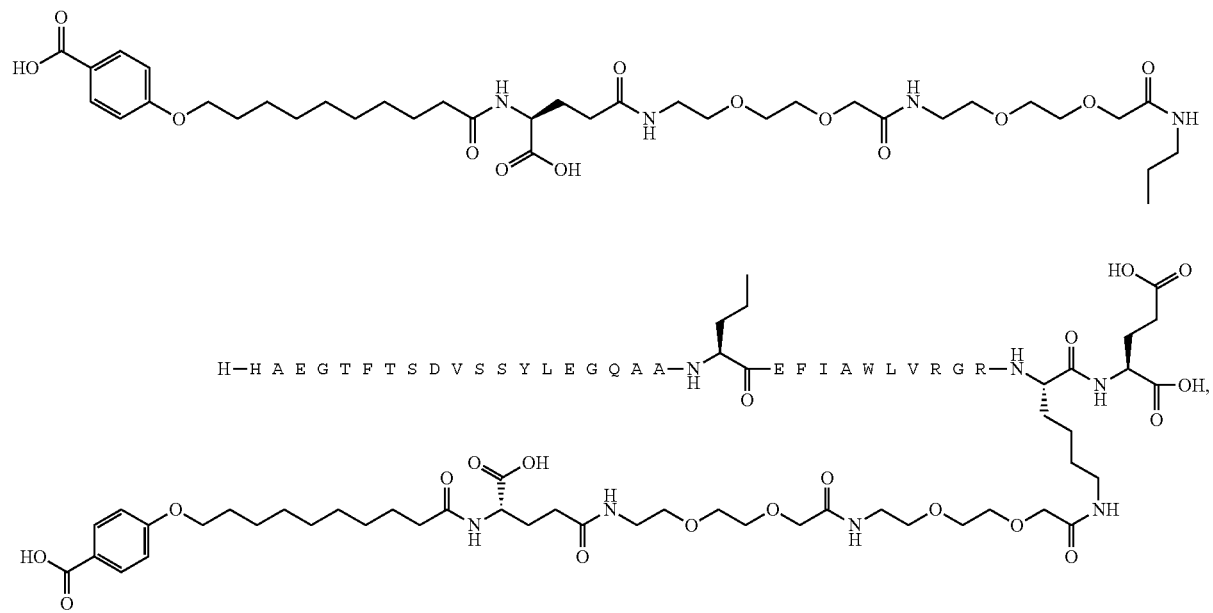
where the amino acid sequence is that of SEQ ID NO: 14,
Chem. 67:
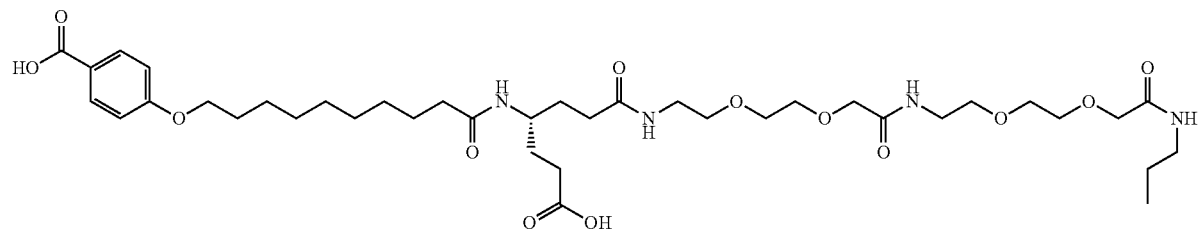

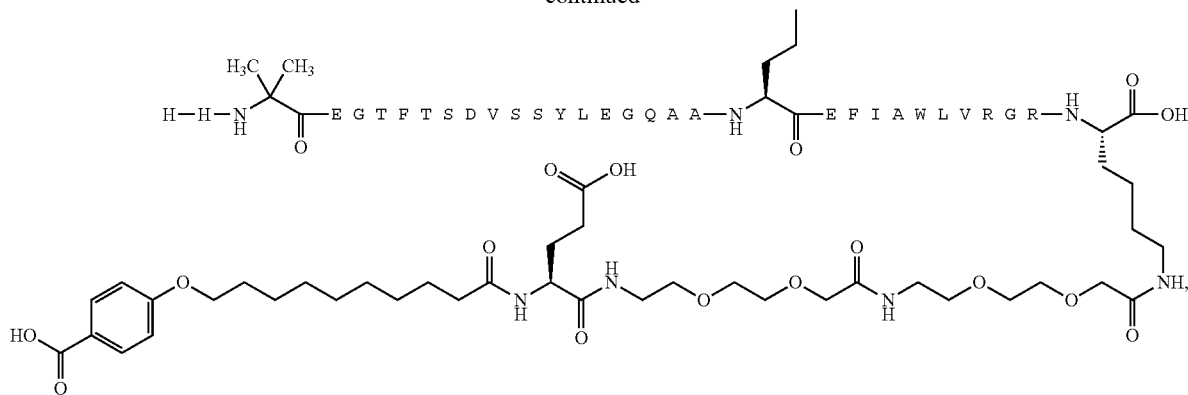

where the amino acid sequence is that of SEQ ID NO: 7, and Chem. 68:

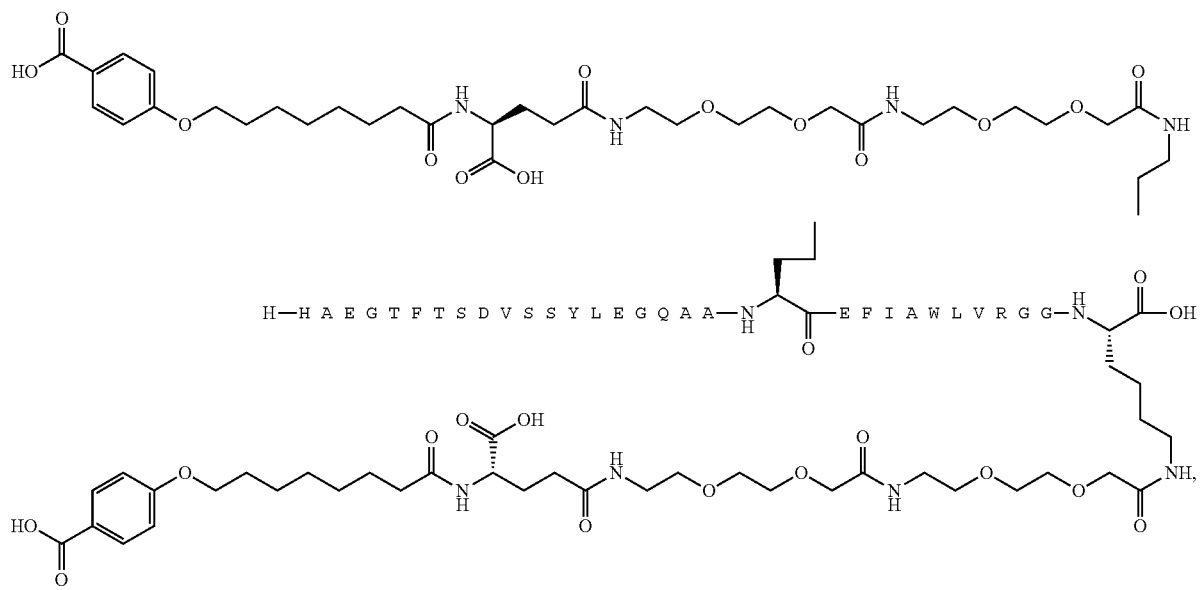

where the amino acid sequence is that of SEQ ID NO: 6, or a pharmaceutically acceptable salt, amide, or ester of any of these compounds.

10. A method for treating type 2 diabetes in a subject in need of such treatment, the method comprising administering a therapeutically effective amount of a derivative according to claim 1 to a subject in need of such treatment.

11. A method for treating type 2 diabetes in a subject in need of such treatment, the method comprising administering a therapeutically effective amount of a compound according to claim 9 to a subject in need of such treatment.

12. A compound according to claim 9 which is

Chem. 20:

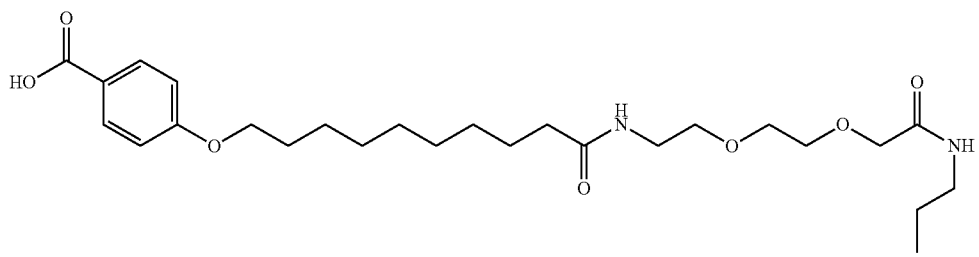

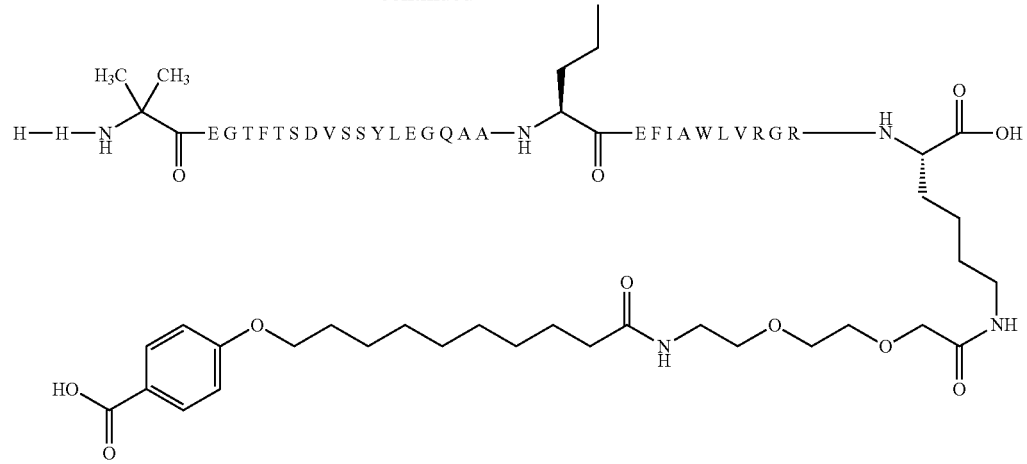
where the amino acid sequence is that of SEQ ID NO: 7, or a pharmaceutically acceptable salt, amide, or ester of the compound.
13. A compound according to claim 9 which is
Chem. 21:
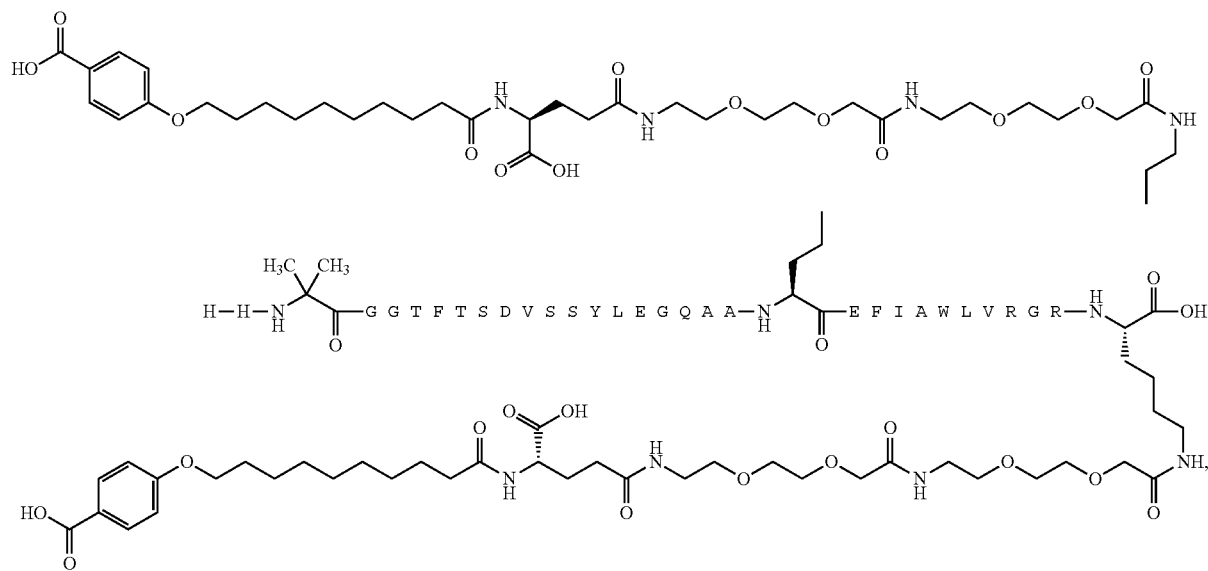
where the amino acid sequence is that of SEQ ID NO: 7, or a pharmaceutically acceptable salt, amide, or ester of the compound.
14. A compound according to claim 9 which is
Chem. 32
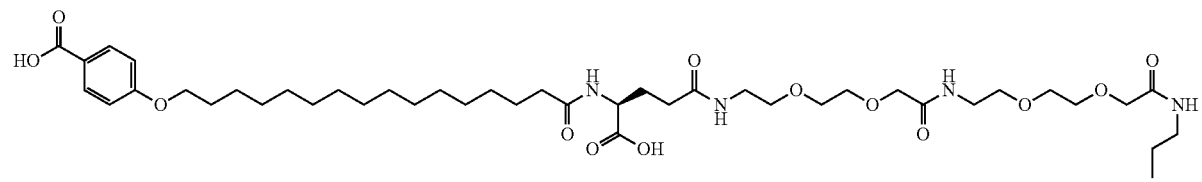

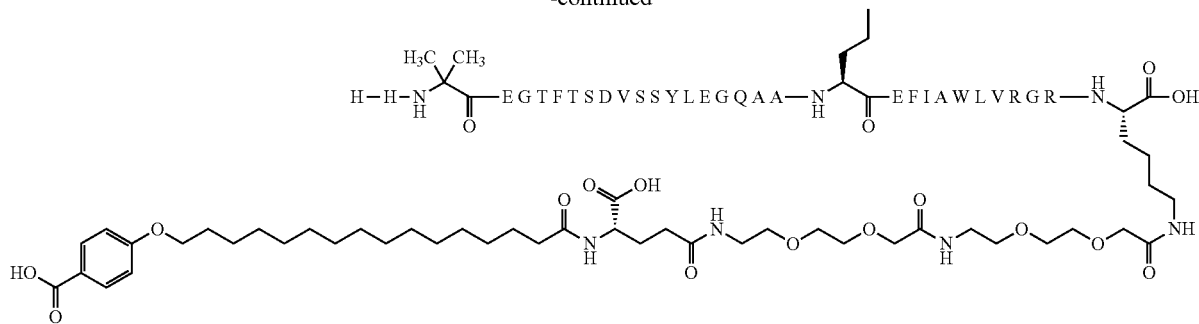
where the amino acid sequence is that of SEQ ID NO: 7, or a pharmaceutically acceptable salt, amide, or ester of the compound.
15. A compound according to claim 9 which is
Chem. 34
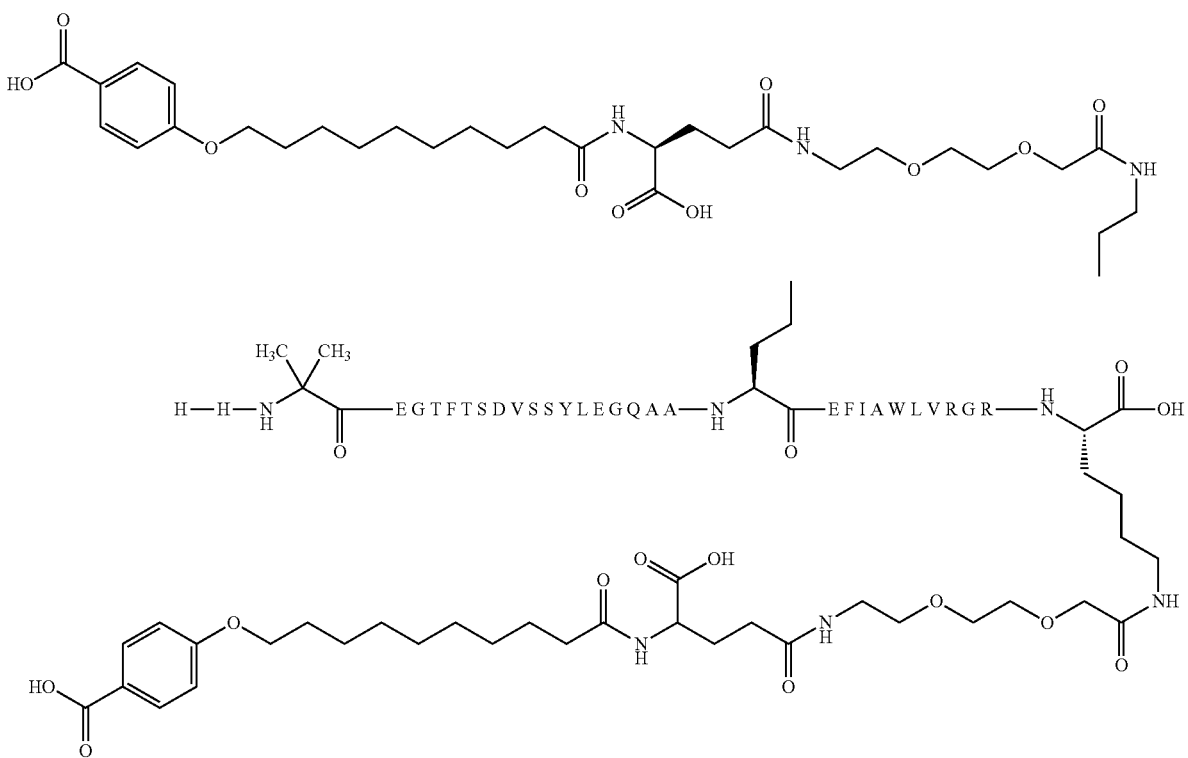
where the amino acid sequence is that of SEQ ID NO: 7, or a pharmaceutically acceptable salt, amide, or ester of the compound.
16. A compound according to claim 9 which is
Chem. 38
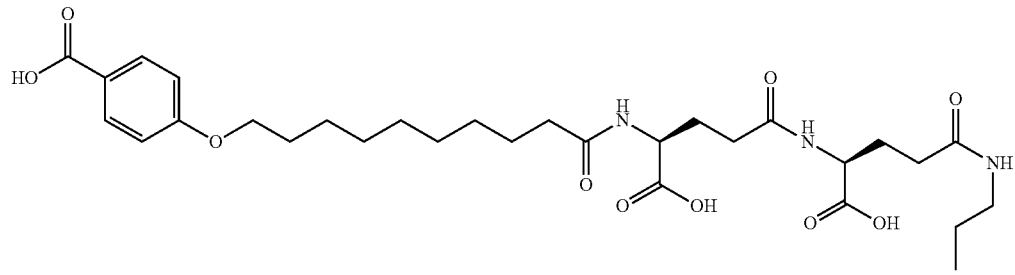

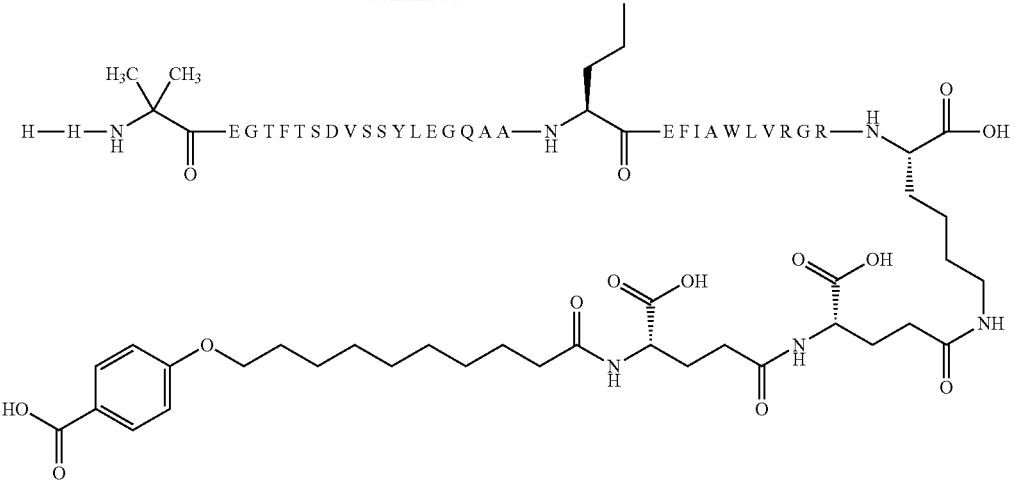
where the amino acid sequence is that of SEQ ID NO: 7, or a pharmaceutically acceptable salt, amide, or ester of the compound.
17. A compound according to claim 9 which is
Chem. 47
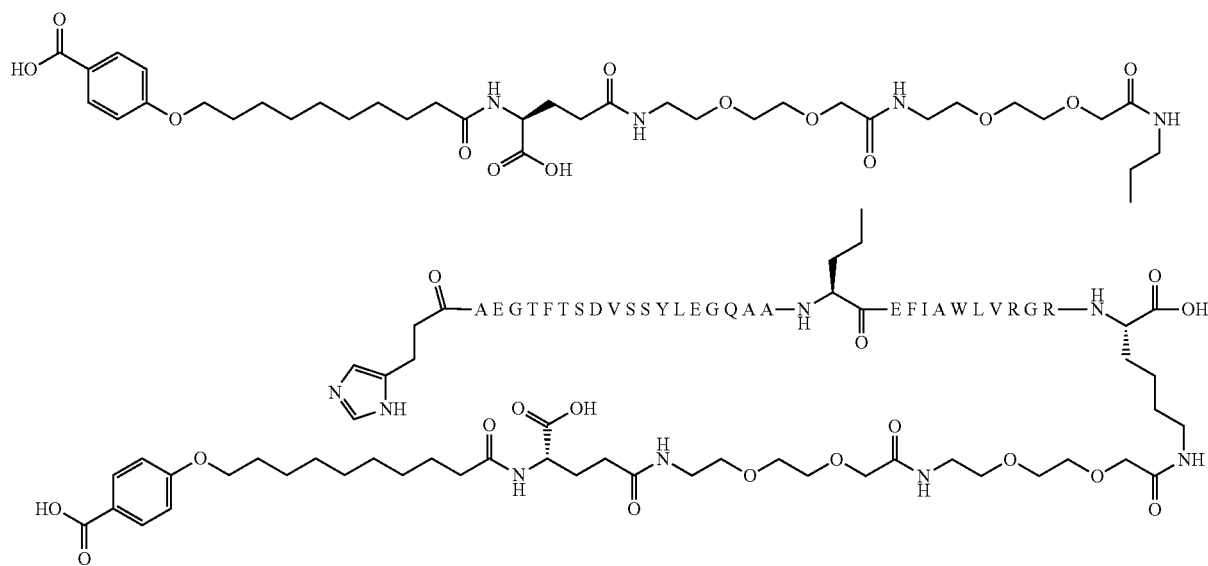
where the amino acid sequence is that of SEQ ID NO: 12, or a pharmaceutically acceptable salt, amide, or ester of the compound.
18. A compound according to claim 9 which is
Chem. 48
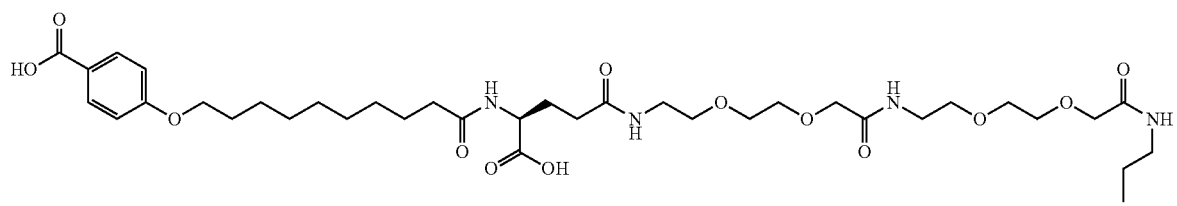

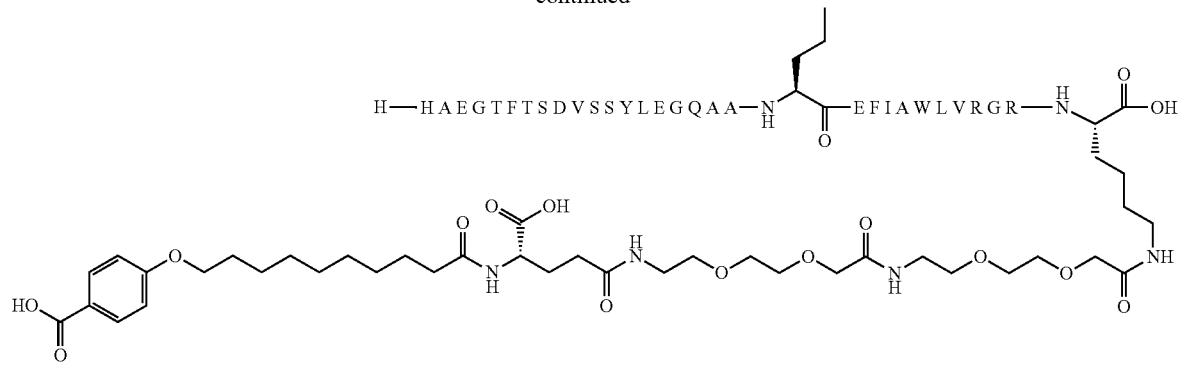
where the amino acid sequence is that of SEQ ID NO: 9, or a pharmaceutically acceptable salt, amide, or ester of the compound.
19. A compound according to claim 9 which is
Chem. 52:
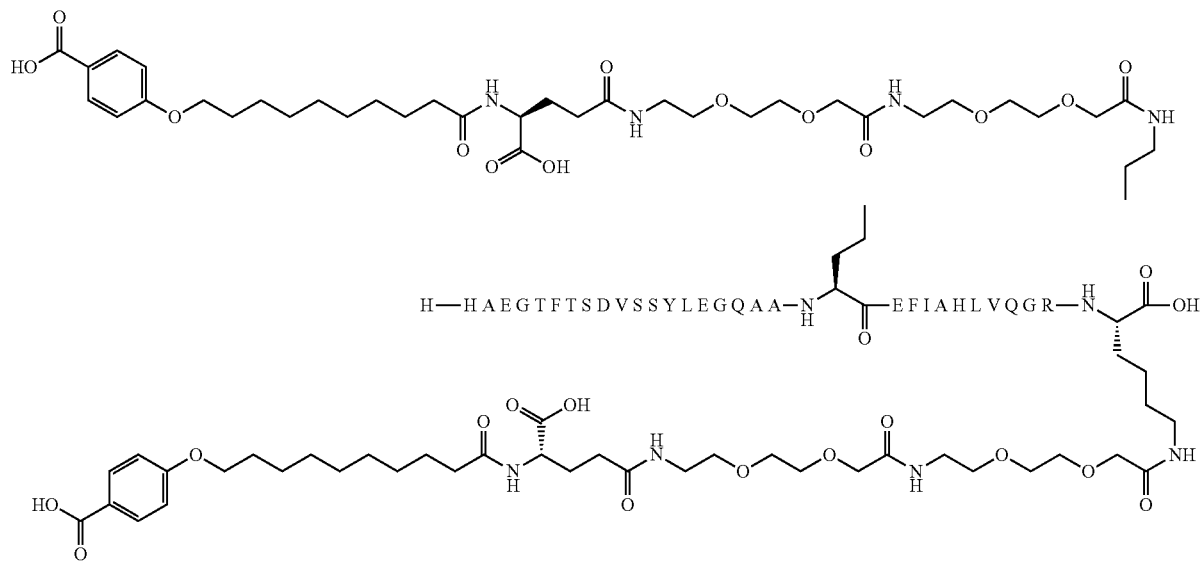
where the amino acid sequence is that of SEQ ID NO: 10, or a pharmaceutically acceptable salt, amide, or ester of the compound.
20. A compound according to claim 1 which is
Chem. 55:
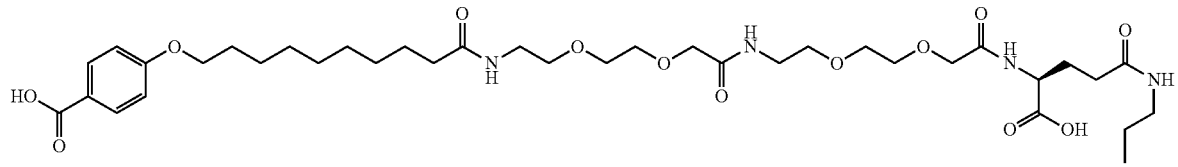

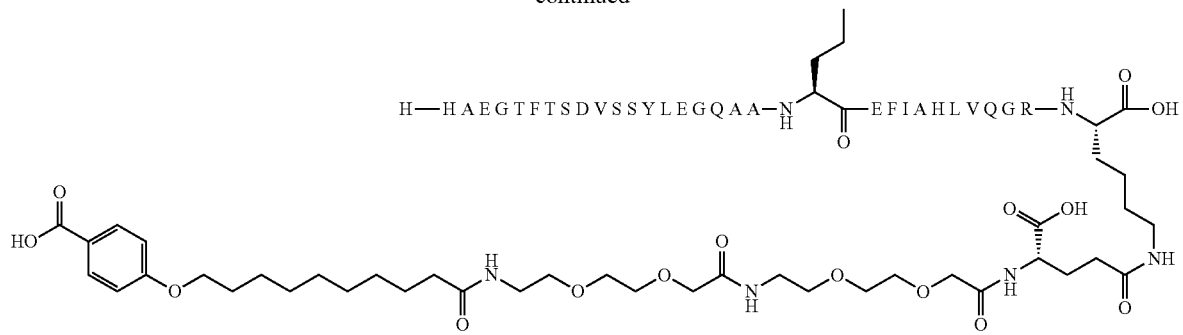
where the amino acid sequence is that of SEQ ID NO: 10, or a pharmaceutically acceptable salt, amide, or ester of the compound.
21. A compound according to claim 1 which is
Chem. 56:
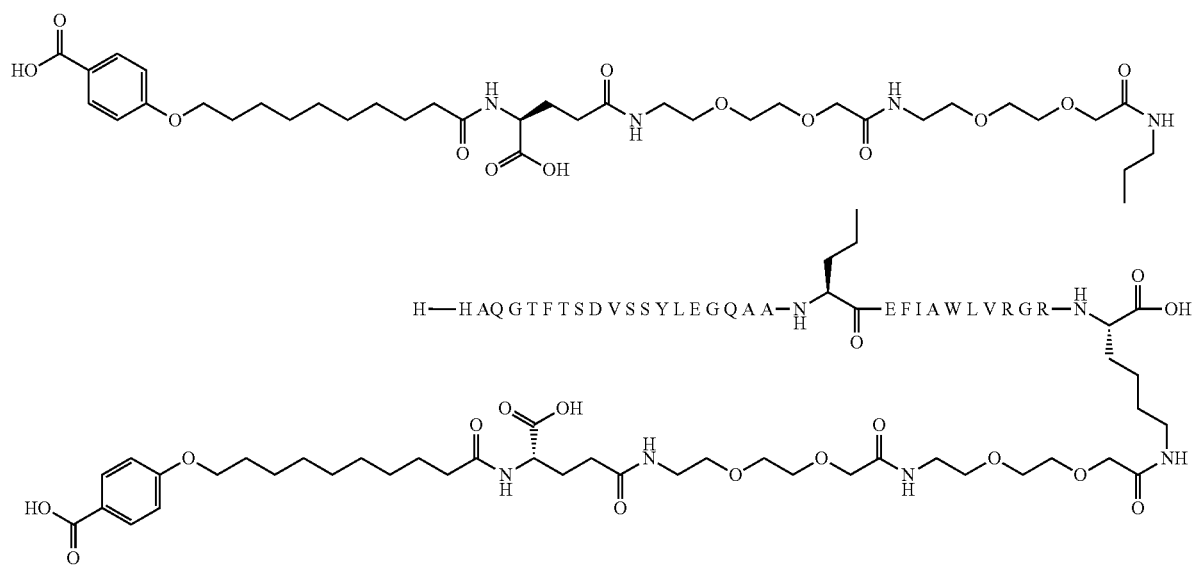
where the amino acid sequence is that of SEQ ID NO: 8, or a pharmaceutically acceptable salt, amide, or ester of the compound.
22. A compound according to claim 9 which is
Chem. 57:
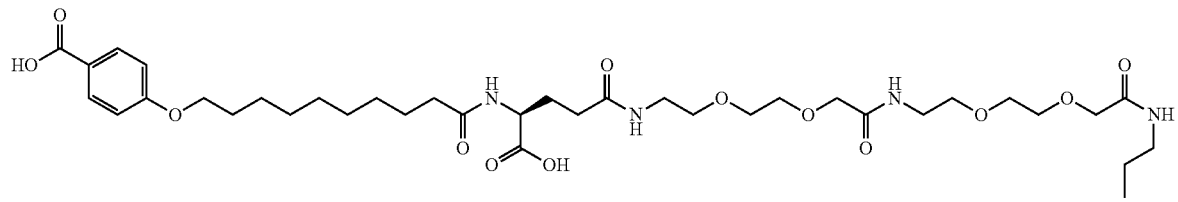

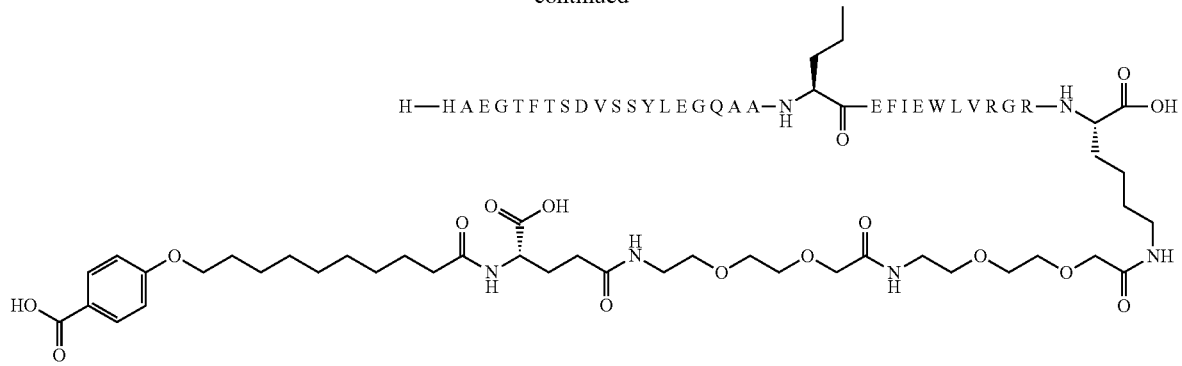
where the amino acid sequence is that of SEQ ID NO: 13, or a pharmaceutically acceptable salt, amide, or ester of the compound.
23. A compound according to claim 9 which is
Chem. 58:
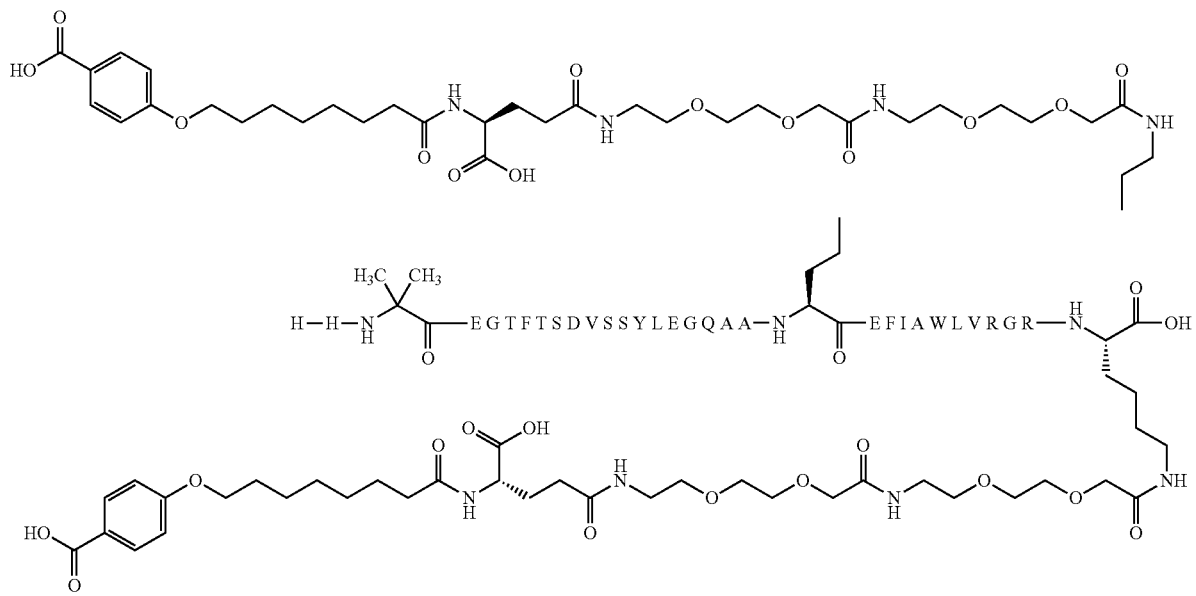
where the amino acid sequence is that of SEQ ID NO: 7, or a pharmaceutically acceptable salt, amide, or ester of the compound.
24. A compound according to claim 9 which is
Chem. 59:
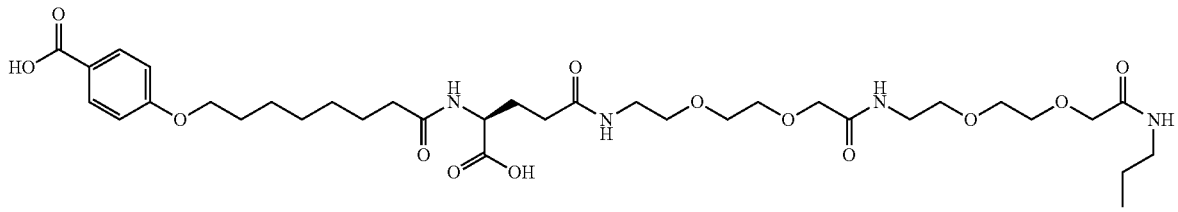

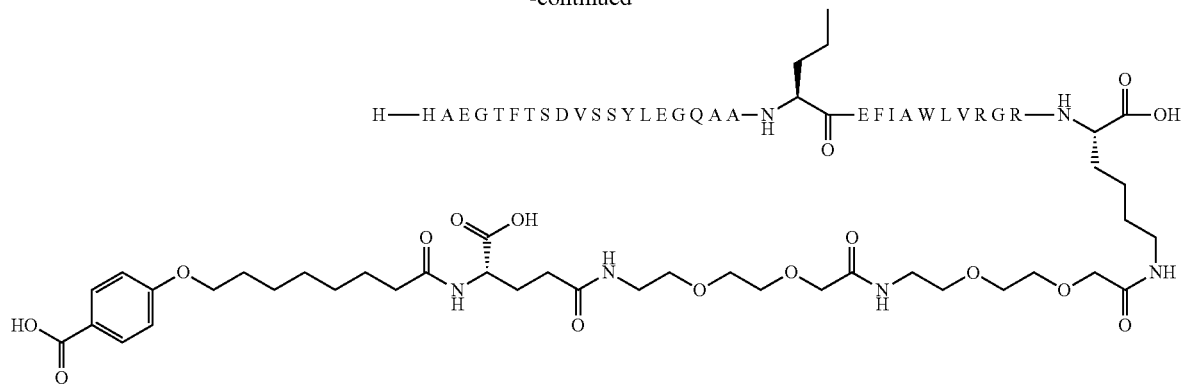
where the amino acid sequence is that of SEQ ID NO: 9, or a pharmaceutically acceptable salt, amide, or ester of the compound.
25. A compound according to claim 9 which is
Chem. 61:
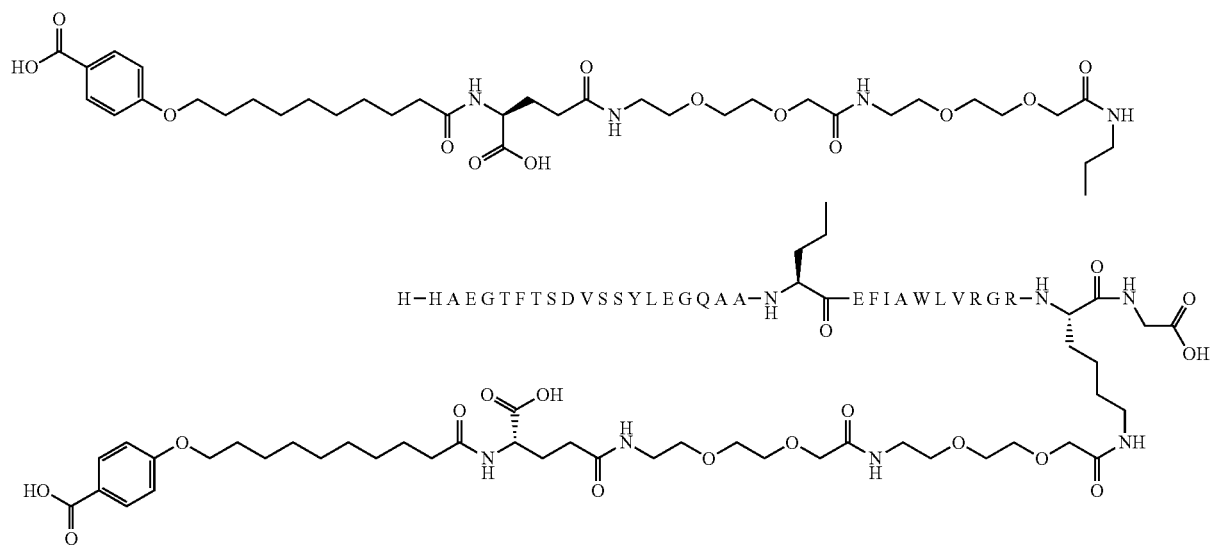
where the amino acid sequence is that of SEQ ID NO: 9, or a pharmaceutically acceptable salt, amide, or ester of the compound.
26. A compound according to claim 9 which is
Chem. 62:
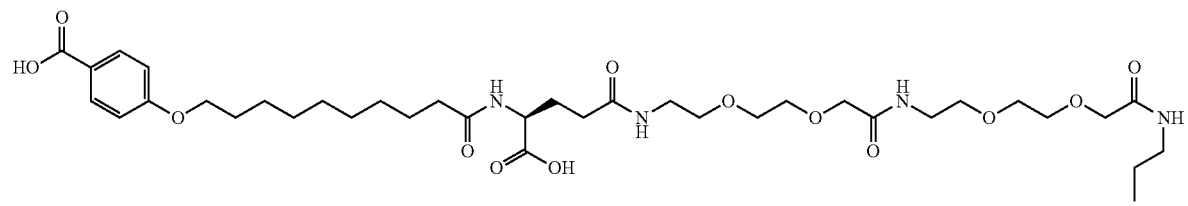

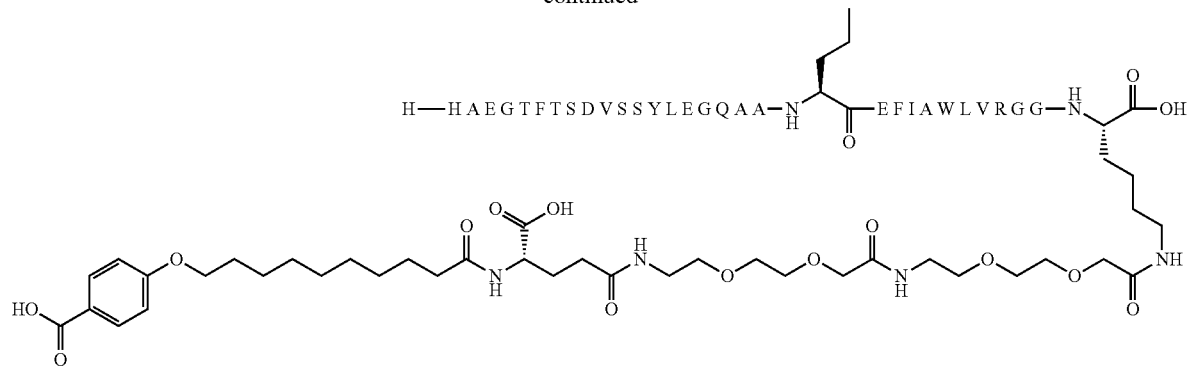
where the amino acid sequence is that of SEQ ID NO: 6, or a pharmaceutically acceptable salt, amide, or ester of the compound.
27. A compound according to claim 9 which is
Chem. 63:
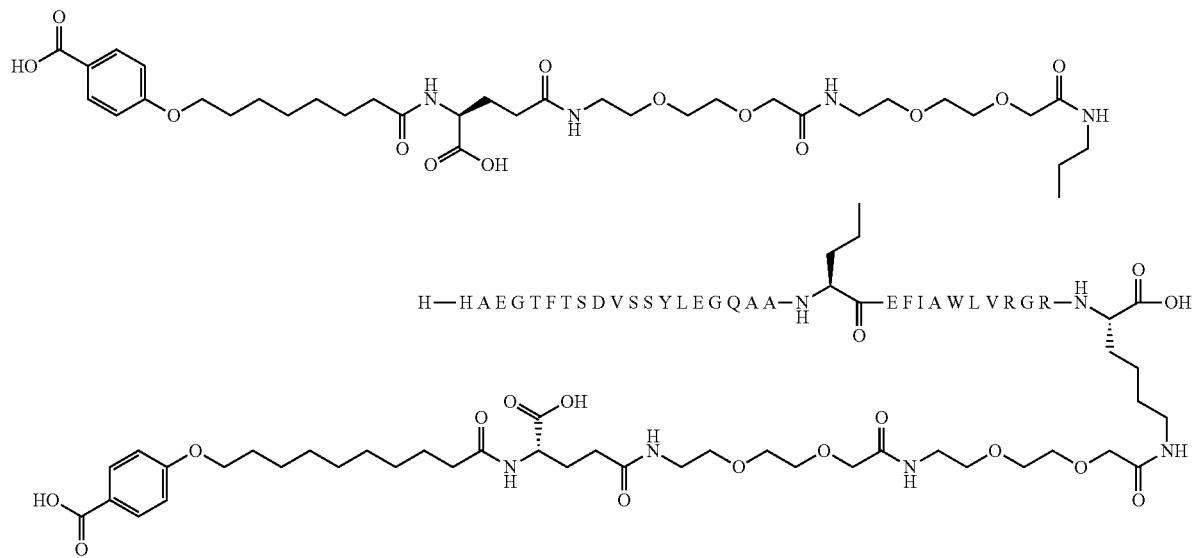
where the amino acid sequence is that of SEQ ID NO: 9, or a pharmaceutically acceptable salt, amide, or ester of the compound.
28. A compound according to claim 9 which is
Chem. 65:
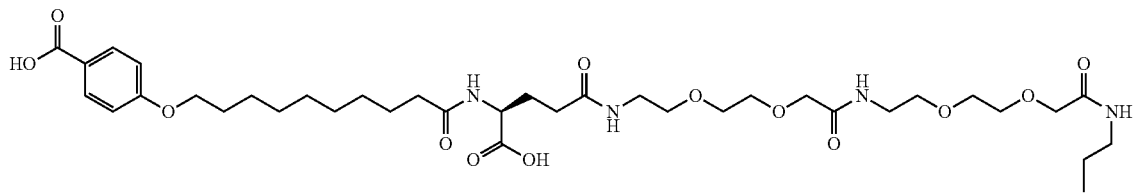

-continued
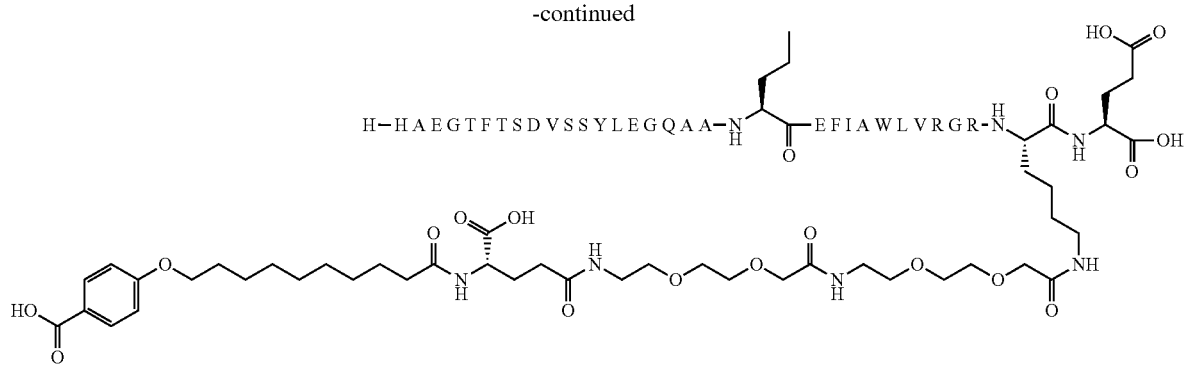
where the amino acid sequence is that of SEQ ID NO: 14, or a pharmaceutically acceptable salt, amide, or ester of the compound.
29. A compound according to claim 9 which is
Chem. 67:
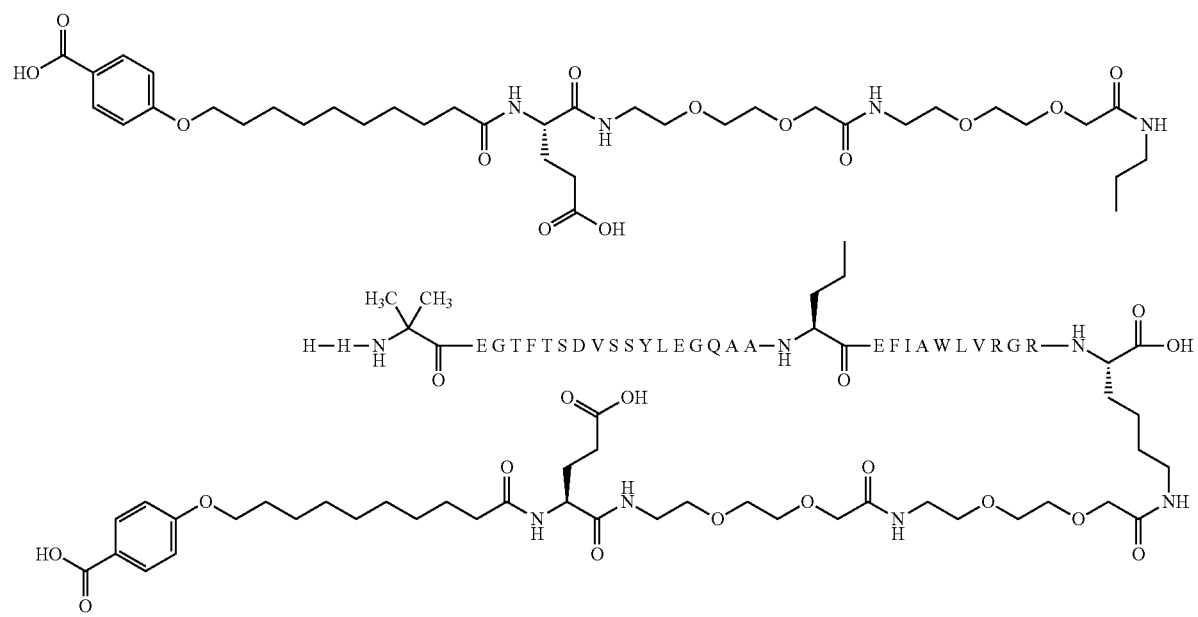
where the amino acid sequence is that of SEQ ID NO: 7, or a pharmaceutically acceptable salt, amide, or ester of the compound.
30. A compound according to claim 9 which is
Chem. 68:
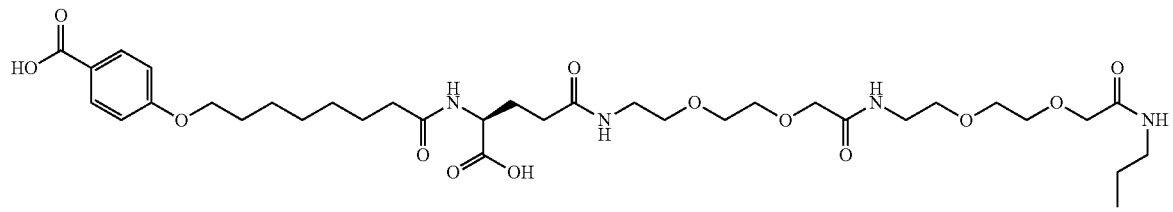

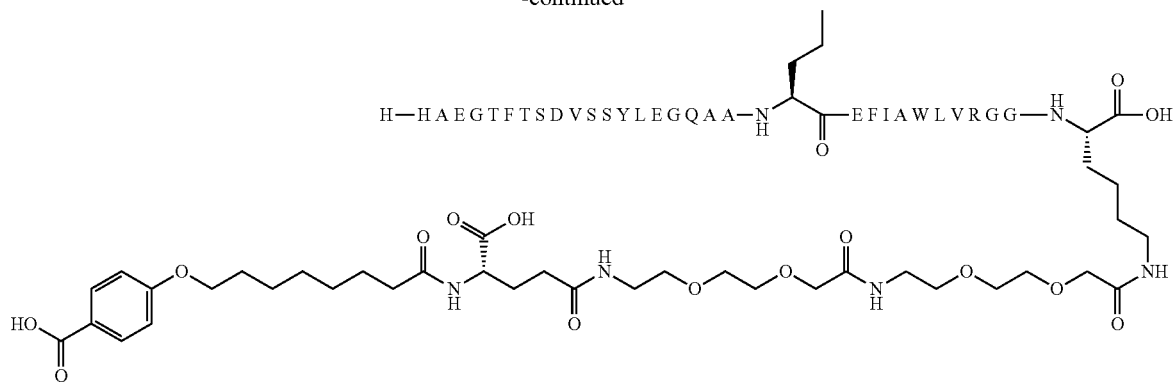
where the amino acid sequence is that of SEQ ID NO: 6, or a pharmaceutically acceptable salt, amide, or ester of the compound.
* * * * *

UNITED STATES PATENT AND TRADEMARK OFFICE
CERTIFICATE OF CORRECTION

| | |
|---|---|
| PATENT NO. | : 8,648,041 B2 |
| APPLICATION NO. | : 12/970196 |
| DATED | : February 11, 2014 |
| INVENTOR(S) | : Patrick W. Garibay et al. |

It is certified that error appears in the above-identified patent and that said Letters Patent is hereby corrected as shown below:

In the Claims

Please replace claim 21, column 237, with the following:

"A compound according to claim 9..."

Signed and Sealed this
Twenty-fourth Day of February, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,648,041 B2  
APPLICATION NO. : 12/970196  
DATED : February 11, 2014  
INVENTOR(S) : Patrick W. Garibay et al.

Page 1 of 1

It is certified that error appears in the above-identified patent and that said Letters Patent is hereby corrected as shown below:

In the Claims

Please replace claim 13, column 229, chem. 21 with the following:

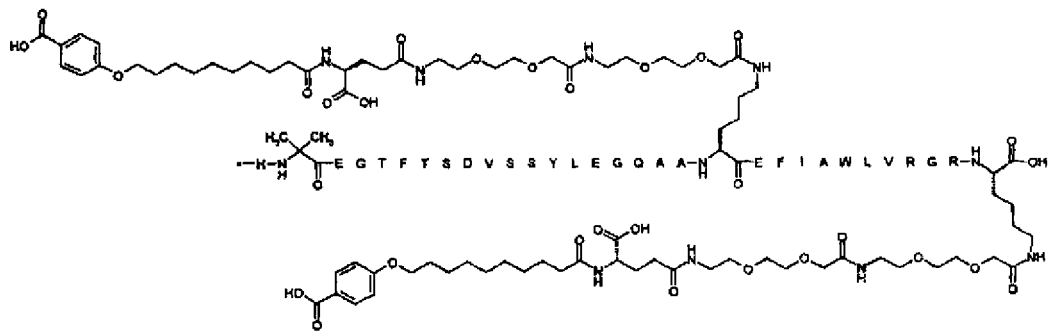

Signed and Sealed this  
Twenty-sixth Day of May, 2015

Michelle K. Lee  
*Director of the United States Patent and Trademark Office*

SEQUENCE LISTING

```
<160> NUMBER OF SEQ ID NOS: 14

<210> SEQ ID NO 1
<211> LENGTH: 31
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: GLP-1(7-37)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Homo sapiens

<400> SEQUENCE: 2

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Lys Glu
            20                  25                  30

<210> SEQ ID NO 3
```

```
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Aib

<400> SEQUENCE: 3

His Xaa Glu Gly Thr Phe Thr Ser Asp Val Ser Ser Tyr Leu Glu Gly
1               5                   10                  15

Gln Ala Ala Lys Glu Phe Ile Ala His Leu Val Gln Gly Arg Lys
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Aib

<400> SEQUENCE: 4

His Xaa Glu Gly Thr Phe Thr Ser Asp Val Ser Ser Tyr Leu Glu Gly
1               5                   10                  15

Arg Ala Ala Lys Glu Phe Ile Ala Trp Leu Val Arg Gly Arg Lys
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Aib

<400> SEQUENCE: 5

His Xaa Gly Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
            20                  25                  30

<210> SEQ ID NO 6
<211> LENGTH: 31
<212> TYPE: PRT
<213> ORGANISM: Homo sapiens

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Lys
            20                  25                  30
```

```
<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 7

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
                20                  25                  30

<210> SEQ ID NO 8
<211> LENGTH: 31
<212> TYPE: PRT
<213> ORGANISM: Homo sapiens

<400> SEQUENCE: 8

His Ala Gln Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
                20                  25                  30

<210> SEQ ID NO 9
<211> LENGTH: 31
<212> TYPE: PRT
<213> ORGANISM: Homo sapiens

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
                20                  25                  30

<210> SEQ ID NO 10
<211> LENGTH: 31
<212> TYPE: PRT
<213> ORGANISM: Homo sapiens

<400> SEQUENCE: 10

His Ala Glu Gly Thr Phe Thr Ser Asp Val Ser Ser Tyr Leu Glu Gly
1               5                   10                  15

Gln Ala Ala Lys Glu Phe Ile Ala His Leu Val Gln Gly Arg Lys
                20                  25                  30

<210> SEQ ID NO 11
<211> LENGTH: 29
<212> TYPE: PRT
<213> ORGANISM: Homo sapiens

<400> SEQUENCE: 11

Glu Gly Thr Phe Thr Ser Asp Val Ser Ser Tyr Leu Glu Gly Gln Ala
1               5                   10                  15
```

```
Ala Lys Glu Phe Ile Ala Trp Leu Val Lys Gly Arg Gly
            20                  25

<210> SEQ ID NO 12
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imidazopropionic acid

<400> SEQUENCE: 12

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
            20                  25                  30

<210> SEQ ID NO 13
<211> LENGTH: 31
<212> TYPE: PRT
<213> ORGANISM: Homo sapiens

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Arg Gly Arg Lys
            20                  25                  30

<210> SEQ ID NO 14
<211> LENGTH: 32
<212> TYPE: PRT
<213> ORGANISM: Homo sapiens

<400> SEQUENCE: 14

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys Glu
            20                  25                  30
```